US008282921B2

(12) United States Patent
Glidden

(10) Patent No.: US 8,282,921 B2
(45) Date of Patent: Oct. 9, 2012

(54) TRNA SYNTHETASE FRAGMENTS

(76) Inventor: Paul Glidden, San Diego, CA (US)

( * ) Notice: Subject to any disclaimer, the term of this patent is extended or adjusted under 35 U.S.C. 154(b) by 221 days.

(21) Appl. No.: 12/492,040

(22) Filed: Jun. 25, 2009

(65) Prior Publication Data

US 2010/0003230 A1  Jan. 7, 2010

Related U.S. Application Data

(63) Continuation-in-part of application No. 12/399,468, filed on Mar. 6, 2009, which is a continuation-in-part of application No. 11/196,019, filed on Aug. 2, 2005, now abandoned, which is a continuation-in-part of application No. 10/962,171, filed on Oct. 7, 2004, now abandoned, and a continuation-in-part of application No. 10/962,217, filed on Oct. 7, 2004, now abandoned, and a continuation-in-part of application No. 10/962,058, filed on Oct. 7, 2004, now abandoned, and a continuation-in-part of application No. 10/961,528, filed on Oct. 7, 2004, now abandoned, and a continuation-in-part of application No. 10/962,375, filed on Oct. 7, 2004, now abandoned, and a continuation-in-part of application No. 10/962,062, filed on Oct. 7, 2004, now abandoned, and a continuation-in-part of application No. 10/962,218, filed on Oct. 7, 2004, now abandoned, and a continuation-in-part of application No. 10/961,529, filed on Oct. 7, 2004, now abandoned, and a continuation-in-part of application No. 10/961,526, filed on Oct. 7, 2004, now abandoned, and a continuation-in-part of application No. 10/961,486, filed on Oct. 7, 2004, now abandoned, and a continuation-in-part of application No. 11/019,969, filed on Dec. 20, 2004, now abandoned, and a continuation-in-part of application No. 10/980,866, filed on Nov. 2, 2004, now abandoned, which is a continuation-in-part of application No. 10/962,218, filed on Oct. 7, 2004, now abandoned.

(60) Provisional application No. 60/598,019, filed on Aug. 2, 2004, provisional application No. 60/624,656, filed on Nov. 2, 2004.

(51) Int. Cl.
*A61K 38/47* (2006.01)
*A61K 48/00* (2006.01)
*C12N 9/22* (2006.01)

(52) U.S. Cl. ............... 424/94.61; 435/199; 435/183; 514/44 R

(58) Field of Classification Search .............. None
See application file for complete search history.

(56) References Cited

U.S. PATENT DOCUMENTS

| | | | |
|---|---|---|---|
| 4,196,265 A | 4/1980 | Koprowski et al. |
| 4,601,980 A | 7/1986 | Goeddel et al. |
| 4,604,359 A | 8/1986 | Goeddel et al. |
| 4,634,677 A | 1/1987 | Goeddel et al. |
| 5,334,531 A | 8/1994 | Del Bue et al. |
| 5,496,713 A | 3/1996 | Honjo et al. |
| 5,637,495 A | 6/1997 | Gorecki et al. |
| 5,714,346 A | 2/1998 | Udaka et al. |
| 5,795,745 A | 8/1998 | Goeddel et al. |
| 2002/0182666 A1 | 12/2002 | Schimmel et al. |
| 2003/0017564 A1 | 1/2003 | Schimmel et al. |
| 2005/0197298 A1 | 9/2005 | Schimmel et al. |
| 2006/0003933 A1 | 1/2006 | Friedlander et al. |
| 2006/0024286 A1 | 2/2006 | Glidden |
| 2006/0024287 A1 | 2/2006 | Glidden |
| 2006/0024288 A1 | 2/2006 | Glidden |
| 2006/0078553 A1 | 4/2006 | Glidden |
| 2006/0078556 A1 | 4/2006 | Glidden |
| 2006/0078886 A1 | 4/2006 | Glidden |
| 2006/0078887 A1 | 4/2006 | Glidden |
| 2006/0079441 A1 | 4/2006 | Glidden |
| 2006/0079472 A1 | 4/2006 | Glidden |
| 2006/0079473 A1 | 4/2006 | Glidden |
| 2006/0079474 A1 | 4/2006 | Glidden |
| 2006/0079672 A1 | 4/2006 | Glidden |
| 2006/0079673 A1 | 4/2006 | Glidden |

FOREIGN PATENT DOCUMENTS

| | | |
|---|---|---|
| BR | 0207449 | 4/2004 |
| CN | 1527719 A | 9/2004 |
| EP | 1377305 | 1/2004 |
| GB | 2327945 | 2/1999 |
| IL | 157558 | 3/2004 |
| JP | 1-196294 | 8/1989 |
| JP | 1-196295 | 8/1989 |
| JP | 1-242105 | 9/1989 |

(Continued)

OTHER PUBLICATIONS

Elbashir, S. et al., "Duplexes of 21-nucleotide RNAs Mediate RNA Interference in Cultured Mammalian Cells," *Nature*, 2001, 494-498, vol. 411.

(Continued)

*Primary Examiner* — Kagnew H Gebreyesus
(74) *Attorney, Agent, or Firm* — Jeffrey A. McKinney; McKinney Law Group APC

(57) ABSTRACT

The present invention relates to compositions and methods for treating conditions associated with angiogenesis. In particular the present invention relates to multi-unit complexes of tRNA synthetase fragments and uses thereof; diverse multi-unit complexes including a tRNA synthetase fragment; compositions and methods for modulating angiogenesis; polynucleotides encoding tRNA synthetase fragments and uses thereof; antibodies and epitopes specific to tRNA synthetase fragments; variants of tRNA synthetase fragments and uses thereof; methods for treating angiogenesis; methods for screening for anti-angiogenic agents; methods of modulating angiogenesis; kits for modulating angiogenesis; and business methods for modulating angiogenesis. Preferably the tRNA synthetase fragments are tryptophanyl tRNA synthetase fragments, and more preferably human tryptophanyl tRNA synthetase fragments.

7 Claims, 33 Drawing Sheets

FOREIGN PATENT DOCUMENTS

| | | |
|---|---|---|
| JP | 4-197436 | 7/1992 |
| JP | 2004532010 | 10/2004 |
| KR | 8902068 | 6/1989 |
| MX | PA03007586 | 12/2003 |
| PL | 364596 | 12/2004 |
| WO | WO01/74841 | 10/2001 |
| WO | WO01/75078 | 10/2001 |
| WO | WO02/067970 | 9/2002 |
| WO | WO03/009813 | 2/2003 |
| WO | WO2004/010959 | 2/2004 |
| WO | WO2004/011900 | 2/2004 |
| ZA | 200307383 | 1/2005 |

OTHER PUBLICATIONS

Epely, S., et al., "Limited Proteolysis of Tryptophanyl-tRNA Synthestase From Beef Pancreas," *European Journal of Biochemistry.*, 1976, 139-146, vol. 61.

Eriani, G., et al., "Partition of tRNA Synthetases into Two Classes Based on Mutually Exclusive Sets of Sequence Motifs," *Nature*, 1990, pp. 203-206, vol. 347.

Erikson, O. et al., "A Conditional Marker Gene Allowing Both Positive and Negative Selection in Plants," *Nature Biotechnology*, 2004, 455-458, vol. 22, No. 4.

Ewalt, K.L., et al., "Activation of Angiogenic Signaling Pathways by Two Human tRNA Synthetases," *Biochemistry*, 2002, 13344-13349, vol. 41.

Ewenson, A. et al., "Ketomethylene Pseudopeptide Analogues of Substance P: Synthesis and Biological Activity," *Journal of Medicinal Chemistry*, 1986, 295-299, vol. 29.

Favorova, O., et al., "Molecular and Cellular Studies of Tryptophanyl-tRNA Synthestases Using Monoclonal Antibodies," *European Journal of Biochemistry*, 1989, 583-588, vol. 184.

Fleckner, J., et al., "Human Interferon Y Potently Induces the Synthesis of a 55-kDa Protein (y2) Highly Homologous to Rabbit Peptide Chain Release Factor and Bovine Tryptophanyl-tRNA Synthetase," *Proceedings of the National Academy of Sciences USA*, 1991, 11520-11524, vol. 88.

Fraley, R. et al., "New Generation Liposomes: The Engineering of an Efficient Vehicle for Intracellular Delivery of Nucleic Acids," *Trends in Biochemical Science*, 1981, 77-80.

Friedlander, M., et al., "Quantative Determination of Retinal Vascular Volumes in Developing Murine Retina," *Retinal Vasculogenesis, Angiogenesis, Remodeling, and Neovascularization Poster Presentation, Hall A*, 2000, vol. 41, No. 4.

Frolova, L. et al., "Cloning and Nucleotide Sequence of the Structural Gene Encoding for Human Tryptophanyl-tRNA Synthetase," *Gene*, 1991, 291-296, vol. 109, No. 2.

Frugier, M. et al., "RNA Recognition by Designed Peptide Creates "Artificial" tRNA Synthetase," *Proceedings of the National Academy of Science*, 2003, 7471-7475, vol. 100, No. 13.

Gasser, C. et al., "Expression of Abbreviated Mouse Dihydrofolate Reductase Genes in Cultured Hamster Cells," *Proceedings of the National Academy of Sciences USA*, 1982, 6522-6526, vol. 79.

Getsios, S. et al., "Regulated Expression of Cadherin-6 and Cadherin-11 in the Glandular Epithelial and Stromal Cells of the Human Endometrium," *Developmental Dynamics*, 1998, 238-247, vol. 211.

Gluzman, Y., "SV40-Transfored Simian Cells Support the Replication of Early SV40 Mutants," *Cell*, 1982, 175-182, vol. 23.

Goodford, P., "A Computational Procedure for Determining Energetically Favorable Binding Sites on Biologically Important Macromolecules," *Journal of Medicinal Chemistry*, 1985, 849-857, vol. 28.

Goodsell, D et al., "Automated Docking of Substrates to Proteins by Simulated Annealing," *Proteins, Structure, Function, and Genetics*, 1990, 195-202, vol. 8.

Gordon, E. et al., "Design of Peptide Derived Amino Alcohols As Transition-State Analog Inhibitors of Angiotensin Converting Enzyme," *Biochemical and Biophysical Research Communications*, 1985, 419-426, vol. 126, No. 1.

Hammond, S. et al., "Post-transcriptional Gene Silencing by Double-stranded RNA," *Nature*, 2001, 110-119, vol. 2.

Hunter, E. et al., "Genetics of Human Cell Lines, IV. DNA-mediated Heritable Transformation of a Biochemical Trait," *Genetics*, 1962, 2026-2034, vol. 48.

Iborra, F., et al., "Structure-Activity Relationships in Tryptophanyl Transfer Ribonucleic Acid Synthetase form Beef Pancreas, "*The Journal of Biological Chemistry*, 1975, pp. 6659-6665, vol. 250, No. 17.

Jia, J. et al., "Two Essential Regions for tRNA Recognition in *Bacillus subtilis* Tryptophanyl-tRNA Synthetase," *Journal of Biochemistry*, 2002, 749-756, vol. 365.

Jones, C. et al., "Current Trends in Molecular Recognition and Bioseparation," *Journal of Chromatography*, 1995, 3-22, vol. 707.

Kise. Y. et al., "A Short Peptide Insertion Crucial for Angiostatic Activity of Human Tryptophanyl-tRNA Synthetase," *Nature Structural & Molecular Biology*, 2004, 149-56, vol. 11, No. 2.

Kisselev, L. et al., "Bovine Tryptophanyl-rRNA Synthetase," *European Journal of Biochemistry*, 1981, 511-517, vol. 120.

Kisselev, L. et al., "Interferon Inducibility of Mammalian Tryptophanyl-tRNA Synthetase: New perspectives," *TIBS*, 1993, 263-267, vol. 18.

Kisselev, L. et al., "Mammalian Tryptophanyl-tRNA Synthetase," *Biochimie*, 1993, 1027-1039, vol. 75, No. 12.

Kleeman, T. et al., "Human Tyrosyl-tRNA Synthetase Shares Amino Acid Sequence Homology With a Putative Cytokine," *The Journal Biological Chemistry*, 1997, 14420-14425, vol. 272, No. 22.

Kuntz, I. et al., "A Geometric Approach to Macromolecule-ligand Interactions," *Journal of Molecular Biology*, 1982, 269-288, vol. 161.

Lazar, E et al., "Transforming Growth Factor α: Mutation of Aspartic Acid 47 and Leucine 48 Results in Different Biological Activities," *Molecular and Cellular Biology*, 1988, 1247-1252, vol. 8, No. 3.

Lemaire, G. et al., "Multiple Forms of Tryptophanyl-tRNA Synthetase From Beef Pancreas," *European Journal of Biochemistry*, 1975, 237-252, vol. 51.

Lin, S. et al., "A Novel mRNA-cDNA Interference Phenomenon for Silencing bcl-2 Expression in Human LNCaP Cells," *Biochemical and Biophysical Research Communications*, 2001, 639-644, vol. 281.

Liu, J. et al., "A New γ-Interferon-Inducible Promoter and Splice Variants of an Anti-Angiogenic Human tRNA Synthetase," *Nucleic Acids Research*, 2004, 719-727, vol. 32, No. 2.

Liu, J. et al., "Mutational Switching of a Yeast tRNA Synthetase Into a Mammalian-like Synthetase Cytokine," *Biochemistry*, 2002, 14232-14237, vol. 41.

Liu, S. et al., "Removal of Endotoxin From Recombinant Protein Preparations," *Clinical Biochemistry*, 1997, 455-463, vol. 30.

Lowy, I. et al., "Isolation of Transforming DNA: Cloning the Hamster aprt Gene," *Cell*, 1980, 817-823, vol. 22.

Mannino, R. et al., "Liposome Mediated Gene Transfer," *BioTechniques*, 1988, 682-689, vol. 6, No. 7.

Miranker, A. et al., "Functionality Maps of Binding Sites: A Multiple Copy Simultaneous Search Method," *Proteins: Structure, Function, and Genetics*, 1992, 29-34, vol. 11.

Moulton, K. et al., "Inhibition of Plaque Neovascularization Reduces Macrophage Accumulation and Progression of Advanced Atherosclerosis," *Proceedings of the National Academy of Sciences*, 2003, 4736-4741, vol. 100, No. 8.

Mulligan, R. et al., "Selection for Animal Cells That Express the *Escherichia coli* Gene Coding for Xanthine-guanine Phosphoribosyltransferase," *Proceedings of the National Academy of Sciences USA*, 1981, 2072-2076, vol. 78, No. 4.

Nagai, U. et al., "Synthesis of a Bicyclic Dipeptide With the Shape of β-turn Central Part," *Tetrahedron Letters*, 1985, 647-650, vol. 26, No. 5.

Nakagawa, S. et al., "Neural Crest Cell-cell Adhesion Controlled by Sequential and Subpopulation-specific Expression of Novel Cadherins," *Development*, 1995, 1321-1332, vol. 121.

Navarro, P. et al., "Differential Localization of VE- and N-Cadherins in Human Endothelial Cells: VE-Cadherin Competes With N-Cadherin for Junctional Localization," *The Journal of Cell Biology*, 1998, 1475-1484, vol. 140, No. 6.

O'Hare, K. et al., "Transformation of Mouse Fibroblasts to Methotrexate Resistance by a Recombinant Plasmid Expressing a Prokaryotic Dihydrofolate," *Proceedings of the National Academy of Sciences USA*, 1981, 1527-1531, vol. 78, No. 3.

Otani, A. et al., "A Fragment of Human TrpRS As a Potent Antagonist of Ocular Angiogenesis," *Proceedings of the National Academy of Science*, 2002, 178-183, vol. 99, No. 1.

Otani, A. et al., "Bone Marrow-derived Stem Cells Target Retinal Astrocytes and Can Promote or Inhibit Retinal Angiogenesis," *Nature Medicine*, 2002, 1004-1010, vol. 8.

Otani, A. et al., "Truncated Fragments of Aminoacyl-tRNA Synthetases are Potent Anglostatic Agents for Retinal Angiogenesis," IOVS, 2001, S93, vol. 42, No. 4.

Paley, E. et al., "A Mammalian Tryptophanyl-tRNA Synthetase Is Associated With Protein Kinase Activity," *European Journal of Biochemistry*, 1997, 780-788, vol. 244.

Park, S. et al., "Dose-dependent Biphasic Activity of tRNA Synthetase-associating Factor, p43, In Angiogenesis," *Journal of Biological Chemistry*, 2002, 45243-45248, vol. 277, No. 47.

Price, P. et al., "Properties of Chromatographically Purified Bovine Pancreatic Deoxyribonuclease," *The Journal of Biological Chemistry*, 1969, 917-922, vol. 244, No. 4.

Ramage, P., et al., "Snags with Tags: Some Observations Made with $(His)_6$-Tagged Proteins," *Life Science News II*, 2002, pp. 1-4, Amersham Biosciences.

Redies, C. et al., "Cadherins in the Developing Central Nervous System: An Adhesive Code for Segmental and Functional Subdivisions," *Developmental Biology*, 1996, 413-423, vol. 180.

Sallafranque, M. et al., "Tryptophanyl-tRNA Synthetase Is a Major Soluble Protein Species in Bovine Pancreas," *Biochimica et Biophysica Acta 882*, 1986, 192-199.

Santerre, R. et al., "Expression of Prokaryotic Genes for Hygromycin B and G418 Resistance as Dominant-selection Markers in Mouse L Cells," *Gene*, 1984, 147-156, vol. 30.

Sato, K. et al., "Synthesis and Antibiotic Activity of a Gramicidin S Analogue Containing Bicyclic β-Turn Dipeptides," *Journal of Chemical Society, Perkin Trans.*, 1986, 1231-1234.

Scheinker, V. et al., "The Effect of tRNA and Tryptophanyl Adenylate on Limited Proteolysis of Beef Pancreas Tryptophanyl-tRNA Synthetase," *Nucleic Acids Research*, 1979, 625-637, vol. 7, No. 3.

Sever, S. et al., "*Escherichia coli* Tryptophanyl-tRNA Synthetase Mutants Selected for Tryptophan Auxotrophy Implicate the Dimer Interface in Optimizing Amino Acid Binding," *Biochemistry*, 1996, 32-40, vol. 35.

Sharp, P., "RNA Interference—2001," *Genes & Development*, 2001, 485-490, vol. 15.

Shaw, A. et al., "Mapping and Identification of Interferon Gamma-regulated HeLa Cell Proteins Separated by Immobilized pHGradient Two-dimensional Gel Electrophoresis," *Electrophoresis*, 1999, 984-993, vol. 20.

Shibata, T. et al., "Identification of Human Cadherin-14, A Novel Neurally Specific Type II Cadherin, by Protein Interaction Cloning," *The Journal of Biological Chemistry*, 1997, 5236-5240, vol. 272, No. 8.

Shimoyama, Y. et al., "Isolation and Sequence Analysis of Human Cadherin-6 Complementary DNA for the Full Coding Sequence and Its Expression in Human Carcinoma Cells," *Cancer Research*, 1995, 2206-2211, vol. 55.

Shimoyama, Y. et al., "Molecular Cloning and Characterization of a Novel Human Classic Cadherin Homologous With Mouse Muscle Cadherin," *The Journal of Biological Chemistry*, 1998, 10011-10018, vol. 273, No. 16.

Subramani, S, et al., "Expression of the Mouse Dihydrofolate Reductase Complementary Deoxyribonucleic Acid in Simian Virus 40 Vectors," *Molecular and Cellular Biology*, 1981, 854-864, vol. 1, No. 9.

Sugimoto, K. et al., "Molecular Cloning and Characterization of a Newly Identified Member of the Cadherin Family, PB-cadherin," *The Journal of Biological Chemistry*, 1996, 11548-11556, vol. 271, No. 19.

Suzuki, S. et al., "Diversity of the Cadherin Family: Evidence for Eight New Cadherins in Nervous Tissue," *Cell Regulation*, 1991, 261-270, vol. 2.

Szymanski, M. et al., "Aminoacyl-tRNA Synthetases Database Y2K," *Nucleic Acids Research*, 2000, 326-328, vol. 28, No. 1.

Tanihara, H. et al., "Cloning of Five Human Cadherins Clarifies Characteristic Features of Cadherin Extracellular Domain and Provides Further Evidence for Two Structurally Different Types of Cadherin," *Cell Adhesion and Communication*, 1994, 15-26, vol. 2.

Tolstrup, A. et al., "Transcriptional Regulation of the Interferon-g-inducible Tryptophanyl-tRNA Synthetase Includes Alternate Splicing," *The Journal of Biological Chemistry*, 1996, 397-403, vol. 270, No. 1.

Turpaev, K. et al., "Alternative Processing of the Tryptophanyl-tRNA Synthetase mRNA From Interferon-treated Human Cells," *European Journal of Biochemistry*, 1996, 732-737, vol. 240.

Turpaev, K. et al., "Ap3A and Ap4A Are Primers for Oligoadenylate Synthesis Catalyzed by Interferon-inducible 2-5A Synthetase," *FEBS Letters*, 1997, 177-181, vol. 408.

Tzima, E. et al., "Biologically Active Fragment of a Human tRNA Synthetase Inhibits Fluid Shear Stress-activated Responses of Endothelial Cells," *Proceedings of the National Academy of Science USA*, 203, 14903-14907, vol. 100, No. 25, 2003.

University of Tennessee, "The Vascular Biology Center of Excellence Announces the Vascular Injury Laboratory," *The Vessel*, 2003, vol. 4, Issue 1.

Urlaub, G, et al., "Isolation of Chinese Hamster Cell Mutants Deficient in Dihydrofolate Reductase Activity," *Proceedings of the National Academy of Sciences USA*, 1980, 4216-4220, vol. 77, No. 7.

Wakasugi, K. et al., "A Human Aminoacyl-tRNA Synthetase as a Regulator of Angiogenesis," *Proceedings of the National Academy of Science USA*, 2002, 173-177, vol. 99, No. 1.

Wakasugi, K. et al., "Highly Differentiated Motifs Responsible for Two Cytokine Activities of a Split Human tRNA Synthetase," *The Journal of Biological Chemistry*, 1999, 23155-23159, vol. 274.

Wakasugi, K. et al., "Induction of Angiogenesis by a Fragment of Human Tryptophanyl-tRNA Synthetase," *The Journal of Biological Chemistry*, 2002, 20124-20126, vol. 277.

Wakasugi, K. et al., "Two Distinct Cytokines Released From a Human Aminoacyl-tRNA Synthetase," *Science*, 1999, 147-151, vol. 284.

Ward, W. et al., "Protein Engineering of Homodimeric Tyrosyl-tRNA Synthetase to Product Active Heterodimers," *The Journal of Biological Chemistry*, 1986, 9576-9578, vol. 261, No. 21.

Watson, J. et al., "Molecular Biology of the Gene," The Benjamin/Cummings Publishing Company, Inc., 1987, 4th Edition, vol. 1. 224-225.

Wilkie, N. et al., "Hybrid Plasmids Containing an Active Thymidine Kinase Gene of Herpes Simplex Virus 1," *Nucleic Acids Research*, 1979, 859-877, vol. 7, No. 4.

Xu, F. et al., "High-level Expression and Single-Step Purification of Human Tryptophanyl-tRNA Synthetase," *Academic Press*, 2001, 296-300, vol. 23.

Yang, X. et al, "Crystal Structure of a Human Aminoacyl-tRNA Synthetase Cytokine," *Proceedings of the National Academy of Science*, 2002, 15369-15374, vol. 99, No. 24.

Yang, X. et al., "Crystal Structures That Suggest Late Development of Genetic Code Components for Differentiating Aromatic Side Chains," *Proceedings of the National Academy of Science*, 2003, 15376-15380, vol. 100, No. 26.

Yang, X. et al., "Relationship of Two Human tRNA Synthetases Used for Cell Signaling," *Trends in Biochemical Sciences*, 2004, 250-256, vol. 29, No. 5.

Yu, Y. et al., "Crystal Structure of Human Tryptophanyl-tRNA Synthetase Catalytic Fragment: Insights Into Substrate Recognition, tRNA Binding, and Angiogenesis Activity," *The Journal Biological Chemistry*, 2004, 8378-8388, vol. 279, No. 9.

Beresten, F., et al., "Molecular and Cellular Studies of Tryptophanyl-tRNA Synthetase Using Monoclonal Antibodies," *European Journal of Biochemistry*, 1989, 575-581, 184.

Brasen, J. et al., "Angiogenesis, Vascular Endothelial Growth Factor and Platelet-Derived Growth factor-BB Expression, Iron Deposition, and Oxidation-Specific Epitopes in Stented Human Coronary Arteries," *Arteriosclerosis, Thrombosis, and Vascular Biology*, 2001, 1720-1726.

Buwitt, U., et al. "Molecular Cloning and Characterization of an Interferon Induced Human Cdna With Sequence Homology to a Mammalian Peptide Chain Release Factor," Embo. J., 1992, 489-496, vol. 11, No. 2.

Caplen, N., "A New Approach to the Inhibition of Gene Expression," Trends in Biotechnology, 2002, 48-51, vol. 20, No. 2.

Cen, S., et al., "Retrovirus-Specific Packaging of Aminoacyl-tRNA Synthetases With Cognate Primer tRNAs," Journal of Virology, 2002, 13111-13115, vol. 76, No. 24.

Chaudhary, V. et al., "A Recombinant Immunotoxin Consisting of Two Antibody Variable Domains Fused to Pseudomonas Exotoxin," Letters to Nature, 1989, 394-397, vol. 339.

Cohen, N. et al., "Molecular Modeling Software and Methods for Medicinal Chemistry," Journal of Medicinal Chemistry, 1990, 883-894, vol. 33, No. 3.

Colbere-Garapin, F. et al., "A New Dominant Hybrid Selective Marker for Higher Eukaryotic Cells," Journal of Molecular Biology, 1981, 1-14, vol. 150.

Dann, J. et al., "Human Renin: A New Class of Inhibitors," Biochemical and Biophysical Research Communications, 1986, 71-77, vol. 134, No. 1.

Dawson, D. et al., "Three Distinct D-Amino Acid Substitutions Confer Potent Antiangiogenic Activity on an Inactive Peptide Derived From a Thrombospondin-1 Type 1 Repeat," Molecular Pharmacology, 1999, 332-338, vol. 55.

Dorrell, M.I., et al., "Adult Bone Marrow-Derived Stem Cells Utilize R-Cadherin to Target Sites of Neovascularization in the Developing Retina," Blood, 2004, 3420-3427, vol. 103.

FIG. 1

| | Size | pI | Charging | Angiogenic | Angiostatic |
|---|---|---|---|---|---|
| Full-Length TrpRS (NH2...COOH, 1-471) | 53Kd | 5.7 | + | – | – |
| Mini TrpRS (splice variant) (48-471) | 48Kd | 58 | + | – | + |
| T1 (clevage product) (71-471) | 46Kd | 59 | + | – | + |
| T2 (clevage product) (94-471) | 43Kd | 68 | + | – | + |

*Note: A mutant of each of the four proteins has been made in which DLT(205-207) is replaced with ELR

```
  1 MPNSEPASLL ELFNSIATQG ELVRSLKAGN ASKDEIDSAV KMLVSLKMSY KAAAGEDYKA DCPPGNPAPT SNHGPDATEA
                                                                                    └→T1
 81 EEDFVDPWTV QTSSAKGIDY DKLIVRFGSS KIDKELINRI ERATGQRPHH FLRRGIFFSH RDMNQVLDAY ENKKPFYLYT
                        └→miniTrpRS
161 GRGPSSEAMH VGHLIPFIFT KWLQDVENVP LVIQMTDDEK YLWKDLTLDQ AYGDAVENAK DIIACGFDIN KTEIFSDLDY
              └→T2
241 MGMSSGFYKN VVKIQKHVTF NQVKGIFGFT DSDCIGKISF PAIQAAPSFS NSFPQIFRDR TDIQCLIPCA IDQDPYFRMT
321 RDVAPRIGYP KPALLHSTFF PALQGAQTKM SAS DPNSSIF LTDTAKQIKT KVNKHAFSGG RDTIEEHRQF GGNCDVDVSF
401 MYLTFFLEDD DKLEQIRKDY TSGAMLTGEL KKALIEVLQP LIAEHQARRK EVTDEIVKEF MTPRKLSFDF Q
```

*Note: All are recombinant constructs and have an N-terminal Met and a C-terminal KLAAALEHHHHHH (SEQ ID NO. 76)

FIG. 5
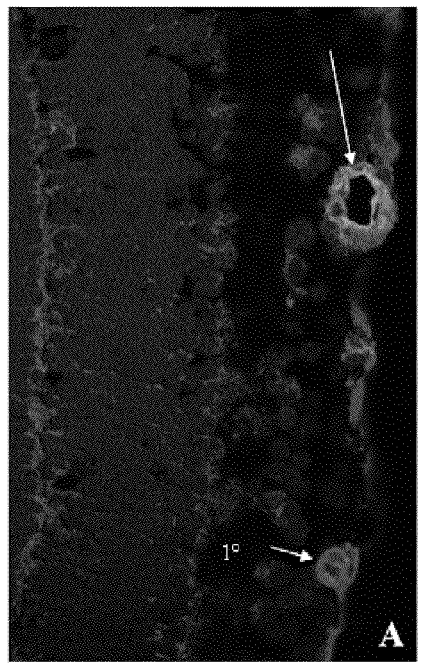
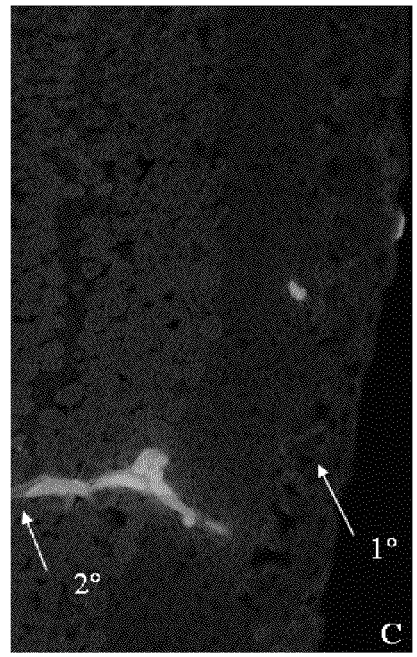
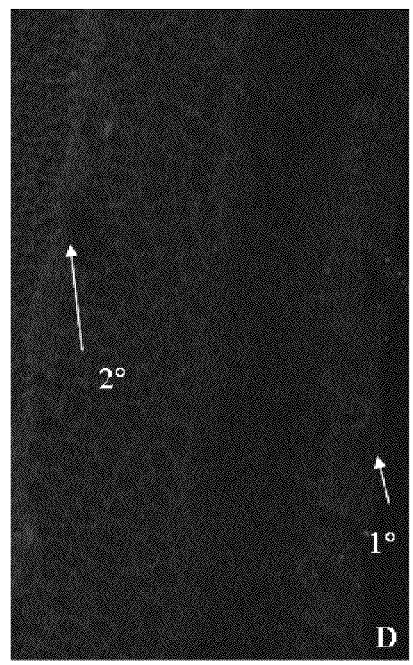

| Lane | Sample |
|---|---|
| 1 | 8 µL Invitrogen BenchMark MW Marker |
| 2 | Blank |
| 3 | 15 µg WRS final sample |
| 4 | 10 µg WRS final sample |
| 5 | 5.0 µg WRS final sample |
| 6 | 2.5 µg WRS final sample |
| 7 | 1.25 µg WRS final sample |
| 8 | 0.625 µg WRS final sample |
| 9 | Blank |
| 10 | 8 µL Invitrogen BenchMark MW Marker |

Experiment: Native Gel Optimization 3 ug     5 ug

Lane 1: T2-WRS
Lane 2: T2-WRS
Lane 3: T2-WRS
Lane 4: Blank
Lane 5: T2-WRS
Lane 6: T2-WRS
Lane 7: T2-WRS

- Novex NuPage Tris-Acetate Gel (No SDS)
- T2-WRS – Lot# PD195-DG30L- dialyzed on 9/27/04
- Samples not heated
- Stacker gel removed because there was no visible protein

FIG. 17

| | CPMs Raw | | | CPMs Less Bkgd | | | PPi (nmole) | | |
|---|---|---|---|---|---|---|---|---|---|
| Time (min) | FL WRS | FLWRS P287D | T2-WRS | FL WRS | FLWRS P287D | T2-WRS | FL WRS | FLWRS P287D | T2-WRS |
| 0 | 268.02 | 173.08 | 202.18 | 0.0 | 0.0 | 0.0 | 0.00 | 0.00 | 0.00 |
| 4 | 5716.81 | 287.16 | 220.21 | 5448.8 | 114.1 | 18.0 | 5.71 | 0.12 | 0.02 |
| 8 | 7862.61 | 269.16 | 232.24 | 7594.6 | 96.1 | 30.1 | 7.95 | 0.10 | 0.03 |
| 12 | 5958.59 | 271.18 | 195.21 | 5690.6 | 98.1 | -7.0 | 5.96 | 0.10 | -0.01 |
| 16 | 7637.51 | 308.23 | 206.24 | 7369.5 | 135.2 | 4.1 | 7.72 | 0.14 | 0.00 |
| 30 | 10138.95 | 211.17 | 136.17 | 9870.9 | 38.1 | -66.0 | 10.34 | 0.04 | -0.07 |

Average SA: 95471.9
nmole ATP/50uL sample: 50.0
cpms/nmol ATP: 1909.34
nmole NAPPi/50uL Sample: 100.0
cpms/nmol NAPPi: 954.7

TRNA SYNTHETASE FRAGMENTS

CROSS REFERENCES

This application is a continuation-in-part of U.S. application Ser. No. 12/399,468, filed on Mar. 6, 2009, which is a continuation-in-part of U.S. application Ser. No. 11/196,019 filed on Aug. 2, 2005 (abandoned), which is: a continuation-in-part of U.S. application Ser. Nos. 10/962,171, 10/962,217, 10/962,058, 10/961,528, 10/962,375, 10/962,062, 10/962,218, 10/961,529, 10/961,526, and 10/961,486, all of which were filed on Oct. 7, 2004 (all abandoned), and a continuation-in-part of U.S. application Ser. No. 11/019,969 filed on Dec. 20, 2004 (abandoned), and a continuation-in-part of U.S. application Ser. No. 10/980,866 filed on Nov. 2, 2004 (abandoned), which is a continuation-in-part of U.S. application Ser. No. 10/962,218 filed on Oct. 7, 2004 (abandoned); and U.S. application Ser. No. 11/196,019 claims the benefit of U.S. Provisional Application No. 60/598,019 filed on Aug. 2, 2004 and U.S. Provisional Application No. 60/624,656 filed on Nov. 2, 2004; all of which applications are incorporated herein by reference in their entirety.

REFERENCE TO SEQUENCE LISTING

The present application is being filed along with a Sequence Listing in electronic format. The Sequence Listing is provided as a file entitled PC22120C.txt, created Sep. 2, 2009, which is 387 KB in size. The information in the electronic format of the Sequence Listing is incorporated herein by reference in its entirety. The content of the sequence listing information recorded in computer readable form is identical to the written sequence listing.

BACKGROUND

Normal tissue growth, which occurs during embryonic development, wound healing, and menstrual cycle is characterized by dependence on new vessel formation for the supply of oxygen and nutrients as well as removal of waste products. Angiogenesis is the name given to the development of new capillaries from pre-existing blood vessels. The extent of angiogenesis is determined by the balance between pro-angiogenic factors and anti-angiogenic factors. Pro-angiogenic factors include, but are not limited to, vascular endothelial growth factor (VEGF), fibroblast growth factor (FGF), interleukin-8 (IL-8), angiogenin, angiotropin, epidermal growth factor (EGF), platelet derived endothelial cell growth factor, transforming growth factor α (TGF-α), transforming growth factor β (TGF-β), and nitric oxide. Anti-angiogenic factors include, but are not limited to, thrombospondin, angiostatin, and endostatin.

While in most normal tissues the balance favors the anti-angiogenic factors and angiogenesis is inhibited, numerous conditions may become manifested upon a switch to an angiogenesis-stimulating phenotype. Such angiogenic conditions include, but are not limited to, age-related macular degeneration (AMD), cancer (both solid and hematologic), developmental abnormalities (organogenesis), diabetic blindness, endometriosis, ocular neovascularization, psoriasis, rheumatoid arthritis (RA), skin discolorations (e.g., hemangioma, nevus flammeus, or nevus simplex) and wound healing.

It is desirable to identify compositions and methods that modulate or inhibit angiogenesis.

SUMMARY OF THE INVENTION

Compositions of and Purification Methods for Low-Endotoxin Therapeutic Agents

The present invention relates to methods for purifying therapeutic agents so that they are substantially free of endotoxins. Also presented herein are preparations suitable for therapeutic administration comprising a pharmaceutical agent, wherein the preparations are substantially free of endotoxins. Such preparations may be used in a variety of therapeutic applications, including, but not limited to applications in the therapy of cancers, applications in the therapy of neovascular disorders, applications in inhibiting angiogenesis, and applications in the therapy of ophthalmic conditions.

In one embodiment, the present invention relates to pharmaceutical preparations suitable for administration to a human comprising a pharmaceutical agent and a pharmaceutically acceptable carrier wherein the amount of endotoxins in the pharmaceutical preparation is less than about 10 endotoxin units per milligram of pharmaceutical agent. In one embodiment, the pharmaceutical agent is a polypeptide.

In another embodiment, the present invention relates to pharmaceutical preparations suitable for administration to a human comprising a polypeptide and a pharmaceutically acceptable carrier wherein the amount of endotoxins in the pharmaceutical preparation is less than about 10 endotoxin units per milligram of polypeptide.

In another embodiment, the present invention relates to pharmaceutical preparations suitable for use in oncological therapy or ophthalmic administration in a human comprising a polypeptide and a pharmaceutically acceptable carrier wherein the amount of endotoxins in the pharmaceutical preparation is less than about 10 endotoxin units per milligram of polypeptide.

In any one of the aforementioned embodiments, the polypeptide is synthesized recombinantly. In another embodiment of these aspects, the polypeptide is produced in and recovered from a transformed prokaryotic cell or its progeny. In another embodiment, the polypeptide is produced in and recovered from a transformed eukaryotic cell or its progeny. In another embodiment, the polypeptide is produced in and recovered from the cytoplasm of the transformed eukaryotic cell or its progeny. In another embodiment, the polypeptide can modulate angiogenesis. In another embodiment, the polypeptide can be used to treat macular degeneration, diabetic retinopathy, or other diseases or conditions associated with unwanted ocular neovascularization. In another embodiment, the polypeptide has an isoelectric point of less than about 8.0. In another embodiment, the polypeptide has an isoelectric point between about 5.5 and about 8.0. In another embodiment, the polypeptide has an isoelectric point between about 6.0 and about 7.5. In another embodiment, the polypeptide comprises a hydrophobic cleft, and in a further refinement of this embodiment, the polypeptide also has an isoelectric point of less than about 8.0.

In any one of the aforementioned embodiments, the polypeptide is all or part of a tryptophan tRNA synthetase. In any one of the aforementioned embodiments, the preparation comprises a T2-TrpRS or a homolog thereof.

In another embodiment, the present invention relates to methods for purifying any of the aforementioned polypeptides or pharmaceutical agents, comprising performing an endotoxin-reduction filtration step after performing a clarification step and prior to performing a buffer exchange step. Further, the endotoxin-reduction filtration step may be performed prior to performing a cation exchange chromatographic step. Alternatively, the endotoxin-reduction filtration step may be performed prior to performing a concentration step.

In another embodiment, the present invention relates to methods for purifying any of the aforementioned polypeptides or pharmaceutical agents, comprising performing an endotoxin-reduction filtration step after performing a clarification step and prior to performing a concentration step. Further, the endotoxin-reduction filtration step may be performed prior to performing a cation exchange chromatographic step. Alternatively, the endotoxin-reduction filtration step may be performed prior to performing a buffer exchange step.

In another embodiment, the present invention relates to methods for purifying any of the aforementioned polypeptides or pharmaceutical agents, comprising performing an endotoxin-reduction filtration step after performing a clarification step and prior to performing a cation-exchange chromatographic step. Alternatively, the endotoxin-reduction filtration step may be performed prior to performing a concentration step. Alternatively, the endotoxin-reduction filtration step may be performed prior to performing a buffer exchange step.

In another embodiment, the present invention relates to methods for purifying any of the aforementioned polypeptides or pharmaceutical agents in which an endotoxin-reduction filtration step is performed prior to performing a concentration step and prior to performing a cation-exchange chromatographic step and prior to a buffer exchange step.

The order of the concentration, buffer exchange, and cation-exchange chromatography steps in any of the aforementioned purification methods may vary, but in one embodiment, at least one concentration step is performed prior to the buffer exchange step. Alternatively, a cation-exchange chromatographic step is performed after the buffer exchange step. Alternatively, at least one concentration step is performed prior to the cation-exchange chromatographic step. Alternatively, the cation-exchange chromatographic step is performed after a buffer exchange step and at least one concentration step. Alternatively, at least one concentration step is performed prior to the buffer exchange step and the cation-exchange chromatographic step. Alternatively, an additional concentration step is performed after any buffer exchange step.

In a further embodiment of any of the aforementioned purification methods, the endotoxin-reduction filtration step is performed after an anion-exchange chromatographic step. In a further embodiment, the anion-exchange chromatographic step comprises use of an anion-exchange resin. In yet a further embodiment, the anion-exchange resin is selected from the group consisting of Q Sepharose, DEAE Sepharose, and ANX Sepharose. In still a further embodiment, the anion-exchange resin is Q Sepharose. In any of these uses of anion-exchange resins, a variety of grades and sizes may be used, including, but not limited to Source grade, fast flow grade and high performance grade.

In an embodiment of any of the aforementioned purification methods that involve a cation-exchange chromatography step, the cation-exchange chromatographic step may comprise use of a cation-exchange resin. In a further embodiment, the cation-exchange resin is selected from the group consisting of CM Sepharose, SP Sepharose, and DEAE Sepharose. In still a further embodiment, the cation exchange resin is CM Sepharose. In any of these uses of cation-exchange resins, a variety of grades and sizes may be used, including, but not limited to Source grade, fast flow grade and high performance grade.

In another embodiment, the present invention relates to methods for purifying a polypeptide suitable for administration to a patient comprising an anion-exchange chromatographic step, a step comprising a means for reducing endotoxins, and a buffer exchange step, wherein the step comprising a means for reducing endotoxins is performed prior to the buffer exchange step. In a further embodiment, the polypeptide suitable for administration to a patient is suitable for ophthalmic administration. In still a further embodiment, the polypeptide suitable for ophthalmic administration is a modulator of angiogenesis. In yet a further embodiment, the polypeptide suitable for ophthalmic administration can be used to treat macular degeneration, diabetic retinopathy or diseases or conditions associated with unwanted ocular neovascularization. In a further refinement of any of the embodiments noted in this paragraph, the polypeptide is substantially free of endotoxins.

In another embodiment, the present invention relates to polypeptide preparations for use in ophthalmic administration comprising the purified polypeptide prepared by a method comprising an anion-exchange chromatographic step, a step comprising a means for reducing endotoxins, and a buffer exchange step, wherein the step comprising a means for reducing endotoxins is performed prior to the buffer exchange step. In a further embodiment, the polypeptide preparation further comprises a pharmaceutically acceptable carrier. In a further embodiment, the polypeptide is all or part of a tRNA synthetase. In yet a further embodiment, the polypeptide is all or part of a tryptophanyl-tRNA synthetase. In yet a further embodiment, the polypeptide is a T2-TrpRS or a homolog thereof. In a further embodiment of any of the polypeptide preparations mentioned in this paragraph, the concentration of endotoxins in the polypeptide preparation is less than about 10 endotoxin units per milligram of polypeptide.

In another embodiment the present invention relates to polypeptide compositions comprising a polypeptide, wherein the polypeptide is all or part of a tRNA synthetase or a homolog thereof, wherein the polypeptide composition is substantially free of endotoxins. In a further embodiment, the polypeptide is all or part of a tryptophanyl-tRNA synthetase. In an alternative aspect are polypeptide compositions comprising a polypeptide, wherein the polypeptide is all or part of a T2-TrpRS or a homolog thereof, wherein the polypeptide composition is substantially free of endotoxins. In a further embodiment of any of the aspects mentioned in this paragraph, the polypeptide composition further comprises a pharmaceutically acceptable carrier.

In another embodiment, the present invention relates to methods for preparing the polypeptide compositions mentioned in the prior paragraph, comprising performing a concentration step on collected polished polypeptide fractions, wherein the collected polished polypeptide fractions are substantially free of endotoxins. In a further embodiment are methods of preparing the collected polished polypeptide fractions of the previous embodiment comprising performing a cation-exchange chromatographic step on an unpolished polypeptide sample thereby producing the collected polished polypeptide fractions of the previous embodiment, wherein the unpolished polypeptide sample is substantially free of endotoxins. In further embodiments are methods of producing the unpolished polypeptide sample of the previous embodiment comprising performing a buffer exchange step on a polypeptide sample in a post-anion exchange buffer thereby producing the unpolished polypeptide sample of the previous embodiment, wherein the polypeptide sample in the post-anion exchange buffer is substantially free of endotoxins. In further embodiments are methods of producing the polypeptide sample in the post-anion exchange buffer of the previous embodiment comprising performing a concentration step on collected polypeptide fractions from an anion-exchange column prior to the buffer exchange step thereby producing the polypeptide sample in the post-anion exchange buffer of the previous embodiment, wherein the collected polypeptide fractions from an anion-exchange column are substantially free of endotoxins. In further embodiments are methods of producing the collected polypeptide fractions from an anion-exchange column of the previous embodiment comprising performing an endotoxin-reduction filtration step prior to the concentration step of the previous embodiment. In a further embodiment are methods comprising performing an anion-exchange chromatographic step prior to the endotoxin-reduction filtration step.

In another embodiment, the present invention relates to methods of treating a patient having an ophthalmic disease or condition comprising administering a therapeutically effective amount of a polypeptide, wherein the level of endotoxins in the therapeutically effective amount of the polypeptide is less than about 10 endotoxin units per milligram of polypeptide. In one embodiment, the ophthalmic disease or condition is associated with unwanted ocular neovascularization. In another embodiment, the polypeptide is isolated from a transformed prokaryotic cell or progeny thereof. In a further embodiment, the isolation comprises an endotoxin-reduction filtration step prior to a polishing step. In still a further embodiment, the isolation further comprises a clarification step prior to the endotoxin-reduction filtration step. In yet a further embodiment, the isolation further comprises a concentration step after the polishing step. In still a further embodiment, the isolation further comprises a buffer-exchange step after the endotoxin-reduction filtration step.

Multi-Unit Complexes and Uses Thereof

The present invention also relates to a composition comprising a multi-unit complex of a tRNA synthetase fragment, or a homolog or analog thereof. Preferably, the multi-unit complex of the tRNA synthetase fragment is isolated and/or soluble. Examples of multi-unit complexes include dimers (including homodimers), trimers etc. A multi-unit complex of the present invention can include a first monomer and a second monomer, wherein the first and the second monomers are covalently linked or non-covalently associated.

A tRNA synthetase fragment of the present invention can be, for example, a tryptophanyl tRNA synthetase fragment, a human tRNA synthetase fragment, or any angiostatic fragment of a tRNA synthetase fragment. In some embodiments, the tRNA synthetase fragment is selected from the group consisting of SEQ ID NOS: 12-17, 24-29, 36-41, 48-53, and any homologs and analogs thereof.

Diverse Multi-Unit Complexes Including a tRNA Synthetase Fragment

In some embodiments, the present invention relates to a composition comprising a first tRNA synthetase fragment or any homolog or analog thereof and a second tRNA synthetase fragment or any homolog or analog thereof, wherein the first tryptophanyl tRNA synthetase fragment has a methionine at its N-terminus and the second tryptophanyl tRNA synthetase does not have a methionine at its N-terminus.

In some embodiments, more than 50% of the composition comprises the first tRNA synthetase fragment. In other embodiments, more than 50% of the composition comprises the second tRNA synthetase fragment.

The first and/or second tRNA synthetase fragments of the present invention may be tryptophanyl tRNA synthetase fragments, human tryptophanyl tRNA synthetase fragments, or any angiostatic fragments of a tRNA synthetase. Examples of angiostatic fragments of a tRNA synthetase include but are not limited to the polypeptide of SEQ ID NOS: 15-17, 27-29, 39-41, 51-53, and any homologs or analogs thereof.

In some embodiments, a composition herein has a pI of about 7.4-7.8. In more preferred embodiments, a composition herein has a pI of about 7.6.

The compositions herein may also include a therapeutic agent. A therapeutic agent of the present invention may be selected from the group consisting of an antineoplastic agent, an anti-inflammatory agent, an antibacterial agent, an antiviral agent, and an anti-angiogenic agent.

Any of the multi-unit complexes of the present invention may be formulated into a pharmaceutical formulation comprising a multi-unit complex and a pharmaceutically acceptable excipient. The formulation can also include a second therapeutic agent selected from the group consisting of: an antineoplastic agent, an anti-inflammatory agent, an antibacterial agent, an angiogenic agent, an antiviral agent, and an anti-angiogenic agent. For ocular administration, a pharmaceutical formulation does not include a preservative. In preferred embodiments, a pharmaceutical formulation is a solution.

Any of the compositions (including pharmaceutical formulations) herein may be lypholized. The compositions (including pharmaceutical formulations) herein may be used to inhibit angiogenesis in a cell by contacting a cell with a composition of the present invention. The compositions herein may also be used to treat an individual suffering from an angiogenic condition by administering to the individual a pharmaceutical formulation of the present invention.

Compositions and Methods for Modulating Angiogenesis

The present invention also relates to pharmaceutical formulations comprising a first tRNA synthetase fragment and a second tRNA synthetase fragment, wherein said first and said second tRNA synthetase fragments are non-covalently dimerized and do not include a marker-sequence, such as hexa-Histidine tag. Such pharmaceutical formulations may have a first tRNA synthetase fragment having a methionine at its N-terminus, and a second tRNA synthetase that does not include a methionine at its N-terminus.

In some embodiments, the first and second tRNA synthetase fragments of such pharmaceutical formulations are tryptophanyl tRNA synthetase fragments. In some embodiments, the first tRNA synthetase fragment is selected from the group consisting of SEQ ID NOS: 15-17, 27-29, 39-41, 51-53, homologs, and analogs thereof. In some embodiments, the second tRNA synthetase fragment is selected from the group consisting of SEQ ID NOS: 12-14, 24-26, 36-38, 48-50, homologs, and analogs thereof. In some embodiments, the first tRNA synthetase fragment is SEQ ID NO: 15, or a homolog or analog thereof and/or the second tRNA synthetase fragment is SEQ ID NO: 12, or a homolog or analog thereof. In some embodiments, the first tRNA synthetase fragment is SEQ ID NO: 27, or a homolog or analog thereof and/or the second tRNA synthetase fragment is SEQ ID NO: 24, or a homolog or analog thereof.

In any of the pharmaceutical formulations herein, the first tRNA synthetase fragment can be less than about 5% by weight of the total amount of the first and second tRNA synthetase fragments. In some embodiments of the pharmaceutical formulations herein, the second tRNA synthetase fragment is at least about 5% by weight of the total amount of the first and second tRNA synthetase fragments. In some embodiments, a pharmaceutical formulation of the present invention has a first tRNA synthetase fragment that is about 50% by weight of the total amount of the first and second tRNA synthetase fragments, and a second tRNA synthetase fragment that is about 50% by weight of the total amount of the first and second tRNA synthetase fragments.

In any of the pharmaceutical formulations herein the endotoxin concentration can be less than 1 endotoxin units per milligram of tRNA synthetase fragments. Moreover, the pharmaceutical formulations herein are preferably substantially free or completely free of detergent and/or preservatives.

The present invention also contemplates a kit that includes a container containing any of the pharmaceutical formulation herein and a set of instruction for modulating angiogenesis. Such kits can also include one or more pre-filled syringes wherein each syringe includes a single dose of such pharmaceutical formulation.

The invention also contemplates methods for modulating angiogenesis in a cell or an organism. Such methods include contacting a cell or organism with a pharmaceutical formulation of the invention. Preferably such angiogenesis is ocular angiogenesis or ocular neovascularization.

The present invention also contemplates a method for treating a patient suffering from a condition comprising administering to said patient a pharmaceutical formulation disclosed herein. Preferably such condition involves ocular angiogenesis or ocular neovascularization. Treatment or prevention may involve administering the pharmaceutical formulations herein locally (e.g., to the eye).

Polynucleotides Encoding tRNA Synthetase Fragments and Uses Thereof

The present invention also relates to a polynucleotide sequence encoding a first tRNA synthetase fragment and a second tRNA synthetase fragment. In some embodiments, at least one of such tRNA synthetase fragments is a tryptophanyl tRNA synthetase fragment. In some embodiments, both of such tRNA synthetase fragments are tryptophanyl tRNA synthetase fragments. The tryptophanyl tRNA synthetase fragments may be mammalian or human and have angiostatic activity.

In some embodiments, a first tRNA synthetase fragment and/or a second tRNA synthetase fragment are selected from the group consisting of SEQ ID NOS: 12-17, 24-29, 36-41, 48-53, and any homologs and analogs thereof. A polynucleotide sequence of the present invention may encode a first and a second tRNA synthetase fragment in tandem. In some embodiments, such polynucleotide sequences also encode a linker. A polynucleotide sequence encoding a linker may be situated between the polynucleotide sequences encoding the first and second tRNA synthetase fragments. A linker of the present invention is long enough to allow the expressed first and second tRNA synthetase fragments to freely rotate and dimerize with one another. The linker and the first and second tRNA synthetase fragments are preferably in the same open reading frame.

In some embodiments, the polynucleotide sequence encoding at least two tRNA synthetase fragments also encodes a leader sequence. A leader of the present invention can be an antibody or antibody fragment that localizes the polypeptide to a particular region. The polynucleotide sequence of the present invention may also encode a prosequence. A prosequence may be cleaved once the encoded tRNA synthetase polypeptides reach a desired location (e.g., the vitreous of an eye).

Preferably, the tRNA synthetase fragment of the present invention is selected from the group consisting of SEQ ID NOS: 12-17, 24-29, 36-41, 48-53, and any homologs or analogs thereof. Such polypeptides may be encoded, for example, by SEQ ID NOS: 18-23, 30-35, 42-47, 54-59, and any homologs and analogs thereof.

The present invention also contemplates an expression vector comprising a polynucleotide sequence disclosed herein, as well as a host cell comprising such expression vector.

In some embodiments, the present invention contemplates a targeted liposome comprising an expression vector of the present invention.

The expression vectors herein may useful for preparing a multi-unit complex. Thus, in some embodiments, the present invention relates to a method for creating a multi-unit complex, wherein the method includes the steps of: providing an expression vector disclosed herein; transfecting a host cell with said expression vector; and maintaining said host cell under condition suitable for expression.

Antibodies and Epitopes Specific to tRNA Synthetase Fragments

The present invention also relates to antibodies that specifically bind to a tRNA synthetase or a fragment, homolog or analog thereof. For example, an antibody of the present invention may bind to an epitope of a tRNA synthetase, or a fragment, homolog, or analog thereof. The tRNA synthetase (or fragment thereof) of the present invention can be a tryptophanyl-tRNA synthetase, a human tRNA synthetase, or any angiostatic fragment of a tRNA synthetase. Preferably, the antibody of the present invention specifically binds to a polypeptide selected from the group consisting of SEQ ID NOS: 12-17, 24-29, 36-41, 48-53 and any homologs and analogs thereof. An antibody of the present invention may be a polyclonal antibody, a monoclonal antibody, a chimeric antibody, an anti-idiotypic antibody, and antibody fragments.

The antibody may bind to an epitope-bearing polypeptide, wherein the epitope-bearing polypeptide comprises about 5 to about 30 amino acids of a tRNA synthetase (or a fragment, homolog, or analog thereof). Such epitope-bearing polypeptides, or epitopes, are preferably N-terminus epitopes or includes the N-terminus of the tRNA synthetase (or a fragment, homolog, or analog thereof).

In some embodiments, the present invention relates to an epitope-bearing polypeptide. An epitope-bearing polypeptide of the present invention can include at least about 5 amino acids of a tRNA synthetase fragment. The tRNA synthetase fragment can be a tryptophanyl tRNA synthetase fragment, a human tryptophanyl tRNA synthetase fragment, or any angiogenic fragment of a tRNA synthetase.

Examples of epitope-bearing polypeptides include a polypeptide comprising, or alternatively consisting of: amino acid residues of from about position 1 to about position 5, about position 1 to about position 15, or about position 1 to about position 25 of SEQ ID NOS: 12-17, 24-29, 36-41, 48-53, and any homologs and analogs thereof; amino acid residues of from about position 10 to about position 15, about position 10 to about position 25, or about position 10 to about position 35 of SEQ ID NOS: 12-17, 24-29, 36-41, 48-53 and any homologs and analogs thereof; amino acid residues of from about position 20 to about position 25, about position 20 to about position 35, or about position 20 to about position 45 of SEQ ID NOS: 12-17, 24-29, 36-41, 48-53 and any homologs and analogs thereof.

In another embodiment, the present invention relates to a polynucleotide sequence encoding one or more of the epitope-bearing polypeptides herein.

Variants of tRNA Synthetase Fragments and Uses Thereof

The present invention also relates to a composition comprising an isolated tRNA synthetase fragment, wherein the tRNA synthetase fragment comprises, consists essentially of, or consists of an amino acid sequence SEQ ID NO: 12, 15, 24, 27, 36, 39, 48 or 51. Preferably, such tRNA synthetase fragment is less than 45 kD, more preferably less than 44 kD, less than 43.9 kD, 43.8 kD, 43.7 kD, 43.6 kD, or more preferably less than 43.5 kD. Preferably such tRNA synthetase fragment is anti-angiogenic.

In some embodiments, a composition comprising an isolated tRNA synthetase fragment, wherein the tRNA synthetase fragment comprises, consists essentially of, or consists of SEQ ID NO: 13, 16, 25, 28, 37, 40, 49 or 52. Preferably, such tRNA synthetase fragment is less than 48 kD, more preferably less than 47 kD, or more preferably less than 46 kD. Preferably such tRNA synthetase fragment is anti-angiogenic.

In some embodiments, the present invention relates to a composition comprising an isolated tRNA synthetase fragment, wherein the tRNA synthetase fragment comprises, consists essentially of, or consists of SEQ ID NO: 14, 17, 26, 29, 38, 41, 50 or 53. Preferably, such tRNA synthetase fragment is less than 53 kD, more preferably less than 52 kD, more preferably less than 51 kD, more preferably less than 50 kD, or more preferably less than 49 kD. Preferably such tRNA synthetase fragment is anti-angiogenic.

In any of the embodiments herein, a tRNA synthetase fragment is preferably isolated. In any of the embodiments herein, a tRNA synthetase fragment is preferably purified. Such purification step may reduce the amount of an endotoxin in a pharmaceutical composition. In some embodiments, the amount of endotoxin in a composition is less than 30, 20, 10, or more preferably 9, 8, 7, 6, 5, 4, 3, 2, or 1 endotoxin units.

Methods for Treating Angiogenesis

The present invention also relates to methods for treating an individual suffering from an angiogenic condition. The methods include the step of administering to such an individual a pharmaceutical formulation comprising a multi-unit complex of a tRNA synthetase fragment or a homolog or analog thereof.

Examples of angiogenic conditions that may be treated by the present invention include, but are not limited to, age-related macular degeneration, cancer, developmental abnormalities, diabetic blindness, endometriosis, ocular neovascularization, psoriasis, rheumatoid arthritis (RA), skin discolorations, such as hymengioma, and wound healing.

The tRNA synthetase fragment used in the method of the present invention may be a tryptophanyl-tRNA synthetase fragment, or a human tryptophanyl-tRNA synthetase fragment, or any angiostatic fragment thereof. Examples of fragments contemplated by the present invention include, but are not limited to, those of SEQ ID NOS: 12-17, 24-29, 36-41, 48-53, and any homologs and analogs thereof.

In some embodiments, the multi-unit complex of the present invention is a dimer or a homodimer. When a multi-unit complex is a dimer, the dimer may include a first monomer and a second monomer, wherein the first monomer and the second monomer are different, homologous, substantially homologous, or identical. The first and a second monomer and the multi-unit complex contemplated herein may be covalently linked or non-covalently linked.

In some embodiments, an individual suffering and/or susceptible to angiogenesis may further be administered or co-administered a therapeutic agent selected from the group consisting of: an antineoplastic agent, an anti-inflammatory agent, an antibacterial agent, an antiviral agent, and an anti-angiogenic agent.

The pharmaceutical formulations used in the method of the present invention may be administered systemically or locally. For systemic administration, the pharmaceutical formulations herein may be administered at a dose of 0.1-100 mg/kg. For topical administration, the pharmaceutical formulations herein may be administered at a dose of 50-1000 µg/cm$^2$. In particularly, for intraocular administration, the pharmaceutical formulations herein may be administered at a dose of 50-1000 µg/eye. When administered to the eye, the pharmaceutical formulations preferably do not include a preservative and are packaged in single unit dosages.

Methods for Screening for Anti-Angiogenic Agents

The present invention also relates to methods for screening for an angiostatic agent wherein the methods include the steps of contacting a receptor of a tRNA synthetase fragment with a member of a library of candidate agents and selecting a candidate agent from the library that selectively binds to the receptor. Candidate agents of a library (two or more agents) may be, for example, polypeptides, peptidomimetic, peptide nucleic acids, nucleic acids, carbohydrates, and small or large, organic or inorganic molecules.

In some embodiments, the above methods of screening further include the step of evaluating the ability of a candidate agent to inhibit angiogenesis. Evaluation can include the step of administering the candidate agent to a retina of a mammal and visualizing neovascularization of said retina.

Examples of tRNA synthetase fragments used in the method of screening include tryptophanyl tRNA synthetase fragments, human tryptophanyl tRNA synthetase fragment, and other angiostatic fragments of a tRNA synthetase.

In some embodiments, the present invention related to methods for obtaining an optimized ligand for a receptor of a tRNA synthetase fragment. Such methods include the steps of obtaining an X-ray structure of said receptor with said fragment; using a computer program to analyze the point of contact between the receptor and the tRNA synthetase fragment; and modifying the tRNA synthetase fragment to increase its affinity to the receptor. Examples of computer programs that may be used in these embodiments include, but are not limited to, GRID, MCSS, AUTODOCK, DOCK, AMBER, QUANTA, and INSIGHT II.

The tRNA synthetase fragment used in the methods for obtaining an optimized ligand may be a tryptophanyl tRNA synthetase fragment, a human tryptophanyl tRNA synthetase fragment, or any angiostatic fragment of a tRNA synthetase. In preferred embodiments, such fragments may be selected from the group consisting of SEQ ID NOS: 12-17, 24-29, 36-41, 48-53, and any homologs or analogs thereof.

Methods of Modulating Angiogenesis

The present invention also relates to methods of modulating angiogenesis. Such methods comprise the step of contacting to a cell or tissue susceptible or experiencing angiogenesis with a multi-unit complex comprising a tRNA synthetase fragment, or a homolog or analog thereof.

A tRNA synthetase fragment of the present invention can be, for example, a tryptophanyl tRNA synthetase fragment, a human tRNA synthetase fragment, or any angiostatic fragment of a tRNA synthetase. Examples of tRNA synthetase fragments contemplated by the present invention include those selected from the group consisting of SEQ ID NOS: 12-17, 24-29, 36-41, 48-53, and any homologs and analogs thereof.

A multi-unit complex of the present invention may be soluble and/or isolated. A multi-unit complex can include two or more monomers. In some examples, a multi-unit complex is a dimer or a homodimer. Two or more monomer units of a multi-unit complex can be covalently linked or non-covalently associated.

In some embodiments, a multi-unit complex can have a first monomer and a second monomer, wherein said first monomer comprises a tRNA synthetase fragment having a methionine at its N-terminus, and wherein said second monomer comprises a tRNA synthetase fragment not having a methionine at its N-terminus. Such compositions can have a pI value of about 7.4-7.8.

Examples of a first monomer include those selected from the group consisting of SEQ ID NOS: 15-17, 27-29, 39-41, 51-53, and any homologs or analogs thereof.

Examples of a second monomer include those selected from the group consisting of SEQ ID NOS: 12-14, 24-26, 36-38, 48-50, and any homologs or analogs thereof.

In some embodiments, a multi-unit complex comprises a first monomer and a second monomer, wherein said first monomer comprises a tRNA synthetase fragment modified to include at least one non-naturally occurring cysteine in its dimerization domain and said second monomer comprises a tRNA synthetase fragment modified to include at least one non-naturally occurring cysteine in its dimerization domain.

Such tRNA synthetase fragments can be, for example, tryptophanyl tRNA synthetase fragments, human tRNA synthetase fragments, or any angiostatic fragment of a tRNA synthetase.

In any of the embodiments herein, a cell or tissue may further be contacted with a second therapeutic agent selected from the group consisting of: an antineoplastic agent, an anti-inflammatory agent, an antibacterial agent, an antiviral agent, and an anti-angiogenic agent.

Kits for Modulating Angiogenesis

The present invention relates to kits for modulating angiogenesis. In some embodiments, a kit of the present invention comprises a container comprising a multi-unit complex wherein at least one unit of said multi-unit complex comprises a tRNA synthetase fragment or a homolog or analog thereof; and written instructions for use thereof in treating an individual. A multi-unit complex can be, for example, a dimer having two units. Monomers of a multi-unit complex can be different from each other, homologous, substantially homologous, or identical. In some embodiments, a multi-unit complex is a dimer having two homologous monomers.

In any of the embodiments herein a tRNA-synthetase fragment can be a tryptophanyl tRNA synthetase fragment, a human tryptophanyl tRNA-synthetase, or any angiostatic fragment of a tRNA synthetase fragment. For example, a tRNA synthetase fragment can be selected from the group consisting of SEQ ID NOS: 12-17, 24-29, 36-41, 48-53, and any homologs and analogs thereof.

Any two monomers within a multi-unit complex may be covalently linked or non-covalently linked. The composition in the first container may be packaged for systemic administration in a single unit dosage. When packaged in single unit dosages, a dose may range between 50-1000 μg/dose.

The kit herein may also include a second therapeutic agent. Such second therapeutic agent may be contained in a second container. Examples of a second therapeutic agent include, but are not limited to an antineoplastic agent, an anti-inflammatory agent, an antibacterial agent, an antiviral agent, and an anti-angiogenic agent.

In some embodiments, a kit of the present invention can include a container, comprising an antibody that specifically binds to an epitope of a tRNA synthetase fragment and written instructions for use thereof. In such examples, the tRNA synthetase fragment is a tryptophanyl tRNA synthetase fragment or a human tryptophanyl tRNA synthetase fragment, or any angiostatic fragment of a tRNA synthetase. In some embodiments, an angiostatic tRNA synthetase fragment is one selected from the group consisting of SEQ ID NOS: 12-17, 24-29, 36-41, 48-53, and any homologs and analogs thereof.

In some embodiments, a kit of the present invention comprises a container comprising a composition of a first tRNA synthetase fragment and a second tRNA synthetase fragment wherein the first tRNA synthetase fragment has a methionine at its N-terminus and wherein the second tRNA synthetase fragment does not have a methionine at its N-terminus; and written instructions for use thereof.

The first tRNA synthetase fragment can be, for example, a tryptophanyl tRNA synthetase fragment, a human tRNA synthetase fragment, or an angiostatic fragment of a tRNA synthetase. The second tRNA synthetase fragment can be, for example, a tryptophanyl tRNA synthetase fragment, a human tRNA synthetase fragment, or an angiostatic fragment of a tRNA synthetase.

Examples of angiostatic tRNA synthetase fragments having a methionine at their N-terminus include, but are not limited to those selected from the group consisting of SEQ ID NOS 15-17, 27-29, 36-38, 48-50 and any homologs and analogs thereof.

Examples of angiostatic tRNA synthetase fragments not having a methionine at their N-terminus include, but are not limited to those selected from the group consisting of SEQ ID NOS 12-14, 24-26, 36-38, 48-50, and any homologs and analogs thereof.

In any of the embodiments herein a composition in the first contain may have a pI of about 7.4-7.8.

Such kits may further include a second therapeutic agent, such as an antineoplastic agent, an anti-inflammatory agent, an antibacterial agent, an antiviral agent, or an anti-angiogenic agent. The second therapeutic agent may be contained in a separate container.

Business Methods for Modulating Angiogenesis

The present invention also relates to business methods for modulating angiogenesis. In some embodiments, the business methods herein include the steps of searching for an agent that modulates or binds to a receptor of a tRNA synthetase fragment; and commercializing said agent.

A tRNA synthetase fragment of the present invention can be, for example, a tryptophanyl tRNA synthetase fragment or a tyrosyl tRNA synthetase. Preferably such fragment is mammalian, or more preferably human. In some embodiments, a tRNA synthetase fragment has angiostatic activity. Examples of such angiostatic tRNA synthetase fragments include but are not limited to a fragment selected from the group consisting of SEQ ID NOS: 12-17, 24-29, 36-41, 48-53, and any homologs and variants thereof.

In any of the embodiments herein, a searching step may involve screening a library of candidate agents to identify an agent that modulates angiogenesis. Such agent can be, for example, a small molecule, a peptide, or a peptidomimetic. In some embodiments, a searching step may involve the use of a computer program to generate a peptidomimetic of said tRNA synthetase fragment.

The present invention also relates to business methods comprising the steps of (i) modifying a tRNA synthetase fragment to enhance its dimerization capabilities; and (ii) commercializing the enhanced tRNA synthetase fragment or dimerized form thereof.

Such tRNA synthetase fragments are preferably angiostatic fragments, tryptophanyl tRNA synthetase fragments, and/or human tRNA synthetase fragments. Examples of such fragments include a fragment selected from the group consisting of SEQ ID NOS: 12-17, 24-29, 36-41, 48-53 and any homologs and analogs thereof.

In some embodiments, the modifying step herein can involve generating an expression vector encoding a tRNA synthetase fragment modified in its dimerization domain to include one or more non-naturally occurring cysteines.

In some embodiments, the modifying step involves generating an expression vector encoding two tRNA synthetase fragments. An expression vector of the present invention may also encode a linker. Such linker may be situated between the first and the second tRNA synthetase fragments.

In some embodiments, the modifying step involves the use of a computer program to optimize the tRNA synthetase fragment. Examples of useful computer programs include, but are not limited to GRID, MCSS, AUTODOCK, DOCK, AMBER, QUANTA, and INSIGHT II.

In some embodiments, the present invention relates to business methods that include the steps of (i) preparing a recombinant tRNA synthetase fragment; and (ii) commercializing said fragment for modulating angiogenesis. Examples of recombinant tRNA synthetase fragments that may be prepared include, but are not limited to, tryptophanyl tRNA synthetase fragments and tyrosyl tRNA synthetase fragments. Preferably such fragments are human. Also, preferably, such fragments can modulate angiogenesis.

Examples of angiostatic fragments include, but are not limited to, SEQ ID NOS: 12-17, 24-29, 36-41, 48-53, and any homologs and analogs thereof.

Any of the angiogenesis-modulating tRNA synthetase fragments herein may be in monomer units or part of a multi-unit complex.

The business methods herein prepare such angiogenesis-modulating tRNA synthetase fragments by first preparing an expression vector encoding such fragments, then transfecting a host cell with said expression vector, and finally maintaining said host cell under a condition that permits the expression of said tRNA synthetase fragment.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 illustrates the amino acid residue sequence of tryptophanyl-tRNA synthetase polypeptide (SEQ ID NO: 63); mini-tryptophanyl-tRNA synthetase polypeptide (SEQ ID NO: 29), which corresponds to amino acid residues 48-471 of SEQ ID NO: 63; T1-tryptophanyl-tRNA-synthetase polypeptide (SEQ ID NO: 25), which corresponds to amino acid residues 71-471 of SEQ ID NO: 63; and T2-tryptophanyl-tRNA synthetase polypeptide (SEQ ID NO: 24), which corresponds to amino acid residues 94-471 of SEQ ID NO: 63.

FIG. 5 is a photomicrograph that illustrates the binding localization of his-tagged T2 (SEQ ID NO: 7) in the retina in a mouse model.

FIG. 17 illustrates counts per minute results from a PPi exchange assay.

DETAILED DESCRIPTION OF THE INVENTION

Definitions

Figure 2:
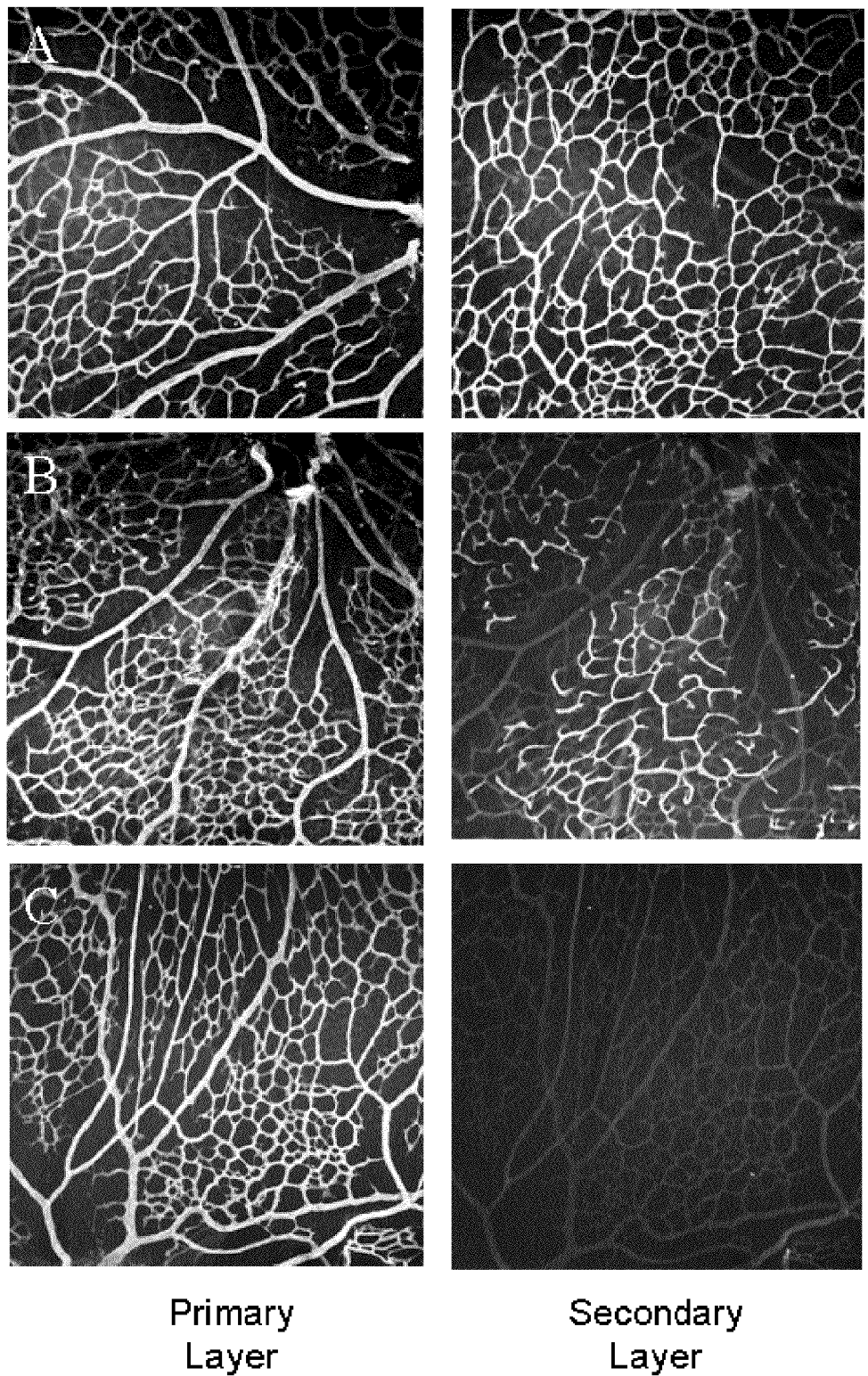
FIG. 2 is a photomicrograph that illustrates retinal vascular development in a mouse model.

The term "amino acid" or "amino acid residue" refers to an amino acid which is preferably in the L-isomeric form. When an amino acid residue is part of a polypeptide chain, the D-isomeric form of the amino acid can be substituted for the L-amino acid residue, as long as the desired functional property is retained. $NH_2$ refers to the free amino group present at the amino terminus of a polypeptide. COOH refers to the free carboxy group present at the carboxyl terminus of a polypeptide.

In keeping with standard polypeptide nomenclature described in *J. Biol. Chem.*, 243:3552-59 (1969) and adopted at 37 C.F.R. §§1.821-1.822, all amino acid residue sequences represented herein by formulae have a left to right orientation in the conventional direction of amino-terminus to carboxyl-terminus. In addition, the phrase "amino acid residue" is broadly defined to include modified and unusual amino acids, such as those referred to in 37 C.F.R. §§1.821-1.822, and incorporated herein by reference. A dash at the beginning or end of an amino acid residue sequence indicates a peptide bond to a further sequence of one or more amino acid residues or to an amino-terminal group such as $NH_2$ or to a carboxyl-terminal group such as COOH.

In a peptide or protein, suitable conservative substitutions of amino acids are known to those of skill in this art and can be made generally without altering the biological activity of the resulting molecule. Those of skill in this art recognize that, in general, single amino acid substitutions in non-essential regions of a polypeptide do not substantially alter biological activity (see, e.g., Watson et al. Molecular Biology of the Gene, 4th Edition, 1987, The Benjamin/Cummings Pub. Co. p. 224).

Such substitutions are preferably made with those set forth as follows:

| Original residue | Conservative substitution(s) |
|---|---|
| Ala | Gly; Ser |
| Arg | Lys |
| Asn | Gln; His |
| Cys | Ser |
| Gln | Asn |
| Glu | Asp |
| Gly | Ala; Pro |
| His | Asn; Gln |
| Ile | Leu; Val |
| Leu | Ile; Val |
| Lys | Arg; Gln; Glu |
| Met | Leu; Tyr, Ile |
| Phe | Met; Leu; Tyr |
| Ser | Thr |
| Thr | Ser |
| Trp | Tyr |
| Tyr | Trp; Phe |
| Val | Ile; Leu |

The term "analog(s)" as used herein refers to a composition that retains the same structure or function (e.g., binding to a receptor) as a polypeptide or nucleic acid herein. Examples of analogs include peptidomimetics, peptide nucleic acids, small and large organic or inorganic compounds, as well as derivatives and variants of a polypeptide or nucleic acid herein. The term "derivative" or "variant" as used herein refers to a peptide or nucleic acid that differs from the naturally occurring polypeptide or nucleic acid by one or more amino acid or nucleic acid deletions, additions, substitutions or side-chain modifications. Amino acid substitutions include alterations in which an amino acid is replaced with a different naturally-occurring or a non-conventional amino acid residue. Such substitutions may be classified as "conservative", in which case an amino acid residue contained in a polypeptide is replaced with another naturally-occurring amino acid of similar character either in relation to polarity, side chain functionality or size.

Substitutions encompassed by the present invention may also be "non-conservative", in which an amino acid residue which is present in a peptide is substituted with an amino acid having different properties, such as naturally-occurring amino acid from a different group (e.g., substituting a charged or hydrophobic amino acid with alanine), or alternatively, in which a naturally-occurring amino acid is substituted with a non-conventional amino acid. Preferably, amino acid substitutions are conservative.

Amino acid substitutions are typically of single residues, but may be of multiple residues, either clustered or dispersed. Additions encompass the addition of one or more naturally occurring or non-conventional amino acid residues. Deletion encompasses the deletion of one or more amino acid residues.

As stated above peptide derivatives include peptides in which one or more of the amino acids has undergone side-chain modifications. Examples of side chain modifications contemplated by the present invention include modifications of amino groups such as by reductive alkylation by reaction with an aldehyde followed by reduction with NaBH$_4$; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5-phosphate followed by reduction with NaBH$_4$.

The guanidine group of arginine residues may be modified by the formation of heterocyclic condensation products with reagents such as 2,3-butanedione, phenylglyoxal and glyoxal. The carboxyl group may be modified by carbodiimide activation via O-acylisourea formation followed by subsequent derivitisation, for example, to a corresponding amide. Sulfhydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH. Any modification of cysteine residues must not affect the ability of the peptide to form the necessary disulphide bonds. It is also possible to replace the sulfhydryl groups of cysteine with selenium equivalents such that the peptide forms a diselenium bond in place of one or more of the disulphide bonds.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitro-tyrosine derivative. Modification of the imidazole ring of a histidine residue may be accomplished by alkylation with iodoacetic acid derivatives or N-carbethoxylation with diethylpyrocarbonate. Proline residue may be modified by, for example, hydroxylation in the 4-position. Other derivatives contemplated by the present invention include a range of glycosylation variants from a completely unglycosylated molecule to a modified glycosylated molecule. Altered glycosylation patterns may result from expression of recombinant molecules in different host cells.

Additional derivatives include alterations that are caused by expression of the polypeptide in bacteria or other host system as well as through chemical modifications. Preferably, the derivatives retain the desired activity. For example, a derivative of T2 may be a truncated version of T2 that retains T2's ability to bind one of its naturally occurring receptors or to inhibit angiogenesis.

The term "antagonist" is used herein to refer to a molecule inhibiting a biological activity. Examples of antagonist molecules include but are not limited to antibodies, antisense nucleic acids, siRNA nucleic acids, and other binding agents.

The term "antibody" or "antibodies" as used herein includes polyclonal antibodies, monoclonal antibodies (mAbs), chimeric antibodies, anti-idiotypic (anti-id) antibodies to antibodies that can be labeled in soluble or bound form, as well as fragments, regions or derivatives thereof (e.g., separate heavy chains, light chains, Fab, Fab', F(ab')2, Fabc, and Fv).

The term "effective amount" as used herein means that amount of composition necessary to achieve the indicated effect.

The terms "gene therapy" and "genetic therapy" refer to the transfer of heterologous nucleic acids to the certain cells, target cells, of a mammal, particularly a human, with a disorder or conditions for which such therapy is sought. The nucleic acid is introduced into the selected target cells in a manner such that the heterologous DNA is expressed and a therapeutic product encoded thereby is produced. Alternatively, the heterologous nucleic acids can in some manner mediate expression of a nucleic acid that encodes the therapeutic product; it can encode a product, such as a peptide or RNA that in some manner mediates, directly or indirectly, expression of a therapeutic product. Genetic therapy can also be used to nucleic acid encoding a gene product replace a defective gene or supplement a gene product produced by the mammal or the cell in which it is introduced. The introduced nucleic acid can encode a therapeutic compound, such as a growth factor inhibitor thereof, or a tumor necrosis factor or inhibitor thereof, such as a receptor thereof, that is not normally produced in the mammalian host or that is not produced in therapeutically effective amounts or at a therapeutically useful time. The heterologous DNA encoding the therapeutic product can be modified prior to introduction into the cells of the afflicted host in order to enhance or otherwise alter the product or expression thereof.

The term "homodimer" as used herein refers to two monomers that are complexed together either covalently or non-covalently wherein the two compounds are identical.

The term "homolog" or "homologous" as used herein refers to homology with respect to structure and/or function. With respect to sequence homology, sequences are homologs if they are at least 50%, preferably at least 60%, more preferably at least 70%, more preferably at least 80%, more preferably at least 90%, more preferably at least 95% identical, more preferably at least 97% identical, or more preferably at least 99% identical. The term "substantially homologous" refers to sequences that are at least 90%, more preferably at least 95% identical, more preferably at least 97% identical, or more preferably at least 99% identical. Homologous sequences can be the same functional gene in different species.

The term "host" as used herein refers to an organism that expresses a nucleic acid of this invention in at least one of its cells. The term "host cell" as used herein refers to a cell which expresses the nucleotide sequences according to this invention.

The term "inhibit" as used herein refers to prevention or any detectable reduction or elimination of a condition.

The term "isolated" as used herein refers to a compound or molecule (e.g., a polypeptide or a nucleic acid) that is relatively free of other compounds or molecules that it normally is associated with in vivo. In general, an isolated polypeptide constitutes at least about 75%, more preferably about 80%, more preferably about 85%, more preferably about 90%, more preferably about 95%, or more preferably about 99% by weight of a sample containing it.

The term "met-tRNA synthetase" as used herein refers to t-RNA synthetase comprising a methionine residue at position 1.

The term "mini-TrpRS" as used herein refers to a polypeptide having an amino acid sequence selected from the group consisting of SEQ ID NOS: 2, 3, 14, 17, 26, 29, 38, 41, 50, 53, and any homologs and analogs thereof.

The term "multi-unit complex" as used herein refers to a complex of one or more monomer units that are complexed together covalently or non-covalently. Examples of multi-unit complexes include dimers, trimers, etc.

The term "Non-met-tRNA synthetase" as used herein refers to t-RNA synthetase without a methionine residue at position 1.

The term "nucleic acid" or "nucleic acid molecule" as used herein refers to an oligonucleotide sequence, polynucleotide sequence, including variants, homologs, fragments, or analogs thereof. A nucleic acid may include DNA, RNA, or a combination thereof. A nucleic acid may be naturally occurring or synthetic, double-stranded or single-stranded, sense or antisense strand.

As used herein the term "operably linked" wherein referring to a first nucleic acid sequence which is operably linked with a second nucleic acid sequence refers to a situation when the first nucleic acid sequence is placed in a functional relationship with the second nucleic acid sequence. For instance, a promoter is operably linked to a coding sequence if the promoter effects the transcription or expression of the coding sequence. Generally, operably linked nucleic acid sequences are contiguous and, where necessary to join two protein coding regions, the open reading frames are aligned.

The term "peptidomimetic" as used herein refers to both peptide and non-peptide agents that mimic aspects of a polypeptide. Non-hydrolyzable peptide analogs of critical residues can be generated using benzodiazepine (see Freidinger et al. in Peptides: Chemistry and Biology, G. R. Marshall ed., ESCOM Publisher: Leiden, Netherlands, 1988), azepine (see Huffman et al. in Peptides: Chemistry and Biology, G. R. Marshall ed., ESCOM Publisher: Leiden, Netherlands, 1988), substituted γ lactam rings (Garvey et al. in Peptides: Chemistry and Biology, G. R. Marshall ed., ESCOM Publisher: Leiden, Netherlands, 1988), keto-methylene pseudopeptides (Ewenson et al. (1986) J Med Chem 29:295; and Ewenson et al. in Peptides: Structure and Function (Proceedings of the 9th American Peptide Symposium) Pierce Chemical Co. Rockland, Ill., 1985), β-turn dipeptide cores (Nagai et al. (1985) Tetrahedron Lett 26:647; and Sato et al. (1986) J Chem Soc Perkin Trans 1:1231), and β-aminoalcohols (Gordon et al. (1985) Biochem Biophys Res Commun 126:419; and Dann et al. (1986) Biochem Biophys Res Commun 134:71).

The term "polypeptide", "peptide", "oligopeptides" or "protein" refers to any composition that includes two or more amino acids joined together by a peptide bond. It will be appreciated that polypeptides often contain amino acids other than the 20 amino acids commonly referred to as the 20 naturally occurring amino acids, and that many amino acids, including the terminal amino acids, may be modified in a given polypeptide, either by natural processes such as glycosylation and other post-translational modifications, or by chemical modification techniques which are well known in the art.

Among the known modifications which may be present in polypeptides of the present invention include, but are not limited to, acetylation, acylation, ADP-ribosylation, amidation, covalent attachment of flavin, covalent attachment of a heme moiety, covalent attachment of a polynucleotide or polynucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, γ-carboxylation, glycation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

The term "receptor" refers to a biologically active molecule that specifically binds to (or with) other molecules. The term "receptor protein" can be used to more specifically indicate the proteinaceous nature of a specific receptor. For example, the term "T2 receptor" refers to a biologically active molecule that specifically binds to (or with) T2.

The term "T1" or "T1-TrpRS" refers to a polypeptide having an amino acid sequence comprising SEQ ID NO: 13, 25, 37, 49, homologs or analogs thereof, and any polynucleotide sequence encoding the same.

The term "T2" or "T2-TrpRS" refers to a polypeptide having an amino acid sequence comprising SEQ ID NO: 12, 24, 36, 48, homologs or analogs thereof, and any polynucleotide sequence encoding the same.

The term "treating" as used herein refers to eliminating, reducing, or alleviating symptoms in a subject, or preventing symptoms from occurring, worsening, or progressing.

The term "TrpRS" or "tryptophanyl tRNA synthetase" as used herein refers to the full length tryptophanyl-tRNA synthetase as illustrated in FIG. 1, wherein amino acid residue 213 is either Gly or Ser and amino acid residue 214 is either Asp or Tyr (independently of the other). Thus, the terms "GD variant" "SD variant" "GY variant" and "SY variant" as used herein refer to TrpRS or a fragment thereof with the corresponding amino acid residues in the above location within the polypeptide.

The term "tRS" as used herein means a tRNA synthetase polypeptide and/or nucleic acids encoding such polypeptide, whether naturally occurring or non-naturally occurring.

The term "truncated tRNA synthetase polypeptides" means polypeptides that are shorter than the corresponding full length tRNA synthetase.

Compositions

Aminoacyl-tRNA synthetases (tRS) are ancient proteins that are essential for decoding genetic information during the process of translation. There are two classes of tRS. The first class, class 1, contains a common loop with the signature sequence KMSKS (and HIGH, as part of a Rossman dinucleotide binding fold of parallel D sheets ("Rossman fold domain")). Sever et al., *Biochem.* 35, 32-40 (1996). The second class, Class II, have an entirely different topology of dinucleotide binding bases on anti-parallel β sheets.

Tryptophanyl-tRNA synthetase (TrpRS) is a Class I tRS. It is believed that expression of TrpRS is stimulated by interferon ("IFN") (e.g., IFN-γ) and/or tumor necrosis factor ("TNF") (e.g., TNF-α). IFN-γ is responsible for antiviral and anti-proliferative state of animal cells. See Kisselev, L., *Biochimie* 75, 1027-1039 (1993). Stimulation of TrpRS by IFN occurs at the transcriptional level by a consensus regulatory sequence designated IFN-stimulated response element ("ISRE"). An examination of ISRE sequences from a number of IFN-response genes indicates a common motif of GGAAAN(N/-)GAAA. Thus the present invention contemplates the use of the compositions herein to treat IFN and/or TNF mediated conditions, and in particular IFN-γ and/or TNF-α mediated conditions.

Mammalian TrpRS molecules have an amino-terminal appended domain. In normal human cells, there are two forms of TrpRS that can be detected: a major form consisting of the full-length molecule (amino acid residues 1-471 of SEQ ID NO: 1) and a minor truncated form ("mini-TrpRS"; a polypeptide comprising amino acid sequence SEQ ID NOS: 3, 14, 19, or 20). In any of the Trp-RS embodiments herein amino acids 213 can be either a Gly or Ser and amino acid 214 can be either an Asp or Tyr. Such variants may be referred to herein as the GD variant, GY variant, SD variant and SY variant.

The minor form is generated by the deletion of the amino-terminal domain through alternative splicing of the pre-mRNA (Tolstrup et al., *J. Biol. Chem.* 270:397-403 (1995)). The amino-terminus of mini-TrpRS has been determined to be the methionine residue at position 48 of the full-length TrpRS molecule. Alternatively, truncated TrpRS can be generated by proteolysis. Lemaire et al., *Eur. J. Biochem.* 51:237-52 (1975). For example, bovine TrpRS is highly expressed in the pancreas and is secreted into the pancreatic juice (Kiselev, Biochimie 75:1027-39 (1993)), thus resulting in the production of a truncated TrpRS molecule. These observations suggest that truncated TrpRS could have a function other than the aminoacylation of tRNA.

Studies indicate that the full-length TrpRS does not inhibit angiogenesis, whereas mini-TrpRS inhibits VEGF-induced cell proliferation and migration (Wakasugi et al., *Proc. Natl. Acad. Sci.* 99: 173-177 (2002)). In particular, a chick CAM assay shows that mini-TrpRS blocks angiogenic activity of VEGF. Thus, removal of the first 47 amino acid residues exposes the anti-angiogenic activity of TrpRS. TrpRS and mini-TrpRS are further described in International Application Nos. PCT/US01/08966 and PCT/US01/8975, both filed Mar. 21, 2001, the disclosures of which are incorporated herein by reference in their entirety.

Additional fragments of TrpRS that have angiostatic activity are referred to herein as T1 and T2. Treatment of TrpRS with PMN elastase results in two additional products: a 47 kDa fragment (super mini-TrpRS or T1; e.g., SEQ ID NO: 13, 16, 25, 28, 37, 40, 49, and 52) and an approximately 43 kDa fragment (T2-TrpRS or T2; e.g., SEQ ID Nos: 12, 15, 24, 27, 36, 39, 48, and 51). Terminal amino acid analysis has revealed Ser-71 and Ser-94, respectively, as the $NH_2$-terminal residues for these fragments. Both T1 and T2 have been shown to be potent antagonists of in vivo angiogenesis as illustrated in the examples below. T1 and T2 are further described in U.S. Provisional Application No. 60/270,951 filed on Feb. 23, 2001, for "Tryptophanyl-tRNA Synthetase Derived Polypeptides Useful for the Regulation of Angiogenesis" as well as U.S. patent application Ser. No. 10/080,839, filed Feb. 22, 2002, and International Application No. PCT/US02/05185, filed Feb. 22, 2002, the disclosures of which are incorporated herein by reference in their entirety. Methods for preparing T2 are further disclosed in U.S. Provisional Application No. 60/598,019, filed Aug. 8, 2004, entitled "Composition of and Purification Methods for Low-Endotoxin Therapeutic Agents", which is incorporated herein by reference in its entirety.

1.) Polypeptides

The present invention relates to compositions comprising a tRNA synthetase fragment having angiogenic or angiostatic (anti-angiogenic) activity.

Preferably such compositions and/or tRNA synthetase fragments are substantially pure. In other embodiments, the compositions and/or tRNA synthetase fragments herein are at least 20%, 30%, 40%, 50%, 55% 60%, 65%, 70%, 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or 99.95% pure. Percent purity refers to the weight of the composition and/or tRNA synthetase fragment per total weight of the composition and/or tRNA synthetase fragment (w/w), respectively. When referring to a composition comprising a tRNA synthetase fragment, the composition is deemed to be, e.g., 80% pure, if 80% of total product is observed under a single chromatographic peak at UV absorbance between 180-220 nm. Similarly, when referring to a tRNA synthetase fragment, the tRNA synthetase fragment is deemed to be, e.g., 90% pure, if 90% of total product is observed under a single chromatographic peak at UV absorbance between 180-220 nm.

In some embodiments, tRNA synthetase fragments (and compositions comprising such fragments) are angiogenic. In some embodiments, tRNA synthetase fragments (and compositions comprising such fragments) are angiostatic. When referring to angiostatic activity, a tRNA synthetase fragment is said to have angiostatic activity as measured by the methods disclosed in Example 18. Preferably, a tRNA synthetase fragment (or composition comprising the tRNA synthetase fragment) has angiostatic activity of more than 10, 15, 20, 25, 30, 35, 40, 45, 50, 55, 60, 65, 70, or 75 angiostatic activity units. In some embodiments, a tRNA synthetase fragment (and compositions comprising thereof) has angiostatic activity greater than 50 angiostatic activity units.

Examples of tRNA synthetase fragments of the present invention include tryptophanyl tRNA synthetase fragments and tyrosyl tRNA synthetase fragments. Such fragments are preferably mammalian, or more preferably human. Such fragments preferably do not include a His-tag (e.g., a series of histidine amino acid residues, commonly added to the C-terminus). Examples of tRNA synthetase fragments that do not include His-tags include SEQ ID NOS: 12-17, 24-29, 36-41, 48-53, and homologs and variants thereof. Removal of His-tag is preferred for pharmaceutical formulations administered to an organism because of the His-tag affinity for certain compounds and effect on solubility of a polypeptide and the potential for the His-tag to be antigenic and potentially elicit an unwanted immunologic effect. However, removal of a His-tag is not trivial and may sometimes affect other aspects of a polypeptide.

Examples of tryptophanyl tRNA synthetase fragments that are contemplated by the present invention include mini-TrpRS, T1, T2 and any angiogenic or angiostatic fragments thereof. Preferably, such polypeptides have an amino acid sequence comprising, consisting essentially of, or consisting of SEQ ID NOS: 12-17, 24-29, 36-41, 48-53, or any homologs, analogs, or fragments thereof. Such fragments may be naturally occurring or non-naturally occurring. Such fragments are preferably isolated and/or purified.

In some embodiments, a composition of the present invention comprises a tRNA synthetase fragment, wherein the tRNA synthetase fragment comprises, consists essentially of, or alternatively consists of an amino acid sequence selected from the group of SEQ ID NO: 12, 15, 24, 27, 36, 39, 48, 51, and any homologs and analogs thereof. Preferably, such tRNA synthetase fragment does not include a His-tag. Preferably, such tRNA synthetase fragment is less than 45 kD, more preferably less than 44 kD, 43.9 kD, 43.8 kD, 43.7 kD, 43.6 kD, or more preferably less than 43.5 kD. Preferably such fragments are anti-angiogenic. Such tRNA synthetase fragment may be isolated and/or purified by the methods herein or other methods known in the art.

In some embodiments, a composition of the present invention comprises a tRNA synthetase fragment, wherein the tRNA synthetase fragment comprises, consists essentially of, or alternatively consists of an amino acid sequence selected from the group of SEQ ID NO: 13, 16, 25, 28, 37, 40, 49, 52, and any homologs and analogs thereof. Preferably, such tRNA synthetase fragment does not include a His-tag. Preferably, such tRNA synthetase fragment is less than 48 kD, more preferably less than 47 kD, or more preferably less than 46 kD. Preferably such tRNA synthetase fragment is anti-angiogenic. Such tRNA synthetase fragment may be isolated and/or purified by the methods herein or other methods known in the art.

In some embodiments, a composition of the present invention comprises a tRNA synthetase fragment, wherein the tRNA synthetase fragment comprises, consists essentially of, or alternatively consists of an amino acid sequence selected from the group consisting of SEQ ID NOs: 14, 17, 26, 29, 38, 41, 50, 53, and any homologs and analogs thereof. Preferably, such tRNA synthetase fragment does not include a His-tag. Preferably, such tRNA synthetase fragment is less than 53 kD, more preferably less than 52 kD, more preferably less than 51 kD, more preferably less than 50 kD, or more preferably less than 49 kD. Preferably, such fragments are greater than 43 kD. Preferably such tRNA synthetase fragment is anti-angiogenic. Such tRNA synthetase fragment may be isolated and/or purified by the methods herein or other methods known in the art.

In any embodiment herein, a tRNA synthetase fragment is preferably isolated. Moreover, in any embodiment herein, a tRNA synthetase fragment is preferably purified. Methods for purifying a tRNA synthetase fragment are described in U.S. Provisional Application No. 60/598,019, which is incorporated herein by reference for all purposes.

In some embodiments, a composition comprising a tRNA synthetase fragment or a tRNA synthetase fragment has an experimental isoelectric point (pI) of less than 10.0, more preferably less than 9.0, or more preferably less than 8.0. In some embodiments, a tRNA synthetase fragment has an isoelectric point of 5.0 to 9.0, more preferably 6.0 to 8.0, or more preferably 7.4 to 7.8. In some embodiments, a tRNA synthetase fragment of the invention has an experimental pI greater than 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, or 7.5. Preferably, a tRNA synthetase fragment of the invention has experimental pI of about 7.6. In some embodiments, a tRNA synthetase fragment herein has a hydrophobic cleft.

The tRNA synthetase fragments herein may be monomer(s) in a multi-unit complex. A multi-unit complex of the present invention can include, for example, at least 2, 3, 4, 5, or 6 monomers. Both the monomer and multi-unit complexes of the present invention may be soluble and may be isolated or purified to homogeneity. A multi-unit complex of the invention comprises at least two monomer units that are associated with each other covalently, non-covalently, or both covalently and non-covalently. A multi-unit complex, made of non-covalently bound monomers, can be broken down to individual monomeric units under certain conditions such as high salt concentrations, detergent, and/or heat. Therefore, in order to maintain multi-unit complex formations one should avoid applying denaturants to the product, such as substantial heat, detergent and/or high salt concentrations.

Monomer units in a multi-unit complex may be different, homologous, substantially homologous, or identical to one another. A multi-unit complex of the invention includes at least one, two, three, four, five or six monomer units that comprise, consist essentially of, or consist of a tRNA synthetase fragment herein.

For example, a composition of the invention can comprise a dimer, wherein each monomer unit of the dimer is selected from the group consisting of SEQ ID NOS: 12-17, 24-29, 36-41, 48-53, and homologs and analogs thereof. Preferably, a composition of the present invention comprises a dimer wherein at least one of the two monomers comprises, consists essentially of, or consists of SEQ ID NO: 24. In some embodiments, both monomer units of a dimer comprise, consist essentially of, or consist of SEQ ID NO: 24.

For example, the present invention contemplates a dimer having two monomers that are T2 fragments. In some embodiments, the present invention contemplates a dimer having two monomers comprising, consisting essentially of, or consisting of SEQ ID NO: 12, 15, 24, 27, 36, 39, 48, 51, or any homologs or analogs thereof. In preferred embodiments, the present invention contemplates a dimer having two monomers comprising, consisting essentially of, or consisting of SEQ ID NO: 12, 24, 36, 48 or homologs or analogs thereof. More preferably, a dimer of the present invention comprises, consists essentially of, or consisting of SEQ ID NO: 24, or any homolog or analog thereof. Preferably each monomer unit does not include a His-tag. In some embodiments, such dimer compositions are isolated and/or purified. In some embodiments, such dimer compositions are soluble. In some embodiments, such dimers are homodimers.

Two or more monomers in a multi-unit complex may be covalently linked. Covalently linked monomers can be linked directly (by bonds) or indirectly (e.g., via a linker). For directly linking the monomers herein, it may be beneficial to modify the polypeptides herein to enhance dimerization. For example, one or more amino acid residues of a tRNA synthetase fragment may be modified by the addition or substitution by one or more cysteines. A tRNA synthetase fragment modified under the present invention is preferably a tryptophanyl tRNA synthetase fragment. Such fragments are preferably mammalian, or more preferably human. Such fragments have angiostatic activity and preferably comprise of, consist essentially of, or consist of a polypeptide having an amino acid sequence selected from the group consisting of SEQ ID NOS: 12-17, 24-29, 36-41, 48-53, and any homologs and analogs thereof. Preferably such amino acid sequence does not include a His-tag. Methods for creating cysteine substitutions, such as by site directed mutagenesis, are known to those skilled in the art.

Preferably, such modification occurs in the dimerization domain of the tRNA synthetase fragment. A dimerization domain refers to that domain which forms covalent and/or non-covalent bonds with a second monomer. For example, the dimerization domain of full length Trp-RS (SEQ ID NO: 1) is between amino acid residues about 230 to about 300, or more preferably between amino acid residues about 237 to about 292. In another example, the dimerization domain for a polypeptide of SEQ ID NO: 13, a T1, is between amino acid residues about 160 to about 230, or more preferably between amino acid residues about 167 to about 222. In another example, the dimerization domain for a polypeptide of SEQ ID NO: 12, 24, 36, or 42, is between amino acid residues about 137 to about 157, or more preferably between amino acid residues about 144 to about 149. For other angiogenic fragments of a tRNA synthetase, the dimerization region may be any region that is homologous to the above regions or SEQ ID NO: 60.

The addition or substitution of cysteines can create disulfide bridges, linking two or more monomers covalently. Preferably, two or more of the modified polypeptide herein are covalently linked to form a multi-unit (monomer) complex. A multi-unit complex comprises at least two, three, four, five, or six monomers. The various monomers in a multi-unit complex may be different, homologous, substantially homologous, or identical to one another. In preferred embodiments, two or more of the various monomers in a multi-unit complex are substantially homologous to one another or identical to one another.

Two or more monomers of the present invention may also be covalently bonded via a linker. A linker of the present invention is preferably long enough to allow the two or more monomer to align in the head-to-tail orientation (N-terminus to C-terminus). In some embodiments, a linker is at least about 3, more preferably about 30, more preferably about 150, more preferably about 300, or more preferably about 450 atoms in length. Linker sequences, which are generally between 2 and 25 amino acids in length, are well known in the art and include, but are not limited to, the glycine(4)-serine spacer (GGGGS ×3) described by Chaudhary et al. (1989). These and other linkers can be used in the present invention.

In some embodiments, a linker can be used to localize a multi-unit complex of the invention. For example, a linker can comprise, consist essentially of, or consist of an antibody fragment or binding agent. In some embodiments, a linker comprises, consists essentially of, or consists of an antibody or antibody fragment or a binding agent that specifically binds to a photoreceptor or another receptor located in the eye.

Examples of non-covalent bonds (associations) include electrostatic bonds, ionic bonds, hydrogen bonds, Van der Waals bonds, and hydrophobic effect.

In any one of the embodiments herein, a polypeptide can be any of the above wherein (i) one or more of the amino acid residues are substituted with a conserved or non-conserved amino acid residue (preferably a conserved amino acid residue) and such substituted amino acid residue is or is not encoded by the genetic code; (ii) one or more of the amino acid residues includes a substituent group; (iii) the polypeptide is fused with another compound, (e.g., a compound to increase the half-life of the polypeptide or target it to a specific receptor, cell, tissue, or organelle), (iv) additional amino acids are fused to the polypeptide, such as a leader or secretory sequence or a sequence which is employed for purification of the polypeptide or a proprotein sequence; or (v) one or more of the amino acid residues are substituted with a non-conserved amino acid residue (preferably cysteine) and such substituted amino acid residue form a disulfide bridge with a second polypeptide (e.g., to form a dimer or homodimer). Such derivatives are deemed to be within the scope of those skilled in the art from the teachings herein.

For example, any of the polypeptides herein can be modified to improve stability and increase potency by means known in the art. For example, L-amino acids can be replaced by D-amino acids, the amino terminus can be acetylated, or the carboxyl terminus modified, e.g., ethylamine-capped (Dawson, D. W., et al., Mol. Pharmacol., 55: 332-338 (1999)) or glycosylated.

In another example, the polypeptides herein can be fused to another protein or portion thereof. For example, mini-TrpRS, T1 or T2 polypeptide or portion thereof, can be operably linked to another polypeptide moiety to enhance solubility. In some embodiments, a polypeptide having an amino acid sequence comprising, consisting essentially of, or consisting of SEQ ID NO: 12-17, 24-29, 36-41, 48-53, or any homologs or analogs thereof is operably linked to another polypeptide moiety to enhance solubility. Preferably such polypeptide does not include a His-tag. Examples of a protein which can be fused with mini-TrpRS, T1 or T2 or portions thereof to enhance solubility include a plasma protein or fragment thereof. In other embodiments, mini-TrpRS, T1 or T2 polypeptide or portion thereof, can be operably linked to another polypeptide moiety to target the molecule to a specific tissue or cell type. For example, mini-TrpRS, T1 or T2 polypeptides or portions thereof, can be operable linked to an antibody that specifically binds the photoreceptor cells in the eye, a particular tumor cell, or a particular organelle. In some embodiments, mini-TrpRS, T1 or T2 polypeptide may be operably linked to a polypeptide moiety that helps reduce immune response, for example, a constant F(c) region of an immunoglobulin.

In another embodiment, the polypeptides herein include a leader sequence. A leader sequence can be used to allow the polypeptide to enter into a specific cell or cell compartment. Thus, the present invention contemplates a polypeptide comprising, consisting essentially of, or consisting of SEQ ID NOS: 12-17, 24-29, 36-41, 48-53, and any analogs and homologs thereof having a leader sequence. In some embodiments, such polypeptide does not include a His-tag.

In another example, the polypeptides herein can be modified for enhanced dimerization. Modifications that enhance dimerization of a polypeptide include alternations (e.g., substitutions or additions) to the naturally occurring sequence which enhances covalent and/or non-covalent interactions of the polypeptide with another monomer. Preferably modifications are made within a dimerization domain.

For tryptophanyl-tRNA synthetase and fragments thereof, the dimerization domain is approximately between amino acid residues 230 and 300, or more preferably approximately between amino acid residues 237 and 292 of the full length Trp-tRS (SEQ ID NO: 1). Such polypeptides (preferably mini-TrpRS, T1, and T2) have enhanced dimerization capabilities. Thus, in some embodiments, the present invention contemplates a mini-TrpRS monomer with a cysteine addition or substitution approximately between amino acid residues 183 and 253, or more preferably approximately between amino acid residues 190 and 245. In some embodiments, the present invention contemplates a T1 monomer with a cysteine addition or substitution approximately between amino acid residues 160 and 230, or more preferably between amino acid residues 167 and 222. In some embodiments, the present invention contemplates a T2 monomer with a cysteine addition or substitution approximately between amino acid residue 137 and 208, or more preferably between amino acid residue 144 and 200.

It is further contemplated by the present invention that any of the cysteine modified polypeptides may dimerize to form tRNA synthetase dimers. In preferred embodiments, such dimerization occurs naturally and/or spontaneously as a result of expressing and/or purifying any of the above polypeptide(s) using a vector that encodes a single tRNA synthetase fragment, and allowing such expressed fragments to naturally dimerize.

Thus, in some embodiments a composition comprises homodimers of preferably identical monomer units. For example, in some embodiments, a composition comprises a dimer of two monomers having SEQ ID NO: 12, a dimer of two monomers having SEQ ID NO: 13, a dimer of two monomers having SEQ ID NO: 14, a dimer of two monomers having SEQ ID NO: 15, a dimer of two monomers having SEQ ID NO: 16, a dimer of two monomers having SEQ ID NO: 17, a dimer of two monomers having SEQ ID NO: 24, a dimer of two monomers having SEQ ID NO: 25, a dimer of two monomers having SEQ ID NO: 26, a dimer of two monomers having SEQ ID NO: 27, a dimer of two monomers having SEQ ID NO: 28, a dimer of two monomers having SEQ ID NO: 29, a dimer of two monomers having SEQ ID NO: 36, a dimer of two monomers having SEQ ID NO: 37, a dimer of two monomers having SEQ ID NO: 38, a dimer of two monomers having SEQ ID NO: 39, a dimer of two monomers having SEQ ID NO: 40, a dimer of two monomers having SEQ ID NO: 41, a dimer of two monomers having SEQ ID NO: 48, a dimer of two monomers having SEQ ID NO: 49, a dimer of two monomers having SEQ ID NO: 50, a dimer of two monomers having SEQ ID NO: 51, a dimer of two monomers having SEQ ID NO: 52, or a dimer of two monomers having SEQ ID NO: 53.

In some embodiments, a composition herein comprises a combination of any of the above identical homodimers. For example, a composition can comprise a dimer of two monomers having SEQ ID NO: 12 and a dimer of two monomers having SEQ ID NO: 24. All other combinations of the dimers above are also contemplated.

In some embodiments, the present invention contemplates a composition comprising a first tRNA synthetase fragment and a second tRNA synthetase fragment, wherein the first tRNA synthetase fragment has a methionine at its N-terminus ("Met-tRS fragment") and wherein the second tRNA synthetase does not have a methionine at its N-terminus ("non-Met-tRS fragment").

Preferably, the tRNA synthetase fragments herein are tryptophanyl-tRNA synthetase fragments. As such in some embodiments, a first tRNA synthetase fragment having a methionine at its N-terminus is a "Met-TrpRS fragment", and the second tRNA synthetase fragment not having a methionine at its N-terminus is a "non-Met-TrpRS fragment".

Examples of Met-TrpRS fragments, or tryptophanyl tRNA synthetase fragments having a methionine at their N-terminus include polypeptides comprising, consisting essentially of, or consisting of an amino acid sequence SEQ ID NOS: 15-17, 27-29, 39-41, 51-53, or any homologs, analogs, or fragments thereof. Preferably such fragments do not include a His-tag.

Examples of Trp-RS fragments, or tryptophanyl tRNA synthetase fragments that do not have methionine at their N-terminus, include polypeptides comprising, consisting essentially of, or consisting SEQ ID NOS: 12-14, 24-26, 36-38, 48-50, or any homologs, analogs, or fragments thereof. All other angiostatic fragments of Trp-tRNA synthetase are contemplated herein. Preferably, such fragments do not include a His-tag.

In some embodiments, the first tRNA synthetase fragment is a polypeptide having an amino acid sequence comprising, consisting essentially of, or consisting of SEQ ID NO: 15, or any homolog, analog, or fragment thereof. Preferably such fragment does not include a His-tag. The second tRNA synthetase fragment may be a polypeptide having an amino acid sequence comprising, consisting essentially of, or consisting of SEQ ID NO: 12, or any homolog, analog, or fragment thereof. Preferably such fragment does not include a His-tag.

In some embodiments, the first tRNA synthetase fragment is a polypeptide having an amino acid sequence comprising, consisting essentially of, or consisting of SEQ ID NO: 16, or any homolog, analog, or fragment thereof. Preferably such fragment does not include a His-tag. The second tRNA synthetase fragment may be a polypeptide having an amino acid sequence comprising, consisting essentially of, or consisting of SEQ ID NO: 13, or any homolog, analog, or fragment thereof. Preferably such fragment does not include a His-tag.

In some embodiments, the first tRNA synthetase fragment is a polypeptide having an amino acid sequence comprising, consisting essentially of, or consisting of SEQ ID NO: 17, or any homolog, analog, or fragment thereof. Preferably such fragment does not include a His-tag. The second tRNA synthetase fragment may be a polypeptide having an amino acid sequence comprising, consisting essentially of, or consisting of SEQ ID NO: 14, or any homolog, analog, or fragment thereof. Preferably such fragment does not include a His-tag.

In some embodiments, the first tRNA synthetase fragment is a polypeptide having an amino acid sequence comprising, consisting essentially of, or consisting of SEQ ID NO: 27, or any homolog, analog, or fragment thereof. Preferably such fragment does not include a His-tag. The second tRNA synthetase fragment may be a polypeptide having an amino acid sequence comprising, consisting essentially of, or consisting of SEQ ID NO: 24, or any homolog, analog, or fragment thereof. Preferably such fragment does not include a His-tag.

In some embodiments, the first tRNA synthetase fragment is a polypeptide having an amino acid sequence comprising, consisting essentially of, or consisting of SEQ ID NO: 28, or any homolog, analog, or fragment thereof. Preferably such fragment does not include a His-tag. The second tRNA synthetase fragment may be a polypeptide having an amino acid sequence comprising, consisting essentially of, or consisting of SEQ ID NO: 25, or any homolog, analog, or fragment thereof. Preferably such fragment does not include a His-tag.

In some embodiments, the first tRNA synthetase fragment is a polypeptide having an amino acid sequence comprising, consisting essentially of, or consisting of SEQ ID NO: 29, or any homolog, analog, or fragment thereof. Preferably such fragment does not include a His-tag. The second tRNA synthetase fragment may be a polypeptide having an amino acid sequence comprising, consisting essentially of, or consisting of SEQ ID NO: 26, or any homolog, analog, or fragment thereof. Preferably such fragment does not include a His-tag.

In some embodiments, the first tRNA synthetase fragment is a polypeptide having an amino acid sequence comprising, consisting essentially of, or consisting of SEQ ID NO: 39, or any homolog, analog, or fragment thereof. Preferably such fragment does not include a His-tag. The second tRNA synthetase fragment may be a polypeptide having an amino acid sequence comprising, consisting essentially of, or consisting of SEQ ID NO: 36, or any homolog, analog, or fragment thereof. Preferably such fragment does not include a His-tag.

In some embodiments, the first tRNA synthetase fragment is a polypeptide having an amino acid sequence comprising, consisting essentially of, or consisting of SEQ ID NO: 40, or any homolog, analog, or fragment thereof. Preferably such fragment does not include a His-tag. The second tRNA synthetase fragment may be a polypeptide having an amino acid sequence comprising, consisting essentially of, or consisting of SEQ ID NO: 37, or any homolog, analog, or fragment thereof. Preferably such fragment does not include a His-tag.

In some embodiments, the first tRNA synthetase fragment is a polypeptide having an amino acid sequence comprising, consisting essentially of, or consisting of SEQ ID NO: 41, or any homolog, analog, or fragment thereof. Preferably such fragment does not include a His-tag. The second tRNA synthetase fragment may be a polypeptide having an amino acid sequence comprising, consisting essentially of, or consisting of SEQ ID NO: 38, or any homolog, analog, or fragment thereof. Preferably such fragment does not include a His-tag.

In some embodiments, the first tRNA synthetase fragment is a polypeptide having an amino acid sequence comprising, consisting essentially of, or consisting of SEQ ID NO: 51, or any homolog, analog, or fragment thereof. Preferably such fragment does not include a His-tag. The second tRNA synthetase fragment may be a polypeptide having an amino acid sequence comprising, consisting essentially of, or consisting of SEQ ID NO: 48, or any homolog, analog, or fragment thereof. Preferably such fragment does not include a His-tag.

In some embodiments, the first tRNA synthetase fragment is a polypeptide having an amino acid sequence comprising, consisting essentially of, or consisting of SEQ ID NO: 52, or any homolog, analog, or fragment thereof. Preferably such fragment does not include a His-tag. The second tRNA synthetase fragment may be a polypeptide having an amino acid sequence comprising, consisting essentially of, or consisting of SEQ ID NO: 49, or any homolog, analog, or fragment thereof. Preferably such fragment does not include a His-tag.

In some embodiments, the first tRNA synthetase fragment is a polypeptide having an amino acid sequence comprising, consisting essentially of, or consisting of SEQ ID NO: 53, or any homolog, analog, or fragment thereof. Preferably such fragment does not include a His-tag. The second tRNA synthetase fragment may be a polypeptide having an amino acid sequence comprising, consisting essentially of, or consisting of SEQ ID NO: 50, or any homolog, analog, or fragment thereof. Preferably such fragment does not include a His-tag.

In some embodiments herein which contain a first tRNA synthetase fragment having a methionine at its N-terminus and a second tRNA synthetase fragment not having a methionine at its N-terminus, the first tRNA synthetase fragment can comprise about 5%, 10%, 15%, 20%, 25%, 30%, 35%, 40%, 45%, 50%, 55%, 60%, 65%, 70%, 75%, 80%, 85%, 90%, or 95% by weight of the total amount tRNA synthetase fragments. In other embodiments, the first tRNA synthetase fragment comprises less than about 5%, 10%, 15%, 20%, 25%, 30%, 35%, 40%, 45%, 50%, 55%, 60%, 65%, 70%, 75%, 80%, 85%, 90%, or 95% by weight of the total amount tRNA synthetase fragments.

In some embodiments herein which contain a first tRNA synthetase fragment having a methionine at its N-terminus and a second tRNA synthetase fragment not having a methionine at its N-terminus, the second tRNA synthetase fragment comprises about 5%, 10%, 15%, 20%, 25%, 30%, 35%, 40%, 45%, 50%, 55%, 60%, 65%, 70%, 75%, 80%, 85%, 90%, or 95% by weight of the total amount tRNA synthetase fragments. In other embodiments, the second tRNA synthetase fragment not having a methionine at its N-terminus comprises at least about 5%, 10%, 15%, 20%, 25%, 30%, 35%, 40%, 45%, 50%, 55%, 60%, 65%, 70%, 75%, 80%, 85%, 90%, or 95% by weight of the total amount tRNA synthetase fragments.

The term "about" as used to describe a percentage by weight of a composition means the percentage by weight +/−4, 3, 2, or 1%.

A composition of the present invention can comprise about 50% by weight of a first tRNA synthetase fragment and about 50% by weight of a second tRNA synthetase fragment. For example, in some embodiments, a composition comprises about 50% by weight of a Met-tRS fragment and about 50% by weight of a non-Met-tRS fragment. In some embodiments, a composition comprises about 50% by weight of a Met-TrpRS fragment and about 50% by weight of a non-Met-TrpRS fragment. In other embodiments, more than 50% of a composition comprises either a Met-Trp-RS fragment or a non-Met-Trp-RS fragment. Preferably the fragments above do not include a His-tag.

Any of the above compositions can further comprise a therapeutic agent, such as an antineoplastic agent, an anti-inflammatory agent, an antibacterial agent, an angiogenic agent, an antiviral agent, and an anti-angiogenic agent. Examples of such agents are disclosed herein. Preferably, the therapeutic agent is an anti-angiogenic agent and is either a VEGF antagonist or an integrin antagonist.

2.) Antibodies

In another aspect, the invention provides a peptide comprising, consisting essentially of, or consisting of an epitope-bearing portion of the polypeptides described herein. The term "epitope" as used herein, refers to a portion of a polypeptide having antigenic or immunogenic activity in an animal, preferably a mammal, and most preferably in a human. Antigenic epitope-bearing peptides of the polypeptides of the invention are useful to raise antibodies, including monoclonal antibodies that bind specifically to a polypeptide of the invention. The term "antigenic epitope," as used herein, is defined as a portion of a protein to which an antibody can specifically bind its antigen as determined by any method well known in the art, for example, by the immunoassays.

Antigenic epitope-bearing polypeptides of the invention preferably contain a sequence of at least about five or about seven, more preferably at least about nine or about eleven amino acids, and more preferably between at least about 5 to about 30 or more preferably between about 10 to about 20 amino acids contained within a tRNA synthetase fragment, or more preferably a tryptophanyl tRNA synthetase fragment. Such fragments are preferably mammalian, or more preferably human. The tRNA fragments herein have angiostatic activity. Examples of human tryptophanyl tRNA synthetase fragments with angiostatic activity include, but are not limited to SEQ ID NOS: 12-17, 24-29, 36-41, 48-53, and homologs and analogs thereof. In this context "about" includes the particularly recited value and values larger or smaller by several (5, 4, 3, 2, or 1) amino acids.

In some embodiments, such epitope-bearing polypeptides are "N-terminus epitopes." The phrase "N-terminus epitopes" as used herein refer to a peptide having an amino acid sequence that is closer to the N-terminus than the C-terminus of a polypeptide of the invention (e.g., SEQ ID NOS: 12-17, 24-29, 36-41, 48-53, and homologs and analogs thereof). In some embodiments, such epitope-bearing polypeptides comprise or consist of the N-terminus of a polypeptide of the invention (e.g., SEQ ID NOS: 12-17, 24-29, 36-41, 48-53, and homologs and analogs thereof).

Examples of such epitope-bearing polypeptides include polypeptide comprising, or alternatively consisting of: amino acid residues of about position 1 to about position 5, about position 1 to about position 15, or about position 1 to about position 25 of SEQ ID NOS: 12-17, 24-29, 36-41, 48-53, and any homologs or analogs thereof; amino acid residues of about position 10 to about position 15, about position 10 to about position 25, or about position 10 to about position 35 of SEQ ID NOS: 12-17, 24-29, 36-41, 48-53, and homologs or analogs thereof; amino acid residues of about position 20 to about position 25, about position 20 to about position 35, or about position 20 to about position 45 of SEQ ID NOS: 12-17, 24-29, 36-41, 48-53 and any homologs and analogs thereof.

The above polypeptides can be used for research purposes (e.g., to distinguish between one fragment and another), for diagnostic purposes (e.g., to identify and quantify angiogenic/angiostatic fragments); and/or for therapeutic purposes (e.g., to inhibit angiostatic activity of an angiostatic tRNA synthetase fragment).

For example, in some embodiments, antibodies of the present invention can distinguish between any two of the following: TrpRS, mini-TrpRS, T1, and T2. In some embodiments, antibodies of the present invention can distinguish between a tRNA synthetase fragment having and not having a methionine in its N-terminus. (For example, an antibody can distinguish between SEQ ID NOS: 12 and 15; or between SEQ ID NOS: 13 and 16; or between SEQ ID NOS: 14 and 17; or homologs or analogs thereof.) In some embodiments, antibodies of the present invention can distinguish between two variants of a tRNA synthetase fragment. (For example, an antibody of the present invention may distinguish between two polypeptide selected from the following group: SEQ ID NOS: 12, 24, 36, and 48.)

Other antibodies that bind the dimerization domain or receptor binding domain may also be useful as therapeutics to treat or prevent a condition associated with diminished vascular growth (an anti-angiogenic condition).

Moreover, calibration of the amount of tRNA fragments that are angiogenic and/or non-angiogenic may permit the diagnosis of angiogenesis-mediated condition.

Polynucleotides encoding these antigenic epitope-bearing peptides are also encompassed by the present invention.

Epitope-bearing polypeptides of the present invention may be used to induce antibodies according to methods well known in the art including, but not limited to, in vivo immunization, in vitro immunization, and phage display methods.

If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde.

For making a polyclonal antibody, animals such as, for example, rabbits, rats, and mice are immunized with either free or carrier-coupled peptides, for instance, by intraperitoneal and/or intradermal injection of emulsions containing about 100 micrograms of an epitope-bearing peptide and possibly a carrier protein and Freund's adjuvant or any other adjuvant known for stimulating an immune response. Several booster injections may be needed, for instance, at intervals of about two weeks, to provide a useful titer of anti-peptide antibody that can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

More preferably, the present invention contemplates monoclonal antibodies that are able to specifically bind to one or more of the polypeptides herein. Monoclonal antibodies can be readily prepared through use of well-known techniques such as those exemplified in U.S. Pat. No. 4,196,265, which is incorporated herein by reference for all purposes. Typically, a technique involves first immunizing a suitable animal with a selected antigen (e.g., a polypeptide or polynucleotide of the present invention) in a manner sufficient to provide an immune response. Rodents such as mice and rats are preferred animals. Spleen cells from the immunized animal are then fused with cells of an immortal myeloma cell. Where the immunized animal is a mouse, a preferred myeloma cell is a murine NS-1 myeloma cell.

The fused spleen/myeloma cells are cultured in a selective medium to select fused spleen/myeloma cells from the parental cells. Fused cells are separated from the mixture of non-fused parental cells, for example, by the addition of agents that block the de novo synthesis of nucleotides in the tissue culture media. This culturing provides a population of hybridomas from which specific hybridomas are selected. Typically, selection of hybridomas is performed by culturing the cells by single-clone dilution in microtiter plates, followed by testing the individual clonal supernatants for reactivity with antigen-polypeptides. The selected clones can then be propagated indefinitely to provide the monoclonal antibody. Preferably, a monoclonal antibody of the present invention is also humanized.

As one of skill in the art will appreciate, and as discussed above, the polypeptides of the present invention comprising an immunogenic or antigenic epitope can be fused to other polypeptide sequences. For example, the polypeptides of the present invention may be fused with the constant domain of immunoglobulins (IgA, IgE, IgG, IgM), or portions thereof (CH1, CH2, CH3, or any combination thereof and portions thereof) resulting in chimeric polypeptides. Such fusion proteins may facilitate purification and may increase half-life in vivo.

The present invention also contemplates fragment, regions or derivatives of the above antibodies. Such fragments include separate heavy chains, light chains, Fab, Fab', F(ab')2, Fabc, and Fv.

3.) Nucleic Acids

The present invention also contemplates polynucleotide sequences encoding any of the polypeptides herein. In some embodiments, a polynucleotide sequence encodes two or more of the polypeptides herein. Preferably, the polynucleotide sequences of the present invention are isolated.

For example, the present invention contemplates polynucleotide sequences that encode one or more, or two or more tRNA synthetase fragments. The tRNA synthetase fragments can be fragments of any one or more of the tRNA synthetases known in the art, but more preferably either of a tryptophanyl tRNA synthetase or a tyrosyl tRNA synthetase. A tRNA synthetase of the present invention is preferably mammalian, or more preferably human. Furthermore, fragments of such tRNA synthetases preferably have angiostatic activity.

For example, in some embodiments, a polynucleotide sequence of the present invention encodes one or more angiostatic fragments of a tRNA synthetase. Examples of angiostatic fragments of a tryptophanyl tRNA synthetase include mini-TrpRS, T1, and T2 and any angiostatic fragments, homologs or analogs thereof. Thus, in some embodiments, a polynucleotide of the present invention encodes a tryptophanyl tRNA synthetase fragment comprising, consisting essentially of, or consisting of a polypeptide selected from the group consisting of SEQ ID NOS: 12-17, 24-29, 36-41, 48-53 or any homologs or analogs thereof. Preferably, a polynucleotide of the present invention encodes a tryptophanyl fragment comprising, consisting essentially of, or consisting of SEQ ID NO: 24 or 27.

Examples of polynucleotide sequences encoding such fragments are the polynucleotide sequence of SEQ ID NOS: 18-23, 30-35, 42-47, 54-59, and homologs and analogs thereof. Additional examples of isolated polynucleotides contemplated by the present invention include the polynucleotides of SEQ ID NOS: 70-75.

As the DNA code is degenerative, such that more than one codon can encode a single amino acid residue, the above polynucleotide sequences are exemplary and not intended to be limiting in any way. Any of the above polynucleotides are preferably isolated.

In some embodiments, a polynucleotide sequence of the present invention encodes two or more of the polypeptides herein. For example, a polynucleotide of the present invention can encode a first tRNA synthetase fragment and a second tRNA synthetase fragment. The first tRNA synthetase fragment can be a polypeptide having an amino acid comprising, consisting essentially of, or consisting of SEQ ID NOS: 12-17, 24-29, 36-41, 48-53, or homologs or analogs thereof. The second tRNA synthetase fragment can be a polypeptide having an amino acid comprising, consisting essentially of, or consisting of SEQ ID NOS: 12-17, 24-29, 36-41, 48-53, or homologs or analogs thereof. The first and the second tRNA synthetase fragments can be different, homologous, substantially homologous, or identical.

In some embodiments, the nucleotide sequences encoding two or more copies of a polypeptide sequence can be fused in tandem. When two nucleotide sequences encoding polypeptides are fused in tandem each polypeptide can have its own orientation such that when the two nucleotide sequences are expressed the encoded polypeptides can result in a C—N, N—N, C—C, or C—N terminal connection. In preferred embodiments, expression of the nucleotide sequences herein result in the N terminus of the second polypeptide being covalently linked to the C-terminus of the first polypeptide.

In some embodiments, a polynucleotide sequence encoding two or more tRNA synthetase fragments may also encode a linker. A nucleotide sequence encoding a linker can be inserted between two nucleotide sequences tRNA synthetase fragments. A nucleotide sequence encoding a linker can be long enough to allow a first tRNA synthetase fragment and a second tRNA synthetase fragment to productively arrange and dimerize with one another. In some embodiments, a nucleotide sequence encoding a linker is at least 9, at least 30, at least around 60, at least around 90, at least around 120, at least around 150, at least around 180, at least around 210, at least around 240, at least around 270, or at least around 300 nucleotides in length.

In some embodiments, a polynucleotide sequence encoding a first tRNA synthetase fragment can be inserted within a polynucleotide sequence encoding a second tRNA synthetase fragment. This will result in translation of a first segment of the first tRNA synthetase fragment, the complete translation of the second tRNA synthetase fragment, and then translation of the remaining segment of the first tRNA synthetase fragment.

In some embodiments, a polynucleotide sequence herein encodes a modified tRNA synthetase fragment. An example of a modified tRNA synthetase fragment is one wherein the fragment has been modified (e.g., by addition or substitution of amino acids) to insert one or more non-naturally occurring cysteines into the fragment. Preferably, the tRNA synthetase fragment is a tryptophanyl tRNA synthetase fragment, or more preferably a fragment selected from the group consisting of SEQ ID NOS: 12-17, 24-29, 36-41, 48-53, and any homologs or analogs thereof.

Preferably, non-naturally occurring cysteine(s) are inserted (e.g., by addition or substitution) into the dimerization domain of the fragment. The insertion of such a cysteine can be made at the nucleic acid level using recombinant technology. Nucleic acid sequences that can be modified by the following invention to include cysteines include, but are not limited to, SEQ ID NOS: 18-23, 30-35, 42-47, 54-59, and any homologs, and analogs thereof.

In some embodiments, a polynucleotide of the invention encodes two or more modified tRNA synthetase fragments. For example, a polynucleotide of the present invention can encode 2 or more tryptophanyl tRNA synthetase fragments wherein each fragment is modified to include at least one non-naturally occurring cysteine in its dimerization domain. Examples of tryptophanyl tRNA synthetase fragments that can be modified as follows include, but are not limited to SEQ ID NOS: 12-17, 24-29, 36-41, 48-53, and any homologs or analogs thereof.

Any of the polynucleotides herein are preferably fused in the same reading frame to a polynucleotide sequence which aids in expression and secretion of a polypeptide from a host cell. This results in an expression vector. An expression vector can be used to express the polynucleotides in a host cell.

In some embodiments, a leader sequence which functions as a secretory sequence for controlling transport of a polypeptide from the cell can be fused after the open reading frame sequence. A polypeptide having a leader sequence is a preprotein and can have the leader sequence cleaved by the host cell to form the mature form of the polypeptide. The polynucleotides can also encode for a proprotein which is the mature protein plus additional 5' amino acid residues. A mature protein having a prosequence is a proprotein and is an inactive form of the protein. Once the prosequence is cleaved an active mature protein remains. Thus, for example, the polynucleotide of the present invention can encode for a mature protein, or for a protein having a prosequence or for a protein having both a prosequence and presequence (leader sequence). Preferably, when a polynucleotide sequence of the present invention encodes a prosequence, such prosequence is cleaved in the vitreous of the eye or at a target cancer cell or tumor.

In some embodiments, the pre or pro sequences encode for antibodies or antibody fragments that bind to a target cell (e.g., photoreceptors). Again, the pre or pro sequence can include a protease cleavage site that will allow for the sequence to be automatically cleaved upon reaching its desired site, thus activating the compositions herein.

The polynucleotides of the present invention can also have the coding sequence fused in frame to a marker sequence which allows for purification of the polypeptide of the present invention. The marker sequence can be a hexa-histidine tag supplied by a pQE-9 vector to provide for purification of the mature polypeptide fused to the marker in the case of a bacterial host, or, for example, the marker sequence can be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The present invention further relates to polynucleotides that hybridize to any of the sequences described herein, preferably under stringent conditions. A stringent condition refers to a condition that allows nucleic acid duplexes to be distinguished based on their degree of mismatch. Such polynucleotides (e.g., antisense and RNAi) can be used to inhibit the expression of an angiostatic tRNA fragment or angiogenic tRNA fragment depending upon the desired outcome. Such polynucleotides can also serve as probes and primers for research and diagnostic purposes.

Antisense nucleic acids are nucleotide sequences which are complementary to the coding strand of a double-stranded cDNA molecule or to an mRNA sequence of a target nucleotide sequence, preferably encoding a positive angiogenesis factor, e.g., VEGF. Antisense nucleic acids can be used as an agent to inhibit angiogenesis in the methods described herein. It inhibits translation by forming hydrogen bonds with a sense nucleic acid. Antisense nucleic acid can be complementary to an entire angiogenic coding region (e.g., VEGF) or only to a portion thereof.

An antisense oligonucleotide herein can be, for example, about 5, 10, 15, 20, 25, 30, 35, 40, 45 or 50 nucleotides in length. An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, β-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, β-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

In some embodiments, double stranded nucleic acids can be used to silence genes associated with angiogenesis (e.g., tryptophanyl tRNA synthetase and/or tyrosyl tRNA synthetase) by RNA interference. RNA interference ("RNAi") is a mechanism of post-transcriptional gene silencing in which double-stranded RNA (dsRNA) corresponding to a gene (or coding region) of interest is introduced into a cell or an organism, resulting in degradation of the corresponding mRNA. The RNAi effect persists for multiple cell divisions before gene expression is regained. RNAi is therefore an extremely powerful method for making targeted knockouts or "knockdowns" at the RNA level. RNAi has proven successful in human cells, including human embryonic kidney and HeLa cells (see, e.g., Elbashir et al. Nature May 24, 2001; 411 (6836):494-8).

In one embodiment, transfection of small (less than 50, more preferably 40, more preferably 30 or more preferably 20 nucleotides (nt) dsRNA specifically inhibits gene expression (reviewed in Caplen (2002) Trends in Biotechnology 20:49-51). Briefly, RNAi is thought to work as follows. dsRNA corresponding to a portion of a gene to be silenced is introduced into a cell. The dsRNA is digested into small dsRNA nucleotide siRNAs, or short interfering RNAs. The siRNA duplexes bind to a nuclease complex to form what is known as the RNA-induced silencing complex, or RISC. The RISC targets the homologous transcript by base pairing interactions between one of the siRNA strands and the endogenous mRNA. It then cleaves the mRNA at about 12 nucleotides from the 3' terminus of the siRNA (reviewed in Sharp et al (2001) Genes Dev 15: 485-490; and Hammond et al. (2001) Nature Rev Gen 2: 110-119).

RNAi technology in gene silencing utilizes standard molecular biology methods. dsRNA corresponding to the sequence from a target gene to be inactivated can be produced by standard methods, e.g., by simultaneous transcription of both strands of a template DNA (corresponding to the target sequence) with T7 RNA polymerase. Kits for production of dsRNA for use in RNAi are available commercially, e.g., from New England Biolabs, Inc. Methods of transfection of dsRNA or plasmids engineered to make dsRNA are routine in the art.

Gene silencing effects similar to those of RNAi have been reported in mammalian cells with transfection of a mRNA-cDNA hybrid construct (Lin et al., Biochem Biophys Res Commun Mar. 2, 2001; 281(3):639-44), providing yet another strategy for gene silencing. In some embodiments, the present invention relates to methods of modulating angiogenesis by contacting a cell or tissue with an RNAi or antisense complementary to a tRNA synthetase (e.g., TyrRS or TrpRS) or a fragment thereof. For example an antisense or RNAi of the present invention can be complementary to a polynucleotide sequence selected from the group consisting of SEQ ID NOS: 18-23, 30-35, 42-47, 54-60, and any homologs and analogs thereof.

The polynucleotides of the present invention are preferably provided in an isolated form, and preferably are purified to homogeneity.

4.) Vectors

The present invention also includes vectors (preferably expression vectors) which include polynucleotides of the present invention, host cells which are genetically engineered with vectors of the invention and the production of polypeptides of the invention by recombinant techniques.

The vectors of the present invention can be constructed using standard recombinant techniques widely available to one skilled in the art. Such techniques can be found in common molecular biology references such as Sambrook, et al., Molecular Cloning: A Laboratory Manual, Cold Spring Harbor Laboratory Press (1989), D. Goeddel, ed., Gene Expression Technology, Methods in Enzymology series, Vol. 185, Academic Press, San Diego, Calif. (1991), and Innis, et al. PCR Protocols: A Guide to Methods and Applications Academic Press, San Diego, Calif. (1990).

In preferred embodiments, the present invention contemplates recombinant construction of a vector which comprises one or more, or more preferably two or more, of the polynucleotide sequences described above. The constructs comprise a vector, such as a plasmid or viral vector, into which one or more, or more preferably two or more, polynucleotide sequence of the invention are inserted, in a forward or reverse orientation. Preferably, two polynucleotide sequences are inserted into a vector in tandem. The polynucleotide sequences can be adjacent to one another or separated by a linker.

5.) Host Cells

Host cells of the invention are cells that express the nucleotide sequences described herein. Representative examples of appropriate hosts include bacterial cells, such as *E. coli, Salmonella typhimurium, Streptomyces*; fungal cells, such as yeast; insect cells, such as *Drosophila* and Sf9; animal cells such as CHO, COS or Bowes melanoma; plant cells, etc. The selection of an appropriate host is deemed to be within the scope of those skilled in the art from the teachings herein.

There are available to one skilled in the art multiple viral and non-viral methods suitable for introduction such nucleotide sequences into a target host cell.

Viral transduction methods can comprise the use of a recombinant DNA or an RNA virus comprising a nucleic acid sequence that drives or inhibits expression of a protein having sialyltransferase activity to infect a target cell. A suitable DNA virus for use in the present invention includes but is not limited to an adenovirus (Ad), adeno-associated virus (AAV), herpes virus, vaccinia virus or a polio virus. A suitable RNA virus for use in the present invention includes but is not limited to a retrovirus or Sindbis virus. It is to be understood by those skilled in the art that several such DNA and RNA viruses exist that can be suitable for use in the present invention.

"Non-viral" delivery techniques that have been used or proposed for gene therapy include DNA-ligand complexes, adenovirus-ligand-DNA complexes, direct injection of DNA, $CaPO_4$ precipitation, gene gun techniques, electroporation, liposomes and lipofection. Any of these methods are widely available to one skilled in the art and would be suitable for use in the present invention. Other suitable methods are available to one skilled in the art, and it is to be understood that the present invention can be accomplished using any of the available methods of transfection. Several such methodologies have been utilized by those skilled in the art with varying success. Lipofection can be accomplished by encapsulating an isolated DNA molecule within a liposomal particle and contacting the liposomal particle with the cell membrane of the target cell. Liposomes are self-assembling, colloidal particles in which a lipid bilayer, composed of amphiphilic molecules such as phosphatidyl serine or phosphatidyl choline, encapsulates a portion of the surrounding media such that the lipid bilayer surrounds a hydrophilic interior. Unilammellar or multilammellar liposomes can be constructed such that the interior contains a desired chemical, drug, or, as in the instant invention, an isolated DNA molecule.

a. Expression

Expression vectors can be used to express the polynucleotides herein in host cells. Expression vectors contain the appropriate polynucleotide sequences, such as those described herein, as well as an appropriate promoter or control sequence, can be employed to transform an appropriate host to permit the host to express the protein. Preferably an expression vector of the present invention expresses a polypeptide selected from the group consisting of SEQ ID NOS: 12-17, 24-29, 36-41, 48-53, and any homologs and analogs thereof. A composition of the present invention may therefore be produced by transfecting a host cell with an expression vector or polynucleotide sequence that encodes a polypeptide comprising, consisting essentially or, or consisting of an amino acid sequence SEQ ID NOS: 12-17, 24-29, 36-41, 48-53, or any homologs or analogs thereof. The host cell is then maintained under a condition which allows the polypeptide or composition of the invention to be produced.

In order to obtain transcription of the polynucleotide sequences herein within a host cell, a transcriptional regulatory region capable of driving gene expression in the target cell is utilized. The transcriptional regulatory region can comprise a promoter, enhancer, silencer or repressor element and is functionally associated with a nucleic acid of the present invention. Preferably, the transcriptional regulatory region drives high level gene expression in the target cell. Transcriptional regulatory regions suitable for use in the present invention include but are not limited to the human cytomegalovirus (CMV) immediate-early enhancer/promoter, the SV40 early enhancer/promoter, the JC polyomavirus promoter, the albumin promoter, PGK and the α-actin promoter coupled to the CMV enhancer, the E. coli lac or trp promoters, the phage lambda $P_L$ promoter and other promoters known to control expression of genes in prokaryotic or eukaryotic cells or their viruses. The expression vector can also contain a ribosome binding site for translation initiation and a transcription terminator.

In addition, the expression vectors may also contain a gene to provide a phenotypic trait for selection of transformed host cells such as dihydrofolate reductase or neomycin resistance for eukaryotic cell culture, or such as tetracycline, kanamycin, or ampicillin resistance in E. coli.

In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example: (a) Bacterial: pQE70, pQE-9 (Qiagen), pBs, phagescript, PsiX174, pBluescript SK, pBsKS, pNH8a, pNH16a, pNH18a, pNH46a (Stratagene), pTrc99A, pKK223-3, pKK233-3, pDR540, and PRIT5 (Pharmacia); (b) Eukaryotic: pWLneo, pSV2cat, pOG44, pXT1, pSG (Stratagene) pSVK3, pBPV, PMSG, pSVL (Pharmacia) and pET20B. In one preferred embodiment, the vector is pET24B which is a kanamycin screening vector. However, any other plasmid or vector can be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, PL and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described construct. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, electroporation, viral transfection (e.g., using adenovirus or a retrovirus), as well as other means known in the art. See Davis, L., et al., Basic Methods in Molecular Biology, 1986; see also WO 0/009813, both of which are incorporated herein by references for all purposes.

The constructs in host cells can be used in a conventional manner to produce the polypeptide products encoded by the recombinant sequence. For example, the present invention contemplates methods for preparing a multi-unit complex that has angiostatic activity. Such method includes the steps of providing an expression vector encoding one or more tRNA synthetase fragments, transfecting a host cell with such expression vector, and maintaining the host cell under conditions suitable for expression. In preferred embodiments, an expression vector used to transfect a host cell encodes one, two or more tRNA synthetase fragments. More preferably, such tRNA synthetase fragments are tryptophanyl tRNA synthetase fragments. In some embodiments, such fragments are derived from mammalian tRNA synthetase, or more preferably, human tRNA synthetase. In some embodiments, the expression vector encodes a tRNA synthetase fragment selected from the group consisting of SEQ ID NOS: 12-17, 24-29, 36-41, 48-53, and any fragments, homologs, and analogs thereof. In some embodiments, such expression vector encodes a second tRNA synthetase fragment, wherein the second tRNA synthetase fragment is also selected from the group consisting of SEQ ID NOS: 12-17, 24-29, 36-41, 48-53, and any fragments, homologs, and analogs thereof. The two tRNA synthetase fragments can be different, homologous, substantially homologous, or identical.

The present invention also contemplates that a host cell (e.g., a bacteria) may or may not cleave the Methionine at the N-terminus of any of the polypeptides herein, depending upon the natural processes within the host cell. As such, it is further contemplated by the present invention that a composition can comprise of a combination of Met- and non-Met-tRNA synthetase fragments. For example, a bacteria transfected with a polynucleotide sequence encoding SEQ ID NO: 15-17, 27-29, 39-41, 51-53, may result in a combination of both Met-tRNA synthetase fragments and non-met tRNA synthetase fragments, all met-tRNA synthetase fragments, or all non-met tRNA synthetase fragments.

Alternatively, the polypeptides of the invention can be synthetically produced by conventional peptide synthesizers.

Proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook. et al., Molecular Cloning: A Laboratory Manual, Second Edition, Cold Spring Harbor, N.Y., (1989), the disclosure of which is hereby incorporated by reference.

Transcription of a polynucleotide sequence encoding the polypeptides of the present invention by higher eukaryotes is increased by inserting an enhancer sequence into the vector. Enhancers are cis-acting elements of DNA, usually about from 10 to about 300 base pairs (bp), that act on a promoter to increase its transcription. Examples include the SV40 enhancer on the late side of the replication origin (bp 100 to 270), a cytomegalovirus early promoter enhancer, a polyoma enhancer on the late side of the replication origin, and adenovirus enhancers.

Generally, recombinant expression vectors will include origins of replication and selectable markers permitting transformation of the host cell, e.g., the ampicillin resistance gene of E. coli, kanamycin for pET24B, and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Following transformation of a suitable host strain and growth of the host strain to an appropriate cell density, the selected promoter is derepressed by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites can be used to provide the required nontranscribed genetic elements.

Thus, in its most basic form, a polypeptide of the present invention can be prepared by providing the appropriate expression vector, transfecting a host cell with such expression vector, and maintaining the host cell under a condition suitable for expression. Preferably, expression vectors used herein include at least one nucleotide sequence encoding a tRNA synthetase fragment, or more preferably a tryptophanyl tRNA synthetase fragment, or any homolog or analog thereof. The vector encoding such tryptophanyl tRNA synthetase fragments may be modified to encode one or more non-naturally occurring cysteines in the dimerization domain of the polypeptide. In some embodiments, an expression vector encodes two or more tRNA synthetase fragments, or more preferably two or more tryptophanyl tRNA synthetase fragments. Such vectors preferably encode a linker situated between the first and second fragments.

Polypeptides are recovered and purified from recombinant cell cultures by methods used heretofore, including ammonium sulfate or ethanol precipitation, acid extraction, anion or cation exchange chromatography, phosphocellulose chromatography, hydrophobic interaction chromatography, affinity chromatography, hydroxyapatite chromatography and lectin chromatography. It is preferred to have low concentrations (approximately 0.1-5 mM) of calcium ion present during purification (Price, et al., J. Biol. Chem., 244:917 (1969)). Protein refolding steps can be used, as necessary, in completing configuration of the mature protein. Finally, high performance liquid chromatography (HPLC) can be employed for final purification steps. Additional purifications methods are disclosed herein.

b. Gene Therapy

The polynucleotides of the present invention can also be employed as gene therapy in accordance with the present invention by expression of such polypeptide in vivo.

Various viral vectors that can be utilized for gene therapy as taught herein include adenovirus, herpes virus, vaccinia, adeno-associated virus (AAV), or, preferably, an RNA virus such as a retrovirus. Preferably, the retroviral vector is a derivative of a murine or avian retrovirus, or is a lentiviral vector. The preferred retroviral vector is a lentiviral vector. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), SIV, BIV, HIV and Rous Sarcoma Virus (RSV). A number of additional retroviral vectors can incorporate multiple genes. All of these vectors can transfer or incorporate a gene for a selectable marker so that transduced cells can be identified and generated. By inserting a zinc finger derived-DNA binding polypeptide sequence of interest into the viral vector, along with another gene that encodes the ligand for a receptor on a specific target cell, for example, the vector is made target specific. Retroviral vectors can be made target specific by inserting, for example, a polynucleotide encoding a protein (dimer). Preferred targeting is accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the zinc finger-nucleotide binding protein polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include but are not limited to PSI-2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced. The vector virions produced by this method can then be used to infect a tissue cell line, such as NIH 3T3 cells, to produce large quantities of chimeric retroviral virions.

c. Zinc Fingers

Another targeted delivery system for polynucleotides encoding zinc finger derived-DNA binding polypeptides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2-4.0 µm, can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.,* 6:77, (1981)).

d. Targeted Liposomes

In some embodiments, targeted liposomes may be used to delivery the polynucleotides herein. In some embodiments, the polynucleotide sequence is an expression vector as described herein. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques,* 6:682, (1988)).

The composition of the liposome is usually a combination of phospholipids, particularly high-phase-transition-temperature phospholipids, usually in combination with steroids, especially cholesterol. Other phospholipids or other lipids can also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine.

The targeting of liposomes has been classified based on anatomical and mechanical factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types. For example, a targeted liposome delivery system can include antibodies that specifically bind to cancer cells, tumor cells, photoreceptor cells, myocardial tissue, etc.

The surface of the targeted delivery system can be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

In general, the compounds bound to the surface of the targeted delivery system will be ligands and receptors which will allow the targeted delivery system to find and "home in" on the desired cells. A ligand can be any compound of interest which will bind to another compound, such as a receptor.

In general, surface membrane proteins which bind to specific effector molecules are referred to as receptors. In the present invention, antibodies are preferred receptors. Antibodies can be used to target liposomes to specific cell-surface ligands. For example, certain antigens expressed specifically on tumor cells, referred to as tumor-associated antigens (TAAs), can be exploited for the purpose of targeting antibody-zinc finger-nucleotide binding protein-containing liposomes directly to the malignant tumor. Since the zinc finger-nucleotide binding protein gene product can be indiscriminate with respect to cell type in its action, a targeted delivery system offers a significant improvement over randomly injecting non-specific liposomes. A number of procedures can be used to covalently attach either polyclonal or monoclonal antibodies to a liposome bilayer. Antibody-targeted liposomes can include monoclonal or polyclonal antibodies or fragments thereof such as Fab, or F(ab')$_2$, as long as they bind efficiently to an the antigenic epitope on the target cells. Liposomes can also be targeted to cells expressing receptors for hormones or other serum factors.

e. Cell Based Therapy

In any of the embodiments herein, cells transfected with the polynucleotides herein can be administered to a patient. In some embodiments, the cells transfected originate from the patient. In other embodiments, the cells transfected do not originate from the patient. In any event, the cells can be transfected by the constructs herein in vivo, ex vivo, or in vitro. In more preferred embodiments, the cells transfected are stem cells. Methods for making hematopoietic stem cells are described in PCT/US2003/024839, which is incorporated herein by reference in its entirety.

Analogs

The present invention contemplates methods for screening for analogs for the compositions herein, and in particular, analogs for mini-TrpRS, T1, and T2. The term "analogs" as used herein means compounds that share structure and/or function, such as, for example, peptidomimetics, and any small or large organic or inorganic compounds. In preferred embodiments, an analog of the present invention is a small organic or inorganic compound that mimics the function and structure of mini-TrpRS, T1, or T2, by having similar interactions with their receptor(s).

Purification

In any of the embodiments herein, and especially for ophthalmic applications, the compositions (e.g., pharmaceutical formulation and/or polypeptides) herein are preferably substantially free of endotoxins.

The levels of endotoxins in a pharmaceutical or polypeptide preparation may be determined by any known technique; such techniques are widespread and commonly used by those of skill in the art in the pharmaceutical and biotechnology fields. For example, the FDA published Good Guidance Practices in February 1997 that noted several methods for quantifying endotoxin levels in a sample, including *Limulus Amebocyte* Lysate tests using chromagenic, endpoint-turbidimetric and kinetic-turbidimetric techniques. All of these techniques, as well as other techniques (including, but not limited to the use of rabbit pyrogen testing colonies) may be appropriately used to determine the endotoxin levels of the samples described herein.

Thus, for example, a pharmaceutical formulation for systemic administration or topical administration can have a concentration of endotoxins that is preferably, less than about 500, 400, 300, 200, 100, 90, 80, 70, 50, 40, 30, 25, 20, or 15, or more preferably less than about 10, 9, 8, 7, 6, 5, 4, 3, 2, or 1, or more preferably less than about 0.5, 0.1, 0.05, 0.01, 0.005, or 0.001 endotoxin units per milligram of product (e.g., polypeptide).

For other forms of administration e.g., intraocular, via inhalation, via eye drops, vaginal, rectal, etc, a pharmaceutical formulation of the present invention preferably has a concentration of endotoxins that is less than 50, 40, 30, 25, 20, or 15, or more preferably less than about 10, 9, 8, 7, 6, 5, 4, 3, 2, or 1, or more preferably less than about 0.5, 0.1, 0.05, 0.01, 0.005, or 0.001 endotoxin units per milligram of a product (e.g., polypeptide).

The amount of endotoxins in a sample refers to the amount of endotoxins (such as measured in endotoxin units (or E.U.s) in a sample relative to the amount of desired polypeptide or pharmaceutical agent in that sample (generally provided per mg of polypeptide or pharmaceutical agent). The amount of endotoxins can be measured by any of a variety of techniques. However, the particular units employed herein are exemplary only, and are used throughout for reasons of consistency and readability. That is, the methods and materials presented herein are not limited by the particular "units" used to present the amount of endotoxins in a sample. Conversion between various units (by way of example only, E.U./mg of polypeptide to E.U./mL of sample) is considered well within the abilities of one of ordinary skill in the art.

In some embodiments, endotoxin reduction is the last or nearly last step in a purification process. In other embodiments, the endotoxin reduction step occurs at an early stage of the purification process (e.g., prior to steps that may lead to strong and/or irreversible binding of endotoxin to polypeptide).

Figure 7:
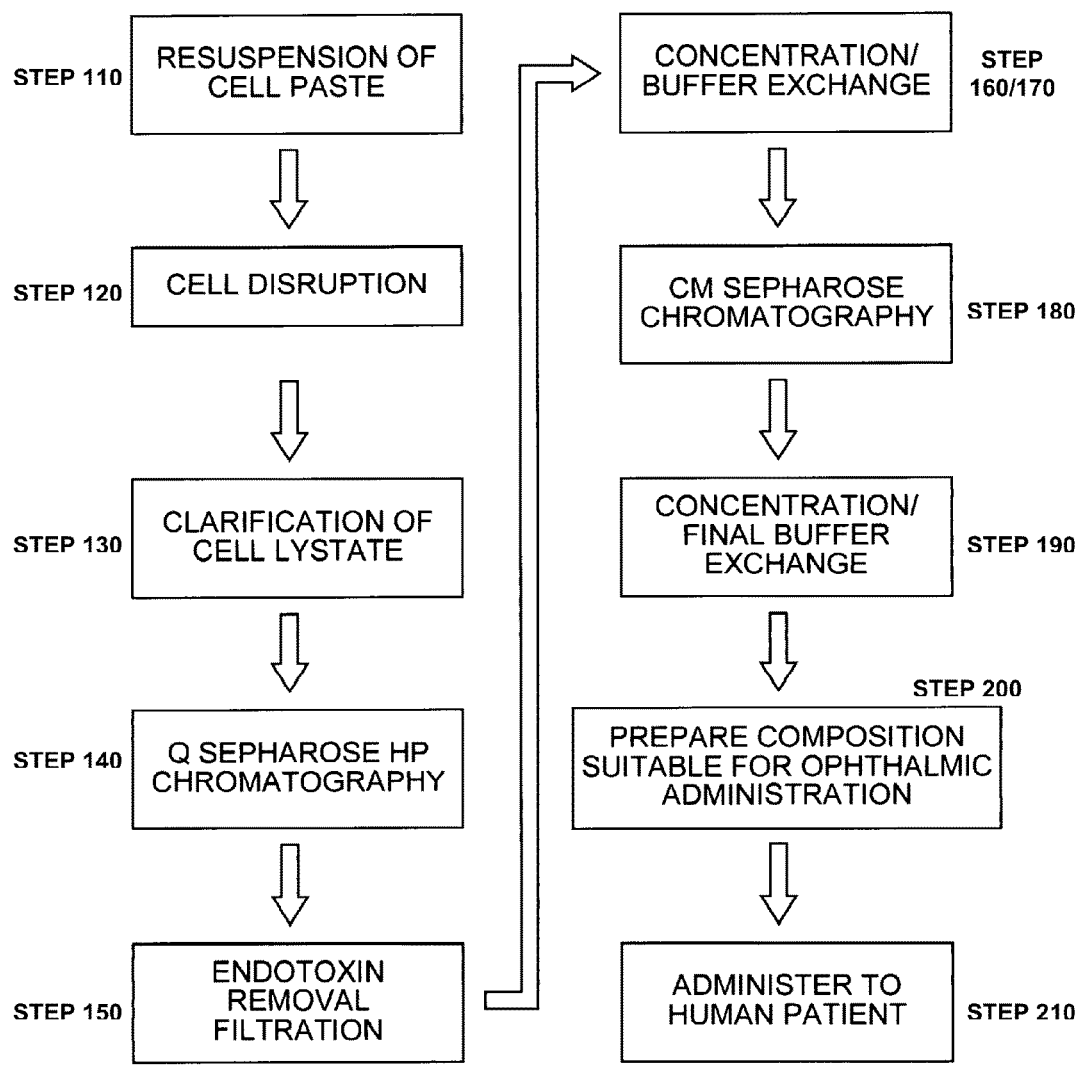
FIG. 7 illustrates a flowchart illustration of one possible method for purifying the compositions herein.

FIG. 7 illustrates a flowchart illustrating a sequence of purification steps (each occurring prior to the next) for purifying a pharmaceutical agent and/or polypeptide of the present invention. When a step occurs "prior to" another step, then the first step has been at least partially completed on a particular sample containing a polypeptide before the subsequent step is initiated.

A cell paste is formed from cells grown in a fermentor (the cell paste may be properly stored until needed). At step 110, the cell paste is resuspended in a buffer. At step 120, the cells are disrupted.

At step 130, cell lysate is clarified. Clarification generally involves removal of insoluble matter (e.g., cellular debris, organelles and membranes) in all or in part from a solution containing a polypeptide of interest (e.g., a cell lysate or homogenate). The methods and compositions described herein are not limited by the technique used to produce the cell paste, lysate, or homogenate (or any other analogous term used in the art for the material). Clarification may be achieved by numerous methods known in the art, including by way of example only, simple filtration, centrifugation, dialysis, depth filtration, ultrafiltration using membranes with cut-offs in the vicinity of 100K (in which the desired product is the filtrate and the retentate is discarded), decanting or other appropriate means known to those of skill in the art for such separations. That is, in general, after clarification, one fraction comprises mostly the insoluble portions of a cell, whereas the other fraction comprises mostly the soluble portions of a cell. In another aspect of a clarification step, a slurry becomes a clarified solution. It is of course appreciated by those in the art that endotoxin reduction does arise non-specifically during a clarification step by means of selecting against inclusion of remaining cell membranes (large fragments). However, clarification, by itself, is not designed to provide a polypeptide preparation that is substantially free of endotoxins.

In step 140, anion-chromatography is performed on the clarified cell lysate. This step can include collecting desired eluant fractions. Anion-exchange chromatography refers to the use of a positively charged surface with which a negatively-charged protein can form an ionic interaction. The protein may then be selectively eluted from the positively charged surface by manipulating the salt concentration and/or the pH of the eluting solvent. Examples of positively charged surfaces include anion-exchange resins.

Examples of anion exchange resins include, but are not limited to, diethylaminoethyl- (DEAE-), the quarternary ammonium- (Q- or QAE-), and the Amberlite-based resins. Different resin substrates, sizes (e.g., fast flow or FF, Source, or high performance or HP), and pore-diameters for anion-exchange resins are commercially available from standard chemical suppliers and their use is considered within the scope of the methods described herein. Preferably, an anion-exchange resin is selected from the group consisting of Q Sepharose, DEAE Sepharose, and ANX Sepharose. In still a further embodiment, the anion-exchange resin is Q-Sepharose. As is appreciated by those of skill in the art, smaller-sized resins may provide cleaner separation of products, but with a consequent trade-off in the speed with which such products are eluted from the chromatography column. Analyzing such trade-offs in selecting an anion-exchange resin is considered well within the ability of one of ordinary skill in the art. The anion-exchange chromatography is preferably performed prior to the reducing of the levels of endotoxins from the collected eluant.

Step 150 involves reducing the levels of endotoxins from the collected eluant fractions. Such step can remove all, substantially all, or some endotoxins from a sample. This step need not necessarily increase the overall purity of the protein (e.g., T1, T2, mini-trpRS). Techniques for endotoxin reduction include, by way of example, ultrafiltration (e.g., using membranes with cut-offs in the vicinity of 100K in which the desired polypeptide product is in the retentate and the filtrate is discarded); reverse-phase, affinity, size-exclusion, hydrophobic interaction and/or anion-exchange chromatography (e.g., including Q Sepharose); sucrose centrifugation gradients; absorption of endotoxin onto activated charcoal, silica, hydroxyapatite, glass, and/or polystyrene; precipitation with isopropanol, ammonium acetate, or polyethylene glycol; phase-separation techniques using surfactants, such as detergents; use of charged-filter surfaces, and proprietary detoxifying media such as Acticlean Etox™, Prosep-Remtox, Mustang E, and CUNO Zeta Plus ZA. The latter are typically provided in devices through which the polypeptide sample flows. In any of the embodiments herein, filtration-based techniques are preferable over column-based techniques based upon the recovery of product in relation to the reduction in endotoxin levels.

In some embodiments, the level of endotoxins is reduced by using ultrafiltration. Ultrafiltration involves separating all or at least some or at least one desired polypeptide(s) from different-sized molecules and/or molecules having a molecular weight different from the desired polypeptide(s). Ultrafiltration may involve a technique known as tangential flow filtration (as opposed to axial flow filtration). By passing the solution over the membrane in a tangential manner and having the ability to recirculate the solution (also called the retentate), the materials can pass through the membrane in a more gentle manner. The ability to pass through the membrane is determined by two factors: the membrane pore size (also known as the molecular weight cut-off), and the transmembrane pressure (set by the user by means of the pumps and valves). Using various embodiments of this set up, the protein of interest may either pass through the membrane (into the filtrate, this is used in clarification systems) or not pass through the membrane (stays in the retentate, this is used in buffer exchanges and concentration systems). In some embodiments, ultrafiltration is used to filter a liquid medium and small solute molecules through a semipermeable membrane having pores with an average cut-off molecular weight ranging from 100 kDa to 1,000 kDa, 200 kDa to 900 kDa, 300 kDa to 800 kDa, or 400 kDa to 500 kDa. In some embodiments, ultrafiltration is used to filter a liquid medium and small solute molecules through a semipermeable membrane having pores with an average cut-off molecular weight of at least 90 kDa, 100 kDa, 200 kDa, 300 kDa, 400 kDa, 500 kDa, 600 kDa, 700 kDa, 800 kDa, 900 kDa, or 1,000 kDa. Performing an ultrafiltration step may include a dialysis process for separating globular proteins in solution from low-molecular weight solutes. Such a step can utilize a semipermeable membrane to retain protein molecules and allow small solute molecules and water to pass through. Such membranes may have a molecular weight cut-offs ranging, by way of example only, from 1 kDa to 100 kDa, 2 kDa to 90 kDa, 3 kDa to 80 kDa, 4 kDa to 70 kDa, 5 kDa to 60 kDa, or 6 kDa to 50 kDa, 7 kDa to 40 kDa, 8 kDa to 30 kDa, or 9 kDa to 20 kDa. In some embodiments, the molecular weight cut-offs may be less than 90 kDa, 85 kDa, 80 kDa, 75 kDa, 70 kDa, 65 kDa, 60 kDa, 55 kDa, 50 kDa, 45 kDa, 40 kDa, 35 kDa, 30 kDa, 25 kDa, 20 kDa, 15 kDa, 10 kDa, 5 kDa, or 1 kDa. Preferably, the molecular weight cut-off for to retain tRNA synthetase molecules and allow small solute molecules and water to pass through is less than 50 kDa, less than 25 kDa, or less than 1 kDa.

In preferred embodiments, the polypeptides purified by the present invention are not modified or denatured during the endotoxin-reduction process. The endotoxin-reduction step is preferably made prior to the buffer exchange step.

In step 160 the filtered eluant fractions are concentrated. Performing a concentration step can result in an increase of concentration of a desired polypeptide or pharmaceutical agent (e.g., any of the polypeptides herein) in the solvent by at least a factor of 2, 3, 4, 5, 6, 7, 8, 9, 10, 20, 30, 40, 50, 100, 200, 300, 400, or 500. Preferably such a concentration-increasing process is conducted after a first chromatography step (e.g., anion-exchange and/or cation-exchange chromatography). Generally, a concentration step involves reducing the relative amount of solvent from a sample. Methods for effecting such a concentration step include, but are not limited to, ultrafiltration, evaporation, lyophilization, and precipitation (followed by resolubilization).

A concentration step will typically be performed at least once, 2, 3, 4, 5, or 6 times during the purification of a polypeptide and/or pharmaceutical agent. For example, if the first ion-exchange chromatography step is an anion-exchange chromatography step, then a concentration step may be performed on the amalgamation of eluted fractions containing the desired polypeptide and/or pharmaceutical agent (in this case, also known as the collected polypeptide fractions from the anion-exchange column). Similarly, if the second ion-exchange chromatography column is a cation-exchange chromatography step (also known as a polishing step), then a concentration step may be performed on the amalgamation of eluted fractions containing the desired polypeptide and/or pharmaceutical agent (in this case, the collected polished polypeptide fractions, or the collected polypeptide fractions from the cation-exchange column).

The concentration step(s) can occur either prior to a buffer exchange step or simultaneous to a buffer exchange step.

In step 170, buffer(s) are exchanged in preparation for a cation-exchange chromatography step. Buffer exchange involves changing of a 'solvent' i.e., the liquid environment of a polypeptide is changed, in whole or in part. Solvents can include micromolecular solutes (e.g. salts) of the medium in which a desired polypeptide is found and/or macromolecule solutes. One suitable technique to perform a buffer exchange is ultrafiltration. Another suitable technique is dialysis of the solution containing the polypeptide against substantially larger quantities of a different buffer. Other buffer exchange techniques include, for example, gel permeation and diafiltration. The buffer exchange step can occur prior to, after, or simultaneously with a concentration step. One example of the latter approach is via the technique known as constant volume diafiltration. A buffer exchange step might be used once or multiple times in purifying a pharmaceutical agent and/or a polypeptide of the invention. By way of example only, if a particular polypeptide sample (i.e., T2 produced by recombinantly expressing vector of SEQ ID NO: 70) comprises an amalgamation of samples collected from an anion-exchange column (i.e., an anion-exchange chromatography step), then this polypeptide sample (known herein as a polypeptide sample in a post-anion exchange buffer) may undergo buffer exchange prior to loading the polypeptide sample through a cation-exchange column (i.e., a cation-exchange chromatography step). Another example wherein a buffer exchange step might be advantageously performed on a polypeptide sample is prior to storage of the finished polypeptide sample, but after the polishing step (e.g., the last ion-exchange chromatography step).

In step 180, a cation-exchange chromatography is performed. This step may include collection of desired eluantfractions. Cation-exchange chromatography refers to the use of a negatively charged surface with which the positively-charged protein can form an ionic interaction. When a cation-exchange chromatography step is performed on a sample that has already undergone an anion-exchange chromatography step, the cation-exchange chromatography step is sometimes referred to as a "polishing step"; the sample loaded onto the cation-exchange column is the unpolished sample and the eluted fractions containing the desired polypeptide sample have been polished and may be referred to as a polished polypeptide sample. The protein may then be selectively eluted from the negatively charged surface by manipulating the salt concentration and/or the pH of the eluting solvent. Examples of negatively charged surfaces include cation-exchange resins.

Examples of cation exchange resins include, by way of example only, carboxymethyl- (CM-) and sulfopropyl- (SP-) based resins. Different resin substrates, sizes (e.g., fast flow or FF, Source, or high performance or HP), and pore-diameters for cation-exchange resins are commercially available from standard chemical suppliers and their use is considered within the scope of the methods described herein. As is appreciated by those of skill in the art, smaller-sized resins may provide cleaner separation of products, but with a consequent trade-off in the speed with which such products are eluted from the chromatography column. Analyzing such trade-offs in selecting a cation-exchange resin is considered well within the ability of one of ordinary skill in the art.

Finally, at step 190, the sample is again concentrated and, optionally, buffers are again exchanged. This results in a polypeptide sample that has reduced endotoxin levels. The low-endotoxin preparation may be further formulated in step 200 prior to administration to an organism (e.g., human) in step 210.

Figure 8:
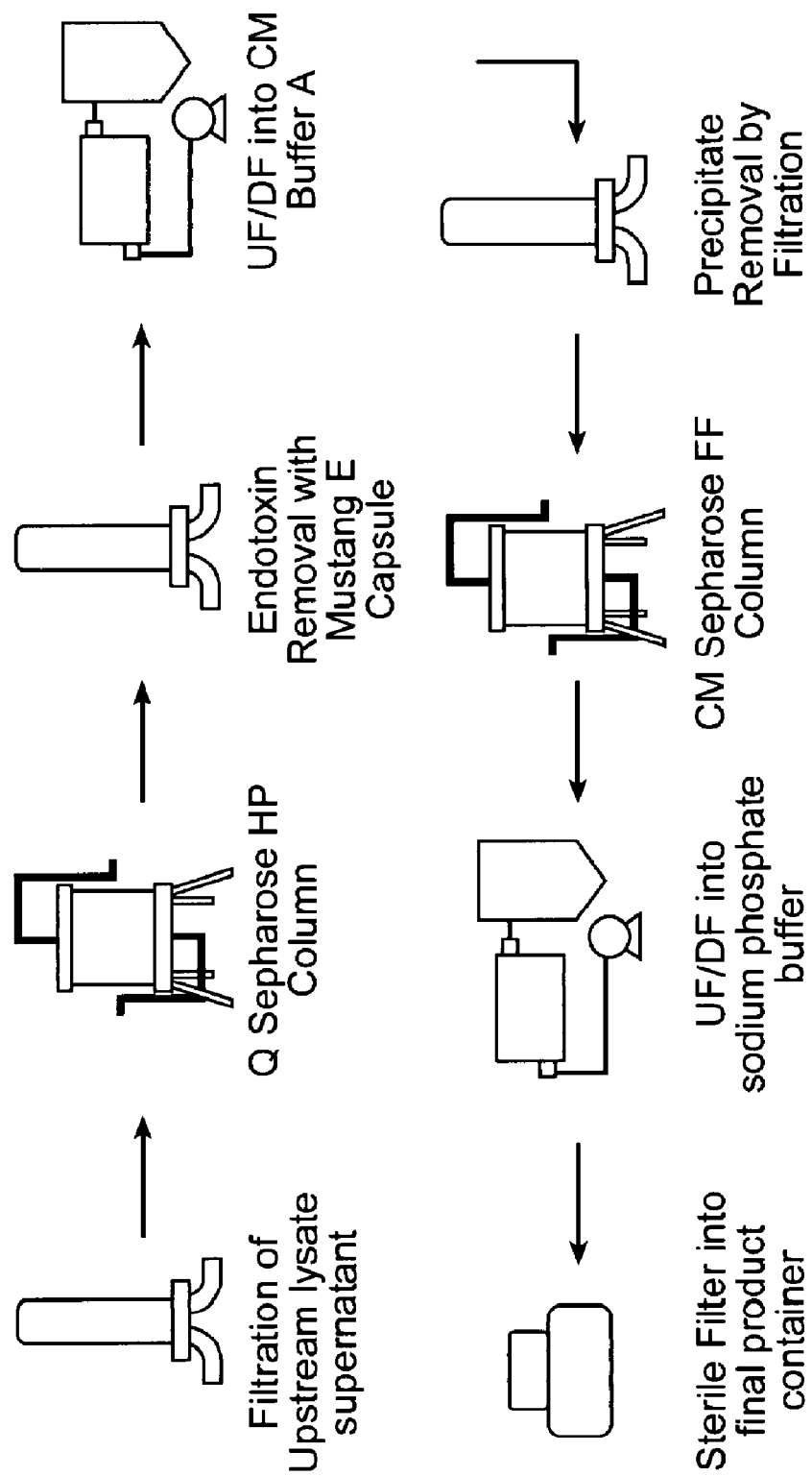
FIG. 8 illustrates another embodiment of the purification methods of the invention.

FIG. 8 is another illustration of the purification methods disclosed herein.

In some aspects of the methods herein, an endotoxin-reduction filtration step is performed after performing a clarification step and prior to performing a buffer exchange step. Furthermore, the endotoxin-reduction filtration step may be performed prior to performing a cation exchange chromatographic step. Alternatively, the endotoxin-reduction filtration step may be performed prior to performing a concentration step.

In some aspects of the methods herein, an endotoxin-reduction filtration step is performed after performing a clarification step and prior to performing a concentration step. Furthermore, the endotoxin-reduction filtration step may be performed prior to performing a cation exchange chromatographic step. Alternatively, the endotoxin-reduction filtration step may be performed prior to performing a buffer exchange step.

In some aspects of the methods herein, an endotoxin-reduction filtration step is performed after performing a clarification step and prior to performing a cation-exchange chromatographic step. Alternatively, the endotoxin-reduction filtration step may be performed prior to performing a concentration step. Alternatively, the endotoxin-reduction filtration step may be performed prior to performing a buffer exchange step.

In some aspects of the methods herein, an endotoxin-reduction filtration step is performed prior to performing a concentration step and prior to performing a cation-exchange chromatographic step and prior to a buffer exchange step.

The order of the concentration, buffer exchange, and cation-exchange chromatography steps in any of the purification methods herein may vary, but in one embodiment, at least one concentration step is performed prior to the buffer exchange step. Alternatively, a cation-exchange chromatographic step is performed after the buffer exchange step. Alternatively, at least one concentration step is performed prior to the cation-exchange chromatographic step. Alternatively, the cation-exchange chromatographic step is performed after a buffer exchange step and at least one concentration step. Alternatively, at least one concentration step is performed prior to the buffer exchange step and the cation-exchange chromatographic step. And alternatively, an additional concentration step is performed after any buffer exchange step.

In a further embodiment of any of the purification methods herein, the endotoxin-reduction filtration step is performed after an anion-exchange chromatographic step. In a further embodiment, the anion-exchange chromatographic step comprises use of an anion-exchange resin. In yet a further embodiment, the anion-exchange resin is selected from the group consisting of Q Sepharose, DEAE Sepharose, and ANX Sepharose. In still a further embodiment, the anion-exchange resin is Q Sepharose. In any of these uses of anion-exchange resins, a variety of grades and sizes may be used, including, but not limited to Source grade, fast flow grade and high performance grade.

In any of the purification methods herein, a cation-exchange chromatographic step may comprise use of a cation-exchange resin. In a further embodiment, the cation-exchange resin is selected from the group consisting of CM Sepharose, SP Sepharose, and DEAE Sepharose. In still a further embodiment, the cation exchange resin is CM Sepharose. In any of these uses of cation-exchange resins, a variety of grades and sizes may be used, including, but not limited to Source grade, fast flow grade and high performance grade.

In an alternative aspect, methods for purifying a polypeptide can comprise an anion-exchange chromatographic step, a step comprising a means for reducing endotoxins, and a buffer exchange step, wherein the step comprising a means for reducing endotoxins is performed prior to the buffer exchange step.

In a further embodiment, the polypeptide suitable for administration to a patient is suitable for ophthalmic administration. In still a further embodiment, the polypeptide suitable for ophthalmic administration is a modulator of angiogenesis. In yet a further embodiment, the polypeptide suitable for ophthalmic administration can be used to treat macular degeneration, diabetic retinopathy or diseases or conditions associated with unwanted ocular neovascularization. In a further refinement of any of the embodiments noted in this paragraph, the polypeptide is substantially free of endotoxins.

In any of the embodiments herein, a purification step can comprise of a concentration step of collected polished polypeptide fractions, wherein the collected polished polypeptide fractions are substantially free of endotoxins. In a further embodiment are methods of preparing the collected polished polypeptide fractions of the previous embodiment comprising performing a cation-exchange chromatographic step on an unpolished polypeptide sample thereby producing the collected polished polypeptide fractions of the previous embodiment, wherein the unpolished polypeptide sample is substantially free of endotoxins. In further embodiments are methods of producing the unpolished polypeptide sample of the previous embodiment comprising performing a buffer exchange step on a polypeptide sample in a post-anion exchange buffer thereby producing the unpolished polypeptide sample of the previous embodiment, wherein the polypeptide sample in the post-anion exchange buffer is substantially free of endotoxins. In further embodiments are methods of producing the polypeptide sample in the post-anion exchange buffer of the previous embodiment comprising performing a concentration step on collected polypeptide fractions from an anion-exchange column prior to the buffer exchange step thereby producing the polypeptide sample in the post-anion exchange buffer of the previous embodiment, wherein the collected polypeptide fractions from an anion-exchange column are substantially free of endotoxins. In further embodiments are methods of producing the collected polypeptide fractions from an anion-exchange column of the previous embodiment comprising performing an endotoxin-reduction filtration step prior to the concentration step of the previous embodiment. In a further embodiment are methods comprising performing an anion-exchange chromatographic step prior to the endotoxin-reduction filtration step.

The purity of the polypeptide sample may be ascertained before, during and/or after any of the aforementioned steps.

As described above a variety of host-expression vector systems may be utilized to express any of the polypeptides herein (e.g., a tRNA synthetase fragment, such as T1, T2, or miniTrpRS, preferably comprising, consisting essentially of, or consisting of a polypeptide of SEQ ID NO: 12-17, 24-29, 36-41, or 48-53). The expression systems that may be used include but are not limited to microorganisms such as bacteria (e.g., *E. coli*, and *B. subtilis*) transformed with recombinant bacteriophage DNA, plasmid DNA or cosmid DNA expression vectors containing a polynucleotide sequence encoding any of the polypeptides herein at least in part; yeast (e.g., *Saccharomyces*, and *Pichia*) transfected with recombinant yeast expression vectors containing a polynucleotide sequence encoding any of the polypeptides herein at least in part; insect cell systems infected with recombinant virus expression vectors (e.g., baculovirus) containing a polynucleotide sequence encoding any of the polypeptides herein at least in part; plant cell systems infected with recombinant virus expression vectors (e.g., cauliflower mosaic virus, CaMV; tobacco mosaic virus, TMV) or transfected with recombinant plasmid expression vectors (e.g., Ti plasmid) containing a nucleotide sequence encoding any of the polypeptides herein at least in part; or mammalian cell systems (e.g., COS, CHO, BHK, 293, 3T3, U937) harboring recombinant expression constructs containing promoters derived from the genome of mammalian cells (e.g., metallothionein promoter) or from mammalian viruses (e.g., the adenovirus late promoter; the vaccinia virus 7.5K promoter).

In eukaryotic systems, a number of selection systems may be used, including but not limited to genes such as the herpes simplex virus thymidine kinase (Wilkie et al., 1979, Nucleic Acids Res., 7:859-77), hypoxanthine-guanine phosphoribosyltransferase (Szybalska & Szybalski, 1962, Proc. Natl. Acad. Sci. USA 48:2026), and adenine phosphoribosyltransferase (Lowy et al., 1980, Cell 22:817) that can be employed in tk-, hprt- or aprt-cells, respectively. Also, antimetabolite resistance can be used as the basis of selection. The following genes exemplify this approach: dhfr, which confers resistance to methotrexate (Subramani S, et al., Mol Cell Biol. 1:854-64 (1981); Gasser et al., Proc Natl. Acad. Sci, 1982, 79(21): 6522-26 (1982); O'Hare et al., (1981), Proc. Natl. Acad. Sci. USA 78:1527), especially in dhfr cells (Urlaub & Chasin, Proc. Natl. Acad. Sci, (1980), 77(7):4216-4220); gpt, which confers resistance to mycophenolic acid (Mulligan & Berg, (1981), Proc. Natl. Acad. Sci. USA 78:2072); neo, which confers resistance to the aminoglycoside G-418 (Colberre-Garapin et al., (1981), J. Mol. Biol. 150:1); hygro, which confers resistance to hygromycin (Santerre et al., (1984), Gene 30:147); the bar gene, which confers resistance to bialaphos; and D-amino acid oxidase, which confers resistance to D-alanine or D-serine (Erikson et al., Nat Biotechnol., (2004), 22(4):455-58).

In bacterial systems, a number of expression vectors may be selected depending upon the use intended for any of the polypeptide herein or homolog or analogs thereof. Suitable bacteria include, by way of example only, gram positive and gram-negative bacteria. In one embodiment, the polypeptide is expressed in *E. coli* bacteria and subsequently isolated from the cells using the purification methods described herein.

The polypeptide can be expressed in a prokaryotic cell using expression systems known to those of skill in the art of biotechnology. Expression systems useful for the practice our methods and compositions are described in U.S. Pat. Nos. 5,795,745; 5,714,346; 5,637,495; 5,496,713; 5,334,531; 4,634,677; 4,604,359; 4,601,980, all of which are incorporated herein by reference in their entirety.

Prokaryotic cells can be grown under a variety of conditions known to the skilled artisan. In one aspect, the cells are grown in a medium suitable for growth of such cells, for example, minimal media or complete (i.e., rich) media. Generally, the medium used to grow the cells should not contain concentrations of salts or other chemicals, for example, urea, that are so high as to interfere with the partitioning of the polypeptide or with the formation of phases during the extraction methods.

Any of the polypeptide herein or homologs or analogs thereof may be expressed in transgenic animals. Animals species including, but not limited to, mice, rats, rabbits, guinea pigs, pigs, micro-pigs, goats, and non-human primates, e.g., baboons, monkeys, and chimpanzees may be used to generate transgenic animals expressing a transgene encoding any of the polypeptide herein or a homolog or analog thereof. Additionally, any of the polypeptide herein, including by way of example only, T1-TrpRS, T2-TrpRS, and mini-TrpRS may be used in the compositions and methods described herein, may also be expressed in transgenic plants.

The purification methods herein are useful for purifying any of the polypeptides herein from a crude mixture that may be rich in contaminants, such as cell extracts or cellular debris. Cells that express the polypeptide herein can be prepared prior to the purification procedure in a variety of ways. For example, one may prepare a paste of frozen dead cells, or one may use living cells that are frozen, or living cells can be used directly in an extraction procedure.

If the polypeptide herein is purified from cells, the cells are disrupted or homogenized prior to extraction of the polypeptide. The purpose for disrupting or homogenizing the cells is to release the polypeptide herein from the cells. A variety of ways to disrupt or homogenize cells of diverse origin are well known in the art, for example, use of bead mills, osmotic shock, french presses, douncing, sonication, microfluidizing, high-pressure homogenization, and freeze fracture. If the polypeptide is secreted from the cells in which it is synthesized, the cells do not have to be lysed but the polypeptide can be extracted from the extracellular fluid or culture medium, e.g., a phase-forming agent may be added directly to the fermentor.

The purification methods described herein may include any techniques for separating the desired pharmaceutical agent or polypeptide from other undesired materials. These techniques include, by way of example only, tangential flow filtration (also known at TFF), depth filtration, ultrafiltration, dialysis, two-phase extractions, decantation, "salting out" techniques, an expanded bed adsorption system, and centrifugation.

In accordance with the compositions and purification methods described herein, the polypeptide can be purified from cells, a cell homogenate, disrupted cells, a crude mixture obtained following chemical synthesis of the polypeptide, or any kind of mixture that contains the polypeptide of interest and contaminants such that purification of the polypeptide is desirable.

Following each purification step, the polypeptide can be detected by a variety of methods including, but not limited to, bioassays, HPLC, amino acid determination or immunological assays, e.g., radioimmunoassay, ELISA, Western blot using antibody binding, SDS-PAGE. Such antibodies include but are not limited to polyclonal antibodies, monoclonal antibodies (mAbs), humanized or chimeric antibodies, single chain antibodies, Fab fragments, F(ab')$_2$ fragments, fragments produced by a Fab expression library, and epitope-binding fragments of any of the above.

The amount of the purified polypeptide and their level of purity can be determined by methods well known in the art. For example, and not by way of limitation, one may examine a polypeptide formulation that was prepared using our purification methods with polyacrylamide gel electrophoresis followed by staining the gel to visualize the total polypeptide in the gel. In one embodiment, the yield and purity of the polypeptide following two-phase extraction are determined using reverse phase HPLC.

The purity of a formulation of a polypeptide prepared using our purification methods may vary depending on the starting material. By way of example only, when purifying a polypeptide that is expressed in *E. coli*, the resulting preparation contains at least about 50% by weight of the polypeptide of interest, more preferably at least about 50%, more preferably at least about 70%, more preferably at least about 85% and preferably at least about 95%, preferably at least about 96%, preferably at least about 97%, preferably at least about 98%%, preferably at least about 99%, or more preferably at least about 99.5%.

All polypeptide purification methods known to the skilled artisan may be used for further purification. Such techniques have been extensively described in Berger and Kimmel, Guide to Molecular Cloning Techniques, Methods in Enzymology, Volume 152, Academic Press, San Diego, Calif. (1987); Molecular Cloning: A Laboratory Manual, 2d ed., Sambrook, J., Fritsch, E. F., and Maniatis, T. (1989); Current Protocols in Molecular Biology, John Wiley & Sons, all Viols., (1989), and periodic updates thereof); New Polypeptide Techniques Methods in Molecular Biology, Walker, J. M., ed., Humana Press, Clifton, N.J., (1988); and Polypeptide Purification: Principles and Practice, 3rd. Ed., Scopes, R. K., Springer-Verlag, New York, N.Y., (1987). Additional methods for further purifying the polypeptide include, but are not limited to ammonium sulfate precipitation, ion exchange, gel filtration, reverse-phase chromatography (and the HPLC or FPLC forms thereof), and hydrophobic interaction chromatography.

Library Screening

In one embodiment, a receptor of any of the compositions herein is used to screen for agents that can modulate the receptor. Preferably the agent is combined with a library of two or more candidate agents. Candidate agents that bind or interact with the receptor can be selected for further evaluation (e.g., by detecting ability to prevent/treat ocular neovascularization in mice or other mammals, see Examples 3 and 4). Examples of candidate agents include polypeptides (e.g., linear, cyclic, natural amino acids, unnatural amino acids, peptidomimetic compounds, and peptide nucleic acids), nucleic acids, carbohydrates, and small or large organic or inorganic molecules. Such libraries can be generated by a person of ordinary skill in the art and tailored for specific assays.

Candidate agents may be obtained from a wide variety of sources including libraries of synthetic or natural compounds. For example, numerous means are available for random and directed synthesis of a wide variety of organic compounds and bio-molecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, or amidification to produce structural analogs.

Agents that bind to the receptor can be then further evaluated for their angiostatic activity using any of the angiogenic assay models disclosed herein or otherwise known in the art. Examples of assays to determine angiogenesis include those described in Example 3 and the Matrigel angiogenesis assay described in Example 4. Agents which have a significant affect on angiogenesis are deemed analogs of the compositions herein.

Molecular Modeling

In some embodiments, the compositions may be modified or new compositions may be designed using computer modeling tools. Once there is confirmation of binding between a ligand (T2 or any of the other homodimers herein) and its receptor(s), modifications of the ligand may allow for increased binding capabilities or rational drug design.

This typically involves solving the crystal structure of the ligand/receptor complex; analyzing the contacts made between the ligand and receptor components; comparing how the ligand would interact with the receptor using computer simulation and the appropriate software; and altering those portions of the ligand that are sterically hindered from or otherwise incompatible with binding to the ligand. The software typically utilized in molecular modeling is capable of achieving each of these steps, as well as suggesting potential replacements for various moieties of the ligand that would increase association with the native second kinase. Preferably, the software can also suggest small organic or inorganic compounds that can be used in lieu of the ligand (e.g., T2) to achieve the same affects.

In preferred embodiments, a molecular modeling system is used to analyze the interaction made by a tryptophanyl tRNA synthetase fragment and its receptor. Subsequently tryptophanyl tRNA synthetase fragment may be modified to improve the binding affinities of these two compounds.

One skilled in the art may use one of several methods to screen chemical moieties to replace portions of the ligand so that binding to the native receptor is optimized. This process may begin by side-by-side visual inspection of the ligand and receptor on the computer screen based on the X-ray structure of the two compounds. Modified ligands may then be tested for their ability to dock to the native receptor using software such as DOCK and AUTODOCK followed by energy minimization and molecular dynamics with standard molecular mechanics force fields, such as CHARMM and AMBER.

Other specialized computer programs that may also assist in the process of replacement fragments include the following:

1. GRID (P. J. Goodford, "A Computational Procedure for Determining Energetically Favorable Binding Sites on Biologically Important Macromolecules", J. Med. Chem., 28, pp. 849-857 (1985)). GRID is available from Oxford University, Oxford, UK.
2. MCSS (A. Miranker et al., "Functionality Maps of Binding Sites: A Multiple Copy Simultaneous Search Method." Proteins: Structure, Function and Genetics, 11, pp. 29-34 (1991)). MCSS is available from Molecular Simulations, Burlington, Mass.
3. AUTODOCK (D. S. Goodsell et al., "Automated Docking of Substrates to Proteins by Simulated Annealing", Proteins: Structure, Function. and Genetics, 8, pp. 195-202 (1990)). AUTODOCK is available from Scripps Research Institute, La Jolla, Calif.
4. DOCK (I. D. Kuntz et al., "A Geometric Approach to Macromolecule-Ligand Interactions", J. Mol. Biol., 161, pp. 269-288 (1982)). DOCK is available from University of California, San Francisco, Calif.

Other molecular modeling techniques may also be employed in accordance with this invention. See, e.g., N. C. Cohen et al., "Molecular Modeling Software and Methods for Medicinal Chemistry, J. Med. Chem., 33, pp. 883-894 (1990).

See also, M. A. Navia et al., "The Use of Structural Information in Drug Design", Current Opinions in Structural Biology, 2, pp. 202-210 (1992).

Once a compound has been designed or selected by the above methods, the efficiency with which that entity may bind to the receptor may be tested and further optimized by computational evaluation.

An entity designed or selected as binding to the native receptor may be further computationally optimized so that in its bound state it would preferably lack repulsive electrostatic interaction with the target receptor. Such non-complementary (e.g., electrostatic) interactions include repulsive charge-charge, dipole-dipole and charge-dipole interactions. Specifically, the sum of all electrostatic interactions between the ligand and the receptor when ligand is bound to the receptor preferably make a neutral or favorable contribution to the enthalpy of binding.

Specific computer software is available in the art to evaluate compound deformation energy and electrostatic interaction. Examples of programs designed for such uses include: Gaussian 92, revision C [M. J. Frisch, Gaussian, Inc., Pittsburgh, Pa. © 1992]; AMBER, version 4.0 [P. A. Kollman, University of California at San Francisco, © 1994]; QUANTA/CHARMM [Molecular Simulations, Inc., Burlington, Mass. © 1994]; and Insight II/Discover (Biosysm Technologies Inc., San Diego, Calif. © 1994). These programs may be implemented, for instance, using a Silicon Graphics workstation, Indigo$_2$ or IBM RISC/6000 workstation model 550. Other hardware systems and software packages will be known to those skilled in the art.

Once the modified ligand has been optimally selected or designed, as described above, substitutions may then be made in some of its atoms or side groups in order to improve or modify its binding properties. Generally, initial substitutions are conservative, i.e., the replacement group will have approximately the same size, shape, hydrophobicity and charge as the original group. Such substituted chemical compounds may then be analyzed for efficiency of fit to the receptor by the same computer methods described in detail, above.

Pharmaceutical Formulations

Any of the compositions and analogs and any salts, prodrugs, or metabolites thereof, can be formulated for administration to an individual by the addition of a pharmaceutically acceptable carrier.

Pharmaceutically acceptable salts are non-toxic salts at the concentration at which they are administered. The preparation of such salts can facilitate the pharmacological use by altering the physical-chemical characteristics of the composition without preventing the composition from exerting its physiological effect. Examples of useful alterations in physical properties include lowering the melting point to facilitate transmucosal administration and increasing the solubility to facilitate the administration of higher concentrations of the drug.

Pharmaceutically acceptable salts include acid addition salts such as those containing sulfate, hydrochloride, phosphate, sulfonate, sulfamate, sulfate, acetate, citrate, lactate, tartrate, methanesulfonate, ethanesulfonate, benzenesulfonate, p-toluenesulfonate, cycloexylsulfonate, cyclohexylsulfamate, and quinate. Pharmaceutically acceptable salts can be obtained from acids such as hydrochloric acid, sulfuric acid, phosphoric acid, sulfonic acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfonic acid, cyclohexylsulfamic acid, and quinic acid. Such salts may be prepared by, for example, reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

Ophthalmically acceptable carriers are agents that have no persistent detrimental effect on the treated eye or the functioning thereof, or on the general health of the subject being treated. Typically, pharmaceutical formulations for intraocular administrations will be substantially free of detergent and/or preservative, or completely free of detergent and/or preservative.

Useful aqueous suspensions for ophthalmic formulations can contain one or more polymers as suspending agents. Useful polymers include water-soluble polymers such as cellulosic polymers, e.g., hydroxypropyl methylcellulose, and water-insoluble polymers such as cross-linked carboxyl-containing polymers. Useful ophthalmic formulations can also comprise of an ophthalmically acceptable mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

Ophthalmically acceptable solubilizing agent to aid in the solubility of any of the compositions herein include agents that result in the formation of a micellar solution or a true solution of the agent. Certain nonionic surfactants, for example polysorbate 80, can be useful as solubilizing agents, as can glycols, polyglycols, e.g., polyethylene glycol 400, and glycol ethers. In general, however, such surfactants and glycols are not used in compositions for intraocular administration except in very low doses because of their potential to cause certain harmful side effects, such as retinal detachment. Accordingly, such surfactants and glycols are preferably not used, or if required, in only small quantities.

Useful ophthalmically acceptable pH adjusting agents or buffering agents include, for example, acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an ophthalmically acceptable range.

Useful ophthalmically acceptable salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Useful ophthalmically acceptable surfactants to enhance physical stability or for other purposes include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

The ophthalmic pharmaceutical formulations herein may also take the form of a solid article that can be inserted between the eye and eyelid or in the conjunctival sac, where it releases the agent. Release is to the lacrimal fluid that bathes the surface of the cornea, or directly to the cornea itself, with which the solid article is generally in intimate contact. Solid articles suitable for implantation in the eye in such fashion are generally composed primarily of polymers and can be biodegradable or non-biodegradable.

In any of the embodiments herein, the pharmaceutically acceptable carrier can be one that does not destroy or affect a multi-unit complex of a tRNA synthetase fragment.

The pharmaceutical formulations herein can further include a therapeutic agent selected from the group consisting of: an antineoplastic agent, an anti-inflammatory agent, an antibacterial agent, an antiviral agent, an angiogenic agent, and an anti-angiogenic agent. Examples of such agents are disclosed herein.

For example, an antineoplastic agent may be selected from the group consisting of Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; Fluorocitabine; Fosquidone; Fostriecin Sodium; Gemcitabine; Gemcitabine Hydrochloride; Gold Au 198; Hydroxyurea; Idarubicin Hydrochloride; Ifosfamide; Imofosine; Interferon Alfa-2a; Interferon Alfa-2b; Interferon Alfa-n1; Interferon Alfa-n3; Interferon β-Ia; Interferon γ-Ib; Iproplatin; Irinotecan Hydrochloride; Lanreotide Acetate; Letrozole; Leuprolide Acetate Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycinl, Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

Anti-angiogenic agents are any agents that inhibit angiogenesis, whether disclosed herein or known in the art. In preferred embodiments, an anti-angiogenic agent is an anti-VEGF agent, such as Macugen™ (Eyetech, New York, N.Y.); or an anti-VEGF antibody.

Pharmaceutical compositions can be formulated by standard techniques using one or more suitable carriers, excipients, and diluents. See, e.g., Remington's Pharmaceutical Sciences, (19$^{th}$ Ed. Williams & Wilkins, 1995) (incorporated herein by reference for all purposes).

Examples of suitable carriers, excipients and diluents include lactose, dextrose, sucrose, sorbitol, mannitol, starches, gum acacia, calcium phosphate, alginates, calcium silicate, microcrystalline cellulose, polyvinyl pyrrolidine, cellulose, tragacanth, gelatin syrup, methylcellulose, methyl and propyl hydroxybenzoates, talc, magnesium stearate, water and mineral oil. Other additives optionally include lubricating agents, wetting agents, emulsifying and suspending agents. An ophthalmic carrier is preferable in sterile, substantially isotonic aqueous solutions.

The pharmaceutical compositions may be formulated to provide immediate, sustained or delayed release of the compound. For applications providing slow release, certain carriers may be particularly preferred. Suitable slow release carriers may be formulated from dextrose, dextran, polylactic acid, and various cellulose derivatives, for example ethylhydroxycellulose in the form of microcapsules.

Various additives may be added to the formulations herein. Such additives include substances that serve for emulsification, preservation, wetting, improving consistency and so forth and which are conventionally employed in pharmaceutical preparations. Other additives include compounds that have surfactant properties, either ionic or non-ionic such as sorbitan monolaurate triethanolamine oleate, polyoxyethylenesorbitan monopalmitate, dioctyl sodium sulfosuccinate, monothioglycerol, thiosorbitol, ethylenediamine tetra-acetic acid, etc.

For non-ocular indications, an excipient may include a preservative. Suitable preservatives for use in non-ocular pharmaceutical preparations include benzalkonium chloride, benzethonium, phenylethyl alcohol, chlorobutanol, thimerosal and the like. Suitable buffers include boric acid, sodium and potassium bicarbonate, sodium and potassium borates, sodium and potassium carbonate, sodium acetate, sodium biphosphate, Tris, and the like, in amounts sufficient to maintain the pH between about pH 3 and about pH 9.5, most preferably between about pH 7 and pH 7.5. Suitable tonicity agents are dextran 40, dextran 70, dextrose, glycerin, potassium chloride, propylene glycol, sodium chloride and the like, such that the sodium chloride equivalent of the ophthalmic solution is in the range of 0.9±0.2%.

Suitable antioxidant and stabilizers include sodium and potassium bisulfite, sodium and potassium metabisulfite, sodium thiosulfate, thiourea and the like. Suitable wetting and clarifying agents include polysorbate 80, polysorbate 20, poloxamer 282 and tyloxapol. Suitable viscosity increasing agents include dextran 40, gelatin, glycerin, hydroxyethyl cellulose, hydroxymethyl propyl cellulose, lanolin, methylcellulose, petrolatum, polyethylene glycol, polyvinyl alcohol, polyvinyl polyvinylpyrrolidone, carboxymethyl cellulose and the like. Stabilizers such as chelating agents that may be used include, for example, EDTA, EGTA, DTPA, DOTA, ethylene diamine, bipyridine, 1,10-phenanthrolene, crown ethers, aza crown, catechols, dimercaprol, D-penicillamine and deferoxamine. Antioxidants that may also act as stabilizers include such compounds as ascorbic acid, sodium bisulfite, ascorbyl palmitate, butylated hydroxyanisole, butylated hydroxytoluene, potassium metabisulfite and sodium metabisulfite.

Formulations can include capsules, gels, cachets, tablets, effervescent or non-effervescent powders or tablets, powders or granules; as a solution or suspension in aqueous or non-aqueous liquid; or as an oil-in-water liquid emulsion or a water-in-oil emulsion. Capsule or tablets can be easily formulated and can be made easy to swallow or chew. Tablets may contain suitable carriers, binders, lubricants, diluents, disintegrating agents, coloring agents, flavoring agents, flow-inducing agents, or melting agents. A tablet may be made by compression or molding, optionally with one or more additional ingredients. Compressed tables may be prepared by compressing the active ingredient in a free flowing form (e.g., powder, granules) optionally mixed with a binder (e.g., gelatin, hydroxypropylmethylcellulose), lubricant, inert diluent, preservative, disintegrant (e.g., sodium starch glycolate, cross-linked carboxymethyl cellulose) surface-active or dispersing agent. Suitable binders include starch, gelatin, natural sugars such as glucose or $\beta$-lactose, corn sweeteners, natural and synthetic gums such as acacia, tragacanth, or sodium alginate, carboxymethylcellulose, polyethylene glycol, waxes, or the like. Tablets may optionally be coated or scored and may be formulated so as to provide slow- or controlled-release of the active ingredient. Tablets may also optionally be provided with an enteric coating to provide release in parts of the gut other than the stomach.

Formulations suitable for topical administration (e.g., wound healing) in the mouth wherein the active ingredient is dissolved or suspended in a suitable carrier include lozenges which may comprise the active ingredient in a flavored carrier, usually sucrose and acacia or tragacanth; gelatin, glycerin, or sucrose and acacia; and mouthwashes comprising the active ingredient in a suitable liquid carrier. Topical applications for administration according to the method of the present invention include ointments, cream, suspensions, lotions, powder, solutions, pastes, gels, spray, aerosol or oil. Alternately, a formulation may comprise a transdermal patch or dressing such as a bandage impregnated with an active ingredient and optionally one or more carriers or diluents.

To be administered in the form of a transdermal delivery system, the dosage administration will, of course, be continuous rather than intermittent throughout the dosage regimen. The topical formulations may desirably include a compound that enhances absorption or penetration of the active ingredient through the skin or other affected areas. Examples of such dermal penetration enhancers include dimethylsulfoxide and related analogs.

Formulations suitable for parenteral administration include aqueous and non-aqueous formulations isotonic with the blood of the intended recipient; and aqueous and non-aqueous sterile suspensions which may include suspending systems designed to target the compound to blood components or one or more organs. The formulations may be presented in unit-dose or multi-dose sealed containers, for example, ampoules or vials. For intraocular formulations, unit dosages are preferred because no preservatives are in the formulation. For other parenteral formulations, preservative may be used, which would allow for multi dose containers Extemporaneous injections solutions and suspensions may be prepared from sterile powders, granules and tablets of the kind previously described. Parenteral and intravenous forms may also include minerals and other materials to make them compatible with the type of injection or delivery system chosen.

Particular parenteral administrations contemplated by the present invention include intraocular and intravitreous administrations to the eye. Pharmaceutical formulations for intraocular and intravitreous administrations include phosphate buffered saline (PBS) and balanced isotonic salt solution (BSS) with or without excipients such as mannitol or sorbitol as protein stabilizers.

In general, water, suitable oil, saline, aqueous dextrose (glucose), or related sugar solutions and glycols such as propylene glycol or polyethylene glycols are suitable carriers for parenteral solutions. Solutions for parenteral administration preferably contain the active ingredient, suitable stabilizing agents and, if necessary, buffer substances. Antioxidizing agents, such as sodium bisulfite, sodium sulfite, or ascorbic acid, either alone or combined, are suitable stabilizing agents. Also used are citric acid salts thereof, or sodium EDTA. In addition, parenteral solutions may contain preservatives, such as benzalkonium chloride, methyl- or propyl-paraben, or chlorobutanol. Suitable pharmaceutical carriers are described in Remington, cited supra.

In any of the embodiments herein, a composition or pharmaceutical formulation herein may be lyophilized.

In any of the embodiments herein, the pharmaceutical formulations preferable have less than about 30, 20 or 10, more preferably less than 9, 8, 7, 6, 5, 4, 3, 2, or 1, or more preferably less 0.1, 0.01, or 0.001 endotoxin unit(s) per milligram of therapeutic agents Indications It is contemplated by the present invention that any of the compositions (including pharmaceutical formulations) herein may be used to modulate angiogenesis in a cell or tissue. Such methods involve contacting the cell or tissue with an appropriate anti-angiogenic (e.g., angiostatic) or angiogenic agent. For example, in some embodiments, a cell or tissue experiencing or susceptible to angiogenesis (e.g., an angiogenic condition) may be contacted with a multi-unit complex of a tRNA synthetase fragment, or a homolog or analog thereof to inhibit an angiogenic condition. In other embodiments, a cell or tissue experiencing or susceptible to insufficient angiogenesis (e.g., an angiostatic condition) may be contacted with an inhibitor of a tRNA synthetase fragment, e.g., an RNAi, antisense nucleic acid, antibody, or other binding agent or agent that interferes with angiostatic activity of a tryptophanyl-tRNA synthetase fragment.

The cells/tissue that may be modulated by the present invention are preferably mammalian cells, or more preferably human cells. Such cells can be of a healthy state or of a diseased state. In some embodiments, a cancerous cell, tumor cell, or a cell experiencing neovascularization is contacted with a composition of the present invention. In some embodiments, a cell experiencing angiogenesis due to an increase in VEGF, interferon $\gamma$, and/or TNF-$\alpha$ is contacted with a composition of the present invention. In one example, a photoreceptor cell is contacted with a multi-unit complex of the present invention.

Angiogenesis can be modulated in a cell or tissue by contacting the cell with a multi-unit complex, such as a dimer, trimer, etc. of the present invention. In preferred embodiments, such multi-unit complex is isolated. Furthermore, in any of the embodiments herein, a multi-unit complex may be soluble.

When modulating angiogenesis, the rate of angiogenesis may be inhibited by contacting a cell or tissue with an effective amount of a multi-unit complex of the present invention. An example of the multi-unit complex of the present invention includes a first monomer and a second monomer. The first and second monomers of the present invention may be different, homologous, substantially homologous, or identical to each other. Any of the monomers of the present invention can comprise a tRNA synthetase fragment. A tRNA synthetase fragment of the present invention can be, for example, a tryptophanyl tRNA synthetase fragment, a human tryptophanyl tRNA synthetase fragment, and/or any angiostatic fragment of a tRNA synthetase. Examples of angiostatic tryptophanyl tRNA synthetase fragments contemplated by the present invention include those selected from the group consisting of SEQ ID NOS: 12-17, 24-29, 36-41, 48-53, and any homologs and analogs thereof.

Units of a multi-unit complex may be covalently linked or non-covalently linked. Covalently linked monomers can be linked by any method disclosed herein, e.g., a linker, a disulfide bond. In some embodiments, two or more monomers are linked by one or more non-naturally occurring cysteines. Such cysteines are preferably located in a dimerization domain of a monomer. In some embodiments, monomers are linked by a linker. A linker of the present invention should be long enough to allow two or more monomers the freedom to productively arrange and dimerize with one another.

When modulating angiogenesis, the rate of angiogenesis may be enhanced by contacting a cell or tissue with an effective amount of an inhibitor of a tRNA synthetase fragment that has angiostatic activity. Examples of such inhibitors include, but are not limited to an antibody, an antisense nucleic acid, a RNAi nucleic acid, a peptidomimetic, a peptide nucleic acid, a peptide, and a small or large organic or inorganic molecule. Such inhibitors may function, for example, by competitively binding to a receptor of said tRNA synthetase fragment; binding to the binding site of said tRNA synthetase fragment; binding to said tRNA synthetase fragment and changing its conformation; inhibiting the expression of said tRNA synthetase, and/or inhibiting the cleavage of a full length tRNA synthetase which forms said tRNA synthetase fragment.

The compositions herein can be used to modulate neovascular stabilization and/or maturation. As such the compositions herein can be used to enhance would healing and regulating vascular endothelial cell function.

It is further contemplated by the present invention that any of the compositions herein may be administered to a patient susceptible to or suffering from a condition associated with increased angiogenesis (vascular formation) ("an angiogenic condition") or a diminished capacity for vascular formation ("an anti-angiogenic condition") (collectively, "angiogenesis-mediated conditions").

Examples of angiogenic conditions that may be treated/prevented by the compositions/methods of the present invention include, but are not limited to, age-related macular degeneration (AMD), neoplastic condition (both solid tumour and haematological disorders), developmental abnormalities (organogenesis), diabetic blindness, endometriosis, ocular neovascularization, psoriasis, rheumatoid arthritis (RA), treat retinopathy of prematurity (ROP) and skin discolorations (e.g., hemangioma, nevus flammeus, or nevus simplex).

Examples of anti-angiogenic conditions that may be treated/prevented by the compositions/methods of the present invention include, but are not limited to, cardiovascular disease (e.g., atherosclerosis (see Moulton, K., *PNAS*, Vol. 100, No. 8: 4736-4741 (2003)), restenosis (see Brasen J H., *Arterioscler. Thromb. Vasc. Biol. Nov;* 21(11):1720-6 (2001)), peripheral vascular disease, peripheral arterial disease, tissue damage after reperfusion of ischemic tissue or cardiac failure (see The U. of Term., *The Vessel,* 4(1) (2003)), chronic inflammation, and wound healing.

For example, the present invention relates to methods for treating or preventing conditions associated with ocular neovascularization using any of the compositions/methods herein. Conditions associated with ocular neovascularization include, but are not limited to, diabetic retinopathy, age related macular degeneration ("ARMD"), rubeotic glaucoma, interstitial keratitis, retinopathy of prematurity, ischemic retinopathy (e.g., sickle cell), pathological myopic, ocular histoplasmosis, pterygia, punitiate inner choroidopathy, and the like.

Examples of neoplastic conditions that may be treatable or preventable by the compositions/methods herein include, but are not limited to, breast cancer; skin cancer; bone cancer; prostate cancer; liver cancer; lung cancer; brain cancer; cancer of the larynx; gallbladder; pancreas; rectum; parathyroid; thyroid; adrenal; neural tissue; head and neck; colon; stomach; bronchi; kidneys; basal cell carcinoma; squamous cell carcinoma of both ulcerating and papillary type; metastatic skin carcinoma; osteo sarcoma; Ewing's sarcoma; veticulum cell sarcoma; myeloma; giant cell tumor; small-cell lung tumor; gallstones; islet cell tumor; primary brain tumor; acute and chronic lymphocytic and granulocytic tumors; hairy-cell leukemia; adenoma; hyperplasia; medullary carcinoma; pheochromocytoma; mucosal neurons; intestinal ganglioneuromas; hyperplastic corneal nerve tumor; marfanoid habitus tumor; Wilm's tumor; seminoma; ovarian tumor; leiomyomater tumor; cervical dysplasia and in situ carcinoma; neuroblastoma; retinoblastoma; soft tissue sarcoma; malignant carcinoid; topical skin lesion; mycosis fungoide; rhabdomyosarcoma; Kaposi's sarcoma; osteogenic and other sarcoma; malignant hypercalcemia; renal cell tumor; polycythemia vera; adenocarcinoma; glioblastoma multiforme; leukemias (including acute myelogenous leukemia); lymphomas; malignant melanomas; epidermoid carcinomas; chronic myeloid lymphoma; gastrointestinal stromal tumors; and melanoma.

Methods of the present invention include a method for treating an individual suffering from an angiogenic condition by administering to the individual a pharmaceutical formulation comprising a multi-unit complex. A multi-unit complex of the present invention is a complex of 2 or more monomers, 3 or more monomers, 4 or more monomers, 5 or more monomers, or 6 or more monomers.

In some embodiments, a monomer of a multi-unit complex is a tRNA synthetase fragment, or a homolog or an analog thereof. Preferably, the tRNA synthetase fragment is a fragment of tryptophanyl tRNA synthetase (SEQ ID NO: 61-64), or any homologs or derivatives thereof. The tRNA synthetase fragment is preferably a fragment from a mammalian tRNA synthetase, or more preferably human tRNA synthetase. In some embodiments, a monomer of the multi-unit complex is selected from the group consisting of SEQ ID NOS: 12-17, 24-29, 36-41, and 48-53. A first monomer and a second monomer of the multi-unit complex can be different, homologous, substantially homologous, or identical. In preferred embodiments, a multi-unit complex is a dimer (with homologous or substantially homologous monomers), or more preferably a homodimer (with identical monomers).

The two or more monomers in a multi-unit complex may be covalently linked, non-covalently associated, or both.

It is further contemplated herein that the compositions herein can specifically interact with at least one angiogenic receptor. An angiogenic receptor is any cell surface receptor that can mediate angiogenesis (including abnormal developmental growth, tumorgenesis, lymphogenesis, and vasculogenesis). Angiogenic receptors of the present invention are preferably located on an endothelium cell, or more preferably vascular endothelium cell. In some embodiments, the compositions herein are used to modulate an angiogenic receptor or to treat an angiogenic-receptor mediated condition.

Known angiogenic receptors include, but are not limited to, growth factor receptors of VEGF, IGF, EGF, PDGF and FGF. Other preferred angiogenic receptors include cell adhesion molecules as described below. Angiogenic receptors also include CXC-receptors or chemokine receptors. Examples of CXC receptors include, but are not limited to, the group consisting of, IL8RA, IL8RB, IL8RBP, CXCR3, CXCR4, BLR1, and CXCR6. Examples of chemokine receptors include, but are not limited to, the group consisting of CCR1-CCR9, GPR2, CCRL1-CCRL2, and FPRL1.

In some embodiments, the methods of treatment disclosed herein further include administering to an individual suffering from an angiogenic condition one or more therapeutic agents selected from the group consisting of antineoplastic agents, antiviral agents, anti-inflammatory agents, antibacterial agents, anti-angiogenic agents, or anti-angiogenic agents.

Such combination treatments can be achieved by either administering to an individual a co-formulating of the compositions herein with the additional therapeutic agent(s) or by administering the compositions herein and the therapeutic agent(s) as two separate pharmaceutical formulations. In embodiments wherein more than one composition/therapeutic agent is administered to an individual, lower dosages of the compositions and/or therapeutic agent(s) may be utilized as a result of the synergistic effect of both active ingredients.

Examples of antineoplastic agents are provided herein and are known in the art.

Antibacterial agents that may be administered to an individual include, but are not limited to, penicillins, aminoglycosides, macrolides, monobactams, rifamycins, tetracyclines, chloramphenicol, clindamycin, lincomycin, imipenem, fusidic acid, novobiocin, fosfomycin, fusidate sodium, neomycin, polymyxin, capreomycin, colistimethate, colistin, gramicidin, minocycline, doxycycline, vancomycin, bacitracin, kanamycin, gentamycin, erythromycin and cephalosporins.

Anti-inflammatory agents that may be administered to an individual include, but are not limited to, NSAIDS (e.g., aspirin (salicylamide), sodium salicylamide, indoprofen, indomethacin, sodium indomethacin trihydrate, Bayer™, Bufferin™, Celebrex™, diclofenac, Ecotrin™, diflunisal, fenoprofen, naproxen, sulindac, Vioxx™), corticosteroids or corticotropin (ACTH), colchicine, and anecortave acetate.

Antiviral agents that may be administered to an individual include, but are not limited to, α-methyl-P-adamantane methylamine, 1,-D-ribofuranosyl-1,2,4-triazole-3 carboxamide, 9-[2-hydroxy-ethoxy]methylguanine, adamantanamine, 5-iodo-2'-deoxyuridine, trifluorothymidine, interferon, adenine arabinoside, CD4,3'-azido-3'-deoxythymidine (AZT), 9-(2-hydroxyethoxymethyl)-guanine (acyclovir), phosphonoformic acid, 1-adamantanamine, peptide T, and 2',3'dideoxycytidine.

Angiogenic agents that may be administered to an individual include, but are not limited to, Angiogenin, Angiopoietin-1, Del-1, Fibroblast growth factors: acidic (aFGF) and basic (bFGF), Follistatin, Granulocyte colony-stimulating factor (G-CSF), Hepatocyte growth factor (HGF)/scatter factor (SF), Interleukin-8 (IL-8), Leptin, Midkine, Placental growth factor, Platelet-derived endothelial cell growth factor (PD-ECGF), Platelet-derived growth factor-BB (PDGF-BB), Pleiotrophin (PTN), Progranulin, Proliferin, Transforming growth factor-α (TGF-α), Transforming growth factor-β (TGF-β), Tumor necrosis factor-α (TNF-α), and Vascular endothelial growth factor (VEGF)/vascular permeability factor (VPF).

Anti-angiogenic agents that may be administered to an individual include antagonists of angiogenic material. The term "antagonists of angiogenic material" is used herein to refer to any molecule that inhibiting the biological activity of an angiogenic material. Examples of antagonists of angiogenic material include, but are not limited to, antibodies that specifically bind the angiogenic material, iRNA that inhibit translation of the angiogenic material, and other agents that bind/interfere with the biological activity of the angiogenic material.

Examples of angiogenic materials include but are not limited to: (1) growth factors and their receptors; (2) remodeling and morphogenic receptors and their ligands; (3) adhesion receptors and their ligands; (4) matrix-degrading enzymes, such as Matrix-Metalo Proteinases (MMPs); (5) signaling molecules, such as Raf and MAPK, PKA, Rhos-family GTPases, PKB; and (6) transcription factors and regulators (e.g., hypoxia inducible factor (HIF)-1, Id 1/3, and Nuclear Factor-B) and homobox gene products (e.g., Hox D3, and B3).

In some embodiments, the angiogenic material is a growth factor and/or its receptor. Examples of growth factors receptors include VEGF receptors (e.g., soluble VEGFR1, VEGFR1 (Flt-1), VEGFR2 (Flk-1), and VEGFR3 (Flt-4)) and their ligands (e.g., VEGF A, B, C, and D). Thus, in some embodiments, an anti-angiogenic agent is an antagonist to a VEGF receptor, such as VEGFR1, VEGFR2, VEGFR3, or an antagonist to a VEGF ligand, such as VEGFA, VEGFB, VEGFC, or VEGFD. In some embodiments, an anti-angiogenic agent is antagonist to a VEGF ligand (e.g., VEGFA-VEGFD). More preferably, an anti-angiogenic agent is antagonist to VEGFA. Examples of anti-VEGF, anti-angiogenic agents include Avastin (Genentech, Inc.), Macugen (EyeTech Pharmaceuticals, Inc.) or Visudyne (Novartis, Crop.) and anti-VEGF monoclonal antibody M293. Additional examples of anti-VEGF anti-angiogenic agents are disclosed in U.S. Pat. Nos. 5,730,977, 6,383,484, 6,403,088, 6,479,654, 6,559,126, and 6,676,941, all of which are incorporated herein by reference for all intended purposes.

Additional examples of growth factors and their receptors include, but are not limited to, angiogenin, angiopoietin-1, Del-1, fibroblast growth factors ("FGF") and FGFR (including acidic aFGF and basic bFGF), follistatin, granulocyte colony-stimulating factor (G-CSF), hepatocyte growth factor (HGF), Interleukin-8 (IL-8), leptin, midkine, placental growth factor, platelet-derived endothelial growth factor (PD-ECGF), platelet-derived growth factor-BB (PDFG-BB), pleiotrophin (PTN), progranulin, proliferin, transforming growth factor (TGF)-α, TGF-β, and tumor necrosis factor (TNF)-α.

In some embodiments, an anti-angiogenic agent of the present invention is an antagonist of a remodeling and morphogenic receptor and/or ligand. Examples of remodeling and morphogenic receptors and ligands include, but are not limited to, the Tie receptors (e.g., Tie1 and Tie2) and their ligands (e.g., ANG-1, ANG-2, and ANG-3/4), as well as the Ephrin receptors (e.g., EphB1, EphB2, EphB3, EphB4, EphB6, EphA4) and their ligands (e.g., ephrin B1, B2, and B3).

In some embodiments, an anti-angiogenic agent of the present invention is an antagonist of an adhesion receptor and/or its ligand. Examples of adhesion receptors and their ligands include, but are not limited to, the integrins, cadherins, semophorins, and fibronectin. There are eighteen α and eight β mammalian subunits which assemble to form 24 different heterodimers of integrin receptors. In some embodiments, an antagonist of an adhesion receptor is an antagonist of a vascular integrin receptor selected from the group consisting of α1β1, α2β1, α3β1, α4β1, α5β1, α6β1, α8β1, α9β1, αVβ1, αVβ3, αVβ5, α6β4, and αVβ8. In more preferred embodiments, an antagonist of an adhesion receptor is an antagonist of a vascular integrin receptor selected from the group consisting of α1β1, α2β1, α5β1, and αVβ3. In more preferred embodiments, an antagonist of an adhesion receptor is an antagonist of αVβ3.

Peptide and antibody antagonists of this integrin inhibit angiogenesis by selectively inducing apoptosis of the proliferating vascular endothelial cells. Integrin antibodies are commercially available from, e.g., Chemicon Internation, Biocompare, Soretec, etc.

Two cytokine-dependent pathways of angiogenesis exist and can be defined by their dependency on distinct vascular cell integrins, αVβ3 and αVβ5. Specifically, basic FGF- and VEGF-induced angiogenesis depend on integrin αVβ3 and αVβ5, respectively, since antibody antagonists of each integrin selectively block one of these angiogenic pathways in the rabbit corneal and chick chorioallantoic membrane (CAM) models. Peptide antagonists that block all αV integrins inhibit FGF- and VEGF-stimulated angiogenesis. While normal human ocular blood vessels do not display either integrin, αVβ3 and αVβ5 integrins are selectively displayed on blood vessels in tissues from patients with active neovascular eye disease. While only αVβ3 was consistently observed in tissue from patients with ARMD, αVβ3 and αVβ5 both were present in tissues from patients with PDR. Systemically administered peptide antagonists of integrins blocked new blood vessel formation in a mouse model of retinal vasculogenesis.

There are many different types of cadherins. The most extensively studied group of cadherins is known as the classical, or type I, cadherins. Cadherins that contain calcium binding motifs within extracellular domain cadherin repeats, but do not contain an HAV CAR sequence, are considered to be nonclassical cadherins. To date, nine groups of nonclassical cadherins have been identified (types II-X). These cadherins are membrane glycoproteins. Type II, or atypical, cadherins include OB-cadherin, also known as cadherin-11 (Getsios et al., *Developmental Dynamics* 211:238-247, (1998)); cadherin-5, also known as VE-cadherin (Navarro et al., *J. Cell Biology* 140:1475-1484 (1998)); cadherin-6, also known as K-cadherin (Shimoyama et al., *Cancer Research* 55:2206-2211 (1995)); cadherin-7 (Nakagawa et al., *Development* 121:1321-1332 (1995); cadherin-8 (Suzuki et al., *Cell Regulation* 2:261-270 (1991)), cadherin-12, also known as Br-cadherin (Tanihara et al., *Cell Adhesion and Communication* 2:15-26, (1994)); cadherin-14 (Shibata et al., *J. Biological Chemistry* 272:5236-5240 (1997)), cadherin-15, also known as M-cadherin (Shimoyama et al., *J. Biological Chemistry* 273:10011-10018 (1998)), and PB-cadherin (Sugimoto et al., *J. Biological Chemistry* 271:11548-11556 (1996)). For a general review of atypical cadherins, see Redies and Takeichi, *Developmental Biology* 180:413-423 (1996) and Suzuki et al., *Cell Regulation* 2:261-270 (1991).

Additional examples of angiogenic receptors include neuropilins (e.g., neuropilin-1 and neuropillin-2), endoglin, PDFGβR, CXCR-4, Tissue Factor ("TF"), thrombin receptor, $G\alpha_{13}$, and EP3. It has been suggested that T2 also binds to neuropilin-1 and 2, see, e.g., International Appl. No. PCT/US02/23868, having publication No. WO 03/009813, which is incorporated herein by reference. Thus, the present invention contemplates methods for identifying other binding partners that can specifically interact with and/or bind tRS, or more preferably T2. Such methods include the use of a yeast two hybrid system, a phage display library system, screening peptide libraries, computer imaging programs, and the like.

In any of the embodiments herein, anti-angiogenic agents can include nucleic acids, polypeptides, peptidomimetics, PNAs, antibodies, fragments of antibodies, small or large organic or inorganic nucleic acids that bind to angiogenesis associated molecules.

Other known anti-angiogenic agents that are found in the body include, but are not limited to, angioarrestin, angiostatin (plasminogen fragment), antiangiogenic antithrombin III, cartilage-derived inhibitor (CDI), CD59 complement fragment, endostatin (collagen XVIII fragment), fibronectin fragment, Gro-β, heparinases, heparin hexasaccharide fragment, human chorionic gonadotropin (hCG), interferon α/β/γ, interferon inducible protein (IP-10), interleukin-12, kringle 5 (plasminogen fragment), metalloproteinase inhibitors (TIMPs), 2-methoxyestradiol, placental ribonuclease inhibitor, plasminogen activator inhibitor, platelet factor-4 (PF4), prolactin 16 kDa fragment, proligerin-related protein (PRP), retinoids, tetrahydrocortisol-S, thrombospondin-1 (TSP-1), transforming growth factor-β, vasculostatin, vasostatin (calreticulin fragment).

Administration

Administration of a composition of the present invention to a target cell in vivo can be accomplished using any of a variety of techniques well known to those skilled in the art.

For example, compositions of the present invention can be administered systemically or locally by any means known in the art (e.g., orally, intraocularly, intravascularly (i.v.), intradermally, intramuscularly, transdermally, transmucosally, enterically, parentally, by inhalation spray, rectally, or topically) in dosage unit formulations and containing conventional pharmaceutically acceptable carriers, adjuvants, and vehicles.

For purposes of this invention the term "ophthalmic administration" encompasses, but is not limited to, intraocular injection, subretinal injection, intravitreal injection, periocular administration, subconjuctival injections, retrobulbar injections, intracameral injections (including into the anterior or vitreous chamber), sub-Tenon's injections or implants, ophthalmic solutions, ophthalmic suspensions, ophthalmic ointments, ocular implants and ocular inserts, intraocular solutions, use of iontophoresis, incorporation in surgical irrigating solutions, and packs (by way of example only, a saturated cotton pledget inserted in the fornix).

As used herein the term parenteral includes subcutaneous, intravenous, intramuscular, intrasternal, infusion techniques or intraperitoneal injections. Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The dosage regimen for treating a disorder or a disease with the vectors of this invention and/or compositions of this invention is based on a variety of factors, including the type of disease, the age, weight, sex, medical condition of the patient, the severity of the condition, the route of administration, and the particular compound employed. Thus, the dosage regimen can vary widely, but can be determined routinely using standard methods.

For systemic administration, the polypeptides (preferably dimers or homodimers) and/or small molecules of the present invention are preferably administered at a dose of at least 0.05, 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10, 20, 30, 40, 50, 75, 100, or 150 mg/kg body weight. In other embodiments, the polypeptides (preferably dimers or homodimers) and/or small molecules herein are administered systemically at a dose of 0.1-100 mg/kg, more preferably 0.5-50 mg/kg, more preferably 1-30 mg/kg body weight, or more preferably 5-20 mg/kg.

For localized administration, the polypeptides (preferably dimers or homodimers) and/or small molecules of the present invention are preferably administered at a dose of at least 50 µg, 100 µg, 150 µg, 200 µg, 250 µg, 300 µg, 350 µg, 400 µg, 450 µg, 500 µg, 550 µg, 600 µg, 650 µg, or 700 µg. In other embodiments, the polypeptides (preferably dimers or homodimers) and/or small molecules herein are administered locally at a dose of 50-1000 µg, more preferably 100-800 µg, more preferably 200-500 µg, or more preferably 300-400 µg per site. In other embodiments, the polypeptides (preferably dimers or homodimers) and/or small molecules herein are administered locally at a dose of at less than 1000 µg, 900 µg, 800 µg, 700 µg, 600 µg, 500 µg, 400 µg, 300 µg, 200 µg, 100 µg, 50 µg, 25 µg, 10 µg, or 5 µg per site.

For example, for dermal administration the polypeptides (e.g., dimers) and/or peptidomimetics and/or small molecules of the present invention are administered at a dose of 50-1000 µg/cm$^2$, more preferably 100-800 µg/cm$^2$, or more preferably 200-500 µg/cm$^2$. In another example, for ocular administration, the polypeptides (e.g., dimers) and/or peptidomimetics and/or small molecules of the present invention are administered at a dose of 50-1000 µg/eye, more preferably 100-800 µg/eye, or more preferably 200-500 µg/eye.

The pharmaceutical compositions preferably include the active ingredient (e.g., T2) in an effective amount, i.e., in an amount effective to achieve therapeutic or prophylactic benefit. The actual amount effective for a particular application will depend on the condition being treated and the route of administration. Determination of an effective amount is well within the capabilities of those skilled in the art, especially in light of the disclosure herein.

Preferably, the effective amount of the active ingredient, e.g., T2, is from about 0.0001 mg to about 500 mg active agent per kilogram body weight of a patient, more preferably from about 0.001 to about 250 mg active agent per kilogram body weight of the patient, still more preferably from about 0.01 mg to about 100 mg active agent per kilogram body weight of the patient, yet still more preferably from about 0.5 mg to about 50 mg active agent per kilogram body weight of the patient, and most preferably from about 1 mg to about 15 mg active agent per kilogram body weight of the patient.

In terms of weight percentage, the formulations of the present invention will preferably comprise the active agent, e.g., T2-TrpRS, in an amount of from about 0.0001 to about 10 wt. %, more preferably from about 0.001 to about 1 wt. %, more preferably from about 0.05 to about 1 wt. %, or more preferably about 0.1 wt. to about 0.5 wt. %. In some ophthalmic formulations, the composition herein is formulated between 0.01-1000 mg/mL, 0.1-100 mg/mL, 1-10 mg/mL, 2-10 mg/mL, 2-9 mg/mL, 3-9 mg/mL, 4-8 mg/mL, 5-8 mg/mL, 5-7 mg/mL, or 6-7 mg/mL. For systemic formulations, the compositions herein can be formulated between 0.001-100 mg/mL, 0.01-10 mg/mL, 0.1-10 mg/mL, 2-10 mg/mL, 2-9 mg/mL, 3-9 mg/mL, 4-8 mg/mL, 5-8 mg/mL, 5-7 mg/mL, or 6-7 mg/mL.

Screening/Diagnosis

In any of the embodiments herein a cell or tissue may be screened for an angiogenesis mediated condition (e.g., an anti-angiogenic condition or an angiogenic condition). This can be accomplished by any technology known in the art. For example, tagged probes, tagged probes described in WO 2004/011900, which is incorporated herein by reference for all purposes, may be used to identify and/or quantify angiostatic and/or angiogenic tRNA synthetase fragments in a sample. Generally, such tagged probes include a binding moiety that is specific to a tRNA synthetase fragment (e.g., mini-Trp-RS, T1, or T2), a detectable reporter (such as a fluorescent group), and optionally a mobility modifier. The mobility modifier and detectable reporter are linked to the binding moiety by a cleavable linker. The binding moiety can be, for example, an antibody specific to a tRNA synthetase fragment disclosed herein (e.g., a polypeptide selected from SEQ ID NOS: 12-17, 24-29, 36-41, 48-53, and any homologs and analogs thereof.

After binding the target agent, the cleavable tags can be cleaved and separated according to their mobility. More than one tagged probe may be used simultaneously to determine the angiogenic state of a cell/tissue/organism.

In some embodiments, a patient may be diagnosed or screened for one or more conditions associated with angiogenesis (an angiogenesis mediated condition) prior to or subsequent a treatment. For example, an individual may be screened for a condition selected from the group consisting of adiposity, cardiovascular diseases, restenosis, cancer, chronic inflammation, tissue damage after reperfusion, neurodegeneration, rheumatoid arthritis, Crohn's disease, Alzheimer's disease, Parkinson's disease, diabetes, endometriosis, psoriasis, failure in wound healing, and ocular neovascularization. If a patient is diagnosed as having such a condition or being susceptible to such a condition, a therapeutically effective amount of the compositions herein may be administered to the patient. Similarly, a patient may be monitored after a therapeutic treatment is administered to see if additional treatments are required.

Methods for diagnosing or screening patients for conditions are known in the art and include detection of single nucleotide polymorphisms (SNPs) or alleles that are associated with resistance or susceptibility to such conditions. In preferred embodiments, such diagnosis is made using a microarray device. Examples of SNPs that may be used to detect/diagnose an individual with an ocular neovascular condition (or susceptibility thereof) are disclosed in U.S. Pat. No. 6,713,300, which is incorporated herein by reference. Additional SNPs related to angiogenesis-mediated conditions can be identified on the dbSNP database maintained by NCBI at <http://www.ncbi.nlm.nih.gov>.

Business Methods

The invention herein also contemplates business methods by providing therapeutics and/or diagnostics for treating individuals suffering from or susceptible to angiogenic conditions. In some embodiments, a business method of the present invention contemplates searching for an agent that modulates or binds to a receptor of tRNA synthetase fragment and commercializing such an agent. A tRNA synthetase fragment is preferably a tryptophanyl tRNA synthetase fragment. The tryptophanyl tRNA synthetase fragments herein are preferably mammalian, or more preferably human. Examples of human tryptophanyl tRNA synthetase fragments include polypeptides that comprise, consist essentially of, or consist of SEQ ID NOS: 12-17, 24-29, 36-41, 48-53, homologs or analogs thereof. Preferably a tRNA synthetase fragment herein is angiostatic. In some embodiments, the step of searching for an agent that modulates or binds to a receptor of tRNA synthetase fragment involves using a computer program to generate peptidomimetics of the tRNA synthetase fragment. In some embodiments the step of searching involves screening a library of candidate agents to identify an agent that modulates or binds to the receptor. There are various forms of libraries available for screening candidate agents. Such libraries include peptide libraries, and small molecule libraries, as well as others disclosed herein or known in the art.

The present invention also contemplates a business method that includes the steps of modifying a tRNA synthetase fragment to enhance its dimerization capabilities and commercializing the enhanced fragment or dimer form thereof. Again, the tRNA synthetase fragment can be tryptophanyl tRNA synthetase fragment, or more preferably a fragment that are polypeptides comprising, consisting essentially of, or consisting of SEQ ID NOS: 12-17, 24-29, 36-41, 48-53, homologs or analogs thereof. In some embodiments, such business methods contemplate the use of a computer program to optimize the tRNA synthetase fragments herein. Examples of computer programs that can be used to optimize a ligand include, but are not limited to GRID, MCSS, AUTODOCK, DOCK, AMBER, QUANTA, and INSIGHT II. In other embodiments, the business methods herein contemplate generating an expression vector that encodes a tRNA synthetase fragment modified to include one or more non-naturally occurring cysteines. Preferably, such modifications occur in the dimerization domain of the fragment. In other embodiments, the business methods herein contemplate generating an expression vector that encodes two tRNA synthetase fragments. Such vectors can also encode a linker that is preferably situated between the two fragments.

The business methods herein also contemplate commercializing fragments of a tRNA synthetase that modulate angiogenesis. In some embodiments, such fragments may inhibit angiogenesis (e.g., angiostatic fragments of a tRNA synthetase). In other embodiments, such fragments may enhance angiogenesis (.e.g., inhibitors of angiostatic fragments of a tRNA synthetase). Preferably, a business method of the present invention contemplates commercializing compositions that can be used to modulate angiogenesis. Such compositions can be any of the compositions described by the present invention. Preferably, such compositions comprise a first tRNA synthetase fragment having a methionine at its N-terminus and a second tRNA synthetase fragment not having a methionine at its N-terminus. The methionine can be naturally occurring or non-naturally occurring. Examples of a first tRNA synthetase fragment having a methionine at its N-terminus include, but are not limited to, SEQ ID NOS: 15-17, 27-29, 39-41, 51-53, and any homologs, analogs, or fragments thereof. Examples of a second tRNA synthetase fragment not having a methionine at its N-terminus include, but are not limited to, SEQ ID NOS: 12-14, 24-26, 36-38, 48-50, and any homologs, analogs, or fragments thereof. In some embodiments, the compositions herein include about 50% by weight of a tRNA synthetase fragment having a methionine at its N-terminus and about 50% by weight of a tRNA synthetase fragment not having a methionine at its N-terminus. Preferably, such compositions are isolated and/or purified. Such tRNA synthetase may under appropriate conditions form dimers.

In one embodiment, the present invention relates to a business method which includes the steps of expressing an expression vector encoding a tRNA synthetase fragment and commercializing said fragment for modulating angiogenesis. A tRNA synthetase fragment of the present invention can be, for example, a tryptophanyl tRNA synthetase fragment, a human tRNA synthetase fragment, or any angiostatic fragment of a tRNA synthetase. Examples of such fragments include but are not limited to SEQ ID NOS: 12-17, 24-29, 36-41, 48-53, and any homologs and analogs thereof.

In some embodiments, the fragments commercialized are part of a multi-unit complex. A multi-unit complex of the present invention can include two or more monomer units covalently bound or non-covalently associated.

In some embodiments, the expression vector also encodes a second tRNA synthetase fragment. The first tRNA synthetase fragment and the second tRNA synthetase fragment can be different, homologous, substantially homologous, or identical. Moreover, in some embodiments, the first tRNA synthetase fragment and the second tRNA synthetase fragment are modified to include at least one non-naturally occurring cysteine. Such non-naturally occurring cysteine is preferably situated in the dimerization domain of the tRNA synthetase fragments.

An expression vector encoding two or more tRNA synthetase fragments can have the two or more fragments aligned in tandem. In some embodiments, the expression vector can also encode a linker. The polynucleotide sequence encoding the linker can be situated between the sequence encoding the first and the sequence encoding the second tRNA synthetase fragments. A linker of the present invention is preferably sufficiently long to allow said first and said second tRNA synthetase fragments to free rotate and dimerize.

The fragments and multi-unit complexes herein can be prepared by transfecting a host cell with the expression vectors disclosed herein, and maintaining the host cell under a condition that permits the expression of the one or more tRNA synthetase fragments.

The business methods herein also contemplate commercializing diagnostics for detection of angiogenesis-mediated conditions (e.g., either an angiostatic or angiogenic condition).

For example, a diagnostic may be commercialized to detect an angiogenic condition, such as an ocular neovascularization condition or AMD, either independently or in combination with an angiostatic composition disclosed herein (e.g., an angiostatic fragment of a tRNA synthetase, more preferably an angiostatic fragment of a tryptophanyl tRNA synthetase, or more preferably mini-trpRS, T1 and/or T2).

Examples of genetic variations and diagnostics that may be used to detect ocular neovascularization conditions include those disclosed in U.S. Pat. No. 6,713,300, which are incorporated herein by reference for all purposes.

In another example, a diagnostic may be commercialized to detect an anti-angiogenic condition, such as a cardiovascular disease, either independently or in combination with an angiogenic composition disclosed herein (e.g., an inhibitor of an angiostatic fragment of a tRNA synthetase, such as a tryptophanyl tRNA synthetase, e.g., mini-trpRS, T1 and/or T2).

In some embodiments, a diagnostic is used to measure the amount of a composition of the present invention (e.g., mini-TrpRS, T1, or T2) in a patient or an organism. Such data can be used for pharmacokinetic or pharmacodynamic studies. Detection of the composition herein can be made using methods such as ELISA, HPLC, and/or any of the antibodies herein. The amount or level of a composition in a patient or organism can subsequently be used to determine if additional treatment should be administered.

In any of the embodiments herein further contemplate the step of partnering with a third party partner to commercialize the compositions and/or diagnostics herein. Examples of partners can include biotech partners, pharmaceutical partners, consumer products partners, agricultural partners, scientific partners, government partners, etc.

In some embodiments, partners can provide funding or research capabilities to, for example, discover analogs of the compositions herein, discover receptors for the compositions herein, optimize the compositions, run clinical trials on the compositions herein, develop inhibitors for the compositions herein, etc.

Kits

The invention also provides a kit comprising one or more containers filled with one or more of the compositions herein. The kits can include written instructions on how to use such compositions (e.g., to modulate angiogenesis or treat a patient suffering from an angiogenic condition).

In one embodiment, a kit comprises a container wherein the container comprises one or more of the compositions herein. Examples of compositions that may be in a container include: a composition comprising an isolated tRNA synthetase fragment having an amino acid sequence comprising, consisting essentially of, or consisting of SEQ ID NOS: 12-17, 24-29, 36-41, 48-53 and any homologs and analogs thereof. Preferably, such tRNA synthetase fragment does not include a His-tag. Moreover, if a tRNA synthetase fragment comprises, consists essentially of, or consists of SEQ ID NOS: 12, 15, 24, 27, 36, 39, 48, 51 or any homologs or analogs thereof, then such tRNA synthetase fragment is preferable less than 45 kD, more preferably less than 44 kD, 43.9 kD, 43.8 kD, 43.7 kD, 43.6 kD, or more preferably less than 43.5 kD. If a tRNA synthetase fragment comprises, consists essentially of, or consists of SEQ ID NOS: 13, 16, 25, 28, 37, 40, 49, 52, or any homologs and analogs thereof, then such tRNA synthetase fragment is preferably less than 48 kD, more preferably less than 47 kD, or more preferably less than 46 kD. If a tRNA synthetase fragment comprises, consists essentially of, or consists of SEQ ID NOS: SEQ ID NO: 14, 17, 26, 29, 38, 41, 50, 53, or any homologs or analogs thereof, then such tRNA synthetase fragment is preferably less than 53 kD, more preferably less than 52 kD, more preferably less than 51 kD, more preferably less than 50 kD, or more preferably less than 49 kD. Preferably a tRNA synthetase fragment in a container is purified.

In some embodiments, a kit of the present invention comprises a container comprising a multi-unit complex, wherein at least one unit of the multi-unit complex comprises a tRNA synthetase fragment or a homolog or analog thereof. A multi-unit complex can be, for example, a dimer having two units. Monomers of a multi-unit complex can be different from each other, homologous, substantially homologous, or identical. In some embodiments, a multi-unit complex is a dimer having two homologous monomers.

In some embodiments, a kit of the present invention includes a container comprising a first tRNA synthetase fragment and a second tRNA synthetase fragment, wherein the first tRNA synthetase fragment has a methionine at its N-terminus. Preferably, such tRNA synthetase fragments are tryptophanyl tRNA synthetase fragments. More preferably, the first tRNA synthetase fragment has an amino acid sequence comprising, consisting essentially of, or consisting of SEQ ID NOS: 15-17, 27-29, 39-41, 51-53, or any homologs, analogs, or fragments thereof. Preferably, such tRNA synthetase fragments do not include a His-tag.

The second tRNA synthetase fragment may or may not have a methionine at its N-terminus. Examples of tRNA synthetase fragments that do not have a methionine at their N-terminus include polypeptide having an amino acid sequence comprising, consisting essentially of, or consisting of SEQ ID NOS: 12-14, 24-26, 36-38, 48-50, or any homologs, analogs, or fragments thereof. Preferably, such tRNA synthetase fragments do not include a His-tag.

In some embodiments, the first and second tRNA synthetase fragments are about 50% by weight of the composition. Other ratios of a first and a second tRNA synthetase fragments may also be utilized.

In any of the embodiments herein a tRNA-synthetase fragment can be a tryptophanyl tRNA synthetase fragment, a human tryptophanyl tRNA-synthetase, and/or any angiostatic fragment of a tRNA synthetase fragment. Such fragments may further form multi-unit complexes that may be covalently or non-covalently linked.

The composition in the first container may be packaged for systemic administration or local administration. Preferably, the compositions are packaged in single unit dosages. When packaged in single unit dosages, a dose may range between 50-1000 μg/dose.

The kit herein may also include a second therapeutic agent. Such second therapeutic agent may be contained in a second container. Examples of a second therapeutic agent include, but are not limited to an antineoplastic agent, an anti-inflammatory agent, an antibacterial agent, an antiviral agent, an angiogenic agent, and an anti-angiogenic agent. In preferred embodiments, a second therapeutic agent is an anti-angiogenic agent.

In any of the kits herein, a composition comprising a tRNA synthetase fragment may have an experimental pI greater than 7.1, 7.2, 7.3, 7.4 or 7.5.

In some embodiments, a kit of the present invention can include a container comprising an antibody that specifically binds to an epitope of a tRNA synthetase fragment and written instructions for use thereof. In such examples, the tRNA synthetase fragment can be a tryptophanyl tRNA synthetase fragment, a human tRNA synthetase fragment, and/or any angiostatic fragment of a tRNA synthetase. In some embodiments, an angiostatic tRNA synthetase fragment is one selected from the group consisting of SEQ ID NOS: 12-17, 24-29, 36-41, 48-53, and any homologs and analogs thereof.

The kits herein can also include one or more syringes or other delivery devices (e.g., stents, implantable depots, etc.). The kits can also include a set of written instructions for use thereof.

EXAMPLES

Example 1

Preparation of Endotoxin-Free Recombinant TrpRS Purified by Laboratory Techniques (Nickel Affinity Column and Triton X-114)

Endotoxin-free recombinant human TrpRS (GD and SY variants) were prepared as follows: Plasmids encoding full-length TrpRS (amino acid residues 1-471 of SEQ ID NO: 1 and the SY variant thereof), or truncated TrpRS, hereinafter referred to as T2 (SEQ ID NO: 12 (GD variant) or SEQ ID NO: 24 (SY variant)), consisting essentially of residues 94-471 of full length TrpRS and a second truncated TrpRS fragment, hereinafter referred to as T1 (SEQ ID NO: 13 (GD variant) or SEQ ID NO: 25 (SY variant)), consisting essentially of residues 71-471 of full length TrpRS were prepared.

Each plasmid also encoded a C-terminal tag consisting of six histidine residues (e.g. amino acid residues 472-484 of SEQ ID NO: 1), and an initial methionine residue. The $His_6$-tagged T1 (SEQ ID NOS: 13 and 25) had the amino acid sequence of SEQ ID NO: 5 (or SY variant thereof), whereas the $His_6$-tagged T2 has the amino acid sequence of SEQ ID NO: 7 (or SY variant thereof).

The above plasmids containing SY and GD variants of T2 were introduced into *E. coli* strain BL 21 (DE 3) (Novagen, Madison, Wis.). Human mature EMAPII, also encoding a C-terminal tag of six histidine residues, was similarly prepared for use. Overexpression of recombinant TrpRS was induced by treating the cells with isopropyl β-D-thiogalactopyranoside for 4 hours. Cells were then lysed and the proteins from the supernatant purified on HIS-BIND® nickel affinity columns (Novagen™) according to the manufacturer's suggested protocol. Following purification, TrpRS proteins were incubated with phosphate-buffered saline (PBS) containing 1 µM $ZnSO_4$ and then free $Zn^{2+}$ was removed (Kisselev et al., *Eur. J. Biochem.* 120:511-17 (1981)).

Endotoxin was removed from protein samples by phase separation using Triton X-114 (Liu et al., *Clin. Biochem.* 30:455-63 (1997)). Protein samples were determined to contain less than 0.01 units of endotoxin per mL using an E-TOX-ATE® gel-clot assay (Sigma, St. Louis, Mo.). Protein concentration was determined by the Bradford assay (Bio-Rad, Hercules, Calif.) using bovine serum albumin (BSA) as a standard.

Example 2

Cleavage of Human TrpRS by PMN Elastase

Cleavage of human full-length TrpRS by PMN elastase was examined. TrpRS was treated with PMN elastase in PBS (pH 7.4) at a protease:protein ratio of 1:3000 for 0, 15, 30, or 60 minutes. Following cleavage, samples were analyzed on 12.5% SDS-polyacrylamide gels. PMN elastase cleavage of a full-length TrpRS of about 53 kDa generated a major fragment of about 46 kDa (SEQ ID NO: 5, T1, having the C-terminal histidine tag, or an SY variant thereof) and a minor fragment of about 43.5 kDa (SEQ ID NO: 7, T2 having the C-terminal histidine tag or the SY variant thereof). In particular, cleavage of full-length TrpRS (SY variant) by PMN elastase generated a major fragment of about 46 kDa (SEQ ID NO: 25) and a minor fragment of about 43.5 kDa (SEQ ID NO: 24).

Western blot analysis with antibodies directed against the carboxyl-terminal $His_6$-tag of the recombinant TrpRS proteins revealed that both fragments, which were apparent at approximately 46 kDa and 43.5 kDa for either the GD or SY variants, possessed the $His_6$-tag at their carboxyl-terminus. Thus, only the amino-terminus of two TrpRS fragments has been truncated. The amino-terminal sequences of the TrpRS fragments were determined by Edman degradation using an ABI Model 494 sequencer. Sequencing of these fragments showed that the N-terminus sequences were S-N-H-G-P for T1 and S-A-K-G-I for T2, indicating that the amino-terminal residues of the major and minor TrpRS fragments were located at positions 71 and 94, respectively, of full-length TrpRS. These human TrpRS constructs for the GD variant are summarized in FIG. 1.

The angiostatic activity of the major and minor TrpRS fragments was analyzed in angiogenesis assays. Recombinant forms of the major and minor TrpRS fragments SEQ ID NO: 5 and 7 (and SY variants thereof), each having a C-terminal histidine tag (amino acid residues 472-484 of SEQ ID NO: 1) were used in these assays. Both GD and SY variants of T2-TrpRS fragments were capable of inhibiting angiogenesis.

Example 3

Truncated Fragments of Trp-RS Show Potent Angiostatic Effect for Retinal Angiogenesis Angiostatic activity of truncated forms derived from full length tryptophanyl-tRNA synthetase was examined, in a post-natal mouse retinal angiogenesis model. Friedlander et al. (Abstracts 709-B84 and 714-B89, IOVS 41(4): 138-139 (Mar. 15, 2000)) reported that postnatal retinal angiogenesis proceeds in stages in the mouse. The present invention provides a method of assaying angiogenesis inhibition by exploiting this staged retinal vascularization.

Endotoxin-free recombinant mini-TrpRS and T2 (e.g., SEQ ID NOS: 12 and 24) were prepared as recombinant proteins. These proteins were injected intravitreally into neonatal Balb/C mice on postnatal (P) day 7 or 8 and the retinas harvested on P12 or P13. Collagen IV antibody and fluorescein-conjugated secondary antibody were used to visualize the vessels in retinal whole mount preparations. Anti-angiogenic activity was evaluated by confocal microscopic examination based upon the effect of injected proteins on formation of the deep, outer, vascular plexus. Intravitreal injection and retina isolation was performed with a dissecting microscope (SMZ 645, Nikon, Japan). An eyelid fissure was created in postnatal day 7 (P7) mice with a fine blade to expose the globe for injection of T2 (5 pmol) or TrpRS (5 pmol). The samples (0.5 µL) were injected with a syringe fitted with a 32-gauge needle (Hamilton Company, Reno, Nev.). The injection was made between the equator and the corneal limbus; during injection the location of the needle tip was monitored by direct visualization to determine that it was in the vitreous cavity. Eyes with needle-induced lens or retinal damage were excluded from the study. After the injection, the eyelids were repositioned to close the fissure.

On postnatal day 12 (P12), animals were euthanized and eyes enucleated. After 10 minutes in 4% paraformaldehyde (PFA) the cornea, lens, sclera, and vitreous were excised through a limbal incision. The isolated retina was prepared for staining by soaking in methanol for 10 minutes on ice, followed by blocking in 50% fetal bovine serum (Gibco, Grand Island, N.Y.) with 20% normal goat serum (The Jackson Laboratory, Bar Harbor, Me.) in PBS for 1 hour on ice. The blood vessels were specifically visualized by staining the retina with a rabbit anti-mouse collagen IV antibody (Chemicon, Temecula, Calif.) diluted 1:200 in blocking buffer for 18 hours at 4° C. An ALEXA FLUOR® 594-conjugated goat anti-rabbit IgG antibody (Molecular Probes, Eugene, Oreg.—1:200 dilution in blocking buffer) was incubated with the retina for 2 hours at 4° C. The retinas were mounted with slow-fade mounting media M (Molecular Probes, Eugene, Oreg.).

Angiostatic activity was evaluated based upon the degree of angiogenesis in the deep, outer retinal vascular layer (secondary layer) that forms between P8 and P12. The appearance of the inner blood vessel network (primary layer) was evaluated for normal development and signs of toxicity. None of the protein constructs used in this example produced any adverse effects on the primary layer.

FIG. 2 provides a photomicrographic depiction of the ability of T2 to inhibit vascularization of the secondary deep network of the mouse retina. In FIG. 2, row A shows the vascular network of a retina exposed to TrpRS, Row B shows the vascular network of a retina exposed to Mini-TrpRS, and row C shows the vascular network of a retina exposed to polypeptide T2 of the present invention. The first (left) column shows the primary superficial network, and the second column shows the secondary deep network. As is evident from FIG. 2, none of the polypeptides affected the primary superficial network, whereas only T2 significantly inhibited vascularization of the secondary deep network.

Most PBS-treated eyes exhibited normal retinal vascular development, but complete inhibition of the outer vascular layer was observed in about 8.2% (n=73) of the treated eyes.

Figure 3:
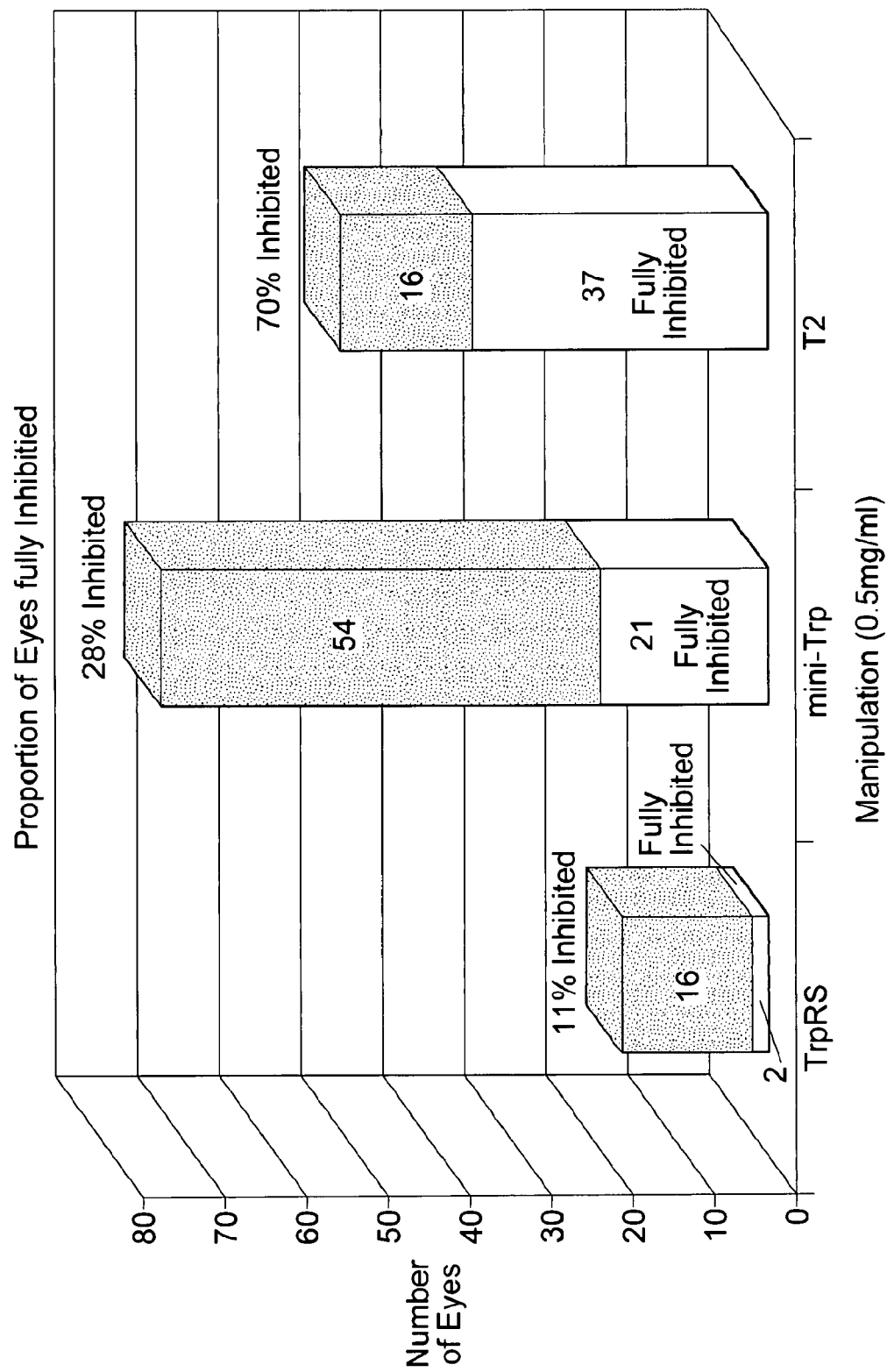
FIG. 3 is a graphical representation of data reported in Example 3, below.

Complete inhibition of the outer network was observed in 28% of mini-TrpRS (0.5 mg/mL)-treated eyes (n=75). The smaller, truncated form (T2) was a far more potent inhibitor of angiogenesis in a dose dependent fashion; 14.3% were completely inhibited after treatment with 0.1 mg/mL of T2 (n=14), 40% after treatment with 0.25 mg/mL (n=20) and 69.8% inhibited completely after 0.5 mg/mL (n=53). The data for the 0.5 mg/mL treatments are presented graphically in FIG. 3. Truncated forms of human TrpRS, especially T2 (e.g., SEQ ID NOS: 12, 24, 36, and 48), have a potent angiostatic effect on retinal vascular development.

Example 4

Matrigel Angiogenesis Assay

Figure 4:
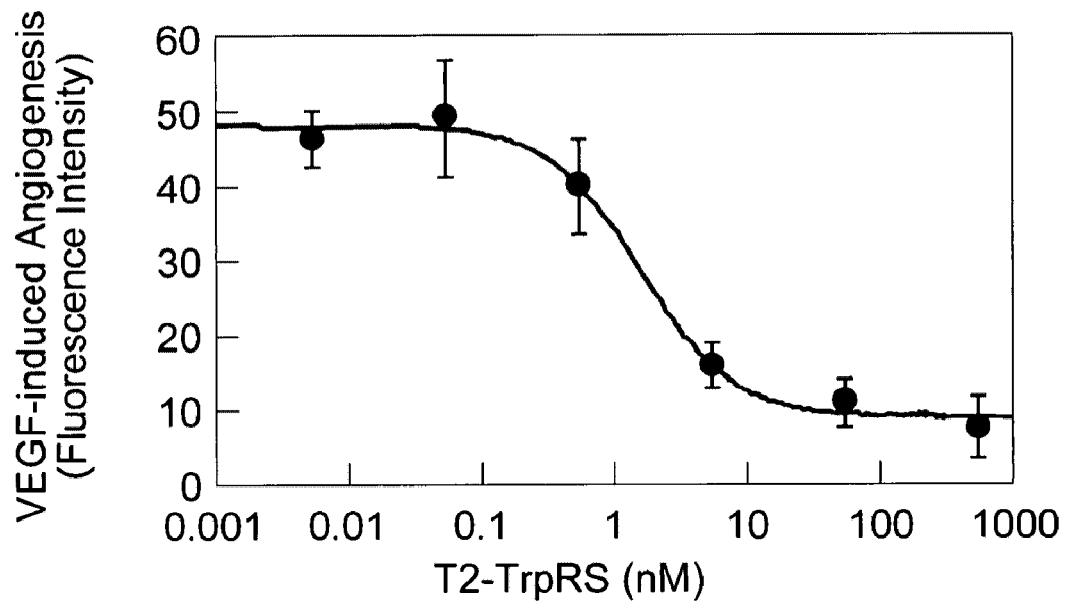
FIG. 4 is a graphical representation of data reported in Example 4, below.

A mouse matrigel angiogenesis assay was used to examine the angiostatic activity of T2 (SEQ ID NO: 7 or SY variant thereof) according to the methods described by Brooks et al. Methods Mol. Biol., 129: 257-269 (1999) and Eliceiri et al. Mol. Cell, 4: 915-924 (1999). It was performed as described with the following modifications. Athymic WEHI mice were subcutaneously implanted with 400 µL growth-factor depleted matrigel (Becton Dickinson, Franklin Lakes, N.J.) containing 20 nM VEGF. The angiostatic activity of T2 was initially tested by including 2.5 µM T2 in the matrigel plug. The potency was determined by including various concentrations of T2 in the plug. On day 5, the mice were intravenously injected with the fluorescein-labeled endothelial binding lectin *Griffonia* (*Bandeiraea*) *Simplicifolia* 1, isolectin B4 (Vector Laboratories, Burlingame, Calif.) and the matrigel plugs were resected. The fluorescein content of each plug was quantified by spectrophotometric analysis after grinding the plug in RIPA buffer (10 mM sodium phosphate, pH 7.4, 150 mM sodium chloride, 1% Nonidet P-40, 0.5% sodium deoxycholate, 0.1% sodium dodecyl sulfate). The data in Example 4 is illustrated in FIG. 4.

Example 5

Localization of T2 Binding within the Retina

To assess the uptake and localization of T2 injected into the retina, ALEXA® 488-labeled (Molecular Probes, Inc., Eugene, Oreg.) T2-TrpRS was injected into the vitreous of the eye on postnatal day 7 (P7). Globes were harvested on P8 and P12 and fixed in 4% PFA for 15 min. The retinas were further dissected free of adherent non-retinal tissue and placed in 4% PFA overnight at 4° C. and then embedded in medium (TISSUE-TEK® O.C.T., Sakura Fine Technical Co., Japan) on dry ice. Cryostat sections (10 micron) were rehydrated with PBS and blocked with 5% BSA, 2% normal goat serum in PBS. Blood vessels were visualized with anti-mouse collagen IV antibody as described above. VECTASHIELD® containing DAPI nuclear stain (Vector Laboratories, Burlingame, Calif.) was used to mount the tissues with a cover slip.

Alternatively, unstained retina sections were incubated with 200 nM ALEXA® 488-labeled full-length TrpRS or ALEXA® 488-labeled T2 in blocking buffer overnight at 4° C. Sections were washed six times for 5 minutes each in PBS, followed by incubation with 1 µg/mL DAPI for 5 minutes for visualization of the nuclei. Pre-blocking with unlabeled T2 was performed by incubating 1 µM unlabeled T2 for 8 hours at 4° C. prior to incubation with ALEXA® 488-labeled T2. Retinas were examined with a multiphoton BioRad MRC1024 confocal microscope. Three dimensional vascular images were produced from a set of Z-series images using the Confocal Assistant software (BioRad, Hercules, Calif.).

Angiostatic Potency of T2 in the Mouse Matrigel Plug Assay

T2 fragments (SEQ ID NO: 7 and its SY variant) were examined to determine whether they had angiostatic activity, even though they had lost aminoacylation activity. The mouse matrigel assay was used to examine the angiostatic activity of T2 in vivo. $VEGF_{165}$-induces the development of blood vessels into the mouse matrigel plug. When T2 was added to the matrigel along with $VEGF_{165}$, angiogenesis was blocked in a dose-dependent manner with a $IC_{50}$ of 1.7 nM as shown in FIG. 4.

ALEXA® 488-labeled T2 Localizes to Retinal Blood Vessels. In order to visualize the intraocular localization of T2, we examined the distribution of ALEXA® 488-labeled T2 following intravitreous injection on postnatal day 7. Retinas were isolated the following day, sectioned and examined using confocal microscopy. The distribution of the injected protein was restricted to blood vessels. This localization was confirmed by co-staining labeled T2 treated eyes with a rabbit, anti-mouse collagen IV antibody (data not shown) and secondarily with an ALEXA FLUOR® 594-labeled goat anti-rabbit IgG antibody. Five days after injection of ALEXA FLUOR® 488-labeled T2 (on P12), the green fluorescence of the labeled T2 was still visible (FIG. 5A). In these retinas, no secondary vascular layer was observed at P12, indicating that the ALEXA FLUOR® 488-labeled T2 retained angiostatic activity comparable to unlabeled T2. Retinas injected on P7 with ALEXA FLUOR® 488-labeled full-length TrpRS developed a secondary vascular layer by P12 but no vascular staining was observed (FIG. 5B). In FIG. 5, ALEXA FLUOR® 488-labeled proteins are green, ALEXA FLUOR® 594-labeled collagen-containing vessels are red, and nuclei are blue.

To further evaluate the binding properties of labeled T2, cross-sectioned slices of normal neonatal retinas were stained with ALEXA FLUOR® 488-labeled T2. Under these conditions, ALEXA FLUOR® 488-labeled T2 only bound to blood vessels (FIG. 5C). The binding was specific as it was blocked by pre-incubation with unlabeled T2 (data not shown). No retinal vessel staining was observed when ALEXA FLUOR® 488-labeled full-length TrpRS was applied to the retinas (FIG. 5D), consistent with the absence of angiostatic activity of the full-length enzyme.

As shown in FIG. 5, ALEXA FLUOR® 488-labeled T2 is angiostatic and localizes to retinal blood vessels. ALEXA FLUOR® 488-labeled T2 (FIG. 5A) or full-length TrpRS (FIG. 5B) were injected (0.5 µL, intravitreous) on postnatal day 7 (P7). The retinas were harvested on P8 and stained with an anti-collagen IV antibody and DAPI nuclear stain, Labeled T2 (upper arrow pointing to vessel in FIG. 5A) localized to blood vessels in the primary superficial network (1°). Note that the secondary deep network is completely absent (2°). While both the primary (1°) and secondary (2°) vascular layers are present in eyes injected with ALEXA FLUOR® 488-labeled full-length TrpRS (arrows in FIG. 5B), no labeling is observed.

In a separate study, frozen sections of P15 retinas were stained with ALEXA FLUOR® 488-labeled T2 (FIG. 5C) or ALEXA FLUOR® 488-labeled full-length TrpRS (FIG. 5D) and imaged in the confocal scanning laser microscope. Labeled T2 selectively localized to blood vessels and appears as a bright green vessel penetrating the primary and secondary retinal vascular layers just below the label "2°" in FIG. 5C. No staining was observed with fluorescently-labeled full-length TrpRS (FIG. 5D).

Full-length TrpRS contains a unique $NH_2$-terminal domain and lacks angiostatic activity. Removing part or this entire domain reveals a protein with angiostatic activity. The $NH_2$-terminal domain, which can be deleted by alternative splicing or by proteolysis, may regulate the angiostatic activity of TrpRS, possibly by revealing a binding site necessary for angiostasis that is inaccessible in full-length TrpRS.

VEGF-induced angiogenesis in the mouse matrigel model was completely inhibited by T2 as was physiological angiogenesis in the neonatal retina. Interestingly, the most potent anti-angiogenic effect of TrpRS fragments in vitro and in CAM and matrigel models is observed in VEGF-stimulated angiogenesis. The neonatal mouse retinal angiogenesis results are consistent with a link between VEGF-stimulated angiogenesis and the angiostatic effects of TrpRS fragments; retinal angiogenesis in this system may be driven by VEGF. In addition, the inhibition observed in the retinal model was specific for newly developing vessels; pre-existing (at the time of injection) primary vascular layer vessels were unaltered by the treatment. While the mechanism for the angiostatic activity of T2 is not known, the specific localization of T2 to the retinal endothelial vasculature and the selective effect of T2 on newly developing blood vessels suggest that T2 may function through an endothelial cell receptor expressed on proliferating or migrating cells. Further understanding of the mechanism of T2 angiostatic activity requires more detailed identification of the mechanism of action.

A variety of cell types that produce, upon interferon-γ stimulation, the angiostatic mini-TrpRS also produce angiostatic factors such as IP-10 and MIG. Thus, these results raise the possibility of a role for TrpRS in normal, physiologically relevant pathways of angiogenesis. Another ubiquitous cellular protein, pro-EMAPII (p43), has two apparently unrelated roles similar to those reported here for TrpRS. Pro-EMAPII assists protein translation by associating with the multisynthetase complex of mammalian aminoacyl tRNA synthetases. It is processed and secreted as EMAPII, and a role for EMAPII as an angiostatic mediator during lung development has been suggested.

Thus, T2 can be utilized in physiologically relevant angiogenic remodeling observed under normal or pathological conditions. In normal angiogenesis, T2 can aid in establishing physiologically important avascular zones present in some organs such as the foveal avascular zone of the central retina. Pathological angiogenesis can occur if the cleavage of full-length TrpRS was inhibited, leading to an overgrowth of vessels.

In ocular diseases, neovascularization can lead to catastrophic loss of vision. These patients can potentially receive great benefit from therapeutic inhibition of angiogenesis. Vascular endothelial growth factor has been associated with neovascularization and macular edema in the retina although it is believed that other angiogenic stimuli also have roles in retinal angiogenesis. We have observed an association between VEGF-stimulated angiogenesis and potent angiostatic activity of TrpRS fragments, making these molecules useful in the treatment of hypoxic, and other, proliferative retinopathies. There has been no report in the literature of an anti-angiogenic agent that completely inhibits angiogenesis 70% of the time, as does the T2 of the present invention (FIG. 5). Another advantage of TrpRS fragments is that they represent naturally occurring and, therefore, potentially non-immunogenic, anti-angiogenics. Thus, these molecules can be delivered via targeted cell- or viral vector-based therapy. Because many patients with neovascular eye diseases have associated systemic ischemic disease, local anti-angiogenic treatment with genetically engineered cells or viral vectors placed directly into the eye is desirable.

In addition to treatment of angiogenic retinopathies, the TrpRS fragments of the present invention, particularly T2-TrpRS and angiogenesis inhibiting fragments thereof, could potentially also inhibit solid tumor growth by preventing vascularization of the tumor. The TrpRS fragments of the present invention block VEGF-induced proliferation and chemotaxis of endothelial cells in vitro, and are thus useful in the treatment of any pathology involving unwanted endothelial cell proliferation and vascularization.

Example 6

Table 6 below summarizes various vector constructs of tRNA synthetase fragments.

TABLE 6

| Name | Antiobiotic Marker | Characteristics Origin |
|---|---|---|
| pAS-001 (SEQ ID NO: 70) | Kan | pET24b+ with a NdeI/HindIII insert of Human T2-TrpRS (SY variant) without 6-His Tag |
| pAS-002 (SEQ ID NO: 71) | Amp | pET20b+ with a NdeI/HindIII insert of Human T2-TrpRS (SY variant), with 6-His Tag |
| pAS-004 (SEQ ID NO: 72) | Amp | pET20b+ with a NdeI/HindIII insert of Human T2-TrpRS, 6-His Tag w/Thrombin Cleavage Site |
| pAS-006 (SEQ ID NO: 73) | Kan | pET24b+ with a NdeI/XhoI insert of Human mini-TyrRS, 6-His Tag |
| pAS-007 (SEQ ID NO: 74) | Kan | pET24b+ with a NdeI/HindIII insert of Human mini-TrpRS (SY variant), 6-His Tag |
| pAS-009 (SEQ ID NO: 75) | Kan | pET24b+ with a NdeI/XhoI insert of Human mini-TyrRS, No His Tag |

The vectors identified in Table 6 were prepared by the following methods:

Plasmid pAS-001. The T2-TrpRS fragment was amplified by PCR using a full-length clone of TrpRS (Invitrogen, clone 3542671) as a template. The oligonucleotides for PCR were based on the T2-TrpRS sequence and contained a 5'-NdeI site and a 3'-HindIII site (in bold italics) (5'GGA GAT ATA CAT ATG AGT GCA AAA GGC ATA GAC TAC 3' and 5'TGC GGC CGC AAG CTT TCA CTG AAA GTC GAA GGA CAG CTT CC 3'). Following amplification, the purified PCR fragment was cleaved with NdeI and HindIII, and then cloned into these same restriction-digested sites of plasmid pET24b+ (Novagen). The resulting plasmid contained a T2-TrpRS sequence, immediately followed by a stop codon. Therefore the His tag sequence was not fused to the T2-TrpRS gene sequence.

Plasmids pAS-002. The T2-TrpRS fragment was amplified by PCR using the full-length TrpRS clone (Invitrogen, clone 3542671) as a template. The oligonucleotides for PCR contained a 5'-NdeI site and a 3'-HindIII site (in bold italics) (5'TGG ACA GTA CAG CAT ATG AGT GCA AAA GGC ATA GAC TAC 3' and 5'TGC GGC CGC AAG CTT CTG AAA GTC GAA GGA CAG CTT CCG 3'). Following amplification, the purified PCR fragment was cleaved with NdeI and HindIII, and then cloned into these same restriction-digested sites of plasmid pET20b+ (Novagen). The resulting plasmid contained an in-frame gene fusion between the carboxy-terminal His tag sequence present in the pET20b+ vector and the T2-TrpRS.

Plasmid pAS-004. PCR based oligonucleotide-mediated introduction of a thrombin cleavage site was used to modify the vector sequence of pAS-002. The oligonucleotides for PCR were based on the T2-TrpRS sequence and contained a thrombin cleavage site (bold italics) (5'-GCT GTC CTT CGA CTT TCA GTC TTC TGG TCT GGT GCC ACG CGG TTC TAA GCT TGC GGC GGC ACT CGA GCA CCA CC 3' and 5'GGT GGT GCT CGA GTG CGG CCG CAA GCT TAG AAC CGC GTG GCA CCA GAC CAG AAG ACT GAA AGT CGA AGG ACA GC 3'). During the PCR reaction, the primers anneal to the same sequence on opposite strands of the plasmid and then were extended with Pfu turbo DNA polymerase (Stratagene), generating plasmids with the thrombin insertion immediately upstream from the 6-His tag. The thrombin cleavage site allows removal of the 6-His tag after protein purification.

Plasmid pAS-006. The mini TyrRS fragment was amplified by PCR using the full-length TyrRS clone (Invitrogen, 4386850) as a template. The oligonucleotides for PCR contained a 5'-NdeI site and a 3'-XhoI site (in bold italics) (5'CCT GCT CAA CAT ATG GGG GAC GCT CCC AGC CCT GAA GAG 3' and 5'CCA GCC GCT CGA GGA TGA CCT CCT CTG GTT CTG MT TC 3'). Following amplification, the purified PCR fragment was cleaved with NdeI and XhoI, and then cloned into these same restriction-digested sites of plasmid pET24b+ (Novagen). The resulting plasmid contained an in-frame gene fusion between the carboxy-terminal His tag sequence present in the pET24b+ vector and the mini TyrRS.

Plasmid pAS-007. The mini-TrpRS fragment was amplified by PCR using the full-length TrpRS clone (Invitrogen, 3542671) as a template. The oligonucleotides for PCR contained a 5'-NdeI site and a 3'-HindIII site (in bold italics) (GTG TCA TTA CAT ATG AGC TAC AAA GCT GCC GCG GGG 3' and 5'CGA TGG GAA GCT TCT GAA AGT CGA AGG ACA GCT TCC G 3'). Following amplification, the purified PCR fragment was cleaved with NdeI and HindIII, and then cloned into these same restriction-digested sites of plasmid pET24b+ (Novagen). The resulting plasmid contained an in-frame gene fusion between the carboxy-terminal His tag sequence present in the pET24b+ vector and the mini TyrRS.

Plasmid pAS-009. The mini TyrRS fragment was amplified by PCR using a full-length clone of TyrRS (Invitrogen, clone 4386850) as a template. The oligonucleotides for PCR were based on the mini TyrRS sequence and contained a 5'-NdeI site and a 3'-XhoI site (in bold italics) (5'CCT GCT CAA CAT ATG GGG GAC GCT CCC AGC CCT GAA GAG 3' and 5'CCA GCC GCT CGA GTC AGA TGA CCT CCT CTG GTT CTG AAT TC 3'). Following amplification, the purified PCR fragment was cleaved with NdeI and XhoI, and then cloned into these same restriction-digested sites of plasmid pET24b+ (Novagen). The resulting plasmid contained a T2-TrpRS sequence, immediately followed by a stop codon. Therefore the His tag sequence was not fused to the T2-TrpRS gene sequence.

In the case of pAS-002 and pAS-007, the gene for either mini TyrRS or T2-TrpRS was fused to a 6-His tag to aid in the purification from the host system for research grade materials. However, the 6-His tag was not used in the final system chosen for the expression and purification of material for pre-clinical development.

Transformations. Plasmids were added to chemically competent E. coli BL21 (DE3) cells (Novagen) and allowed to incubate on ice for 30 minutes. After the incubation, the cells/DNA mixture was heat shocked for 45 seconds at 42° C. The cells were allowed to recover at 37° C. on a rotator for 30 minutes and then plated on LB plates with the appropriate antibiotic.

Protein Purification. Expression of research grade (His tagged proteins) the protein in BL21 (DE3) was induced at $A_{600}$=0.6 by addition of 1 mM isopropyl β-D-thiogalactopyranoside (Novagen) for 4 hours. Cells were harvested by centrifugation, lysed on ice by sonication in column buffer (20 mM Tris-HCl (pH 7.9), 500 mM NaCl, 30 mM imidazole and 5 mM β-mercaptoethanol), and the lysate was cleared by centrifugation at 35,000 g for 30 minutes. The supernatant was loaded onto a Ni-NTA affinity column (Qiagen) pre-equilibrated with column buffer. The column was washed with column buffer containing 0.1% Triton-X 114 (Sigma) to dissociate lipopolysaccharide (LPS) from the protein, followed by additional column buffer to remove residual detergent. The protein was eluted with a gradient of 30-250 mM imidazole in column buffer and stored in PBS (pH 7.5)/50% Glycerol and 2 mM DTT. Purified proteins were assayed for endotoxin by the Limulus Amebocyte Lysate (LAL) assay (BioWhittaker). All purified proteins were more than 95% pure as judged by polyacrylamide gel electrophoresis (4-12% Bis-Tris NuPAGE Gels, Invitrogen). Protein concentration was determined by Bradford assay using the Bio-Rad Protein Assay reagent (Bio-Rad).

Additional variants disclosed herein can be constructed by a person of ordinary skill in the art using similar methods as described above.

Example 7

Preparation of Endotoxin-Free TrpRS Purified by Using a Linear Gradient Column Chromatography System and an Endotoxin Filter E. coli cells were transfected with a vector of SEQ ID NO: 70 identified in Example 6 above. The T2 protein product produced was purified to about 95% purity by the following methods:

Cell Disruption and Clarification of Lysate

In the following cell disruption and lysate clarification procedure, all steps were performed at 4° C. and the pH of all buffers adjusted at 4° C.

The total mass of cell paste collected from the fermentation tank was divided into seven batches, each batch containing approximately 90 g of cell paste. The cell paste for each batch was mixed for approximately 3 minutes with 950 mL of cold Lysis Buffer (25 mM Tris pH 8.0, 10% Glycerol, 1 mM EDTA) using a homogenizer.

The suspension for each batch was then passed twice through an Avestin EmulsiFlex C-50 high pressure homogenizer at 10,000 to 20,000 PSI and collected on ice, taking care that the temperature of the lysate did not exceed 10° C. The homogenizer was then flushed with lysis buffer to remove the residual lysate.

The lysate (~1150 mL) for each batch was then centrifuged at 38,250 g for 55 minutes. The supernatant (~1100 mL) was retained and the pellets were discarded. For each batch, the supernatant was loaded on the Q sepharose HP column as quickly as possible (see Q Sepharose chromatography). All of the above steps for the cell disruption and clarification for any additional batches of cells was performed, followed by immediate loading onto the Q Sepharose column following clarification.

Q Sepharose Chromatography

The supernatant from the centrifugation process was loaded onto a 2.2 L (13 cm diameter, 16.6 cm height) Q Sepharose High Performance column. The column load of the protein should not exceed 5 mL of lysate per mL of resin. The column was pre-equilibrated with 2.5 L of Buffer B (25 mM Tris pH 8.0, 10% glycerol, 1M NaCl) followed by 11 L of Buffer A (25 mM Tris pH 8.0, 10% glycerol). The load flow rate (for the soluble material) was 20-50 mL/min (~10-25 cm/hr) and the column flow through collected.

The column was washed with 30 column volumes (66 L) of Buffer A at 60 mL/min (~30 cm/hr). The column was then eluted with a 20 column volume (44 L) linear gradient, from Buffer A to 20% Buffer B at 100 mL/min (~50 cm/hr) and 500 mL fractions were collected during the elution peak ('Q fractions'). The Q fractions were analyzed by SDS-PAGE (for both the amount of T2-TrpRS in the fraction and the relative purity of the material) and the fractions containing the greatest amounts of purified T2-TrpRS were pooled. Reverse-phase HPLC represents one possible alternative to the use of SDS-PAGE for fraction analysis.

Endotoxin Reduction Filtration

The total pool of Q fractions was filtered at 4° C. through 2 Pall endotoxin reduction filtration cartridges with a Mustang E membrane at 10 mL/min, collecting the flow through. The sample was split between the two filter cartridges and only exposed to the filter membrane once. Approximately 93% of the total protein was recovered following the endotoxin reduction filtration.

Concentration and Buffer Exchange

The endotoxin reduction filtered pool (8500 mL) was concentrated to <1 L using a Cross-Flow (Ultrafiltration) filter (molecular weight cut off of 10,000) at pressures of 5-7 psi. The filtrate was collected and checked by Bradford assay for leaking polypeptide. The concentrated pool (<1 L) was diluted five-fold with CM Buffer A (25 mM HEPES pH 8.0, 10% glycerol) to increase the volume of the sample to 5 L. The conductivity of the final dilution pool was 1.02 mS, whereas the conductivity of the CM Buffer A was 0.74 mS.

CM Sepharose Chromatography

The sample from the buffer exchange process was loaded onto a 1300 mL (13 cm diameter, 9.8 cm height) CM Sepharose Fast Flow column, pre-equilibrated with 6.5 L of Buffer A (25 mM HEPES pH 8.0, 10% glycerol); the load flow rate was 90 mL/min (~40 cm/hr). The column was washed with 15 column volumes (19.5 L) of Buffer A at 70 mL/min (~30 cm/hr). The column was then eluted with a 20 column volume (26 L) linear gradient, from Buffer A to 50% Buffer B (25 mM HEPES pH 8.0, 10% glycerol, 1M NaCl) at 100 mL/min (~50 cm/hr) and 500 mL fractions were collected during the elution peak. The CM fractions were analyzed by SDS-PAGE (for both the amount of T2-TrpRS in the fraction and the relative purity of the material), and fractions containing the greatest amounts of purified T2-TrpRS were pooled. Reverse-phase HPLC represents one possible alternative to the use of SDS-PAGE for fraction analysis.

Final Sample Concentration and Buffer Exchange

The pooled CM fractions (5500 mL) were concentrated to ~150 mL using a Cross-Flow (Ultrafiltration) filter (molecular weight cut off of 10,000 daltons) at pressures of 2-7 psi. The filtrate fractions were collected and checked by Bradford assay for leaking polypeptide. The concentrated pool (145 mL) was dialyzed against 15 L of final storage buffer (5 mM sodium phosphate pH 7.4, 150 mM NaCl, 50% glycerol) using dialysis tubing having a 6000-8000 daltons molecular weight cut off at 4° C. (~16 hours).

Figure 9:
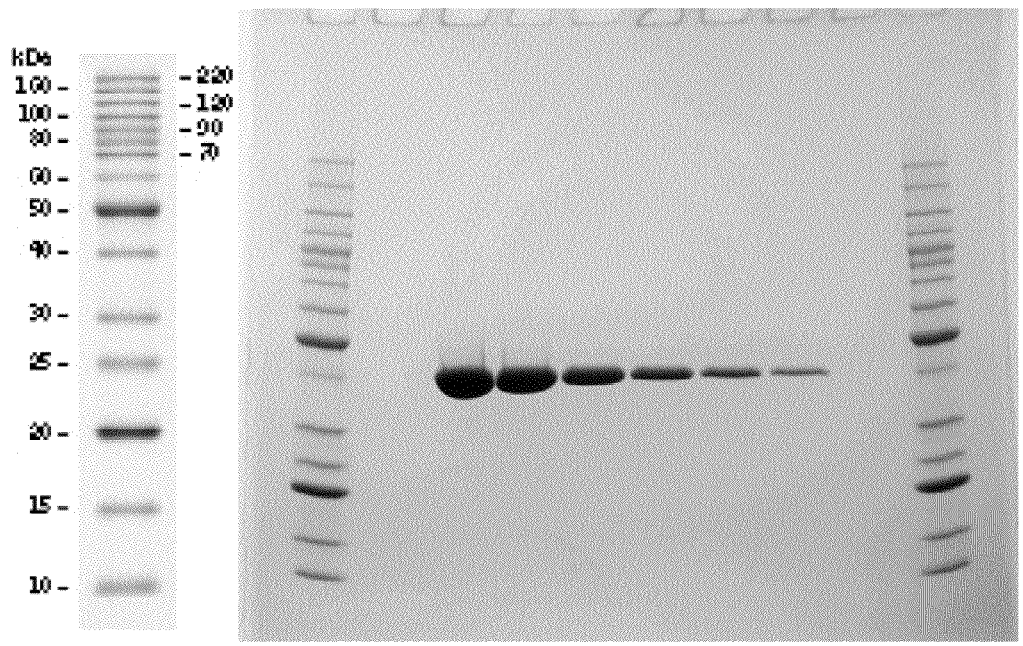
FIG. 9 illustrates a 4-20% Tris-Glycine SDS-PAGE analysis (reducing reconditions) demonstrating purity of a polypeptide produced by a bacteria host cell transfected with a vector of SEQ ID NO: 70, encoding SEQ ID NO: 27 and further purified using one of the methods disclosed herein.

The dialyzed pool (~50 mL) was removed from dialysis and assays were completed on the sample. The final volume of the concentrated sample was 52 mL and the final concentration of the sample was 26.3 mg/mL based on the standard Bradford assay. Final denaturing SDS-PAGE analysis of the sample was completed for a purity determination and is illustrated in FIG. 9. Lanes 1 and 10 illustrate the Invitrogen BenchMark MW Protein Markers. The two heavy molecular weight markers and the three lighter molecular weight markers in between them are identified on the left side of the gel. Their molecular weights vary from 20 kDa to 50 kDa. Lanes 2 and 9 are blank. Lanes 3-8 illustrate various amounts of final T2-TrpRS product. As can be visualized, the T2-TrpRS product produced by *E. coli* transfection of SEQ ID NO: 70 had molecular weight of about 43 kDa. The endotoxin level of this sample, measured using a PyroGene™ endotoxin assay from Invitrogen Corporation, was determined to be 6.25 E.U./mg of protein.

Table 2 below illustrates analysis of T2-TrpRS product from various stages of the purification protocol described above.

TABLE 2

Analysis of T2-TrpRS

| Fraction | Volume (mL) | Protein (mg/mL) | Total Protein (mg) | Recovery % | Purity % |
|---|---|---|---|---|---|
| Q HP pool | 8500 | 0.4 | 3400 | — | >85% |
| Q HP pool post endotoxin filter | 8800 | 0.36 | 3168 | 93% | >85% |
| CM load | 4800 | 0.663 | 3182 | 93.6% | >85% |
| CM pool | 5500 | 0.345 | 1897.5 | 55.8% | >95% |
| CM pool concentrated | 145 | 13.36 | 1937.2 | 57% | >95% |
| Final sample | 52 | 26.3 | 1367.6 | 40.2% | >95% |

Example 8

Preparation of Endotoxin-Free TrpRS Purified by Using a Scaled-Up Manufacturing Process, Including Batch Elution Column Chromatography and an Increased Area of an Endotoxin Filter Low endotoxin T2-TrpRS was produced by expression in an *E. coli* host (BL21-DE3) using a T7 driven plasmid having SEQ ID NO: 70. The cells were grown under cGMP conditions to produce both the Master Cell Bank (MCB) and the Working Cell Bank (WCB).

Growth medium (yeast extract 46.4 g/L, glycerol 4 g/L, and glucose 4 g/L) was prepared and filter sterilized. Kanamycin was added to the solution at a final concentration 50 μg/mL of medium. Growth medium aliquots of 250 mL were transferred into seven sterile 1 L flasks and used for inoculation.

A single stage inoculum was used for the process. A WCB vial was thawed prior to inoculation. Four shake flasks were selected for further process procedures. Fifty (50) mL of media was removed from the 3 shaker flasks not used for further processing for bioburden testing. A 0.2 mL aliquot of the WCB was added to each of four, 1 L shaker flasks containing 0.25 L of growth medium. A sterile pipet tip was used between each flask. The flasks were incubated at 37° C., 200 rpm in an environmentally controlled shaker for 8-10 hours. One flask of the four was used to monitor growth, and the other three were used to inoculate the fermentor. During the shaker flask incubation, the fermentor was filled with fermentation medium, heat-sterilized and allowed to cool. The composition of the fermentation medium was as follows: yeast extract 37.1 g/L, KH$_2$PO$_4$ 6.67 g/L, K$_2$HPO$_4$ 9.67 g/L, Na$_2$HPO$_4$ 18.6 g/L, NH$_4$Cl 1.47 g/L, and NaCl 0.736 g/L.

Additional materials such as the feeding solution (MgSO$_4$ anhydrous 7.3 g/L, glycerol 160 g/L, CaCl$_2$ 0.22 g/L, glucose 32.0 g/L) and trace elements solution (FeCl$_3$.6H$_2$O 27.0 g/L, ZnCl$_2$ 1.3 g/L, CuCl$_2$.2H$_2$O 1.0 g/L, CoCl$_2$ 2.0 g/L, (NH$_4$)$_6$Mo$_7$O$_{24}$.4H$_2$O 2.0 g/L, boric acid 0.5 g/L, concentrated HCl 100 mL/L) were added to the reaction mixture at the correct proportions (0.147 L/L and 0.0022 mL/L, respectively). Pluronic L-61 Antifoam solution (25%, v/v) was added to the fermentor at a ratio of 0.02 mL/L fermentation solution. Additional kanamycin was added to the fermentor to maintain the selection for transfected cells. The pH of the solution was brought to 7.0, using either ammonium hydroxide or phosphoric acid, and the temperature was maintained at 37° C.

After the culture of the sample flask reaches an OD$_{600}$ of 3, the contents of the three other shake flasks were pooled and used to inoculate the fermentation medium in the fermentor. The contents of the inoculum pool, minus the volume of samples, were added to the fermentor. The OD$_{600}$ was measured immediately after inoculation and at 1 hour intervals. The agitation was increased, and the oxygen was supplemented as necessary to maintain the dissolved oxygen (DO) above 30% using automatic controls. When the fermentor reached an OD$_{600}$ of 10, the pre-induction samples were taken and processed.

Induction was performed by addition of IPTG to a final concentration of 0.1 mM. The growth was monitored every hour until the glycerol was exhausted. The consumption of the glycerol resulted in a spike in the DO at 6-8 hours post induction. At that point, samples were taken and processed. The remaining slurry was prepared for cell harvest.

The harvest procedure began with decreasing the temperature setting to 10° C. The pH and DO controls were stopped and the stirrer was slowed to 100 rpm. When the temperature of the slurry reached 25° C., the contents of the fermentor were distributed to centrifuge bottles. The slurry was centrifuged at 4000 (nominal 3300×g) rpm for 15 minutes at 2-8° C. The cell pellets were collected, weighed and resuspended in Cell Lysis Buffer (tris base 3.02 g/L, EDTA 0.29 g/L and glycerol 100 g/L, pH 8.0) such that for every 1 g of cell paste, 10 mL of buffer was used, and stored at 2-8° C. until lysis. The suspended cells were then homogenized with 3 passes through an Avestin Emulsiflux 50 at >9000 psi at 2-8° C. The homogenized slurry was dispensed into centrifuge bottles and centrifuged at 4000 rpm for 45 minutes at 2-8° C. The supernatant was collected and stored at 2-8° C. pending further processing.

The general downstream processing methods are diagramed in FIG. 8. The purification method followed the general theme of the following steps: supernatant clarification; Q Sepharose high performance column chromatography; Mustang E filtration; concentration/buffer exchange; CM Sepharose fast flow column chromatography; concentration/buffer exchange; and sterile filtration and filling.

Supernatant Clarification

Lysis buffer was flushed through a 0.45/0.2 micron sterile capsule filter (Sartobran P, 2 sq. ft membrane) while maintaining a pressure of <20 psig. All air is purged from the system. The supernatant was passed through the system at a rate of 130-150 mL/min. The pump speed was adjusted to achieve <25 psi backpressure. The resulting solution was called the "Clarified Supernatant".

Q Sepharose High Performance (HP) Column Chromatography

The first column chromatography system was designed to increase the purity of the protein by selecting for its binding and elution characteristics. During this step, the protein purity increased to approximately 90% and the endotoxins were reduced to approximately 5% of the starting content (EU/mg protein).

Q sepharose HP resin was loaded into an Amersham BPG 200/500 column and sanitized with 0.5 N sodium hydroxide. The approximate volume of the resin bed was 5 L. The column was connected to an Amersham 6 mm Bioprocess Chromatography system. All solutions were primed, and the system was flushed with a minimum of five (5) column volumes of the loading buffer (25 mM tris+10% (w/w) glycerol, pH 8.0). The Clarified Supernatant was loaded onto the column at a flow rate of 9.4 L/hour. The column was washed with wash buffer (25 mM tris+10% (w/w) glycerol+30 mM NaCl, pH 8.0) at a rate of 9.4 L/hour until 12 column volumes of solution passed through the column and the absorbance ($A_{280nm}$) dropped to <0.05 AU. The product was eluted from the column by passing the elution buffer (25 mM tris+10% (w/w) glycerol+80 mM NaCl, pH 8.0) through the column at a rate of 15 L/hour. The product was eluted in a volume of nine (9) column volumes, which was collected as six (6) 1000 mL fractions (F1-F6), followed by twenty (20) 2000 mL fractions (F7-F26). The peak was collected until the absorbance ($A_{280nm}$) returned to 0.04 AU above baseline. Samples were taken from each fraction and analyzed for T2-TrpRS content. The fractions were stored at 2-8° C. until all analyses were completed. When the fractions containing ≧20% purity of T2-TrpRS were identified, they were combined into one container and renamed the "Q Sepharose HP Pool". The column was cleaned by passing regeneration buffer (25 mM tris+10% (w/w) glycerol+1 M NaCl, pH 8.0) through the column for a minimum of five (5) column volumes at a rate of 9.1 L/hour. Thereafter, the column was sanitized by passing 0.5 N sodium hydroxide through the column at a rate of 17 L/hour for five (5) column volumes. The column was stored in 0.1 N sodium hydroxide.

Mustang E Filtration

The Mustang E filtration system was a solid phase filtration system specifically designed to remove endotoxin from the solution. This step did not result in any appreciable increase in the amount of T2-TrpRS compared to the total amount of protein, i.e., the purity of T2-TrpRS relative to other polypeptides in solution.

A Pall Mustang E capsule (NP6MSTGEP1) was connected to a peristaltic pump and flushed with Water for Injection (WFI). The pressure was maintained at <20 psig, and the air was released by opening the purge valve on the non-sterile (inlet) side of the filter. Approximately three (3) L of WFI was passed through the filter. The Q Sepharose HP Pool was passed through the filter into a depyrogenated carboy at a rate that produces an inlet pressure of <20 psig. When less than 500 mL of the Q Sepharose HP Pool remained, two (2) L of Q sepharose wash buffer (25 mM tris+10% (w/w) glycerol+30 mM NaCl, pH 8.0) was added to the pool. The pump setting was reduced and the remaining material was filtered. The resulting filtrate was named the "Mustang E Filtrate".

Concentration/Buffer Exchange

This ultrafiltration/diafiltration system was designed to reduce the volume and change the buffer system to that of the next chromatography system (CM Sepharose Fast Flow Column Chromatography).

A Pellicon 2 Ultrafiltration Diafiltration (UFDF) system was fitted with five (5) 10 kDa 0.1 m$^2$ cross flow filters. The system was flushed with a minimum of 20 L of WFI, and the clear water flux rate (CWF) was calculated at a transmembrane pressure (TMP) of 10 psig. The system was sanitized with a minimum of 10 L of 0.5 N sodium hydroxide at a TMP of 5 psig. The sodium hydroxide was flushed from the system with WFI. The system was flushed with a minimum of 10 L of CM sepharose fast flow (FF) loading buffer (25 mM HEPES+ 10% (w/w) glycerol, pH 8.0). The system was loaded with a fresh solution of CM sepharose FF loading buffer, and the Mustang E Filtrate was connected to the inlet line. The Mustang E Filtrate was concentrated to a final volume of 15 L at a TMP of 10-12 psig. When the concentration was complete, the diafiltration into the CM sepharose FF loading buffer began using six times the volume of the concentrated Mustang E Filtrate. When the conductivity of the solution reached 1.3 mS/cm, the diafiltration was complete. The final solution was designated "UFDF #1 Retentate". The system was cleaned with 0.5 N sodium chloride and WFI between uses and stored in 0.1 N sodium hydroxide.

CM Sepharose Fast Flow Column Chromatography

The second column chromatography system was designed to increase the purity of the protein by selecting for its binding and elution characteristics. During this step, the protein purity increased to ≧98% and the endotoxins were reduced to <10 EU/mg protein.

CM sepharose FF resin was loaded into an Amersham BPG 200/500 column and sanitized with 0.5 N sodium hydroxide. The approximate volume of the resin bed was 3.2 L. The column was connected to an Amersham 6 mm Bioprocess Chromatography system. All solutions were primed, and the system was flushed with a minimum of five (5) column volumes of the loading buffer (25 mM HEPES+10% (w/w) glycerol, pH 8.0). The UFDF #1 Retentate was passed through a Opticap 4 inch capsule filter (0.2 μm pore size) at <20 psig, and the solution was relabeled "UFDF #1 Retentate Filtrate". The latter solution was immediately loaded onto the CM sepharose column at 31.4 L/hour. Thereafter, the column was washed with 15 column volumes of the loading buffer at the same flow rate until the absorbance ($A_{280nm}$) drops to <0.01 AU and the full volume of wash buffer was used. The product was eluted from the column by passing elution buffer (25 mM HEPES+1.0 M NaCl+10% glycerol, pH 8.0) at a rate of 31.4 L/hour for six (6) column volumes. The elution volume was collected as fractions (F1, F2, etc) in 1 L increments until the absorbance ($A_{280nm}$) falls to 0.01 AU above baseline. Samples were taken from each fraction and analyzed for T2-TrpRS content. The fractions were stored at 2-8° C. until all analyses was completed (not to exceed 24 hours). The column was cleaned by passing regeneration buffer (25 mM HEPES+10% (w/w) glycerol+1 M NaCl, pH 8.0) through the column for a minimum of five (5) column volumes at a rate of 31.4 L/hour. Thereafter, the column was sanitized by passing 0.5 N sodium hydroxide through the column at a rate of 31.4 L/hour for five (5) column volumes. The column was stored in 0.1 N sodium hydroxide.

Concentration/Buffer Exchange

This ultrafiltration/diafiltration system was designed to reduce the volume and change the buffer system to that of the final drug substance formulation (5 mM sodium phosphate+ 150 mM sodium chloride, pH 7.4).

A Pellicon 2 Ultrafiltration Diafiltration (UFDF) system was fitted with one (1) 10 kDa 0.1 m² cross flow filter. The system was flushed with a minimum of 10 L of WFI, and the CWF was calculated at a TMP of 5 psig. The system was sanitized with a minimum of 5 L of 0.5 N sodium hydroxide at a TMP of 5 psig. The sodium hydroxide was flushed from the system with WFI. The system was flushed with a minimum of 2 L of final drug substance formulation buffer. The system was loaded with a fresh solution of final drug substance formulation buffer, and the CM elution fractions identified as having >95% T2-TrpRS content purity were recombined and gently mixed and designated the "CM Sepharose Elution Pool". In the Ultrafiltration mode, the CM Sepharose Elution Pool was concentrated to a target of 15.0 g/L at a TMP of 10-12 psig. When the concentration was complete, diafiltration into the final drug substance formulation buffer began using eight times the volume of the concentrated CM Sepharose Elution Pool. When the diafiltration was complete, the system was drained, and a sample was sent to Quality Control for a stat measurement of protein concentration and purity. If the concentration was in the range of 10-15 mg/mL, the UFDF step was completed. If the concentration fell outside of this range, the system was reinitiated and corrective measures taken to adjust the concentration into the specified range. The system was cleaned with 0.5 N sodium chloride and WFI between uses and stored in 0.1 N sodium hydroxide.

Sterile Filtration and Filling

The final solution was passed through a Millipak 20 (0.22 μm) filter into sterile 1 L PETG bottles. Endotoxin units were measured at 0.003 E.U. per mg protein.

Figure 6:
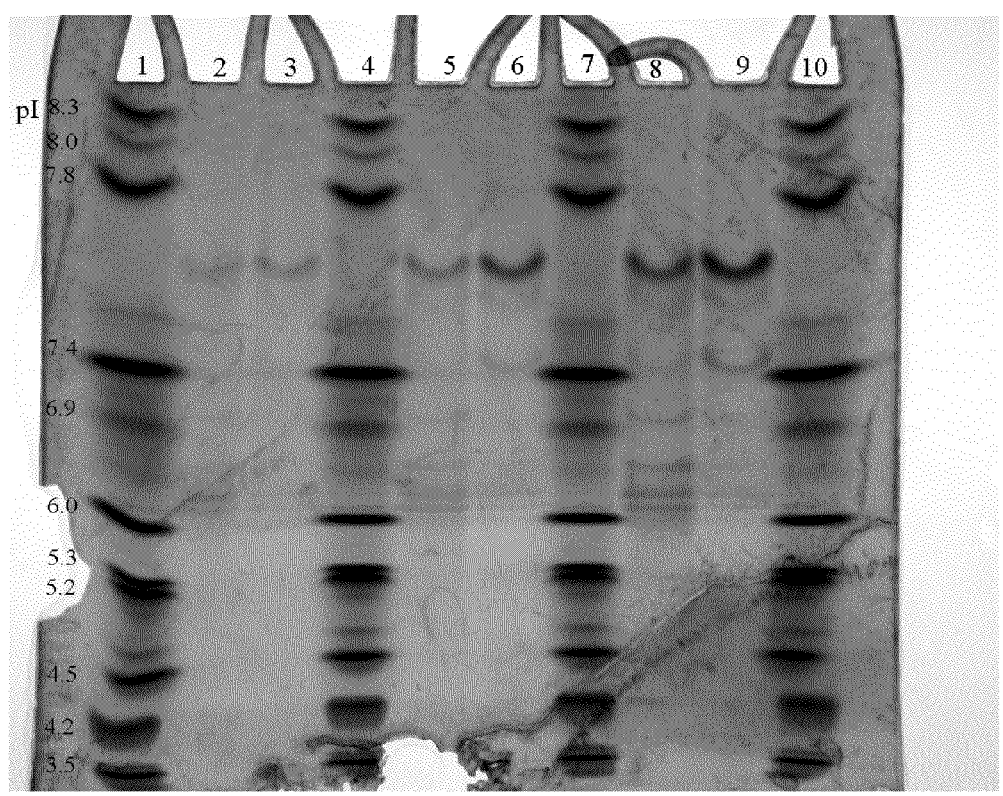
FIG. 6 illustrates experimental pl of a polypeptide recombinantly produced by an expression vector encoding SEQ ID NO: 27.

FIG. 6 illustrates measurements of experimental pI (the effective charge) of a product produced recombinantly by *E. coli* after transfected with a vector of SEQ ID NO: 70 produced by the methods of Example 7 and 8. Sample 1 was produced by the methods of Example 7 and Sample 2 was produced by the methods of Example 8. The purity of Sample 1 is about 95% and the purity of Sample 2 is greater than 99%. Samples were diluted 1:1 with Novex pH 3-10 sample buffer. The marker used was an IEF Marker from Invitrogen™.

The following Table 1 is a summary of each lane.

TABLE 1

| Lane No. | Sample | Load |
|---|---|---|
| 1 | Marker | 5 μL |
| 2 | Sample 1 | 1 μg |
| 3 | Sample 2 | 1 μg |
| 4 | Marker | 5 μL |
| 5 | Sample 2 | 2 μg |
| 6 | Sample 1 | 2 μg |
| 7 | Marker | 5 μL |
| 8 | Sample 2 | 4 μg |
| 9 | Sample 1 | 4 μg |
| 10 | Marker | 5 μL |

While the theoretical pI for monomer T2 having SEQ ID NO: 24 or 27 is 7.1, the experimental pI for the recombinantly produced product was measured at about 7.6, as is illustrated by FIG. 6. This suggests that some of the negative charges of the primary sequence are "hidden" or inaccessible to the local environment.

Example 10

Figure 10:
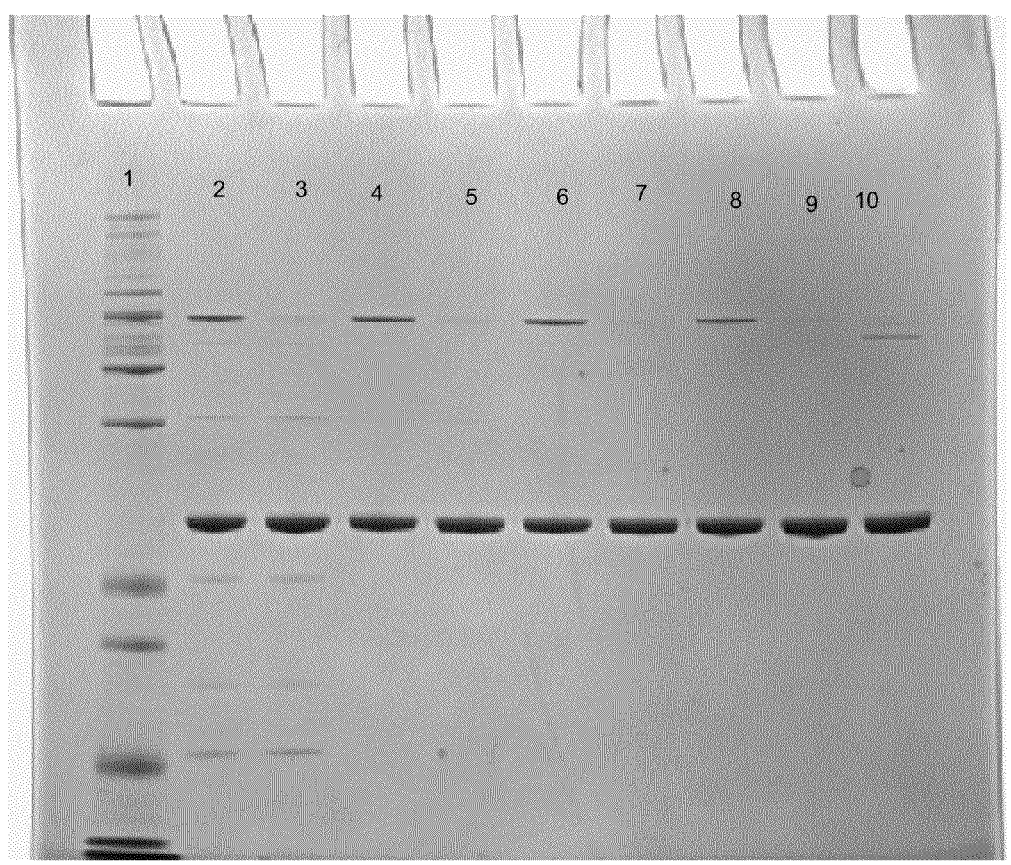
FIG. 10 illustrates an SDS-PAGE gel of samples produced by recombinantly expressing in *E. coli* a vector of SEQ ID NO: 70, which encodes SEQ ID NO: 27, wherein some product is heated.

FIG. 10 illustrates an SDS page gel of T2-TrpRS produced by recombinantly expressing a vector of SEQ ID NO: 70 in *E. coli*. The T2-TrpRS material produced by this method was approximately 99% pure and contained approximately 0.003 E.U./mg protein.

Lane 1 is a Mark 12 Ladder. Lane 2 illustrates a sample of the Load material at the processing step prior to the final purification step using a CM-sepharose column that was not heated prior to starting the gel separation. Lane 3 is the same material after heat has been applied to the sample at or near 100° C. for at least 5 minutes. Lanes 4, 6, and 8 are fractions from the CM-sepharose column without heating the sample prior to starting the gel separation. The T2-TrpRS-containing elution fractions being tested represent early, middle, and late elution from the CM-sepharose column after application of the elution buffer. There were five elution fractions in this study. Lanes 5, 7, and 9 are the fractions of Lanes 4, 6, and 8, respectively, but with heat denaturation of the protein prior to starting gel separation. Lane 10 is a Reference Standard (product approximately 95% pure) also prepared by recombinantly expressing a polynucleotide encoding SEQ ID NO: 27 in *E. coli*.

As is visualized by the gel, Lanes 2, 4, 6, 8, and 10, all include an upper band at roughly 86 kDa. This band disappears when the samples were heated in Lanes 3, 5, 7 and 9. All lanes include a band at roughly 43 kD, which is believed to be the monomer form of the product. This is most likely to occur because the product produced by recombinantly expressing SEQ ID NO: 27 in *E. coli* is a multi-unit complex such as a dimer that is non-covalently associated. Heating results in dissociation of the dimer and visualization of the protein's monomer components.

Example 11

Figure 11:
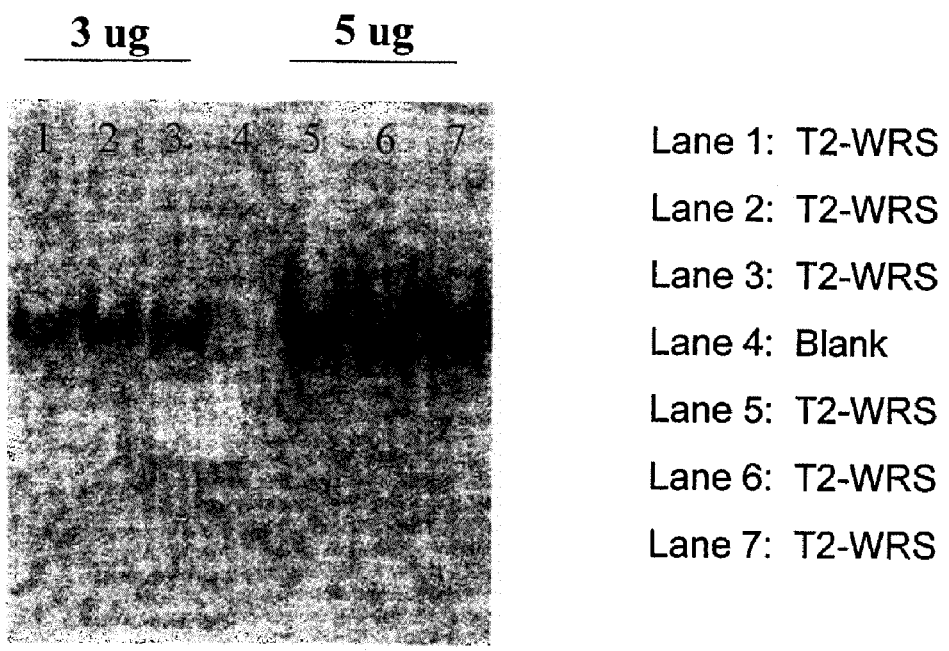
FIG. 11 illustrates a native PAGE gel of a product produced by recombinantly expressing in *E. coli* a vector of SEQ ID NO: 70, which encodes SEQ ID NO: 27.

FIG. 11 illustrates a native gel of T2-TrpRS produced by recombinantly expressing a vector of SEQ ID NO: 70 in *E. coli*, which was further purified to about 99% purity and approximately 0.003 E.U./mg protein.

The gel was a Novex NuPage Tris-Acetate Gel, which did not include SDS or detergent which could disrupt non-covalent bonds. Lanes 1-3 illustrate the product at lower concentrations than Lanes 5-7 (3 μg and 5 μg/lane, respectively). As can be visualized, the samples all run as a single band. This suggests that the purified product is a single form of the molecule (i.e., monomer and dimer do not exist simultaneously using this mode of detection).

Example 12

A sizing HPLC column was used to detect the molecular weight and complexity of a T2-TrpRS product produced by recombinantly expressing vector of SEQ ID NO: 70. The T2-TrpRS product was purified to about 99% and 0.003 E.U./mg protein.

The HPLC column used was Amersham Superdex 200 10/300 GL™, which is a cross linked agarose and dextran column. The mobile phase was 0.2 M Potassium Phosphate and 0.15 Potassium Chloride (pH 6.5). The flow rate (mL/min) was 0.5. Detection was made at three different wavelengths: 215, 254 and 280 nm.

Calibration was made using blue dextran, β-amylase, alcohol dehydrogenase, albumin, carbonic anhydrase, cytochrome c, and sodium azide.

Table 3 below illustrates molecular weight (MW), log MW, retention time (RT), and elution volume for each of the calibrants. Void Volume ($V_0$) was measured as the elution volume of blue dextran at 8.667; Internal Volume ($V_i$) was measured as the elution volume of sodium azide at 26.977, and Total Volume ($W_m$) was 35.654.

TABLE 3

Molecular Weight and Retention Time

| Sample | MW | LogMW | Rt | Elution Volume, ml |
|---|---|---|---|---|
| Blue Dextran | | | 17.353 | 8.677 |
| Sodium Azide | | | 53.954 | 26.977 |
| β-amylase alcohol | 200000 | 5.30103 | 23.307 | 11.654 |
| dehydrogenase | 150000 | 5.176091 | 25.546 | 12.773 |
| albumin | 66000 | 4.819544 | 28.508 | 14.254 |
| carbonic anhydrase | 29000 | 4.462398 | 32.687 | 16.344 |
| cytochrome c | 12400 | 4.093422 | 34.681 | 17.341 |

Table 4 bellow illustrates distribution coefficient for each of the calibrants.

TABLE 4

Distribution Coefficient

| Distribution Coefficient | KD = (Vr − Vo)/(Vm − Vo) = (Vr − Vo)/Vi |
|---|---|
| blue dextran | 0.000 |
| β-amylase alcohol dehydrogenase | 0.110 |
| | 0.152 |
| albumin | 0.207 |
| carbonic anhydrase | 0.284 |
| cytochrome c | 0.321 |
| sodium azide | 0.678 |

Figure 12:
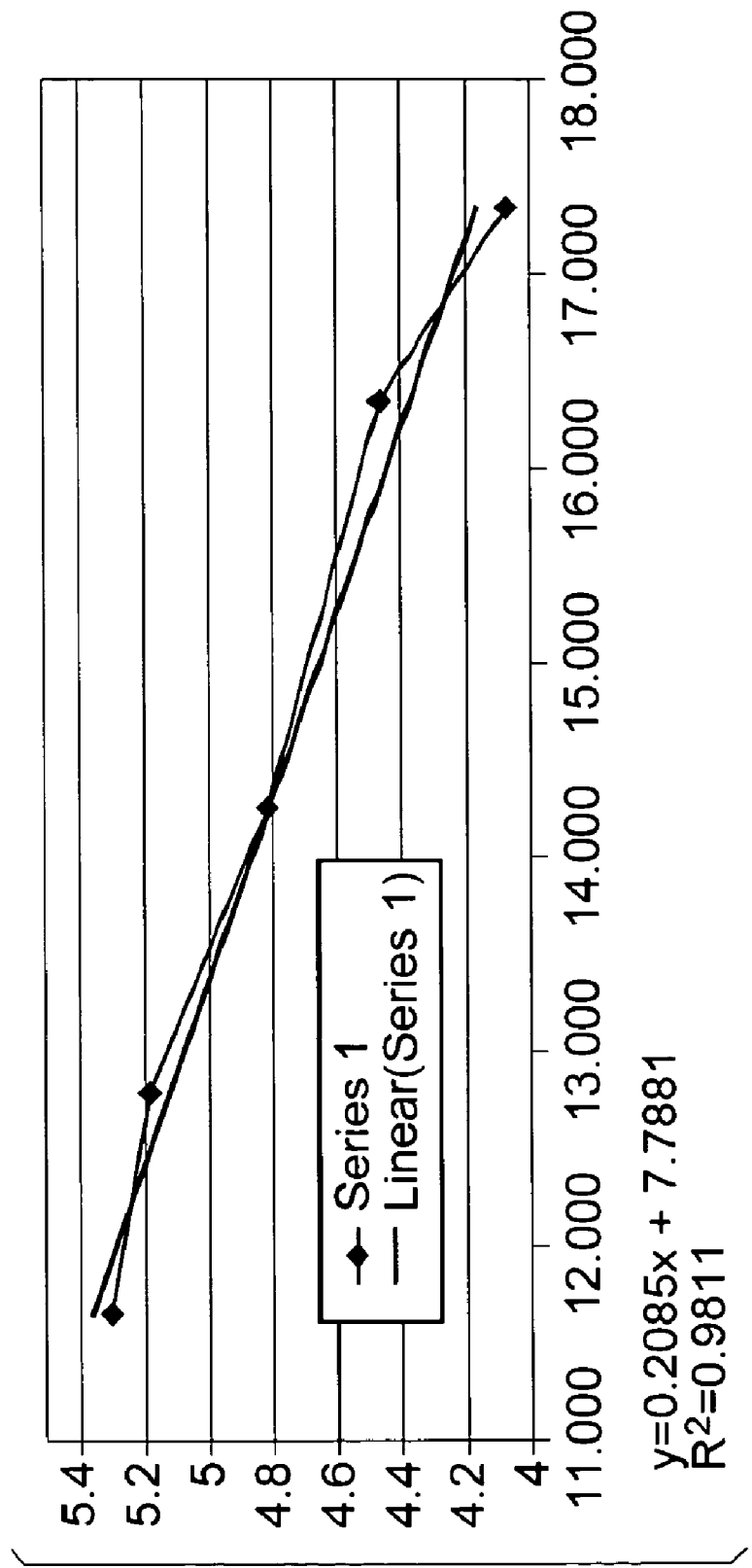
FIG. 12 illustrates a calibration curve wherein the x-axis is the retention time of calibrants per minute and the y-axis is the log MW.

FIG. 12 illustrates a calibration curve wherein the x-axis is the retention time of calibrants per minute and the y-axis is the log MW.

Figure 13:
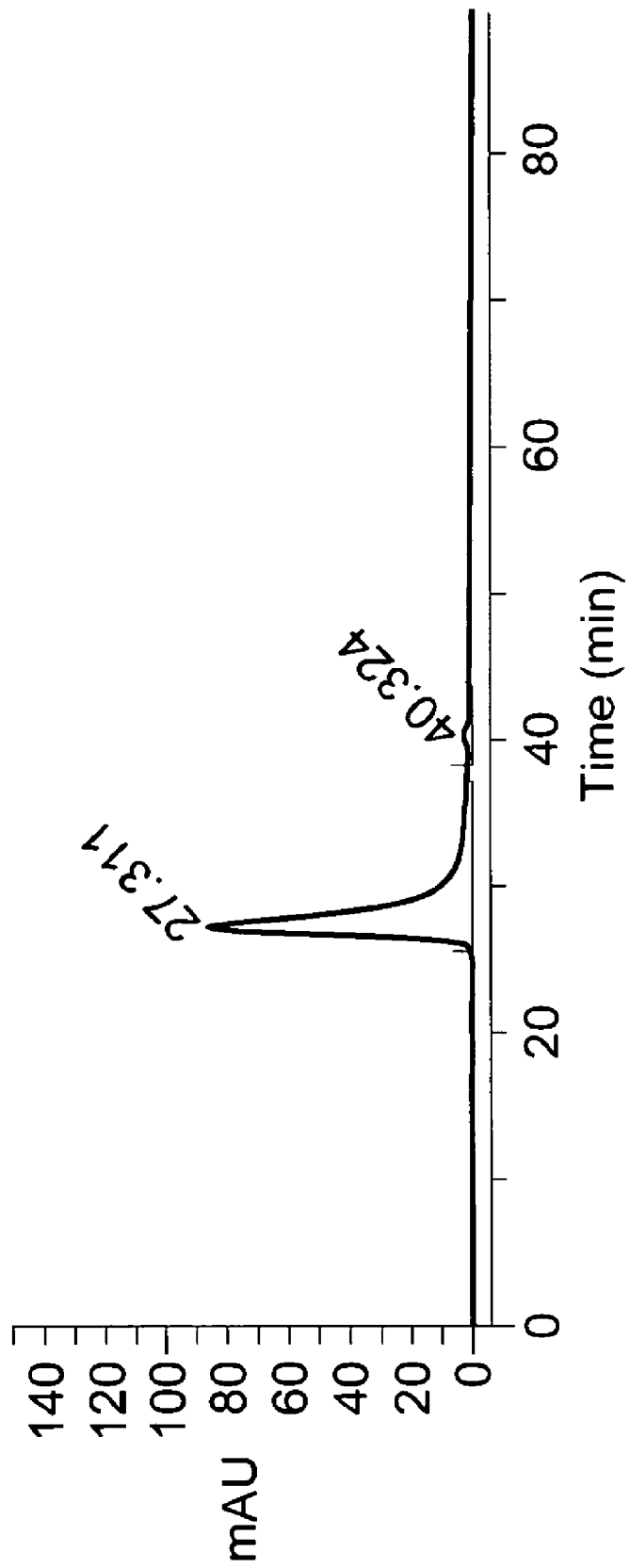
FIG. 13 illustrates a product produced by recombinantly expressing in *E. coli* a vector of SEQ ID NO: 70, which encodes SEQ ID NO: 27, as detected at UV absorbance of 215 nm.
Figure 14:
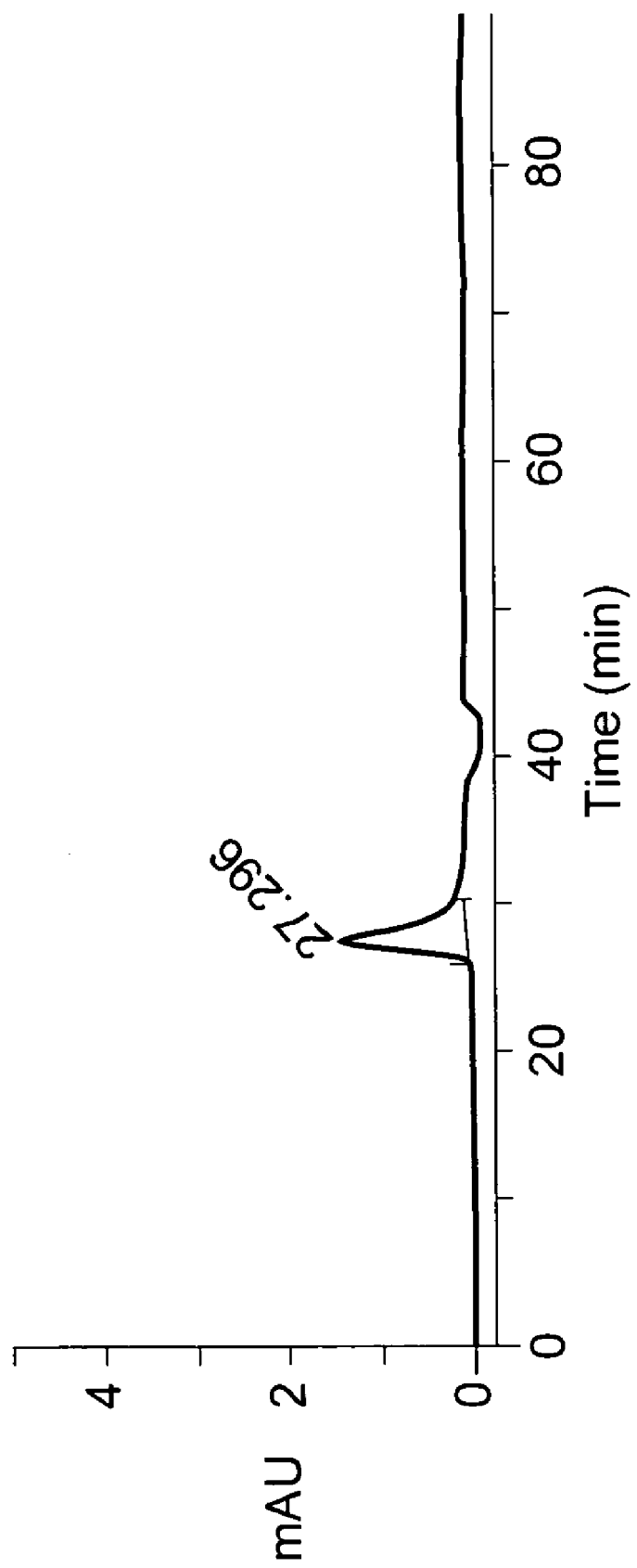
FIG. 14 illustrates a product produced by recombinantly expressing in *E. coli* a vector of SEQ ID NO: 70, which encodes SEQ ID NO: 27, as detected at UV absorbance of 254 nm.
Figure 15:
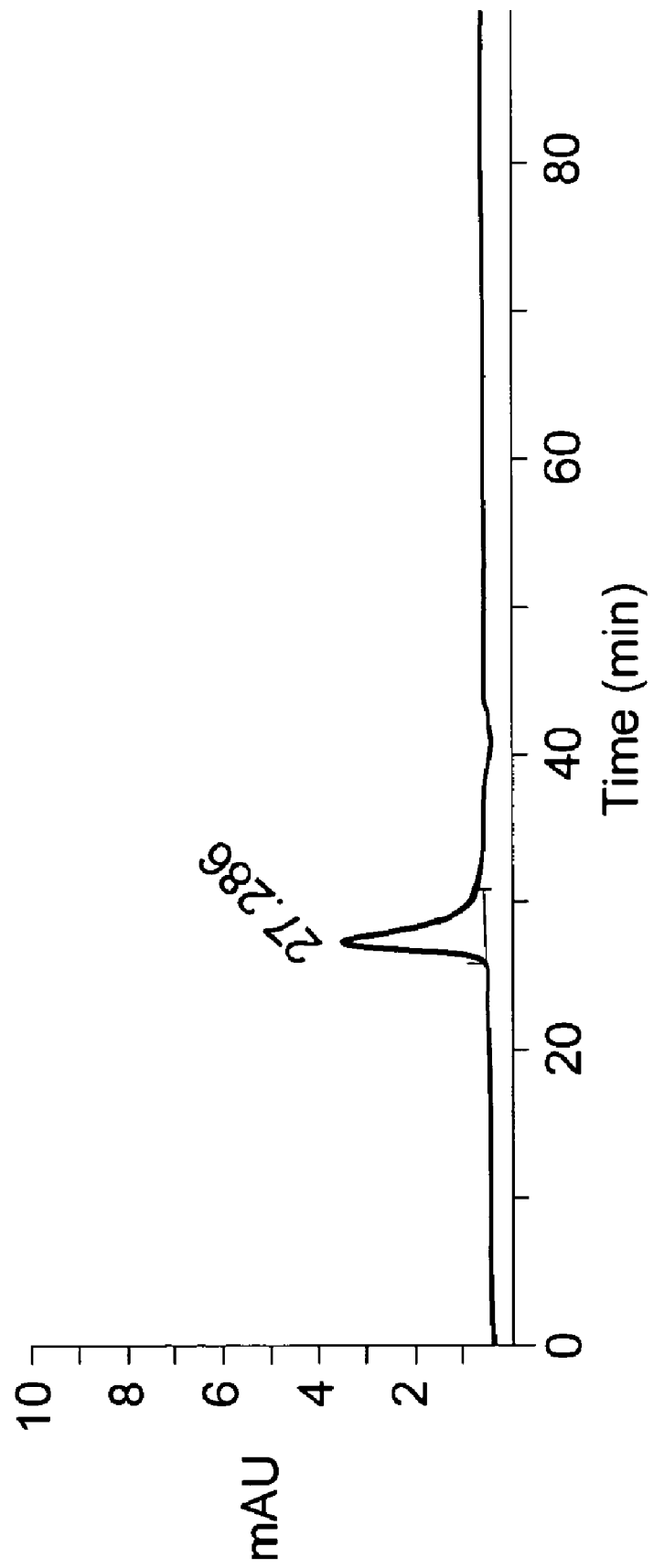
FIG. 15 illustrates a product produced by recombinantly expressing in *E. coli* a vector of SEQ ID NO: 70, which encodes SEQ ID NO: 27, as detected at UV absorbance of 280 nm.

A sample of the purified protein product from expression of SEQ ID NO: 70 was loaded onto the column to identify its molecular weight. Products with larger molecular weight come off of the column sooner than products having lower molecular weight. As is illustrated in FIGS. 13-15, the recombinantly produced product had a retention time of about 27.3 minutes. FIG. 13 illustrates the product detected at UV absorbance of 215 nm. FIG. 14 illustrates the product detected at UV absorbance of 254 nm. FIG. 15 illustrates the product as detected at UV absorbance of 280 nm.

Table 5 below illustrates calculations of the molecular weight of the recombinantly produced product. It was calculated that the product had a molecular weight of 87.283 kD. This confirmed that the product is composed of two monomer units, each approximately 43 kDa.

TABLE 5

Molecular Weight of Sample

| Sample | Rt | Elution Volume, mL | logMW | MW |
|---|---|---|---|---|
| Reference Sample 100x dilution with mobile phase | 27.311 | 13.656 | 4.940928 | 87283 |

Calibration Curve
Slope −0.2085
Intercept 7.7881
R2 0.9811
Flow rate 0.5

Example 13

A reverse phase HPLC was conducted to analyze the purity and establish identity of a product produced by recombinantly expressing a polynucleotide encoding a T2 fragment (e.g., SEQ ID NO: 27) herein. The HPLC system used included a Vydac Protein C4 column, 2.1×150 mm, 5 μm, Part #214TP5215 and a UV detector capable of detection at 210 nm. The mobile phase A (diluent), included 0.1% TFA in water, which was prepared by mixing 1 mL TFA with 1 L water. The mobile phase B, included 0.1% TFA in acetonitrile, which was prepared by mixing 1 mL TFA with 1 L acetonitrile. The acetonitrile is less hydrophobic than water and therefore interferes with lipid interactions of proteins and the column resin surface. After the Vydac column is installed, a diluent is injected as a blank sample. Various amounts of reference material (e.g., purified T2 to about 99% purity) may further be injected to create a standard curve. Later, a sample of a partially purified T2 product (e.g., a product obtained by recombinantly expressing a polynucleotide encoding SEQ ID NO: 27) that has been left at room temperature for three days is injected at a volume of 25 μL. A gradient set of the two mobile phases (A and B) is made as follows:

TABLE 6

HPLC Reverse Gradient Set Up

| Time, minute | % A | % B |
|---|---|---|
| 0 | 85 | 15 |
| 5 | 85 | 15 |
| 25 | 30 | 70 |
| 26 | 5 | 95 |
| 31 | 5 | 95 |
| 32 | 85 | 15 |
| 37 | 85 | 15 |

Figure 20:
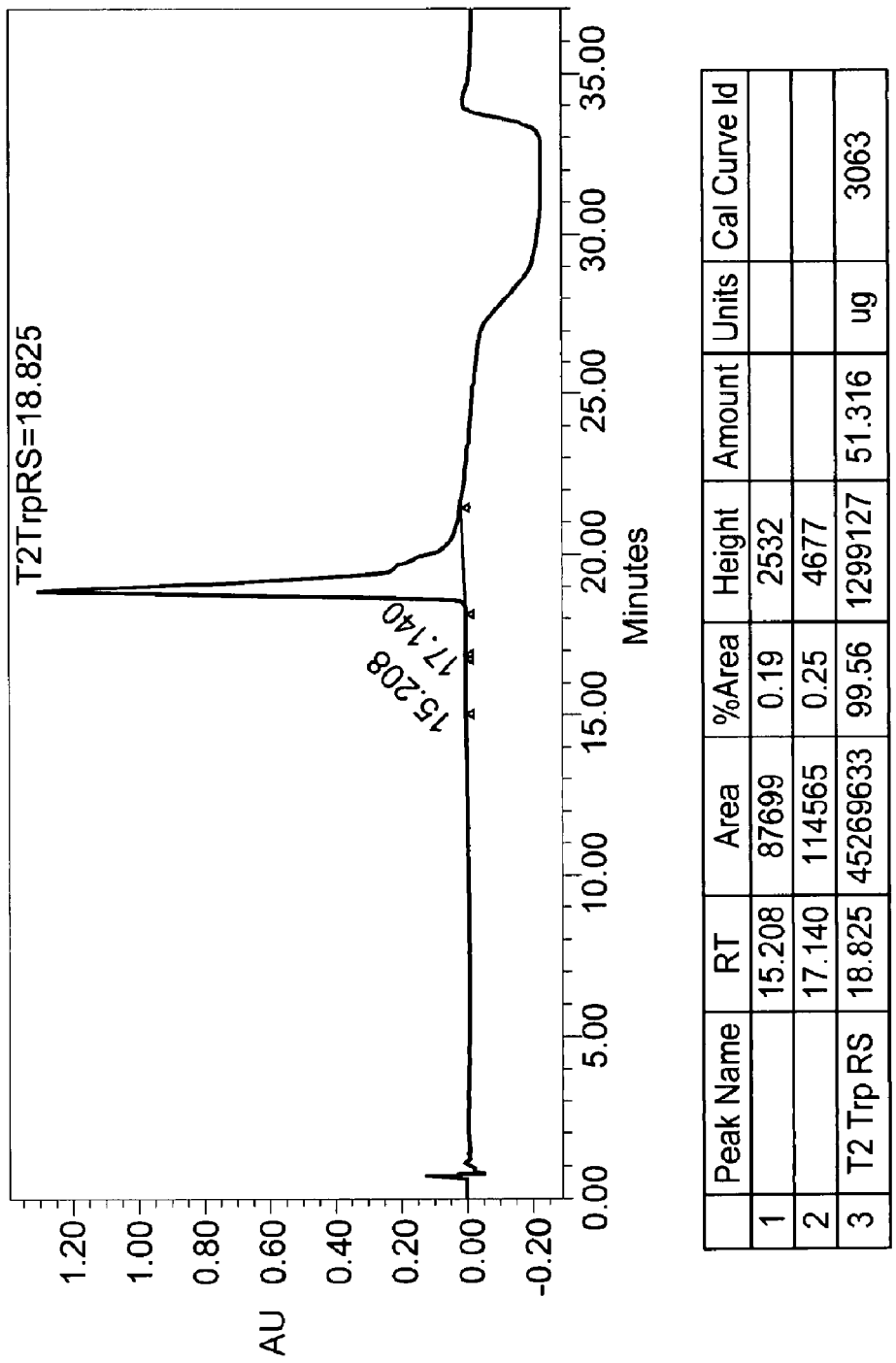
FIG. 20 illustrates results from a reverse phase HPLC column of a product produced by *E. coli* expression of a polynucleotide encoding SEQ ID NO: 27, purified to reduce endotoxin levels.

The column flow rate of the column is maintained at 0.50 mL/minute and the column temperature is maintained at 40° C. The main product peak retention time can be identified by comparing sample retention time to reference material retention time. Results from the reverse phase HPLC column are illustrated in FIG. 20. The x-axis illustrates retention rate in minutes. The y-axis illustrates absorbance units.

A single peak at roughly 18.825 illustrates that the product is one species (roughly 99.56% of the area under the curve was at a retention time of 18.825 min.±1 min.). It also demonstrates that the product, which is a dimer does not cleave or fall apart when left at room temperature for three days.

Example 14

Edman degradation was performed on two T2-TrpRS products produced by E. coli expression of vector of SEQ ID NO: 70. The first product was purified to about 95% purity and the second product was purified to about 99.5% purity. Both products had an N-terminal sequence that began with SAK.

Example 15

About 0.5 μL of products produced by E. coli transfected with a vector of SEQ ID NO: 70, and purified to about 95%±4% purity (Product A) and to about 99.5%±0.5% purity (Product B) were subjected to MALDI-TOF (Voyager DE-STR) mass spectrum analysis.

Figure 21:
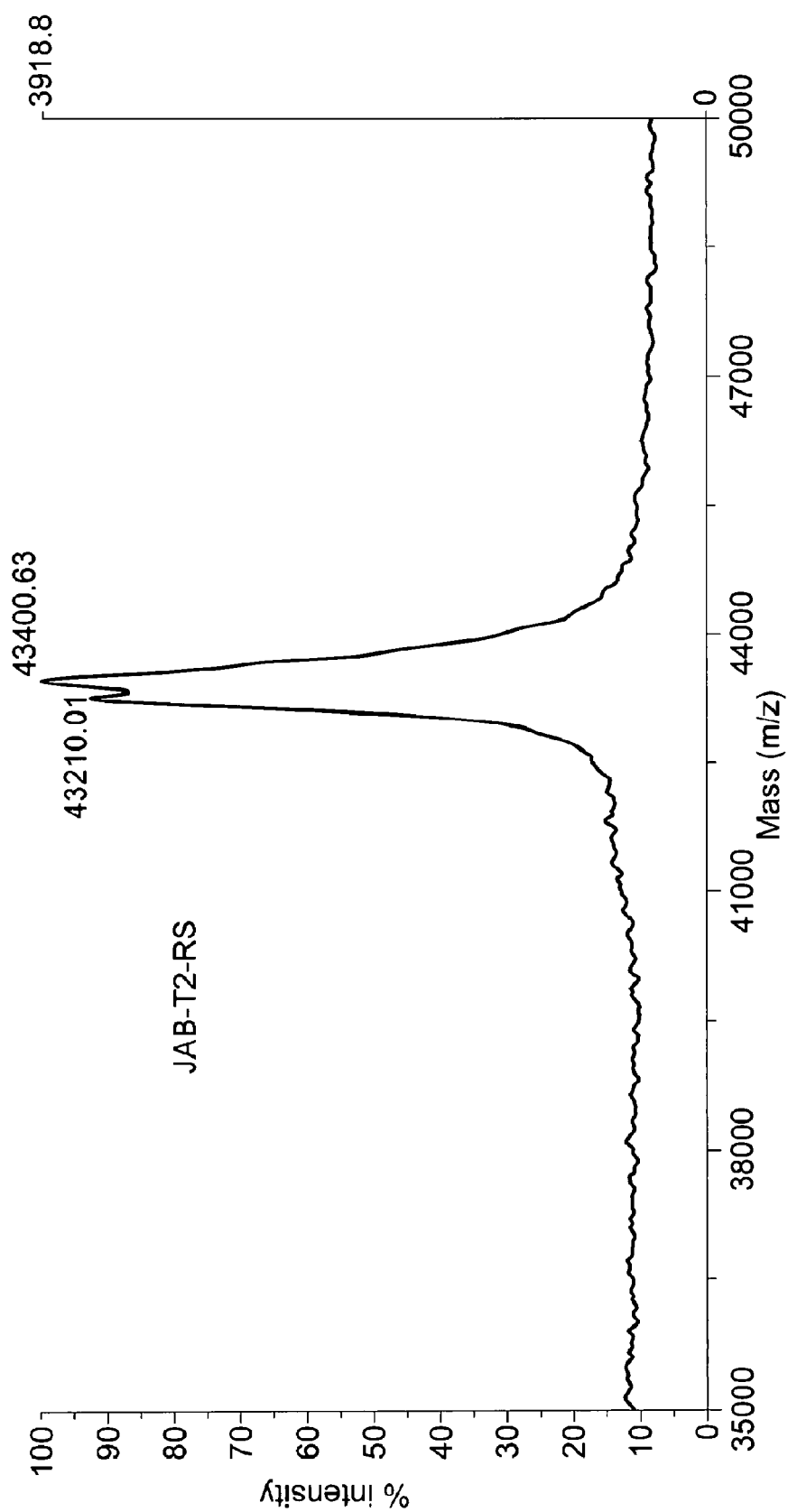
FIG. 21 illustrates MALDI-TOF spectrum of a product produced by recombinant *E. coli* expression of vector SEQ ID NO: 70, which is then purified to about 95% purity ±4%.
Figure 22:
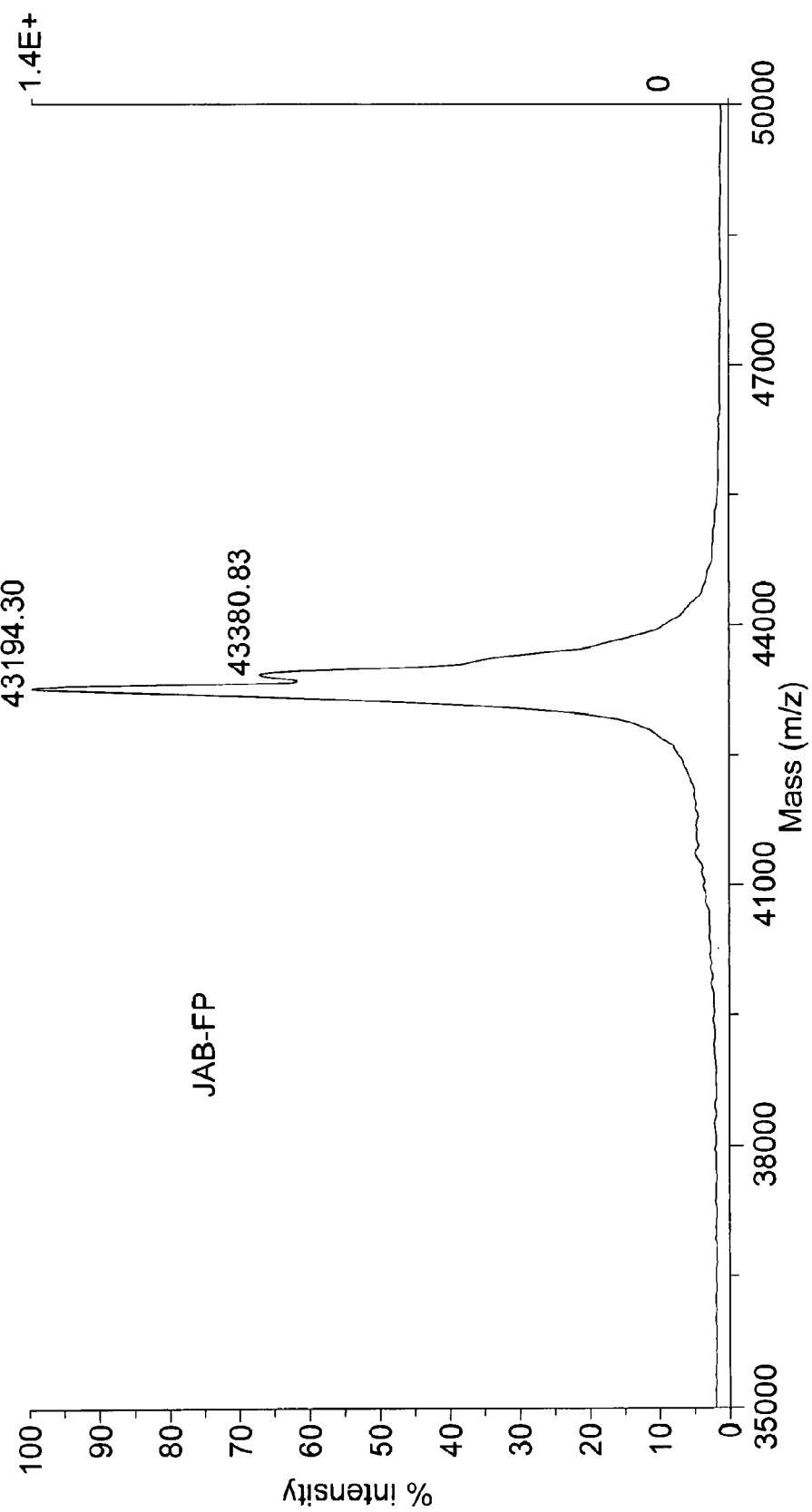
FIG. 22 illustrates a MALDI-TOF spectrum of a product produced by recombinant *E. coli* expression of vector SEQ ID NO: 70, which is then purified to about 99%±1% purity.

Two major masses were observed in the MALDI-TOF spectra for both the Product A (43210/43400 Da±30 Da) and Product B (43194/43380 Da±30 Da). The potentially doubly charged ions may indicate the presence of more than one protein mass per sample. FIG. 21 illustrates MALDI-TOF spectrum of Product A. FIG. 22 illustrates MALDI-TOF spectrum of Product B. The two peaks may be a result from having some product containing an N-formyl methionine not cleaved after protein translation; a matrix effect from the MALDI-TOF device; or other chemical or post-translational modification of the product.

Example 16

T2-TrpRS product produced by transfection of E. coli with a vector of SEQ ID NO: 70 was analyzed using electrospray (ESI) mass spectra (QSTARpulsar, Applied Biosystems) and MALDI-TOFF mass spectra (Voyager De STR, Applied Biosystems) to further characterize the resulting T2-TrpRS product, to determine whether the ends were modified, and to determine whether the N-terminus had methionine, no methionine, or a modified methionine.

Figure 23:
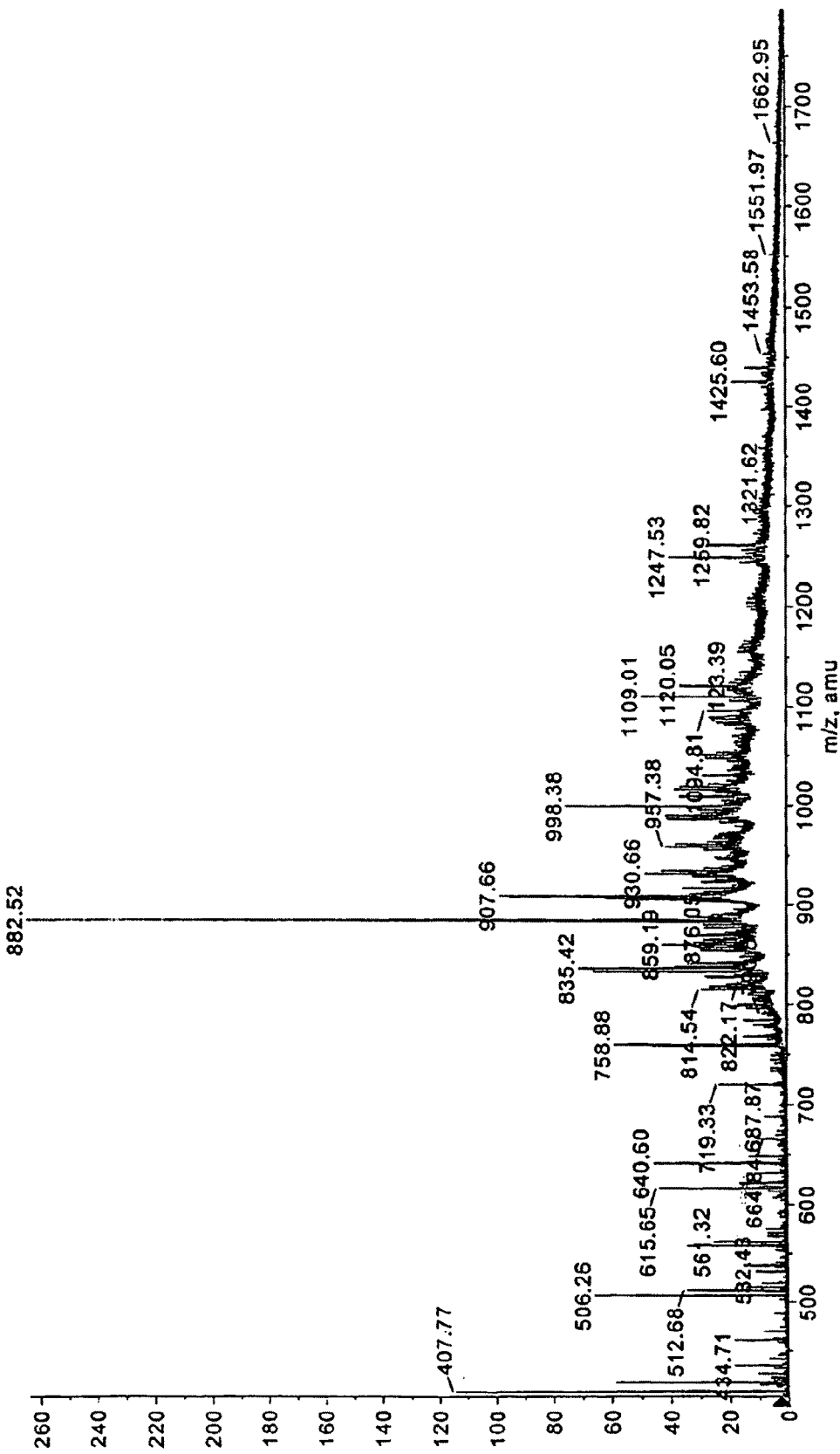
FIG. 23 illustrates mass spectrum of a product produced by recombinant expression of SEQ ID NO: 70 in *E. coli*, followed by purification to greater than 99% purity and removal of substantially all endotoxins, which is then digested by GluC.

FIG. 23 illustrates mass spectrum of the T2-TrpRS product produced by transfection of E. coli with a vector of SEQ ID NO: 70, and further purification of the product to about 99.5% purity and 0.003 E.U./mg protein, digested by GluC.

Figure 24:
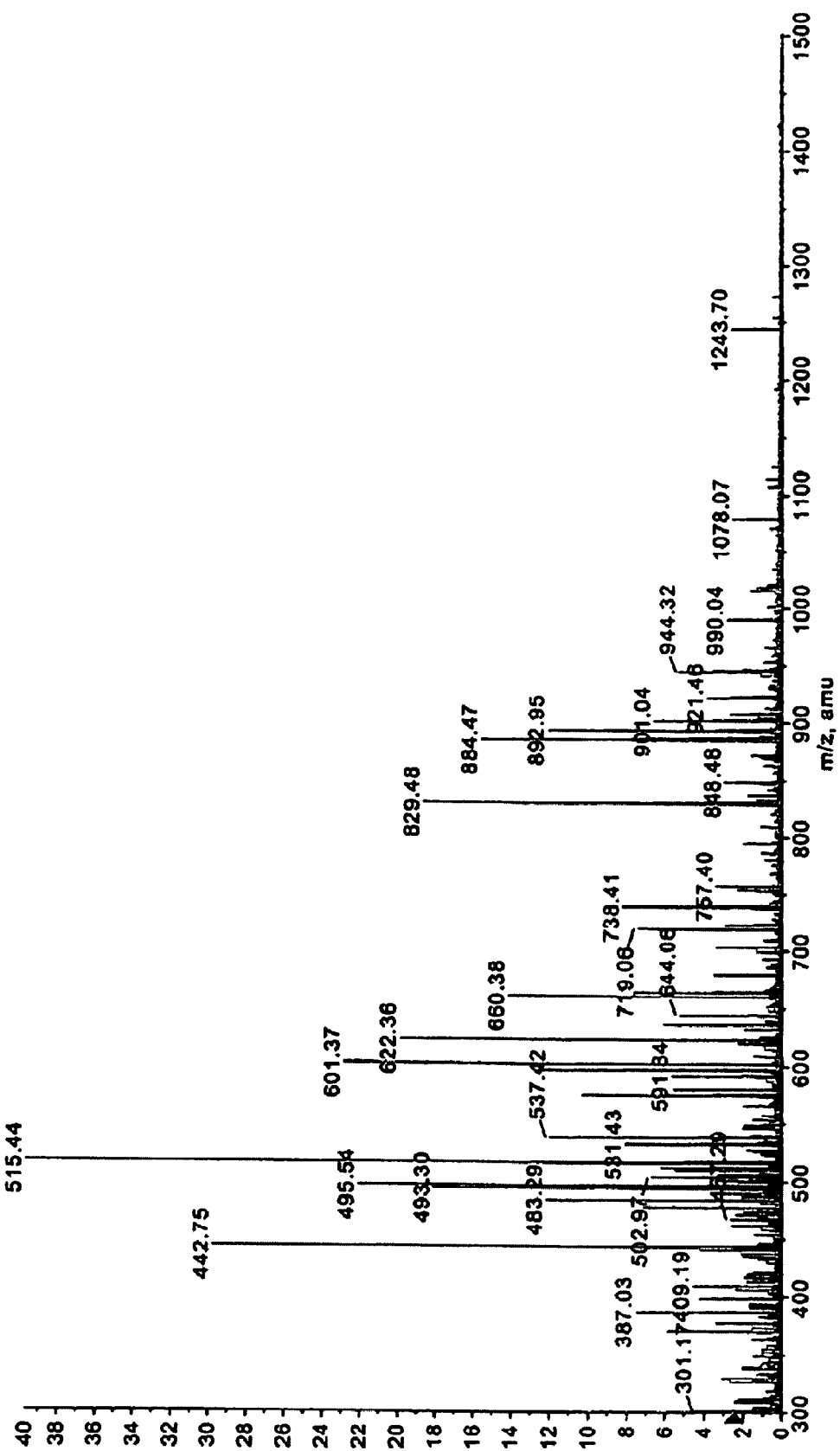
FIG. 24 illustrates mass spectrum of a product produced by recombinant expression of SEQ ID NO: 70 in *E. coli*, followed by purification to greater than 99% purity and removal of substantially all endotoxins, which is then digested with trypsin.

FIG. 24 illustrates mass spectrum of the T2-TrpRS product produced by transfection of E. coli with a vector of SEQ ID NO: 70, and further purification of the product to about 99.5% purity and 0.003 E.U./mg protein, digested with trypsin.

Figure 25:
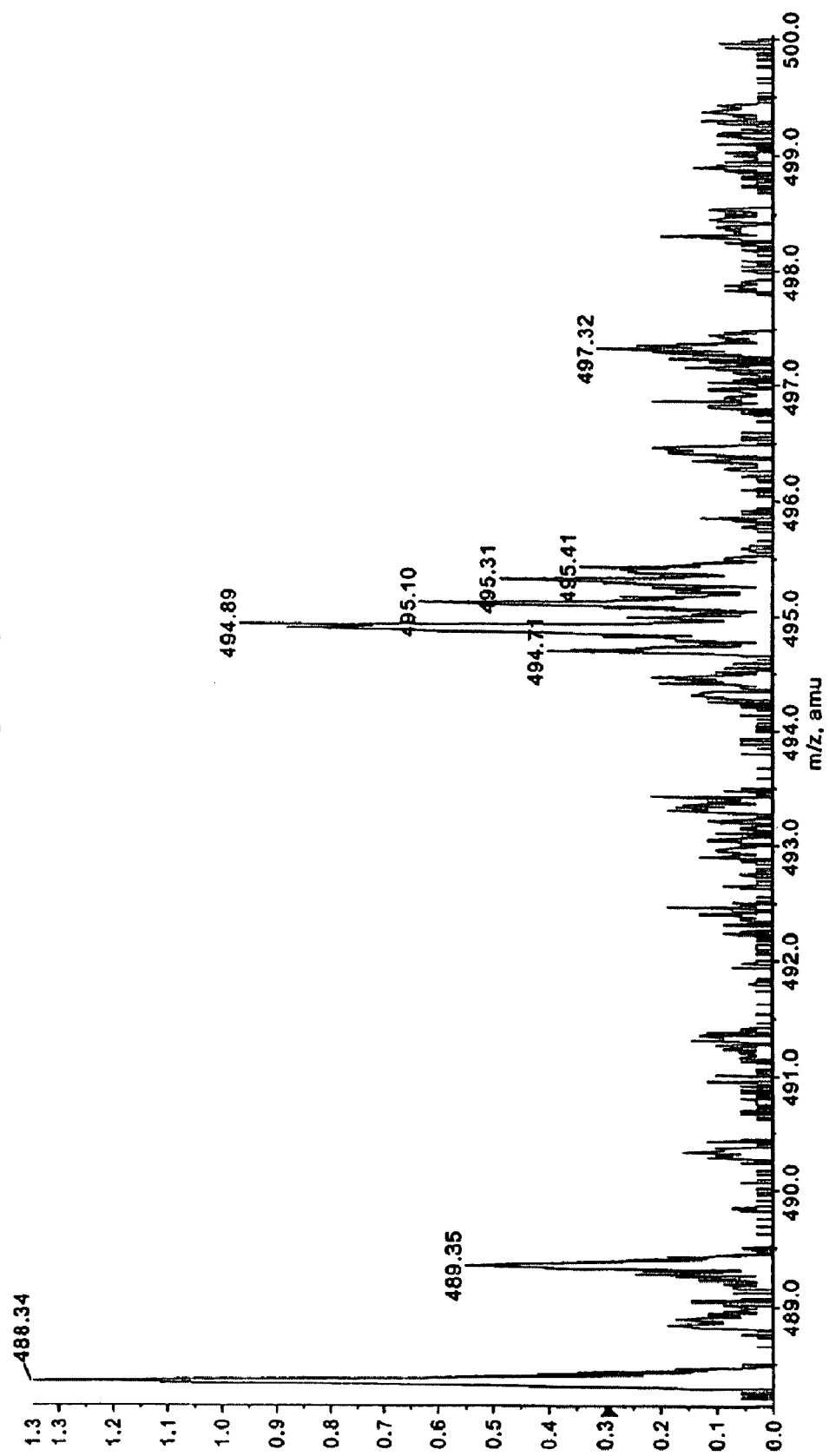
FIG. 25 illustrates mass spectrum of a product produced by recombinant expression of SEQ ID NO: 70 in *E. coli*, followed by purification to greater than 99% purity and removal of substantially all endotoxins, which is then digested with GluC showing the N-terminal peptide without a methionine at 494 m/z (Mr=2468).

FIG. 25 illustrates mass spectrum of the T2-TrpRS product produced by transfection of E. coli with a vector of SEQ ID NO: 70, and further purification of the product to about 99.5% purity and 0.003 E.U./mg protein, digested with GluC showing the N-terminal peptide without a methionine at 494 m/z (Mr=2468). A mass corresponding to N-terminus with methionine or a formyl, oxidized, methylated or acetylated methoinine was not observed. It is noted that the charge state of this peptide is 5. The isotopic masses in this series differ by ⅕ or 0.2 Da. Overall, the signal intensity of the N-terminus without a methionine was below 10 counts even when the protein concentration was as high as 0.4 μg/μL.

Figure 26:
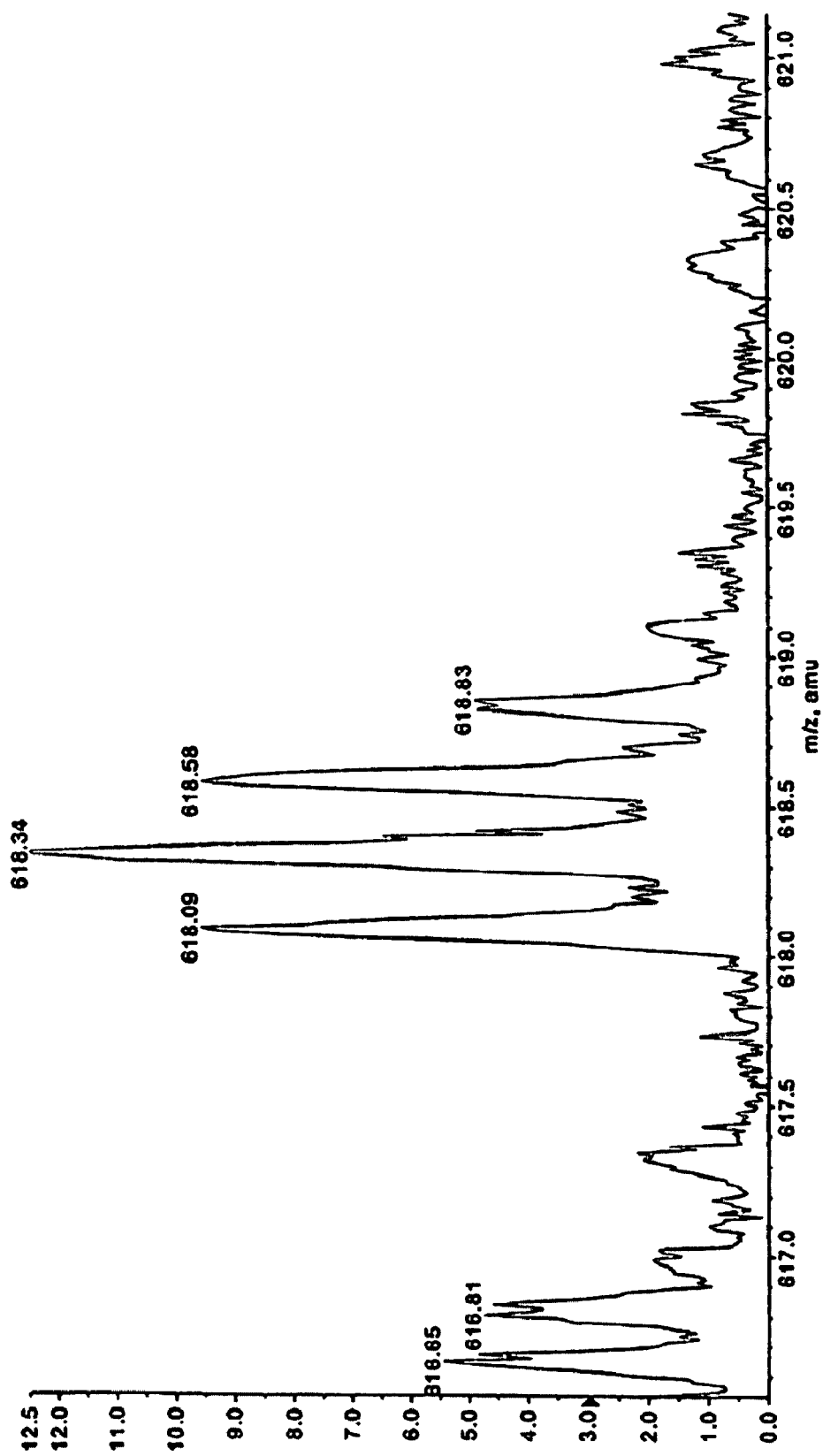
FIG. 26 illustrates mass spectrum of a product produced by recombinant expression of SEQ ID NO: 70 in *E. coli*, followed by purification to greater than 99% purity and removal of substantially all endotoxins, which is then digested with GluC showing N-terminal peptide without a methionine at 618 m/z (Mr=2468).

FIG. 26 illustrates mass spectrum of T2-TrpRS product produced by transfection of E. coli with a vector of SEQ ID NO: 70, and further purification of the product to about 99.5% purity and 0.003 E.U./mg protein, digested with GluC showing N-terminal peptide without a methionine at 618 m/z (Mr=2468). It was noted that the charge state of this T2-TrpRS product was 4. The isotopic masses in this series differed by ¼ or 0.25 Da. Overall, spectra for T2-TrpRS product produced showed that the protein was partially digested.

Figure 27:
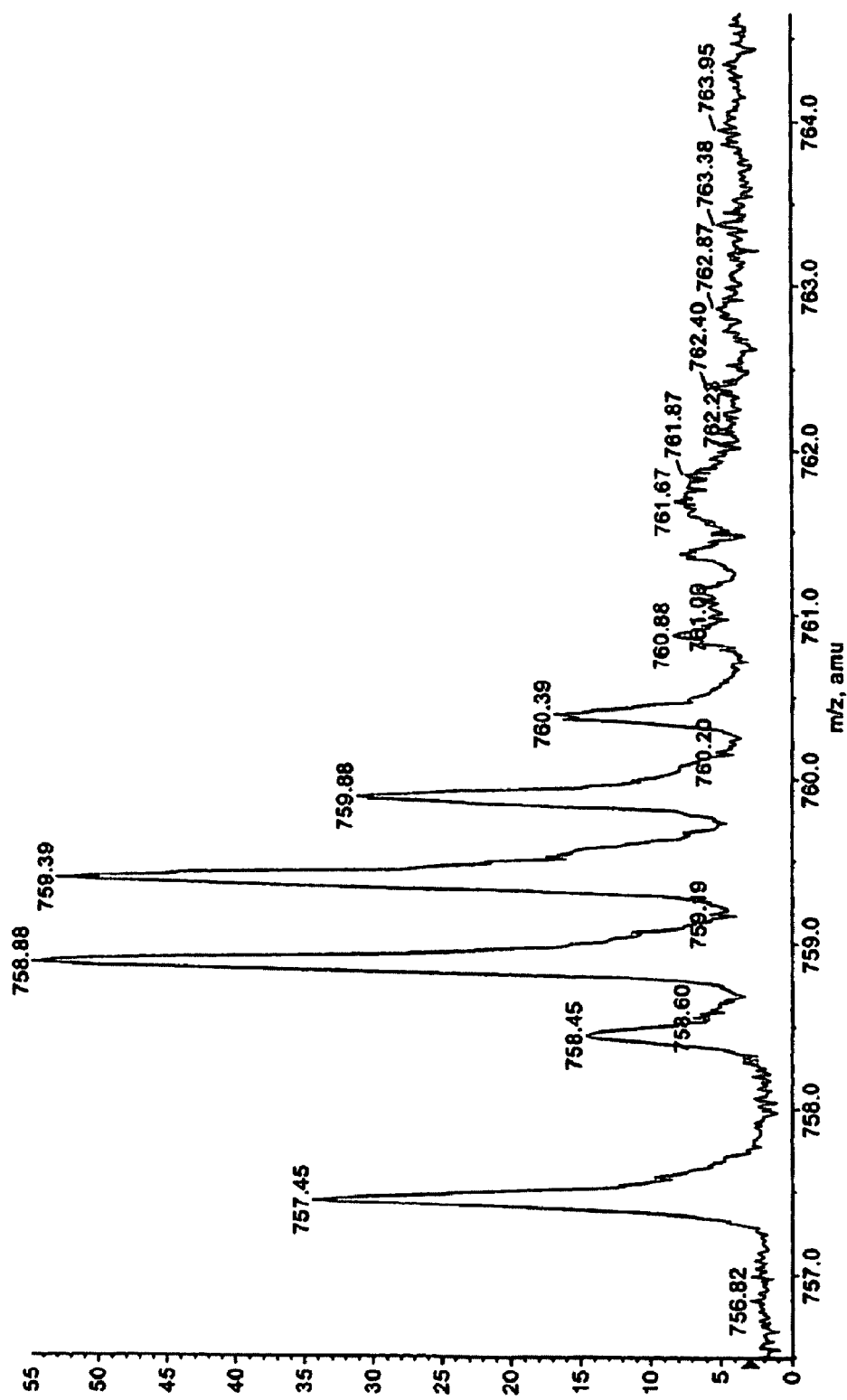
FIG. 27 illustrates the mass spectrum of a product produced by recombinant expression of SEQ ID NO: 70 in *E. coli*, followed by purification to greater than 99% purity and removal of substantially all endotoxins, which is then digested with GluC, showing the N-terminal peptide without a methionine.

FIG. 27 illustrates the mass spectrum of a GluC digested T2-TrpRS product produced by transfection of E. coli with a vector of SEQ ID NO: 70, and further purification of the product to about 99.5% purity and 0.003 E.U./mg protein, showed a C-terminal peptide without an N-terminal methionine. This peptide was at m/z=759. As this peptide is doubly charged the mass of it was also doubled or Mr=1516.

Figure 28:
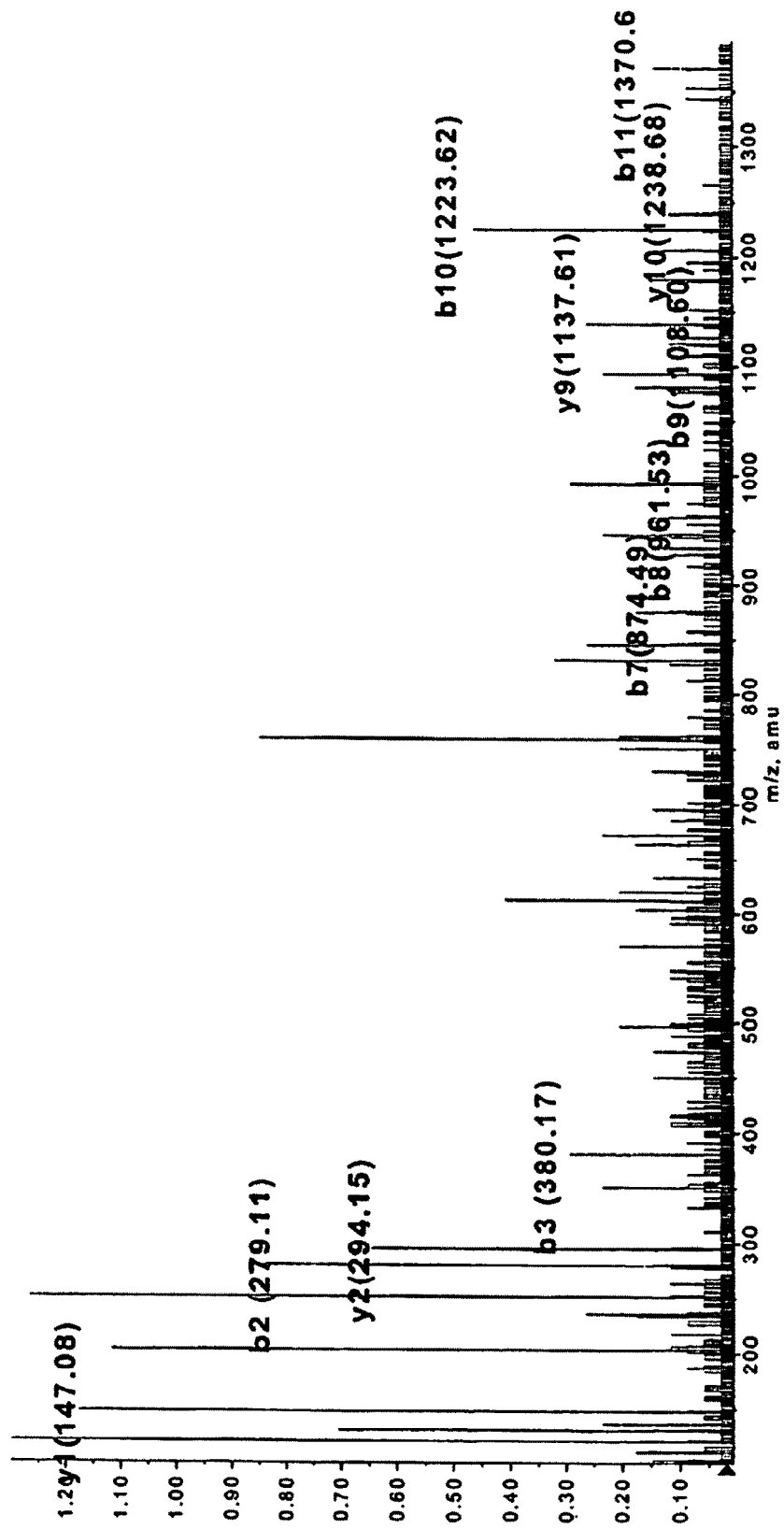
FIG. 28 illustrates a fragmentation of the doubly charged mass at m/z=759 of a product produced by recombinant expression of SEQ ID NO: 70 in *E. coli*, followed by purification to greater than 99% purity and removal of substantially all endotoxins.

FIG. 28 illustrates a fragmentation of the doubly charged mass at m/z=759 from FIG. 28. Only single charged fragments were labeled. Analysis of this spectrum confirms that the C-terminus of the T2-TrpRS product produced by recombinantly expressing the vector of SEQ ID NO: 70 had a sequence of SEQ ID NO: 69. Searching the non-redundant database with this fragmentation data returned a significant hit for human protein IFP53. The sequence of the peptide matched 100% the C-terminal peptide of the T2-TrpRS product produced by transfection of E. coli with a vector of SEQ ID NO: 70. These results indicated that the T2-TrpRS product produced by transfection of E. coli with a vector of SEQ ID NO: 70 did not have ragged ends and that the C-terminus of the recombinant product was SEQ ID NO: 69, without a His-tag.

Figure 29:
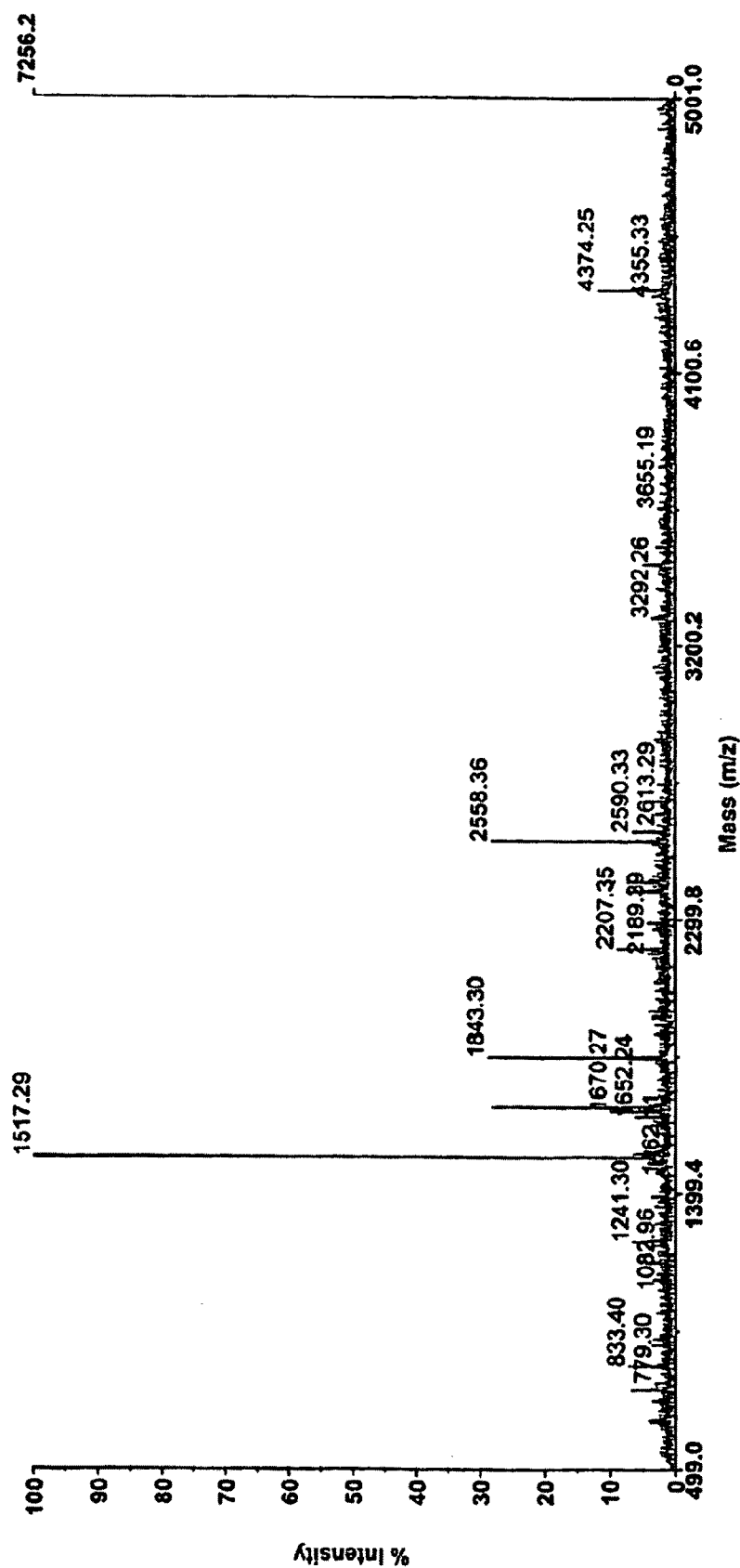
FIG. 29 illustrates a MALDI-TOF mass spectrum of a product produced by recombinant expression of SEQ ID NO: 70 in *E. coli*, followed by purification to greater than 99% purity and removal of substantially all endotoxins, which is then digested by GluC.

FIG. 29 illustrates MALDI-TOF mass spectrum of T2-TrpRS product recombinantly produced in *E. coli* with a vector of SEQ ID NO: 70, wherein the product was purified to about 99.5% purity and endotoxin were removed leaving 0.003 E.U./mg protein. The product was then digested by GluC.

Figure 30:
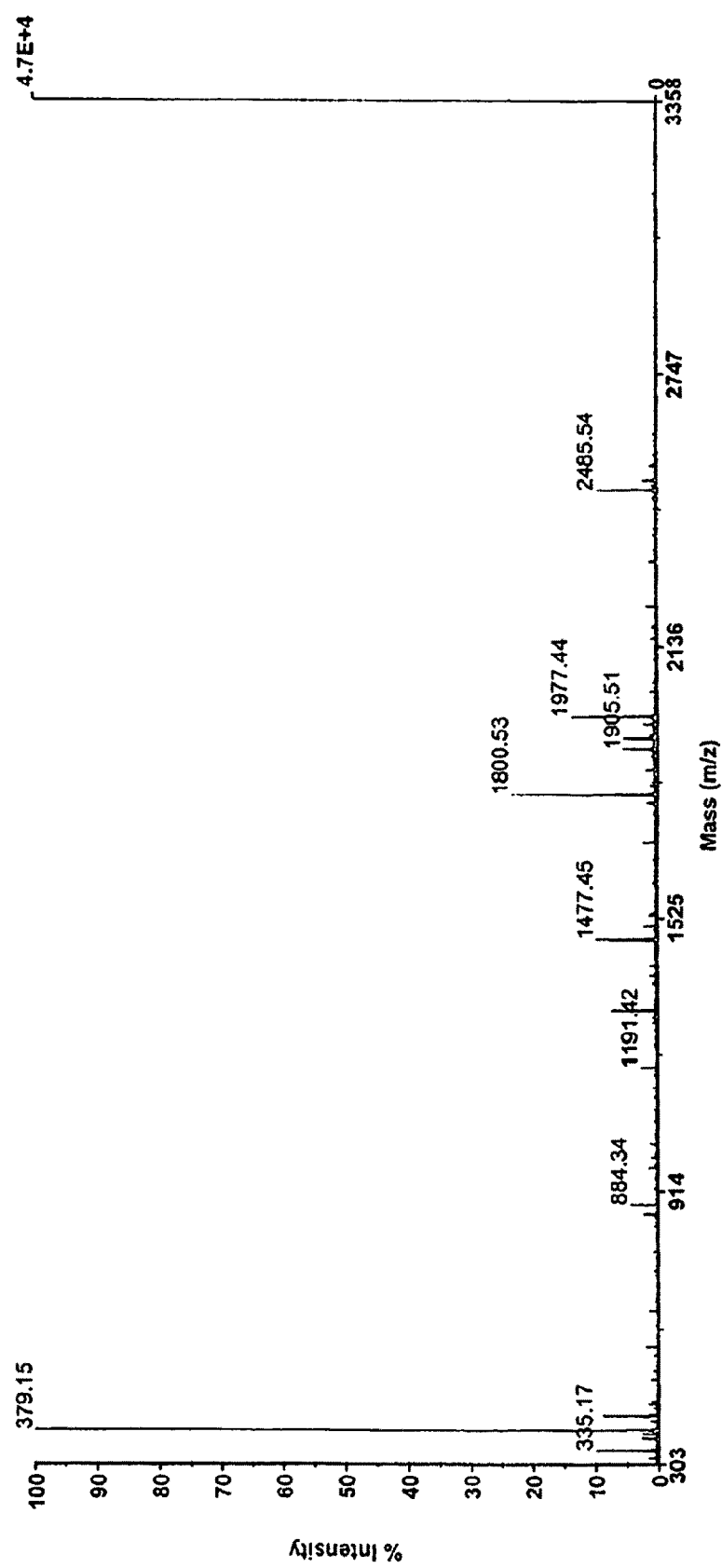
FIG. 30 illustrates a MALDI-TOF mass spectrum of a product produced by recombinant expression of SEQ ID NO: 70 in *E. coli*, followed by purification to greater than 99% purity and removal of substantially all endotoxins, which is then digested by trypsin.

FIG. 30 illustrates MALDI-TOF mass spectrum of T2-TrpRS product recombinantly produced in *E. coli* with a vector of SEQ ID NO: 70, wherein the product was purified to about 99.5% purity and endotoxin were removed leaving 0.003 E.U./mg protein. The product was then digested by trypsin.

These MALDI-TOF spectra did not show masses that would correspond to an N-terminus with or without Met.

Figure 31:
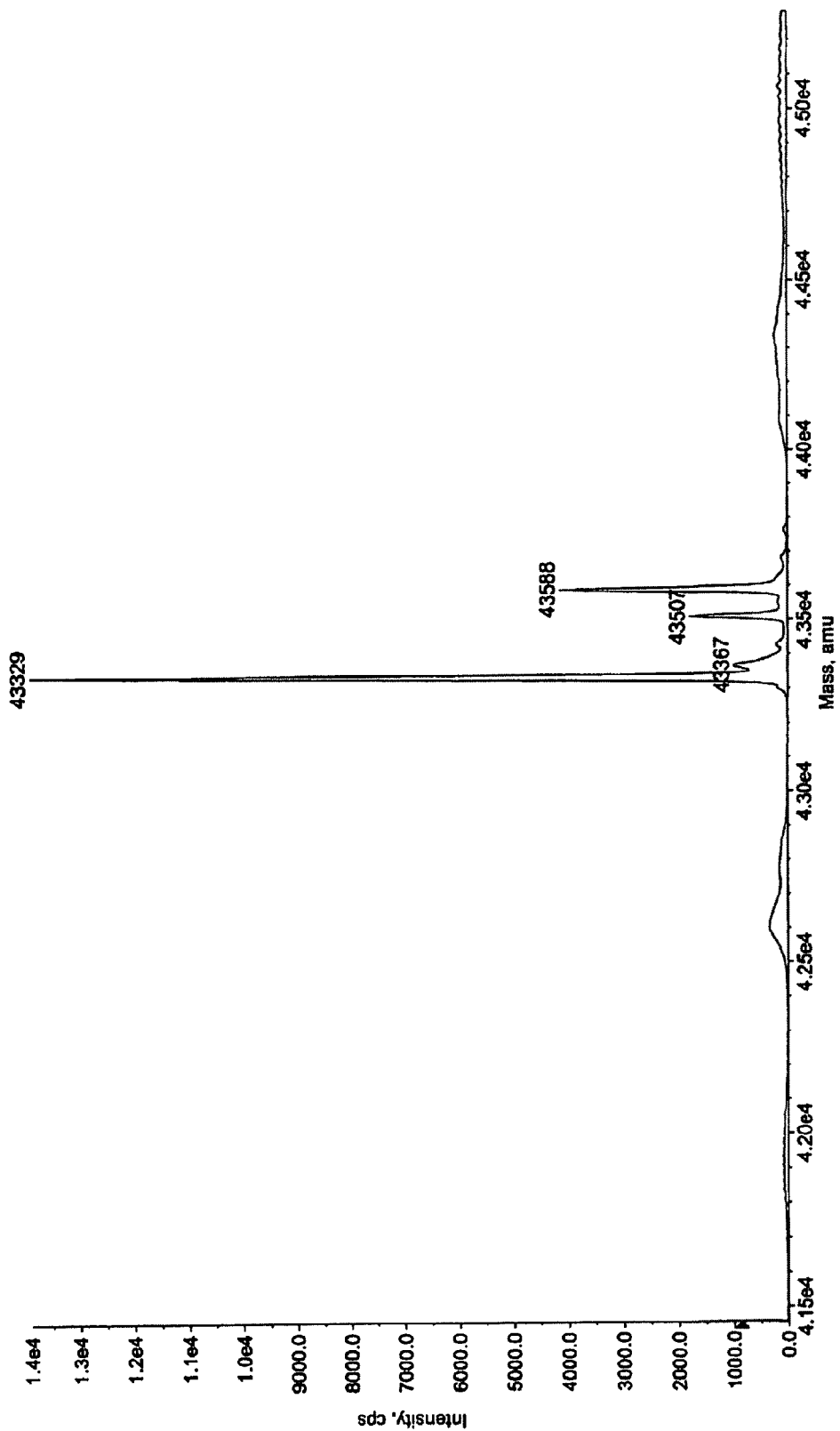
FIG. 31 illustrates an electrospray ionization spectrum of a product produced by recombinant expression of SEQ ID NO: 70 in *E. coli*, followed by purification to greater than 99% purity and removal of substantially all endotoxins, which is then desalted with a $C_4$ ZipTip (Millipore).
Figure 32:
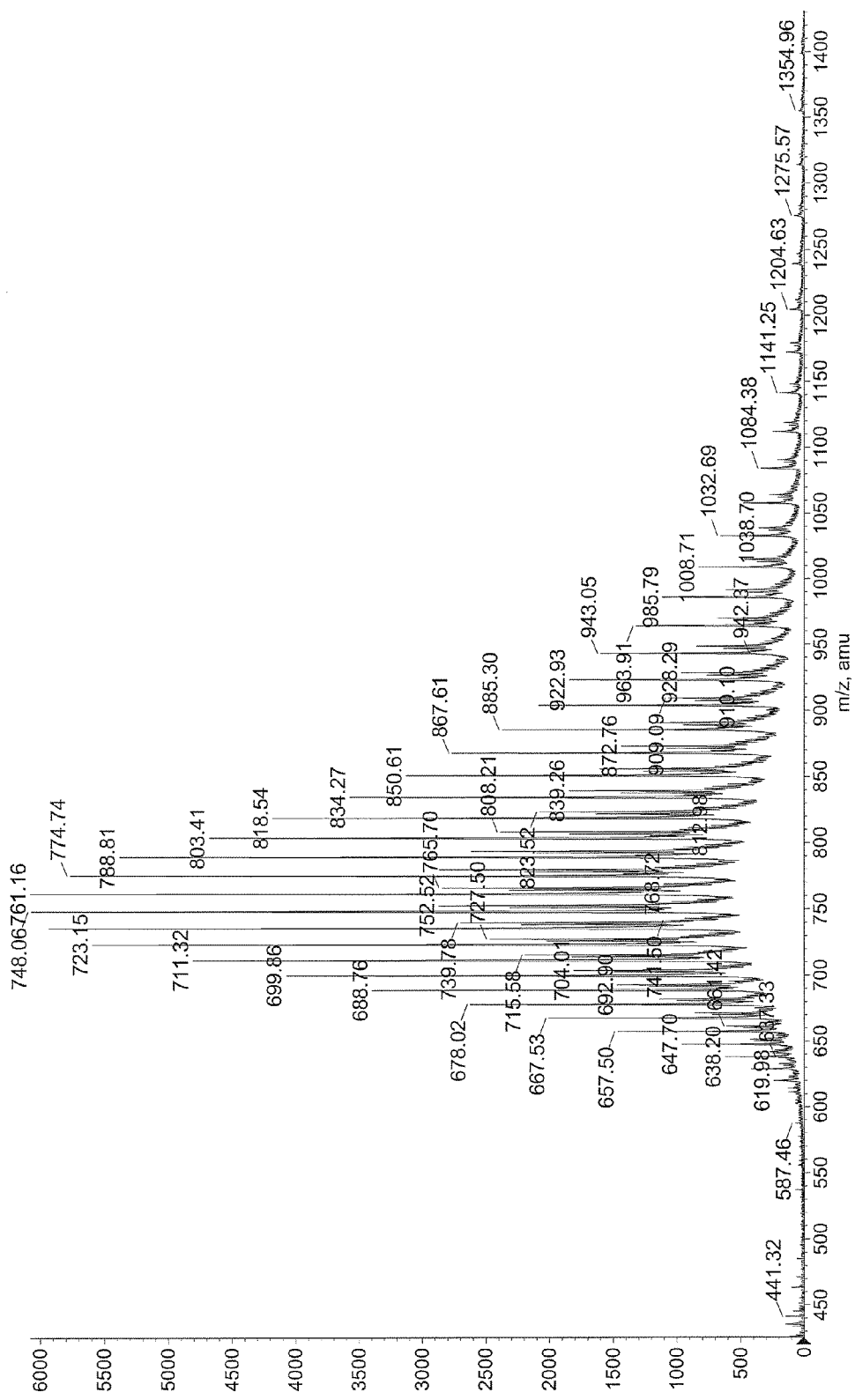
FIG. 32 illustrates the convoluted electrospray spectrum.

FIG. 31 illustrates an electrospray ionization spectrum of a T2-TrpRS product produced by transfection of *E. coli* with a vector of SEQ ID NO: 70, purification to about 99.5% purity, and removal of endotoxins to about 0.003 E.U./mg protein. The product was desalted with a $C_4$ ZipTip (Millipore). This spectrum illustrates several series of possible multiply-charged ions. When convoluted, as is illustrated in FIG. 32, these data show a major component with molecular mass of 43,329 Da and is consistent with the theoretical mass of 43,329 Da for the expected protein minus the N-terminus Met residue. In addition, two notable additional species are also assigned with masses of 43,507 Da and 43,588 Da. The mass difference between these components is close to that expected for phosphorylation although the difference between the major component (43329 Da) and the component with mass (43507 Da) cannot be readily assigned.

Figure 33:
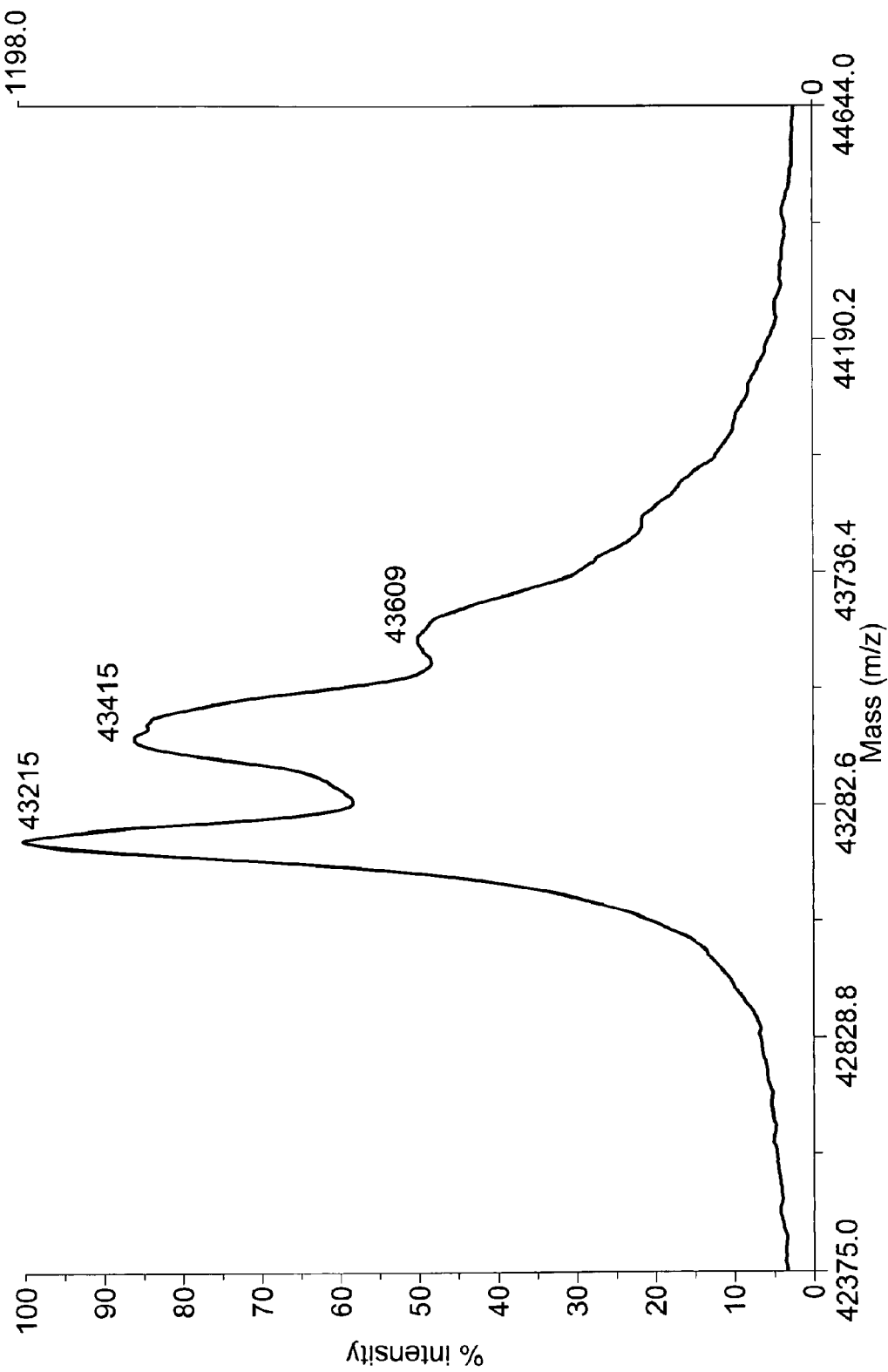
FIG. 33 illustrates a MALDI-TOF mass spectrum of a product produced by recombinant expression of SEQ ID NO: 70 in *E. coli*, followed by purification to greater than 99% purity and removal of substantially all endotoxins, which is then desalted with a $C_4$ preparatory column (ZipTip, Millipore).

FIG. 33 illustrates a MALDI-TOF mass spectrum of a T2-TrpRS product produced by transfection of *E. coli* with a vector of SEQ ID NO: 70, purification to about 99.5% purity, and removal of endotoxins to about 0.003 E.U./mg protein. The product was desalted with a $C_4$ ZipTip (Millipore). The spectrum has major singly-charged pseudomolecular ion clusters having centers at m/z 43215 and 43415, with the associated doubly-charged ions at m/z 21621 and 21715. Expansions of the singly charged region suggests the 43415 Da cluster to be composed of more than one species and may correspond to the two higher mass species observed in the electrospray spectrum of FIG. 31.

Example 17

Quantitative Measurements of Enzymatic Aminoacylation Activity

FIG. 13 illustrates a PPi exchange assay. TrpRS covalently links tryptophan to its cognate tRNA in a two-step mechanism which is energetically driven by consumption of ATP: The PPi exchange assay measures the enzyme's catalysis of inorganic pyrophosphate (PPi) incorporation into Tryptophanyl-AMP.

The products of this reaction are free tryptophan and free ATP. (This is the reverse reaction of the one used to activate amino acids for attachment to tRNA.) It is used as a measure of enzyme activity in the first half reaction catalyzed by amino acyl tRNA synthetases. As such, it is commonly used to evaluate enzymes for activity. The other (or second half of the reaction) is the subsequent attachment of the amino acid to tRNA. The complete two-step enzyme reaction that measures the overall incorporation of Trp onto tRNA is called an "aminoacylation assay" and can be summarized as follows:

First reaction: Trp+ATP reversibly yields Trp-AMP+PPi
Second reaction: Trp-AMP+tRNA yields Trp-tRNA+AMP
Overall: Trp+ATP+tRNA yields Trp-tRNA+AMP+PPi In the first step (termed amino acid activation), TrpRS activates the amino acid through a condensation reaction with ATP to generate Trp-AMP with the release of pyrophosphate (PPi). In the second step, the activated amino acid is attached to the 3' end of the cognate tRNA to yield the aminoacylated tRNA (Trp-tRNA) and the release of AMP.

Therefore, the catalytic activity of TrpRS can be characterized in a tryptophan-dependent ATP-PPi exchange (Eq. 1) and aminoacylation assays (sum of Eqs. 1 and 2).

The PPi exchange reactions assess the reverse of amino acid activation by measuring the incorporation of $[^{32}P]$-PPi into ATP (Eq. 1). In contrast, aminoacylation assays (sum of Eqs. 1 and 2) measures the amount of $[^{3}H]$-Tryptophan ligated to its cognate tRNA.

PPi exchange reaction-PPi exchange reactions were performed at 100 mM Tris HCl, pH 7.8, 10 mM potassium fluoride, 2 mM magnesium chloride, 1 mM ATP, 2 mM sodium PPi, $[^{32}P]$-sodium PPi, 1 mM tryptophan, and 5 mM β-mercaptoethanol. Reactions were initiated by the addition of 0.2 μM enzyme and carried out at room temperature. At each time point, samples were quenched in 4% charcoal, 11% perchloric acid, and 200 mM sodium PPi. The charcoal was collected and washed twice with 1% perchloric acid and 200 mM sodium PPi prior to scintillation counting.

Counts per minute ("CPM's") measuring the incorporation of $[^{32}P]$-PPi into ATP were detected for full length TrpRS and T2 produced. FIG. 17 (left) illustrates CPMs for full-length TrpRS ("FL WRS"; SEQ ID NO: 63 or 64); a variant of the full-length wherein Pro 287 is converted to an Asp ("FLWRS/P287D"), and of T2-TrpRS derived by recombinantly expressing the vector of SEQ ID NO: 70 in *E. coli* according to the methods herein) ("T2-WRS"). FIG. 17 (center) illustrates CPMs less background are data wherein the CPM units at time zero have been subtracted out. FIG. 17 (right) illustrates final CPM of $[^{32}P]$-PPi.

Figure 16:
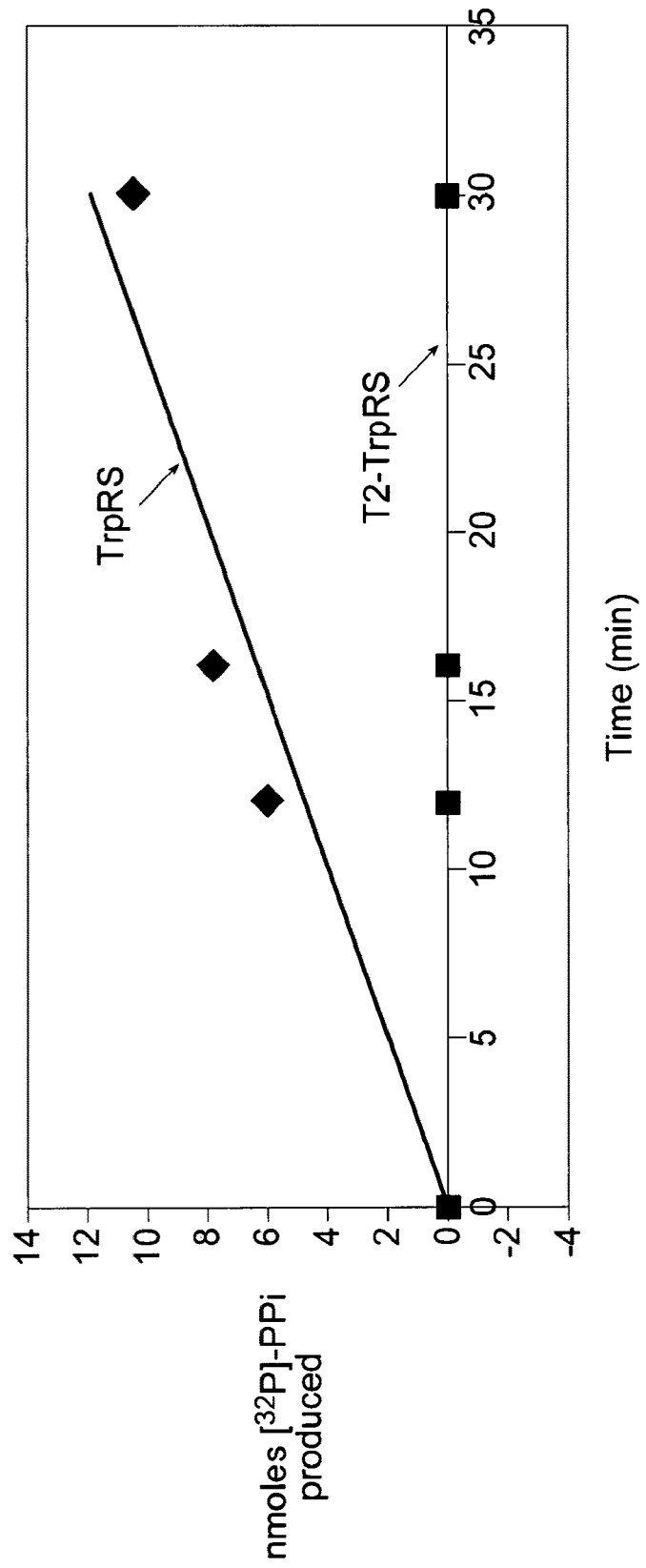
FIG. 16 illustrates results from a PPi exchange assay.

As illustrated by FIG. 16, full-length TrpRS incorporated substantially more $[^{32}P]$-PPi into ATP than the T2-TrpRS. This result suggests that T2 is largely "inactive" as compared to the full-length TrpRS in its tRNA synthetase activity.

Example 18

Quantitative Measurements of Angiostatic Activity

Immediately after birth (P0), retinal vasculature is virtually absent in the mouse. By about three weeks post-natally (P21) the retina has attained an adult pattern of retinal vessels through a stereotypical, biphasic developmental pattern of angiogenesis. Initially, spoke-like peripapillary vessels grow radially from the central retinal artery and vein, becoming progressively interconnected by a capillary plexus that forms between them. The second phase of retinal vessel formation begins around postnatal day 8 (P8) when collateral branches sprout from capillaries of the superficial plexus and penetrate into the retina. Vascular branches then anastamose laterally to form a planar "deep vascular plexus" at the outer edge of the inner nuclear layer, which is in place by P12. An intermediate vascular plexus also forms at the inner edge of the inner nuclear layer between P14 and P20. The development of these vascular networks in the neonatal mouse is strikingly similar to the events occurring in the third trimester human fetus.

Figure 18:
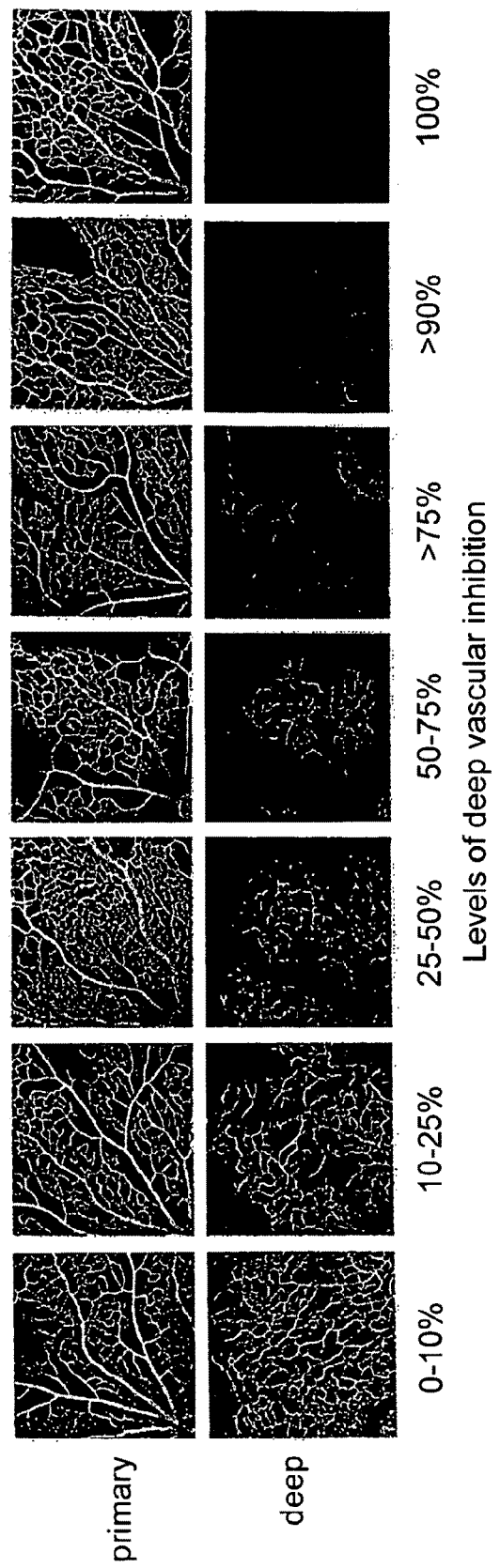
FIG. 18 illustrates various inhibition levels in a post-natal mouse.

The reproducibility of this process and its easy accessibility in post-natal animals provide an opportunity to test the efficacy of anti-angiogenic compounds in a physiologically relevant model of angiogenesis. The angiostatic activity of T2-TrpRS or other angiostatic molecules was tested by intravitreal injections at P8, just prior to formation of the deep vascular sprouts, and was evaluated based upon the degree of vascular formation in the deep retinal vascular plexus by P12. The appearance of the superficial vascular plexus (primary layer) was evaluated for signs of toxicity and any adverse effects of the drug on the pre-established vasculature. For each retina, the levels of inhibition were graded based on the relative levels of inhibition throughout the entire retina. FIG. 18 illustrates various percentages of inhibition by compounds injected at P8 prior to development of the deep vascular plexus, and the effects of neovascularization assessed 4 days later.

Figure 19:
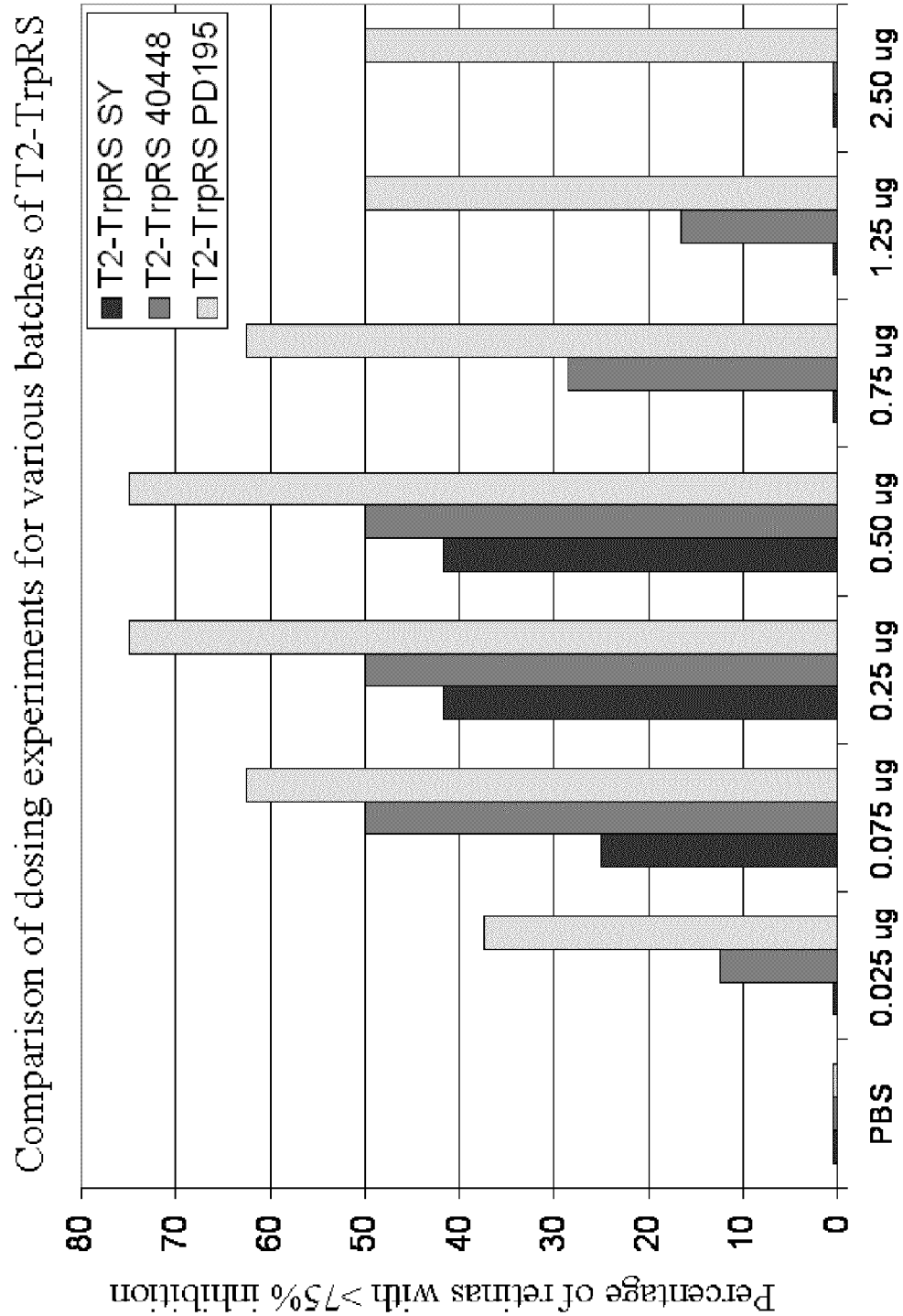
FIG. 19 illustrates a comparison of percentage inhibition of angiogenesis by the product produced by *E. coli* expression of SEQ ID NO: 71, SEQ ID NO: 70, which is purified to about 95% purity and, SEQ ID NO: 70, which is purified to about 100% purity at various dosages.

FIG. 19 illustrates a comparison of percentage inhibition of angiogenesis by three different T2 manufacture lots at various dosages. On the far left of each dosage comparison is inhibition by "T2-TrpRS SY", a product produced by expressing a polynucleotide encoding SEQ ID NO: 27 with the addition of a C-terminal $His_6$-tag in $E.\ coli$ followed by purification using laboratory techniques (nickel affinity column and Triton X-114 as described above in Example 1). In the center of each dose comparison is "T2-TrpRS 40448," a product produced by expressing a polynucleotide encoding SEQ ID NO: 27 (without a C-terminal $His_6$-tag) in $E.\ coli$ followed by purification using a linear gradient column chromatography system and an endotoxin filter such that the sample is about 95% pure. On the far right of each dose comparison level is inhibition by "T2-TrpRS PD195", a product produced by expressing a vector of SEQ ID NO: 70 (without a C-terminal $His_6$-tag) in $E.\ coli$, followed by purification using a scaled-up manufacturing process, including batch elution column chromatography and an increased area of an endotoxin filter, such that the sample is about 99% pure and further reduced endotoxin levels.

A slight bell-shaped efficacy curve is apparent, with maximum efficacies occurring from injections of 0.25 or 0.50 µg/eye, (5.22 or 10.44 picomoles respectively). Significant improvements in efficacy have been made with each new manufacturing protocol to date ($1^{st}$=T2-TrpRS SY, $2^{nd}$=T2-TrpRS 40448, $3^{rd}$=T2-TrpRS PD195-DG30L (PD195)). In addition, with each new manufactured batch, the efficacy curve became significantly broader (FIG. 19). These improvements are likely to be the result of improved purification methods which have yielded nearly 100% levels of purity by the T2-TrpRS PD195 batch.

The y-axis of FIG. 19 illustrates percentage of retinas with >75% inhibition. This percentage inhibition can also be referred to herein in activity units. For example, if 50% of retinas experienced >75% inhibition, the protein activity is deemed at 50 activity units, if 70% of retinas experiences >75% inhibition, the protein activity is deemed at 70 activity units.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

SUMMARY OF SEQUENCES

SEQ ID NO: 1.—Met-TrpRS-His tag (amino acid plus nucleic acid vector) (the GD variant)

SEQ ID NO: 2.—Met-mini-Trp-His tag (amino acid plus nucleic acid) (the GD variant)

SEQ ID NO: 3.—Met-mini-TrpRS-His tag (amino acid) (the GD variant)

SEQ ID NO: 4.—Met-T1-His tag (amino acid plus nucleic acid vector) (the GD variant)

SEQ ID NO: 5.—Met-T1-His tag (amino acid) (the GD variant)

SEQ ID NO: 6.—Met-T2-His tag (amino acid plus nucleic acid vector) (the GD variant)

SEQ ID NO: 7.—Met-T2-His tag (amino acid) (the GD variant)

SEQ ID NO: 8.—SNHGP (beginning sequence of T1) (the GD variant)

SEQ ID NO: 9.—SAKGI (beginning sequence of T2) (the GD variant)

SEQ ID NO: 10.—HVGH (internal sequence)

SEQ ID NO: 11.—KMSAS (internal sequence)

SEQ ID NO: 12.—T2 (the GD variant)

SEQ ID NO: 13.—T1 (the GD variant)

SEQ ID NO: 14.—mini-TrpRS (the GD variant)

SEQ ID NO: 15.—Met-T2 (the GD variant)

SEQ ID NO: 16.—Met-T1 (the GD variant)

SEQ ID NO: 17.—Met-mini-TrpRS (the GD variant)

SEQ ID NO: 18.—nucleic acid encoding T2 (the GD variant)

SEQ ID NO: 19.—nucleic acid encoding Met-T2 (the GD variant)

SEQ ID NO: 20.—nucleic acid encoding T1 (the GD variant)

SEQ ID NO: 21.—nucleic acid encoding Met-T1 (the GD variant)

SEQ ID NO: 22.—nucleic acid encoding mini-TrpRS (the GD variant)

SEQ ID NO: 23.—nucleic acid encoding Met-mini-TrpRS (the GD variant)

SEQ ID NO: 24.—T2 (the SY variant)

SEQ ID NO: 25.—T1 (the SY variant)

SEQ ID NO: 26.—mini-TrpRS (the SY variant)

SEQ ID NO: 27.—Met-T2 (the SY variant)

SEQ ID NO: 28.—Met-T1 (the SY variant)

SEQ ID NO: 29.—Met-mini-TrpRS (the SY variant)

SEQ ID NO: 30.—nucleic acid encoding T2 (the SY variant)

SEQ ID NO: 31.—nucleic acid encoding Met-T2 (the SY variant)

SEQ ID NO: 32.—nucleic acid encoding T1 (the SY variant)

SEQ ID NO: 33.—nucleic acid encoding Met-T1 (the SY variant)

SEQ ID NO: 34.—nucleic acid encoding mini-TrpRS (the SY variant)

SEQ ID NO: 35.—nucleic acid encoding Met-mini-TrpRS (the SY variant)

SEQ ID NO: 36.—T2 (the GY variant)

SEQ ID NO: 37.—T1 (the GY variant)

SEQ ID NO: 38.—mini-TrpRS (the GY variant)

SEQ ID NO: 39.—Met-T2 (the GY variant)

SEQ ID NO: 40.—Met-T1 (the GY variant)

SEQ ID NO: 41.—Met-mini-TrpRS (the GY variant)

SEQ ID NO: 42.—nucleic acid encoding T2 (the GY variant)

SEQ ID NO: 43.—nucleic acid encoding Met-T2 (the GY variant)

SEQ ID NO: 44.—nucleic acid encoding T1 (the GY variant)

SEQ ID NO: 45.—nucleic acid encoding Met-T1 (the GY variant)
SEQ ID NO: 46.—nucleic acid encoding mini-TrpRS (the GY variant)
SEQ ID NO: 47.—nucleic acid encoding Met-mini-TrpRS (the GY variant)
SEQ ID NO: 48.—T2 (the SD variant)
SEQ ID NO: 49.—T1 (the SD variant)
SEQ ID NO: 50.—mini-TrpRS (the SD variant)
SEQ ID NO: 51.—Met-T2 (the SD variant)
SEQ ID NO: 52.—Met-T1 (the SD variant)
SEQ ID NO: 53.—Met-mini-TrpRS (the SD variant)
SEQ ID NO: 54.—nucleic acid encoding T2 (the SD variant)
SEQ ID NO: 55.—nucleic acid encoding Met-T2 (the SD variant)
SEQ ID NO: 56.—nucleic acid encoding T1 (the SD variant)
SEQ ID NO: 57.—nucleic acid encoding Met-T1 (the SD variant)
SEQ ID NO: 58.—nucleic acid encoding mini-TrpRS (the SD variant)
SEQ ID NO: 59.—nucleic acid encoding Met-mini-TrpRS (the SD variant)
SEQ ID NO: 60.—Dimerization domain (from T2 144-199)
SEQ ID NO: 61.—Full Length GD variant, with N-terminal Met, and no His-tag
SEQ ID NO: 62.—Full Length GD variant, without N-terminal Met, and no His-tag
SEQ ID NO: 63.—Full Length SY variant, with N-terminal Met, and no His-tag
SEQ ID NO: 64.—Full Length SY variant, without N-terminal Met, and no His-tag
SEQ ID NO: 65.—Full Length GY variant, with N-terminal Met, and no His-tag
SEQ ID NO: 66.—Full Length GY variant, without N-terminal Met, and no His-tag
SEQ ID NO: 67.—Full Length SD variant, with N-terminal Met, and no His-tag
SEQ ID NO: 68.—Full Length SD variant, without N-terminal Met, and no His-tag
SEQ ID NO: 69.—C-terminus: FMTPRKLSFDFQ.
SEQ ID NO: 70.—Plasmid 01-pET24b+ with a NdeI/HindIII insert of Human T2-TrpRS (SY variant) without 6-His Tag
SEQ ID NO: 71.—Plasmid 02: pET20b+ with a NdeI/HindIII insert of Human T2-TrpRS (SY variant), with 6-His Tag
SEQ ID NO: 72.—Plasmid 04 pET20b+ with a NdeI/HindIII insert of T2-TrpRS (SY variant), 6-His Tag with Thrombin Cleavage Site
SEQ ID NO: 73.—Plasmid 06 pET24b+ with a NdeI/XhoI insert of Human mini-TyrRS, 6-His Tag.
SEQ ID NO: 74.—Plasmid 07 pET24b+ with a NdeI/HindIII insert of Human mini-TrpRS, (SY variant) 6-His Tag
SEQ ID NO: 75.—Plasmid 09: pET24b+ with a NdeI/XhoI insert of Human mini-TyrRS, No His Tag.
SEQ ID NO: 76.—a C-terminal KLMALEHHHHHH.

What is claimed is:

1. A method for purifying a multiunit complex comprising a first tryptophanyl tRNA synthetase fragment and a second tryptophanyl tRNA synthetase fragment, wherein the purified complex comprises less than 10 endotoxin units per milligram of synthetase fragment, and wherein the method comprises performing an endotoxin-reduction filtration step after performing a clarification step and prior to performing at least one of the steps selected from: a buffer exchange; a concentration step; and a cation-exchange chromatographic step, wherein said endotoxin-reduction filtration step does not include the use of a detergent.

2. A method for purifying a multiunit complex comprising a first tryptophanyl tRNA synthetase fragment and a second tryptophanyl tRNA synthetase fragment, wherein the purified complex comprises less than 10 endotoxin units per milligram of synthetase fragment, and wherein the method comprises performing an endotoxin-reduction filtration step after performing an anion-exchange chromatographic step, wherein said endotoxin-reduction filtration step does not include the use of a detergent.

3. The method according to claim 1, wherein said first tRNA synthetase fragment and said second tRNA synthetase fragments are identical.

4. The method according to claim 3, wherein said first tRNA synthetase fragment consists of SEQ ID NO: 27.

5. The method according to claim 1, wherein said first tRNA synthetase fragment consists of SEQ ID NO: 27 and said second tRNA synthetase fragment consists of SEQ ID NO: 24 or SEQ ID NO: 27.

6. The method according to claim 1, wherein said first tRNA synthetase fragment and said second tRNA synthetase fragment are each independently selected from the group consisting of SEQ ID Nos. 24, SEQ ID No. 25, SEQ ID No. 26, SEQ ID No. 27, SEQ ID No. 28, SEQ ID No. 29, SEQ ID No. 36, SEQ ID No. 37, SEQ ID No. 38, SEQ ID No. 39, SEQ ID No. 40, SEQ ID No. 41, SEQ ID No. 48, SEQ ID No. 49, SEQ ID No. 50, SEQ ID No. 51, SEQ ID No. 52 and SEQ ID No. 53, or homologs thereof, and wherein said first and second fragments are covalently dimerized.

7. The method according to claim 1, wherein said multiunit complex has greater than 50 angiostatin activity unites; and at least 99% level of purity.

* * * * *

SEQUENCE LISTING

```
<160> NUMBER OF SEQ ID NOS: 76

<210> SEQ ID NO 1
<211> LENGTH: 484
<212> TYPE: PRT
<213> ORGANISM: Artificial Sequence
<220> FEATURE:
<223> OTHER INFORMATION: Recombinant human trpRS

<400> SEQUENCE: 1

Met Pro Asn Ser Glu Pro Ala Ser Leu Leu Glu Leu Phe Asn Ser Ile
1               5                   10                  15

Ala Thr Gln Gly Glu Leu Val Arg Ser Leu Lys Ala Gly Asn Ala Ser
            20                  25                  30

Lys Asp Glu Ile Asp Ser Ala Val Lys Met Leu Val Ser Leu Lys Met
        35                  40                  45

Ser Tyr Lys Ala Ala Ala Gly Glu Asp Tyr Lys Ala Asp Cys Pro Pro
    50                  55                  60

Gly Asn Pro Ala Pro Thr Ser Asn His Gly Pro Asp Ala Thr Glu Ala
65                  70                  75                  80

Glu Glu Asp Phe Val Asp Pro Trp Thr Val Gln Thr Ser Ser Ala Lys
                85                  90                  95

Gly Ile Asp Tyr Asp Lys Leu Ile Val Arg Phe Gly Ser Ser Lys Ile
            100                 105                 110

Asp Lys Glu Leu Ile Asn Arg Ile Glu Arg Ala Thr Gly Gln Arg Pro
        115                 120                 125

His His Phe Leu Arg Arg Gly Ile Phe Phe Ser His Arg Asp Met Asn
    130                 135                 140

Gln Val Leu Asp Ala Tyr Glu Asn Lys Lys Pro Phe Tyr Leu Tyr Thr
```

```
                145                 150                 155                 160
Gly Arg Gly Pro Ser Ser Glu Ala Met His Val Gly His Leu Ile Pro
                    165                 170                 175
Phe Ile Phe Thr Lys Trp Leu Gln Asp Val Phe Asn Val Pro Leu Val
                180                 185                 190
Ile Gln Met Thr Asp Asp Glu Lys Tyr Leu Trp Lys Asp Leu Thr Leu
            195                 200                 205
Asp Gln Ala Tyr Gly Asp Ala Val Glu Asn Ala Lys Asp Ile Ile Ala
        210                 215                 220
Cys Gly Phe Asp Ile Asn Lys Thr Phe Ile Phe Ser Asp Leu Asp Tyr
225                 230                 235                 240
Met Gly Met Ser Ser Gly Phe Tyr Lys Asn Val Val Lys Ile Gln Lys
                245                 250                 255
His Val Thr Phe Asn Gln Val Lys Gly Ile Phe Gly Phe Thr Asp Ser
            260                 265                 270
Asp Cys Ile Gly Lys Ile Ser Phe Pro Ala Ile Gln Ala Ala Pro Ser
        275                 280                 285
Phe Ser Asn Ser Phe Pro Gln Ile Phe Arg Asp Arg Thr Asp Ile Gln
    290                 295                 300
Cys Leu Ile Pro Cys Ala Ile Asp Gln Asp Pro Tyr Phe Arg Met Thr
305                 310                 315                 320
Arg Asp Val Ala Pro Arg Ile Gly Tyr Pro Lys Pro Ala Leu Leu His
                325                 330                 335
Ser Thr Phe Phe Pro Ala Leu Gln Gly Ala Gln Thr Lys Met Ser Ala
            340                 345                 350
Ser Asp Pro Asn Ser Ser Ile Phe Leu Thr Asp Thr Ala Lys Gln Ile
        355                 360                 365
Lys Thr Lys Val Asn Lys His Ala Phe Ser Gly Gly Arg Asp Thr Ile
    370                 375                 380
Glu Glu His Arg Gln Phe Gly Gly Asn Cys Asp Val Asp Val Ser Phe
385                 390                 395                 400
Met Tyr Leu Thr Phe Phe Leu Glu Asp Asp Lys Leu Glu Gln Ile
                405                 410                 415
Arg Lys Asp Tyr Thr Ser Gly Ala Met Leu Thr Gly Glu Leu Lys Lys
                420                 425                 430
Ala Leu Ile Glu Val Leu Gln Pro Leu Ile Ala Glu His Gln Ala Arg
            435                 440                 445
Arg Lys Glu Val Thr Asp Glu Ile Val Lys Glu Phe Met Thr Pro Arg
        450                 455                 460
Lys Leu Ser Phe Asp Phe Gln Lys Leu Ala Ala Ala Leu Glu His His
465                 470                 475                 480
His His His His
```

```
<210> SEQ ID NO 2
<211> LENGTH: 4877
<212> TYPE: DNA
<213> ORGANISM: Artificial Sequence
<220> FEATURE:
<223> OTHER INFORMATION: Recombinant human mini-TrpRS nucleotide
      construct
<220> FEATURE:
<221> NAME/KEY: CDS
<222> LOCATION: (3428)..(4738)

<400> SEQUENCE: 2
tggcgaatgg gacgcgccct gtagcggcgc attaagcgcg gcgggtgtgg tggttacgcg    60
```

| | |
|---|---|
| cagcgtgacc gctacacttg ccagcgccct agcgcccgct cctttcgctt tcttcccttc | 120 |
| ctttctcgcc acgttcgccg gctttccccg tcaagctcta aatcgggggc tcccttagg | 180 |
| gttccgattt agtgctttac ggcacctcga ccccaaaaaa cttgattagg gtgatggttc | 240 |
| acgtagtggg ccatcgccct gatagacggt ttttcgccct ttgacgttgg agtccacgtt | 300 |
| ctttaatagt ggactcttgt tccaaactgg aacaacactc aaccctatct cggtctattc | 360 |
| ttttgattta tagggatttt tgccgatttc ggcctattgg ttaaaaaatg agctgattta | 420 |
| acaaaatttt aacgcgaatt ttaacaaaat attaacgttt acaatttcag gtggcacttt | 480 |
| tcggggaaat gtgcgcggaa cccctatttg tttattttc taaatacatt caaatatgta | 540 |
| tccgctcatg agacaataac cctgataaat gcttcaataa tattgaaaaa ggaagagtat | 600 |
| gagtattcaa catttccgtg tcgcccttat tccctttttt gcggcatttt gccttcctgt | 660 |
| ttttgctcac ccagaaacgc tggtgaaagt aaaagatgct gaagatcagt tgggtgcacg | 720 |
| agtgggttac atcgaactgg atctcaacag cggtaagatc cttgagagtt ttcgccccga | 780 |
| agaacgtttt ccaatgatga gcacttttaa agttctgcta tgtggcgcgg tattatcccg | 840 |
| tattgacgcc gggcaagagc aactcggtcg ccgcatacac tattctcaga atgacttggt | 900 |
| tgagtactca ccagtcacag aaaagcatct tacggatggc atgacagtaa gagaattatg | 960 |
| cagtgctgcc ataaccatga gtgataacac tgcggccaac ttacttctga caacgatcgg | 1020 |
| aggaccgaag gagctaaccg cttttttgca caacatgggg gatcatgtaa ctcgccttga | 1080 |
| tcgttgggaa ccggagctga atgaagccat accaaacgac gagcgtgaca ccacgatgcc | 1140 |
| tgcagcaatg gcaacaacgt tgcgcaaact attaactggc gaactactta ctctagcttc | 1200 |
| ccggcaacaa ttaatagact ggatggaggc ggataaagtt gcaggaccac ttctgcgctc | 1260 |
| ggcccttccg gctggctggt ttattgctga taaatctgga gccggtgagc gtgggtctcg | 1320 |
| cggtatcatt gcagcactgg ggccagatgg taagccctcc cgtatcgtag ttatctacac | 1380 |
| gacgggagt caggcaacta tggatgaacg aaatagacag atcgctgaga taggtgcctc | 1440 |
| actgattaag cattggtaac tgtcagacca agtttactca tatatacttt agattgattt | 1500 |
| aaaacttcat ttttaattta aaaggatcta ggtgaagatc ctttttgata atctcatgac | 1560 |
| caaaatccct aacgtgagt tttcgttcca ctgagcgtca gaccccgtag aaaagatcaa | 1620 |
| aggatcttct tgagatcctt ttttttctgcg cgtaatctgc tgcttgcaaa caaaaaaacc | 1680 |
| accgctacca gcggtggttt gtttgccgga tcaagagcta ccaactcttt ttccgaaggt | 1740 |
| aactggcttc agcagagcgc agataccaaa tactgtcctt ctagtgtagc cgtagttagg | 1800 |
| ccaccacttc aagaactctg tagcaccgcc tacatacctc gctctgctaa tcctgttacc | 1860 |
| agtggctgct gccagtggcg ataagtcgtg tcttaccggg ttggactcaa gacgatagtt | 1920 |
| accggataag gcgcagcggt cgggctgaac ggggggttcg tgcacacagc ccagcttgga | 1980 |
| gcgaacgacc tacaccgaac tgagatacct acagcgtgag ctatgagaaa gcgccacgct | 2040 |
| tcccgaaggg agaaaggcgg acaggtatcc ggtaagcggc agggtcggaa caggagagcg | 2100 |
| cacgagggag cttccagggg gaaacgcctg gtatctttat agtcctgtcg ggtttcgcca | 2160 |
| cctctgactt gagcgtcgat ttttgtgatg ctcgtcaggg gggcggagcc tatggaaaaa | 2220 |
| cgccagcaac gcggcctttt tacggttcct ggccttttgc tggccttttg ctcacatgtt | 2280 |
| ctttcctgcg ttatcccctg attctgtgga taaccgtatt accgcctttg agtgagctga | 2340 |
| taccgctcgc cgcagccgaa cgaccgagcg cagcgagtca gtgagcgagg aagcggaaga | 2400 |
| gcgcctgatg cggtattttc tccttacgca tctgtgcggt atttcacacc gcatatatgg | 2460 |

```
tgcactctca gtacaatctg ctctgatgcc gcatagttaa gccagtatac actccgctat        2520
cgctacgtga ctgggtcatg gctgcgcccc gacacccgcc aacacccgct gacgcgccct        2580
gacgggcttg tctgctcccg gcatccgctt acagacaagc tgtgaccgtc tccgggagct        2640
gcatgtgtca gaggttttca ccgtcatcac cgaaacgcgc gaggcagctg cggtaaagct        2700
catcagcgtg gtcgtgaagc gattcacaga tgtctgcctg ttcatccgcg tccagctcgt        2760
tgagtttctc cagaagcgtt aatgtctggc ttctgataaa gcgggccatg ttaagggcgg        2820
ttttttcctg tttggtcact gatgcctccg tgtaaggggg atttctgttc atgggggtaa        2880
tgataccgat gaaacgagag aggatgctca cgatacgggt tactgatgat gaacatgccc        2940
ggttactgga acgttgtgag ggtaaacaac tggcggtatg gatgcggcgg gaccagagaa        3000
aaatcactca gggtcaatgc cagcgcttcg ttaatacaga tgtaggtgtt ccacagggta        3060
gccagcagca tcctgcgatg cagatccgga acataatggt gcagggcgct gacttccgcg        3120
tttccagact ttacgaaaca cggaaaccga agaccattca tgttgttgct caggtcgcag        3180
acgttttgca gcagcagtcg cttcacgttc gctcgcgtat cggtgattca ttctgctaac        3240
cagtaaggca accccgccag cctagccggg tcctcaacga caggagcacg atcatgcgca        3300
cccgtggcca ggacccaacg ctgcccgaga tctcgatccc gcgaaattaa tacgactcac        3360
tatagggaga ccacaacggt ttccctctag aaataatttt gtttaacttt aagaaggaga        3420 tatacat atg agc tac aaa gct gcc gcg ggg gag gat tac aag gct gac           3469
        Met Ser Tyr Lys Ala Ala Ala Gly Glu Asp Tyr Lys Ala Asp
          1               5                  10 tgt cct cca ggg aac cca gca cct acc agt aat cat ggc cca gat gcc           3517
Cys Pro Pro Gly Asn Pro Ala Pro Thr Ser Asn His Gly Pro Asp Ala
 15              20                  25                  30 aca gaa gct gaa gag gat ttt gtg gac cca tgg aca gta cag aca agc           3565
Thr Glu Ala Glu Glu Asp Phe Val Asp Pro Trp Thr Val Gln Thr Ser
                 35                  40                  45 agt gca aaa ggc ata gac tac gat aag ctc att gtt cgg ttt gga agt           3613
Ser Ala Lys Gly Ile Asp Tyr Asp Lys Leu Ile Val Arg Phe Gly Ser
             50                  55                  60 agt aaa att gac aaa gag cta ata aac cga ata gag aga gcc acc ggc           3661
Ser Lys Ile Asp Lys Glu Leu Ile Asn Arg Ile Glu Arg Ala Thr Gly
 65                  70                  75 caa aga cca cac cac ttc ctg cgc aga ggc atc ttc ttc tca cac aga           3709
Gln Arg Pro His His Phe Leu Arg Arg Gly Ile Phe Phe Ser His Arg
         80                  85                  90 gat atg aat cag gtt ctt gat gcc tat gaa aat aag aag cca ttt tat           3757
Asp Met Asn Gln Val Leu Asp Ala Tyr Glu Asn Lys Lys Pro Phe Tyr
 95                 100                 105                 110 ctg tac acg ggc cgg ggc ccc tct tct gaa gca atg cat gta ggt cac           3805
Leu Tyr Thr Gly Arg Gly Pro Ser Ser Glu Ala Met His Val Gly His
                115                 120                 125 ctc att cca ttt att ttc aca aag tgg ctc cag gat gta ttt aac gtg           3853
Leu Ile Pro Phe Ile Phe Thr Lys Trp Leu Gln Asp Val Phe Asn Val
            130                 135                 140 ccc ttg gtc atc cag atg acg gat gac gag aag tat ctg tgg aag gac           3901
Pro Leu Val Ile Gln Met Thr Asp Asp Glu Lys Tyr Leu Trp Lys Asp
145                 150                 155 ctg acc ctg gac cag gcc tat ggc gat gct gtt gag aat gcc aag gac           3949
Leu Thr Leu Asp Gln Ala Tyr Gly Asp Ala Val Glu Asn Ala Lys Asp
        160                 165                 170 atc atc gcc tgt ggc ttt gac atc aac aag act ttc ata ttc tct gac           3997
Ile Ile Ala Cys Gly Phe Asp Ile Asn Lys Thr Phe Ile Phe Ser Asp
175                 180                 185                 190
```

| | | | | | | | | | | | | | | | | |
|---|---|---|---|---|---|---|---|---|---|---|---|---|---|---|---|---|
| ctg | gac | tac | atg | ggg | atg | agc | tca | ggt | ttc | tac | aaa | aat | gtg | gtg | aag | 4045 |
| Leu | Asp | Tyr | Met | Gly | Met | Ser | Ser | Gly | Phe | Tyr | Lys | Asn | Val | Val | Lys | |
| | | | | 195 | | | | 200 | | | | | 205 | | | |
| att | caa | aag | cat | gtt | acc | ttc | aac | caa | gtg | aaa | ggc | att | ttc | ggc | ttc | 4093 |
| Ile | Gln | Lys | His | Val | Thr | Phe | Asn | Gln | Val | Lys | Gly | Ile | Phe | Gly | Phe | |
| | | 210 | | | | | 215 | | | | | 220 | | | | |
| act | gac | agc | gac | tgc | att | ggg | aag | atc | agt | ttt | cct | gcc | atc | cag | gct | 4141 |
| Thr | Asp | Ser | Asp | Cys | Ile | Gly | Lys | Ile | Ser | Phe | Pro | Ala | Ile | Gln | Ala | |
| | | 225 | | | | 230 | | | | | 235 | | | | | |
| gct | ccc | tcc | ttc | agc | aac | tca | ttc | cca | cag | atc | ttc | cga | gac | agg | acg | 4189 |
| Ala | Pro | Ser | Phe | Ser | Asn | Ser | Phe | Pro | Gln | Ile | Phe | Arg | Asp | Arg | Thr | |
| | 240 | | | | | 245 | | | | | 250 | | | | | |
| gat | atc | cag | tgc | ctt | atc | cca | tgt | gcc | att | gac | cag | gat | cct | tac | ttt | 4237 |
| Asp | Ile | Gln | Cys | Leu | Ile | Pro | Cys | Ala | Ile | Asp | Gln | Asp | Pro | Tyr | Phe | |
| 255 | | | | | 260 | | | | | 265 | | | | | 270 | |
| aga | atg | aca | agg | gac | gtc | gcc | ccc | agg | atc | ggc | tat | cct | aaa | cca | gcc | 4285 |
| Arg | Met | Thr | Arg | Asp | Val | Ala | Pro | Arg | Ile | Gly | Tyr | Pro | Lys | Pro | Ala | |
| | | | | 275 | | | | | 280 | | | | | 285 | | |
| ctg | ttg | cac | tcc | acc | ttc | ttc | cca | gcc | ctg | cag | ggc | gcc | cag | acc | aaa | 4333 |
| Leu | Leu | His | Ser | Thr | Phe | Phe | Pro | Ala | Leu | Gln | Gly | Ala | Gln | Thr | Lys | |
| | | | | 290 | | | | | 295 | | | | | 300 | | |
| atg | agt | gcc | agc | gac | cca | aac | tcc | tcc | atc | ttc | ctc | acc | gac | acg | gcc | 4381 |
| Met | Ser | Ala | Ser | Asp | Pro | Asn | Ser | Ser | Ile | Phe | Leu | Thr | Asp | Thr | Ala | |
| | | | 305 | | | | | 310 | | | | | 315 | | | |
| aag | cag | atc | aaa | acc | aag | gtc | aat | aag | cat | gcg | ttt | tct | gga | ggg | aga | 4429 |
| Lys | Gln | Ile | Lys | Thr | Lys | Val | Asn | Lys | His | Ala | Phe | Ser | Gly | Gly | Arg | |
| | | | 320 | | | | | 325 | | | | | 330 | | | |
| gac | acc | atc | gag | gag | cac | agg | cag | ttt | ggg | ggc | aac | tgt | gat | gtg | gac | 4477 |
| Asp | Thr | Ile | Glu | Glu | His | Arg | Gln | Phe | Gly | Gly | Asn | Cys | Asp | Val | Asp | |
| 335 | | | | | 340 | | | | | 345 | | | | | 350 | |
| gtg | tct | ttc | atg | tac | ctg | acc | ttc | ttc | ctc | gag | gac | gac | gac | aag | ctc | 4525 |
| Val | Ser | Phe | Met | Tyr | Leu | Thr | Phe | Phe | Leu | Glu | Asp | Asp | Asp | Lys | Leu | |
| | | | | 355 | | | | | 360 | | | | | 365 | | |
| gag | cag | atc | agg | aag | gat | tac | acc | agc | gga | gcc | atg | ctc | acc | ggt | gag | 4573 |
| Glu | Gln | Ile | Arg | Lys | Asp | Tyr | Thr | Ser | Gly | Ala | Met | Leu | Thr | Gly | Glu | |
| | | | 370 | | | | | 375 | | | | | 380 | | | |
| ctc | aag | aag | gca | ctc | ata | gag | gtt | ctg | cag | ccc | ttg | atc | gca | gag | cac | 4621 |
| Leu | Lys | Lys | Ala | Leu | Ile | Glu | Val | Leu | Gln | Pro | Leu | Ile | Ala | Glu | His | |
| | | | 385 | | | | | 390 | | | | | 395 | | | |
| cag | gcc | cgg | cgc | aag | gag | gtc | acg | gat | gag | ata | gtg | aaa | gag | ttc | atg | 4669 |
| Gln | Ala | Arg | Arg | Lys | Glu | Val | Thr | Asp | Glu | Ile | Val | Lys | Glu | Phe | Met | |
| | 400 | | | | | 405 | | | | | 410 | | | | | |
| act | ccc | cgg | aag | ctg | tcc | ttc | gac | ttt | cag | aag | ctt | gcg | gcc | gca | ctc | 4717 |
| Thr | Pro | Arg | Lys | Leu | Ser | Phe | Asp | Phe | Gln | Lys | Leu | Ala | Ala | Ala | Leu | |
| 415 | | | | | 420 | | | | | 425 | | | | | 430 | |
| gag | cac | cac | cac | cac | cac | cac | tgagatccgg ctgctaacaa agcccgaaag | | | | | | | | | 4768 |
| Glu | His | His | His | His | His | His | | | | | | | | | | |
| | | | | | 435 | | | | | | | | | | | | gaagctgagt tggctgctgc caccgctgag caataactag cataaccect tggggcctct    4828 aaacgggtct tgaggggttt tttgctgaaa ggaggaacta tatccggat             4877

<210> SEQ ID NO 3
<211> LENGTH: 437
<212> TYPE: PRT
<213> ORGANISM: Artificial Sequence
<220> FEATURE:
<223> OTHER INFORMATION: Recombinant human mini-TrpRS protein construct

<400> SEQUENCE: 3

Met Ser Tyr Lys Ala Ala Ala Gly Glu Asp Tyr Lys Ala Asp Cys Pro
1               5                   10                  15

```
Pro Gly Asn Pro Ala Pro Thr Ser Asn His Gly Pro Asp Ala Thr Glu
            20                  25                  30

Ala Glu Glu Asp Phe Val Asp Pro Trp Thr Val Gln Thr Ser Ser Ala
            35                  40                  45

Lys Gly Ile Asp Tyr Asp Lys Leu Ile Val Arg Phe Gly Ser Ser Lys
            50                  55                  60

Ile Asp Lys Glu Leu Ile Asn Arg Ile Glu Arg Ala Thr Gly Gln Arg
 65                  70                  75                  80

Pro His His Phe Leu Arg Arg Gly Ile Phe Phe Ser His Arg Asp Met
                85                  90                  95

Asn Gln Val Leu Asp Ala Tyr Glu Asn Lys Lys Pro Phe Tyr Leu Tyr
            100                 105                 110

Thr Gly Arg Gly Pro Ser Ser Glu Ala Met His Val Gly His Leu Ile
            115                 120                 125

Pro Phe Ile Phe Thr Lys Trp Leu Gln Asp Val Phe Asn Val Pro Leu
            130                 135                 140

Val Ile Gln Met Thr Asp Asp Glu Lys Tyr Leu Trp Lys Asp Leu Thr
145                 150                 155                 160

Leu Asp Gln Ala Tyr Gly Asp Ala Val Glu Asn Ala Lys Asp Ile Ile
                165                 170                 175

Ala Cys Gly Phe Asp Ile Asn Lys Thr Phe Ile Phe Ser Asp Leu Asp
            180                 185                 190

Tyr Met Gly Met Ser Ser Gly Phe Tyr Lys Asn Val Val Lys Ile Gln
            195                 200                 205

Lys His Val Thr Phe Asn Gln Val Lys Gly Ile Phe Gly Phe Thr Asp
            210                 215                 220

Ser Asp Cys Ile Gly Lys Ile Ser Phe Pro Ala Ile Gln Ala Ala Pro
225                 230                 235                 240

Ser Phe Ser Asn Ser Phe Pro Gln Ile Phe Arg Asp Arg Thr Asp Ile
                245                 250                 255

Gln Cys Leu Ile Pro Cys Ala Ile Asp Gln Asp Pro Tyr Phe Arg Met
            260                 265                 270

Thr Arg Asp Val Ala Pro Arg Ile Gly Tyr Pro Lys Pro Ala Leu Leu
            275                 280                 285

His Ser Thr Phe Phe Pro Ala Leu Gln Gly Ala Gln Thr Lys Met Ser
            290                 295                 300

Ala Ser Asp Pro Asn Ser Ser Ile Phe Leu Thr Asp Thr Ala Lys Gln
305                 310                 315                 320

Ile Lys Thr Lys Val Asn Lys His Ala Phe Ser Gly Gly Arg Asp Thr
                325                 330                 335

Ile Glu Glu His Arg Gln Phe Gly Gly Asn Cys Asp Val Asp Val Ser
            340                 345                 350

Phe Met Tyr Leu Thr Phe Phe Leu Glu Asp Asp Lys Leu Glu Gln
            355                 360                 365

Ile Arg Lys Asp Tyr Thr Ser Gly Ala Met Leu Thr Gly Glu Leu Lys
            370                 375                 380

Lys Ala Leu Ile Glu Val Leu Gln Pro Leu Ile Ala Glu His Gln Ala
385                 390                 395                 400

Arg Arg Lys Glu Val Thr Asp Glu Ile Val Lys Glu Phe Met Thr Pro
                405                 410                 415

Arg Lys Leu Ser Phe Asp Phe Gln Lys Leu Ala Ala Ala Leu Glu His
            420                 425                 430

His His His His His
```

-continued

435

<210> SEQ ID NO 4
<211> LENGTH: 4811
<212> TYPE: DNA
<213> ORGANISM: Artificial Sequence
<220> FEATURE:
<223> OTHER INFORMATION: Recombinant human Met-T1-His tag nucleotide
      construct
<220> FEATURE:
<221> NAME/KEY: CDS
<222> LOCATION: (3428)..(4672)

<400> SEQUENCE: 4

```
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcgggggc tccctttagg     180 gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta taagggattt tgccgatttc ggcctattgg ttaaaaaatg agctgattta     420
acaaaaattt aacgcgaatt ttaacaaaat attaacgttt acaatttcag gtggcacttt     480
tcggggaaat gtgcgcggaa cccctatttg tttattttc taaatacatt caaatatgta     540
tccgctcatg agacaataac cctgataaat gcttcaataa tattgaaaaa ggaagagtat     600
gagtattcaa catttccgtg tcgcccttat cccttttttt gcggcatttt gccttcctgt     660
ttttgctcac ccagaaacgc tggtgaaagt aaaagatgct gaagatcagt tgggtgcacg     720
agtgggttac atcgaactgg atctcaacag cggtaagatc cttgagagtt ttcgccccga     780
agaacgtttt ccaatgatga gcacttttaa agttctgcta tgtggcgcgg tattatcccg     840
tattgacgcc gggcaagagc aactcggtcg ccgcatacac tattctcaga atgacttggt     900
tgagtactca ccagtcacag aaaagcatct tacggatggc atgacagtaa gagaattatg     960
cagtgctgcc ataaccatga gtgataacac tgcggccaac ttacttctga acgatcgg     1020 aggaccgaag gagctaaccg cttttttgca acatggggg gatcatgtaa ctcgccttga     1080
tcgttgggaa ccggagctga atgaagccat accaaacgac gagcgtgaca ccacgatgcc     1140
tgcagcaatg gcaacaacgt tgcgcaaact attaactggc gaactactta ctctagcttc     1200
ccggcaacaa ttaatagact ggatggaggc ggataaagtt gcaggaccac ttctgcgctc     1260
ggcccttccg gctggctggt ttattgctga taaatctgga gccggtgagc gtgggtctcg     1320
cggtatcatt gcagcactgg ggccagatgg taagccctcc cgtatcgtag ttatctacac     1380
gacggggagt caggcaacta tggatgaacg aaatagacag atcgctgaga taggtgcctc     1440
actgattaag cattggtaac tgtcagacca agtttactca tatatacttt agattgattt     1500
aaaacttcat ttttaattta aaaggatcta ggtgaagatc ctttttgata atctcatgac     1560
caaaatccct taacgtgagt tttcgttcca ctgagcgtca gaccccgtag aaaagatcaa     1620
aggatcttct tgagatcctt ttttttctgcg cgtaatctgc tgcttgcaaa caaaaaaacc     1680
accgctacca gcggtggttt gtttgccgga tcaagagcta ccaactcttt ttccgaaggt     1740
aactggcttc agcagagcgc agataccaaa tactgtcctt ctagtgtagc cgtagttagg     1800
ccaccacttc aagaactctg tagcaccgcc tacatacctc gctctgctaa tcctgttacc     1860
agtggctgct gccagtggcg ataagtcgtg tcttaccggg ttggactcaa gacgatagtt     1920
```

```
accggataag gcgcagcggt cgggctgaac gggggggttcg tgcacacagc ccagcttgga   1980
gcgaacgacc tacaccgaac tgagatacct acagcgtgag ctatgagaaa gcgccacgct   2040
tcccgaaggg agaaaggcgg acaggtatcc ggtaagcggc agggtcggaa caggagagcg   2100 cacgaggag cttccagggg gaaacgcctg gtatctttat agtcctgtcg ggtttcgcca   2160
cctctgactt gagcgtcgat ttttgtgatg ctcgtcaggg gggcggagcc tatggaaaaa   2220
cgccagcaac gcggccttt tacggttcct ggccttttgc tggccttttg ctcacatgtt   2280
ctttcctgcg ttatccctg attctgtgga taaccgtatt accgctttg agtgagctga   2340 taccgctcgc cgcagccgaa cgaccgagcg cagcgagtca gtgagcgagg aagcggaaga   2400
gcgcctgatg cggtatttc tccttacgca tctgtgcggt atttcacacc gcatatatgg   2460
tgcactctca gtacaatctg ctctgatgcc gcatagttaa gccagtatac actccgctat   2520
cgctacgtga ctgggtcatg gctgcgcccc gacacccgcc aacacccgct gacgcgccct   2580
gacgggcttg tctgctcccg gcatccgctt acagacaagc tgtgaccgtc tccgggagct   2640
gcatgtgtca gaggttttca ccgtcatcac cgaaacgcgc gaggcagctg cggtaaagct   2700
catcagcgtg gtcgtgaagc gattcacaga tgtctgcctg ttcatccgcg tccagctcgt   2760
tgagtttctc cagaagcgtt aatgtctggc ttctgataaa gcgggccatg ttaagggcgg   2820
ttttttcctg tttggtcact gatgcctccg tgtaagggg atttctgttc atggggtaa   2880 tgataccgat gaaacgagag aggatgctca cgatacgggt tactgatgat gaacatgccc   2940
ggttactgga acgttgtgag ggtaaacaac tggcggtatg gatgcggcgg gaccagagaa   3000
aaatcactca gggtcaatgc cagcgcttcg ttaatacaga tgtaggtgtt ccacagggta   3060
gccagcagca tcctgcgatg cagatccgga acataatggt gcagggcgct gacttccgcg   3120
tttccagact ttacgaaaca cggaaaccga agaccattca tgttgttgct caggtcgcag   3180
acgttttgca gcagcagtcg cttcacgttc gctcgcgtat cggtgattca ttctgctaac   3240
cagtaaggca accccgccag cctagccggg tcctcaacga caggagcacg atcatgcgca   3300
cccgtggcca ggacccaacg ctgcccgaga tctcgatccc gcgaaattaa tacgactcac   3360
tatagggaga ccacaacggt ttccctctag aaataatttt gtttaacttt aagaaggaga   3420 tatacat atg agt aat cat ggc cca gat gcc aca gaa gct gaa gag gat   3469
        Met Ser Asn His Gly Pro Asp Ala Thr Glu Ala Glu Glu Asp
         1               5                  10 ttt gtg gac cca tgg aca gta cag aca agc agt gca aaa ggc ata gac   3517
Phe Val Asp Pro Trp Thr Val Gln Thr Ser Ser Ala Lys Gly Ile Asp
 15              20                  25                  30 tac gat aag ctc att gtt cgg ttt gga agt agt aaa att gac aaa gag   3565
Tyr Asp Lys Leu Ile Val Arg Phe Gly Ser Ser Lys Ile Asp Lys Glu
             35                  40                  45 cta ata aac cga ata gag aga gcc acc ggc caa aga cca cac cac ttc   3613
Leu Ile Asn Arg Ile Glu Arg Ala Thr Gly Gln Arg Pro His His Phe
         50                  55                  60 ctg cgc aga ggc atc ttc ttc tca cac aga gat atg aat cag gtt ctt   3661
Leu Arg Arg Gly Ile Phe Phe Ser His Arg Asp Met Asn Gln Val Leu
 65                  70                  75 gat gcc tat gaa aat aag aag cca ttt tat ctg tac acg ggc cgg ggc   3709
Asp Ala Tyr Glu Asn Lys Lys Pro Phe Tyr Leu Tyr Thr Gly Arg Gly
             80                  85                  90 ccc tct tct gaa gca atg cat gta ggt cac ctc att cca ttt att ttc   3757
Pro Ser Ser Glu Ala Met His Val Gly His Leu Ile Pro Phe Ile Phe
 95                  100                 105                 110 aca aag tgg ctc cag gat gta ttt aac gtg ccc ttg gtc atc cag atg   3805
Thr Lys Trp Leu Gln Asp Val Phe Asn Val Pro Leu Val Ile Gln Met
```

```
                    115                 120                 125
acg gat gac gag aag tat ctg tgg aag gac ctg acc ctg gac cag gcc       3853
Thr Asp Asp Glu Lys Tyr Leu Trp Lys Asp Leu Thr Leu Asp Gln Ala
            130                 135                 140 tat ggc gat gct gtt gag aat gcc aag gac atc atc gcc tgt ggc ttt       3901
Tyr Gly Asp Ala Val Glu Asn Ala Lys Asp Ile Ile Ala Cys Gly Phe
        145                 150                 155 gac atc aac aag act ttc ata ttc tct gac ctg gac tac atg ggg atg       3949
Asp Ile Asn Lys Thr Phe Ile Phe Ser Asp Leu Asp Tyr Met Gly Met
160                 165                 170 agc tca ggt ttc tac aaa aat gtg gtg aag att caa aag cat gtt acc       3997
Ser Ser Gly Phe Tyr Lys Asn Val Val Lys Ile Gln Lys His Val Thr
175                 180                 185                 190 ttc aac caa gtg aaa ggc att ttc ggc ttc act gac agc gac tgc att       4045
Phe Asn Gln Val Lys Gly Ile Phe Gly Phe Thr Asp Ser Asp Cys Ile
                195                 200                 205 ggg aag atc agt ttt cct gcc atc cag gct gct ccc tcc ttc agc aac       4093
Gly Lys Ile Ser Phe Pro Ala Ile Gln Ala Ala Pro Ser Phe Ser Asn
            210                 215                 220 tca ttc cca cag atc ttc cga gac agg acg gat atc cag tgc ctt atc       4141
Ser Phe Pro Gln Ile Phe Arg Asp Arg Thr Asp Ile Gln Cys Leu Ile
        225                 230                 235 cca tgt gcc att gac cag gat cct tac ttt aga atg aca agg gac gtc       4189
Pro Cys Ala Ile Asp Gln Asp Pro Tyr Phe Arg Met Thr Arg Asp Val
240                 245                 250 gcc ccc agg atc ggc tat cct aaa cca gcc ctg ttg cac tcc acc ttc       4237
Ala Pro Arg Ile Gly Tyr Pro Lys Pro Ala Leu Leu His Ser Thr Phe
255                 260                 265                 270 ttc cca gcc ctg cag ggc gcc cag acc aaa atg agt gcc agc gac cca       4285
Phe Pro Ala Leu Gln Gly Ala Gln Thr Lys Met Ser Ala Ser Asp Pro
                275                 280                 285 aac tcc tcc atc ttc ctc acc gac acg gcc aag cag atc aaa acc aag       4333
Asn Ser Ser Ile Phe Leu Thr Asp Thr Ala Lys Gln Ile Lys Thr Lys
            290                 295                 300 gtc aat aag cat gcg ttt tct gga ggg aga gac acc atc gag gag cac       4381
Val Asn Lys His Ala Phe Ser Gly Gly Arg Asp Thr Ile Glu Glu His
        305                 310                 315 agg cag ttt ggg ggc aac tgt gat gtg gac gtg tct ttc atg tac ctg       4429
Arg Gln Phe Gly Gly Asn Cys Asp Val Asp Val Ser Phe Met Tyr Leu
320                 325                 330 acc ttc ttc ctc gag gac gac gac aag ctc gag cag atc agg aag gat       4477
Thr Phe Phe Leu Glu Asp Asp Asp Lys Leu Glu Gln Ile Arg Lys Asp
335                 340                 345                 350 tac acc agc gga gcc atg ctc acc ggt gag ctc aag aag gca ctc ata       4525
Tyr Thr Ser Gly Ala Met Leu Thr Gly Glu Leu Lys Lys Ala Leu Ile
                355                 360                 365 gag gtt ctg cag ccc ttg atc gca gag cac cag gcc cgg cgc aag gag       4573
Glu Val Leu Gln Pro Leu Ile Ala Glu His Gln Ala Arg Arg Lys Glu
            370                 375                 380 gtc acg gat gag ata gtg aaa gag ttc atg act ccc cgg aag ctg tcc       4621
Val Thr Asp Glu Ile Val Lys Glu Phe Met Thr Pro Arg Lys Leu Ser
        385                 390                 395 ttc gac ttt cag aag ctt gcg gcc gca ctc gag cac cac cac cac cac       4669
Phe Asp Phe Gln Lys Leu Ala Ala Ala Leu Glu His His His His His
400                 405                 410 cac tgagatccgg ctgctaacaa agcccgaaag gaagctgagt tggctgctgc             4722
His
415 caccgctgag caataactag cataacccct tggggcctct aaacgggtct tgaggggttt      4782
```
tttgctgaaa ggaggaacta tatccggat                                              4811

<210> SEQ ID NO 5
<211> LENGTH: 415
<212> TYPE: PRT
<213> ORGANISM: Artificial Sequence
<220> FEATURE:
<223> OTHER INFORMATION: Recombinant human Met-T1-His tag protein
      construct

<400> SEQUENCE: 5

Met Ser Asn His Gly Pro Asp Ala Thr Glu Ala Glu Asp Phe Val
1               5                   10                  15

Asp Pro Trp Thr Val Gln Thr Ser Ala Lys Gly Ile Asp Tyr Asp
                20                  25                  30

Lys Leu Ile Val Arg Phe Gly Ser Ser Lys Ile Asp Lys Glu Leu Ile
                35                  40                  45

Asn Arg Ile Glu Arg Ala Thr Gly Gln Arg Pro His His Phe Leu Arg
50                  55                  60

Arg Gly Ile Phe Phe Ser His Arg Asp Met Asn Gln Val Leu Asp Ala
65                  70                  75                  80

Tyr Glu Asn Lys Lys Pro Phe Tyr Leu Tyr Thr Gly Arg Gly Pro Ser
                85                  90                  95

Ser Glu Ala Met His Val Gly His Leu Ile Pro Phe Ile Phe Thr Lys
                100                 105                 110

Trp Leu Gln Asp Val Phe Asn Val Pro Leu Val Ile Gln Met Thr Asp
                115                 120                 125

Asp Glu Lys Tyr Leu Trp Lys Asp Leu Thr Leu Asp Gln Ala Tyr Gly
                130                 135                 140

Asp Ala Val Glu Asn Ala Lys Asp Ile Ile Ala Cys Gly Phe Asp Ile
145                 150                 155                 160

Asn Lys Thr Phe Ile Phe Ser Asp Leu Asp Tyr Met Gly Met Ser Ser
                165                 170                 175

Gly Phe Tyr Lys Asn Val Val Lys Ile Gln Lys His Val Thr Phe Asn
                180                 185                 190

Gln Val Lys Gly Ile Phe Gly Phe Thr Asp Ser Asp Cys Ile Gly Lys
                195                 200                 205

Ile Ser Phe Pro Ala Ile Gln Ala Ala Pro Ser Phe Ser Asn Ser Phe
210                 215                 220

Pro Gln Ile Phe Arg Asp Arg Thr Asp Ile Gln Cys Leu Ile Pro Cys
225                 230                 235                 240

Ala Ile Asp Gln Asp Pro Tyr Phe Arg Met Thr Arg Asp Val Ala Pro
                245                 250                 255

Arg Ile Gly Tyr Pro Lys Pro Ala Leu Leu His Ser Thr Phe Phe Pro
                260                 265                 270

Ala Leu Gln Gly Ala Gln Thr Lys Met Ser Ala Ser Asp Pro Asn Ser
                275                 280                 285

Ser Ile Phe Leu Thr Asp Thr Ala Lys Gln Ile Lys Thr Lys Val Asn
                290                 295                 300

Lys His Ala Phe Ser Gly Gly Arg Asp Thr Ile Glu Glu His Arg Gln
305                 310                 315                 320

Phe Gly Gly Asn Cys Asp Val Asp Val Ser Phe Met Tyr Leu Thr Phe
                325                 330                 335

Phe Leu Glu Asp Asp Asp Lys Leu Glu Gln Ile Arg Lys Asp Tyr Thr
                340                 345                 350

Ser Gly Ala Met Leu Thr Gly Glu Leu Lys Lys Ala Leu Ile Glu Val

```
                        355                 360                 365
Leu Gln Pro Leu Ile Ala Glu His Gln Ala Arg Arg Lys Glu Val Thr
            370                 375                 380

Asp Glu Ile Val Lys Glu Phe Met Thr Pro Arg Lys Leu Ser Phe Asp
385                 390                 395                 400

Phe Gln Lys Leu Ala Ala Ala Leu Glu His His His His His His
                405                 410                 415

<210> SEQ ID NO 6
<211> LENGTH: 4742
<212> TYPE: DNA
<213> ORGANISM: Artificial Sequence
<220> FEATURE:
<223> OTHER INFORMATION: Recombinant human Met-T2-His tag nucleotide
      construct
<220> FEATURE:
<221> NAME/KEY: CDS
<222> LOCATION: (3428)..(4603)

<400> SEQUENCE: 6
tggcgaatgg gacgcgccct gtagcggcgc attaagcgcg gcgggtgtgg tggttacgcg     60
cagcgtgacc gctacacttg ccagcgccct agcgcccgct cctttcgctt tcttcccttc    120
ctttctcgcc acgttcgccg gctttccccg tcaagctcta atcggggggc tccctttagg    180
gttccgattt agtgctttac ggcacctcga ccccaaaaaa cttgattagg gtgatggttc    240
acgtagtggg ccatcgccct gatagacggt ttttcgccct tgacgttgg agtccacgtt     300 ctttaatagt ggactcttgt tccaaactgg aacaacactc aacctatct cggtctattc     360 ttttgattta aagggatttt tgccgatttc ggcctattgg ttaaaaatg agctgattta     420 acaaaaattt aacgcgaatt ttaacaaaat attaacgttt acaatttcag gtggcacttt    480
tcggggaaat gtgcgcggaa cccctatttg tttatttttc taaatacatt caaatatgta    540
tccgctcatg agacaataac cctgataaat gcttcaataa tattgaaaaa ggaagagtat    600
gagtattcaa catttccgtg tcgcccttat ccctttttt gcggcatttt gccttcctgt     660
ttttgctcac ccagaaacgc tggtgaaagt aaaagatgct gaagatcagt tgggtgcacg    720
agtgggttac atcgaactgg atctcaacag cggtaagatc cttgagagtt tcgccccga     780 agaacgtttt ccaatgatga gcacttttaa agttctgcta tgtggcgcgg tattatcccg    840
tattgacgcc gggcaagagc aactcggtcg ccgcatacac tattctcaga atgacttggt    900
tgagtactca ccagtcacag aaaagcatct tacggatggc atgacagtaa gagaattatg    960
cagtgctgcc ataaccatga gtgataacac tgcggccaac ttacttctga caacgatcgg   1020
aggaccgaag gagctaaccg cttttttgca acatggggg gatcatgtaa ctcgccttga   1080
tcgttgggaa ccggagctga atgaagccat accaaacgac gagcgtgaca ccacgatgcc   1140
tgcagcaatg gcaacaacgt tgcgcaaact attaactggc gaactactta ctctagcttc   1200
ccggcaacaa ttaatagact ggatggaggc ggataaagtt gcaggaccac ttctgcgctc   1260
ggcccttccg gctggctggt ttattgctga taaatctgga gccggtgagc gtgggtctcg   1320
cggtatcatt gcagcactgg ggccagatgg taagccctcc cgtatcgtag ttatctacac   1380
gacggggagt caggcaacta tggatgaacg aaatagacag atcgctgaga taggtgcctc   1440
actgattaag cattggtaac tgtcagacca agtttactca tatatacttt agattgattt   1500
aaaacttcat ttttaattta aaaggatcta ggtgaagatc ctttttgata atctcatgac   1560
caaaatccct taacgtgagt tttcgttcca ctgagcgtca gaccccgtag aaaagatcaa   1620
aggatcttct tgagatcctt ttttttctgcg cgtaatctgc tgcttgcaaa caaaaaaacc   1680
```

```
accgctacca gcggtggttt gtttgccgga tcaagagcta ccaactcttt ttccgaaggt   1740
aactggcttc agcagagcgc agataccaaa tactgtcctt ctagtgtagc cgtagttagg   1800
ccaccacttc aagaactctg tagcaccgcc tacatacctc gctctgctaa tcctgttacc   1860
agtggctgct gccagtggcg ataagtcgtg tcttaccggg ttggactcaa gacgatagtt   1920
accggataag gcgcagcggt cgggctgaac gggggggttcg tgcacacagc ccagcttgga   1980
gcgaacgacc tacaccgaac tgagatacct acagcgtgag ctatgagaaa gcgccacgct   2040
tcccgaaggg agaaaggcgg acaggtatcc ggtaagcggc agggtcggaa caggagagcg   2100
cacgagggag cttccagggg gaaacgcctg gtatctttat agtcctgtcg ggtttcgcca   2160
cctctgactt gagcgtcgat ttttgtgatg ctcgtcaggg gggcggagcc tatggaaaaa   2220
cgccagcaac gcggcctttt tacggttcct ggccttttgc tggccttttg ctcacatgtt   2280
ctttcctgcg ttatcccctg attctgtgga taaccgtatt accgcctttg agtgagctga   2340
taccgctcgc cgcagccgaa cgaccgagcg cagcgagtca gtgagcgagg aagcggaaga   2400
gcgcctgatg cggtattttc tccttacgca tctgtgcggt atttcacacc gcatatatgg   2460
tgcactctca gtacaatctg ctctgatgcc gcatagttaa gccagtatac actccgctat   2520
cgctacgtga ctgggtcatg gctgcgcccc gacacccgcc aacacccgct gacgcgccct   2580
gacgggcttg tctgctcccg gcatccgctt acagacaagc tgtgaccgtc tccgggagct   2640
gcatgtgtca gaggttttca ccgtcatcac cgaaacgcgc gaggcagctg cggtaaagct   2700
catcagcgtg tcgtgaagc gattcacaga tgtctgcctg ttcatccgcg tccagctcgt   2760
tgagtttctc cagaagcgtt aatgtctggc ttctgataaa gcgggccatg ttaagggcgg   2820
ttttttcctg tttggtcact gatgcctccg tgtaaggggg attctgttc atggggtaa   2880 tgataccgat gaaacgagag aggatgctca cgatacgggt tactgatgat gaacatgccc   2940
ggttactgga acgttgtgag ggtaaacaac tggcggtatg gatgcggcgg gaccagagaa   3000
aaatcactca gggtcaatgc cagcgcttcg ttaatacaga tgtaggtgtt ccacagggta   3060
gccagcagca tcctgcgatg cagatccgga acataatggt gcagggcgct gacttccgcg   3120
tttccagact ttacgaaaca cggaaaccga agaccattca tgttgttgct caggtcgcag   3180
acgttttgca gcagcagtcg cttcacgttc gctcgcgtat cggtgattca ttctgctaac   3240
cagtaaggca accccgccag cctagccggg tcctcaacga caggagcacg atcatgcgca   3300
cccgtggcca ggacccaacg ctgcccgaga tctcgatccc gcgaaattaa tacgactcac   3360
tatagggaga ccacaacggt ttccctctag aaataatttt gtttaacttt aagaaggaga   3420 tatacat atg agt gca aaa ggc ata gac tac gat aag ctc att gtt cgg     3469
        Met Ser Ala Lys Gly Ile Asp Tyr Asp Lys Leu Ile Val Arg
        1               5                   10 ttt gga agt agt aaa att gac aaa gag cta ata aac cga ata gag aga     3517
Phe Gly Ser Ser Lys Ile Asp Lys Glu Leu Ile Asn Arg Ile Glu Arg
15                  20                  25                  30 gcc acc ggc caa aga cca cac cac ttc ctg cgc aga ggc atc ttc ttc     3565
Ala Thr Gly Gln Arg Pro His His Phe Leu Arg Arg Gly Ile Phe Phe
                35                  40                  45 tca cac aga gat atg aat cag gtt ctt gat gcc tat gaa aat aag aag     3613
Ser His Arg Asp Met Asn Gln Val Leu Asp Ala Tyr Glu Asn Lys Lys
            50                  55                  60 cca ttt tat ctg tac acg ggc cgg ggc ccc tct tct gaa gca atg cat     3661
Pro Phe Tyr Leu Tyr Thr Gly Arg Gly Pro Ser Ser Glu Ala Met His
65                  70                  75 gta ggt cac ctc att cca ttt att ttc aca aag tgg ctc cag gat gta     3709
```

-continued

| | | | | | | | | | | | | | | |
|---|---|---|---|---|---|---|---|---|---|---|---|---|---|---|
| Val | Gly | His | Leu | Ile | Pro | Phe | Ile | Phe | Thr | Lys | Trp | Leu | Gln | Asp | Val |
| | 80 | | | | 85 | | | | | 90 | | | | | |

```
ttt aac gtg ccc ttg gtc atc cag atg acg gat gac gag aag tat ctg    3757
Phe Asn Val Pro Leu Val Ile Gln Met Thr Asp Asp Glu Lys Tyr Leu
 95             100                 105                 110 tgg aag gac ctg acc ctg gac cag gcc tat ggc gat gct gtt gag aat    3805
Trp Lys Asp Leu Thr Leu Asp Gln Ala Tyr Gly Asp Ala Val Glu Asn
             115                 120                 125 gcc aag gac atc atc gcc tgt ggc ttt gac atc aac aag act ttc ata    3853
Ala Lys Asp Ile Ile Ala Cys Gly Phe Asp Ile Asn Lys Thr Phe Ile
         130                 135                 140 ttc tct gac ctg gac tac atg ggg atg agc tca ggt ttc tac aaa aat    3901
Phe Ser Asp Leu Asp Tyr Met Gly Met Ser Ser Gly Phe Tyr Lys Asn
     145                 150                 155 gtg gtg aag att caa aag cat gtt acc ttc aac caa gtg aaa ggc att    3949
Val Val Lys Ile Gln Lys His Val Thr Phe Asn Gln Val Lys Gly Ile
 160                 165                 170 ttc ggc ttc act gac agc gac tgc att ggg aag atc agt ttt cct gcc    3997
Phe Gly Phe Thr Asp Ser Asp Cys Ile Gly Lys Ile Ser Phe Pro Ala
175                 180                 185                 190 atc cag gct gct ccc tcc ttc agc aac tca ttc cca cag atc ttc cga    4045
Ile Gln Ala Ala Pro Ser Phe Ser Asn Ser Phe Pro Gln Ile Phe Arg
             195                 200                 205 gac agg acg gat atc cag tgc ctt atc cca tgt gcc att gac cag gat    4093
Asp Arg Thr Asp Ile Gln Cys Leu Ile Pro Cys Ala Ile Asp Gln Asp
         210                 215                 220 cct tac ttt aga atg aca agg gac gtc gcc ccc agg atc ggc tat cct    4141
Pro Tyr Phe Arg Met Thr Arg Asp Val Ala Pro Arg Ile Gly Tyr Pro
     225                 230                 235 aaa cca gcc ctg ttg cac tcc acc ttc ttc cca gcc ctg cag ggc gcc    4189
Lys Pro Ala Leu Leu His Ser Thr Phe Phe Pro Ala Leu Gln Gly Ala
 240                 245                 250 cag acc aaa atg agt gcc agc gac cca aac tcc tcc atc ttc ctc acc    4237
Gln Thr Lys Met Ser Ala Ser Asp Pro Asn Ser Ser Ile Phe Leu Thr
255                 260                 265                 270 gac acg gcc aag cag atc aaa acc aag gtc aat aag cat gcg ttt tct    4285
Asp Thr Ala Lys Gln Ile Lys Thr Lys Val Asn Lys His Ala Phe Ser
             275                 280                 285 gga ggg aga gac acc atc gag gag cac agg cag ttt ggg ggc aac tgt    4333
Gly Gly Arg Asp Thr Ile Glu Glu His Arg Gln Phe Gly Gly Asn Cys
         290                 295                 300 gat gtg gac gtg tct ttc atg tac ctg acc ttc ttc ctc gag gac gac    4381
Asp Val Asp Val Ser Phe Met Tyr Leu Thr Phe Phe Leu Glu Asp Asp
     305                 310                 315 gac aag ctc gag cag atc agg aag gat tac acc agc gga gcc atg ctc    4429
Asp Lys Leu Glu Gln Ile Arg Lys Asp Tyr Thr Ser Gly Ala Met Leu
 320                 325                 330 acc ggt gag ctc aag aag gca ctc ata gag gtt ctg cag ccc ttg atc    4477
Thr Gly Glu Leu Lys Lys Ala Leu Ile Glu Val Leu Gln Pro Leu Ile
335                 340                 345                 350 gca gag cac cag gcc cgg cgc aag gag gtc acg gat gag ata gtg aaa    4525
Ala Glu His Gln Ala Arg Arg Lys Glu Val Thr Asp Glu Ile Val Lys
             355                 360                 365 gag ttc atg act ccc cgg aag ctg tcc ttc gac ttt cag aag ctt gcg    4573
Glu Phe Met Thr Pro Arg Lys Leu Ser Phe Asp Phe Gln Lys Leu Ala
         370                 375                 380 gcc gca ctc gag cac cac cac cac cac cac tgagatccgg ctgctaacaa     4623
Ala Ala Leu Glu His His His His His His
     385                 390 agcccgaaag gaagctgagt tggctgctgc caccgctgag caataactag cataacccct  4683
```

-continued

```
tggggcctct aaacgggtct tgaggggttt tttgctgaaa ggaggaacta tatccggat    4742
```

<210> SEQ ID NO 7
<211> LENGTH: 392
<212> TYPE: PRT
<213> ORGANISM: Artificial Sequence
<220> FEATURE:
<223> OTHER INFORMATION: Recombinant human Met-T2-His tag protein construct

<400> SEQUENCE: 7

```
Met Ser Ala Lys Gly Ile Asp Tyr Asp Lys Leu Ile Val Arg Phe Gly
1               5                   10                  15

Ser Ser Lys Ile Asp Lys Glu Leu Ile Asn Arg Ile Glu Arg Ala Thr
                20                  25                  30

Gly Gln Arg Pro His His Phe Leu Arg Arg Gly Ile Phe Phe Ser His
            35                  40                  45

Arg Asp Met Asn Gln Val Leu Asp Ala Tyr Glu Asn Lys Lys Pro Phe
        50                  55                  60

Tyr Leu Tyr Thr Gly Arg Gly Pro Ser Ser Glu Ala Met His Val Gly
65                  70                  75                  80

His Leu Ile Pro Phe Ile Phe Thr Lys Trp Leu Gln Asp Val Phe Asn
                85                  90                  95

Val Pro Leu Val Ile Gln Met Thr Asp Asp Glu Lys Tyr Leu Trp Lys
                100                 105                 110

Asp Leu Thr Leu Asp Gln Ala Tyr Gly Asp Ala Val Glu Asn Ala Lys
            115                 120                 125

Asp Ile Ile Ala Cys Gly Phe Asp Ile Asn Lys Thr Phe Ile Phe Ser
        130                 135                 140

Asp Leu Asp Tyr Met Gly Met Ser Ser Gly Phe Tyr Lys Asn Val Val
145                 150                 155                 160

Lys Ile Gln Lys His Val Thr Phe Asn Gln Val Lys Gly Ile Phe Gly
                165                 170                 175

Phe Thr Asp Ser Asp Cys Ile Gly Lys Ile Ser Phe Pro Ala Ile Gln
            180                 185                 190

Ala Ala Pro Ser Phe Ser Asn Ser Phe Pro Gln Ile Phe Arg Asp Arg
        195                 200                 205

Thr Asp Ile Gln Cys Leu Ile Pro Cys Ala Ile Asp Gln Asp Pro Tyr
    210                 215                 220

Phe Arg Met Thr Arg Asp Val Ala Pro Arg Ile Gly Tyr Pro Lys Pro
225                 230                 235                 240

Ala Leu Leu His Ser Thr Phe Phe Pro Ala Leu Gln Gly Ala Gln Thr
                245                 250                 255

Lys Met Ser Ala Ser Asp Pro Asn Ser Ser Ile Phe Leu Thr Asp Thr
            260                 265                 270

Ala Lys Gln Ile Lys Thr Lys Val Asn Lys His Ala Phe Ser Gly Gly
        275                 280                 285

Arg Asp Thr Ile Glu Glu His Arg Gln Phe Gly Gly Asn Cys Asp Val
    290                 295                 300

Asp Val Ser Phe Met Tyr Leu Thr Phe Phe Leu Glu Asp Asp Lys
305                 310                 315                 320

Leu Glu Gln Ile Arg Lys Asp Tyr Thr Ser Gly Ala Met Leu Thr Gly
                325                 330                 335

Glu Leu Lys Lys Ala Leu Ile Glu Val Leu Gln Pro Leu Ile Ala Glu
            340                 345                 350
```

His Gln Ala Arg Arg Lys Glu Val Thr Asp Glu Ile Val Lys Glu Phe
            355                 360                 365

Met Thr Pro Arg Lys Leu Ser Phe Asp Phe Gln Lys Leu Ala Ala Ala
        370                 375                 380

Leu Glu His His His His His His
385                 390

<210> SEQ ID NO 8
<211> LENGTH: 5
<212> TYPE: PRT
<213> ORGANISM: Homo sapiens

<400> SEQUENCE: 8

Ser Asn His Gly Pro
1               5

<210> SEQ ID NO 9
<211> LENGTH: 5
<212> TYPE: PRT
<213> ORGANISM: Homo sapiens

<400> SEQUENCE: 9

Ser Ala Lys Gly Ile
1               5

<210> SEQ ID NO 10
<211> LENGTH: 4
<212> TYPE: PRT
<213> ORGANISM: Homo sapiens

<400> SEQUENCE: 10

His Val Gly His
1

<210> SEQ ID NO 11
<211> LENGTH: 5
<212> TYPE: PRT
<213> ORGANISM: Homo sapiens

<400> SEQUENCE: 11

Lys Met Ser Ala Ser
1               5

<210> SEQ ID NO 12
<211> LENGTH: 378
<212> TYPE: PRT
<213> ORGANISM: Homo sapiens

<400> SEQUENCE: 12

Ser Ala Lys Gly Ile Asp Tyr Asp Lys Leu Ile Val Arg Phe Gly Ser
1               5                   10                  15

Ser Lys Ile Asp Lys Glu Leu Ile Asn Arg Ile Glu Arg Ala Thr Gly
            20                  25                  30

Gln Arg Pro His His Phe Leu Arg Arg Gly Ile Phe Phe Ser His Arg
        35                  40                  45

Asp Met Asn Gln Val Leu Asp Ala Tyr Glu Asn Lys Lys Pro Phe Tyr
    50                  55                  60

Leu Tyr Thr Gly Arg Gly Pro Ser Ser Glu Ala Met His Val Gly His
65                  70                  75                  80

Leu Ile Pro Phe Ile Phe Thr Lys Trp Leu Gln Asp Val Phe Asn Val
                85                  90                  95

Pro Leu Val Ile Gln Met Thr Asp Asp Glu Lys Tyr Leu Trp Lys Asp

-continued

```
                100                 105                 110
Leu Thr Leu Asp Gln Ala Tyr Gly Asp Ala Val Glu Asn Ala Lys Asp
            115                 120                 125

Ile Ile Ala Cys Gly Phe Asp Ile Asn Lys Thr Phe Ile Phe Ser Asp
130                 135                 140

Leu Asp Tyr Met Gly Met Ser Ser Gly Phe Tyr Lys Asn Val Val Lys
145                 150                 155                 160

Ile Gln Lys His Val Thr Phe Asn Gln Val Lys Gly Ile Phe Gly Phe
                165                 170                 175

Thr Asp Ser Asp Cys Ile Gly Lys Ile Ser Phe Pro Ala Ile Gln Ala
            180                 185                 190

Ala Pro Ser Phe Ser Asn Ser Phe Pro Gln Ile Phe Arg Asp Arg Thr
        195                 200                 205

Asp Ile Gln Cys Leu Ile Pro Cys Ala Ile Asp Gln Asp Pro Tyr Phe
    210                 215                 220

Arg Met Thr Arg Asp Val Ala Pro Arg Ile Gly Tyr Pro Lys Pro Ala
225                 230                 235                 240

Leu Leu His Ser Thr Phe Phe Pro Ala Leu Gln Gly Ala Gln Thr Lys
                245                 250                 255

Met Ser Ala Ser Asp Pro Asn Ser Ser Ile Phe Leu Thr Asp Thr Ala
            260                 265                 270

Lys Gln Ile Lys Thr Lys Val Asn Lys His Ala Phe Ser Gly Gly Arg
        275                 280                 285

Asp Thr Ile Glu Glu His Arg Gln Phe Gly Gly Asn Cys Asp Val Asp
    290                 295                 300

Val Ser Phe Met Tyr Leu Thr Phe Phe Leu Glu Asp Asp Lys Leu
305                 310                 315                 320

Glu Gln Ile Arg Lys Asp Tyr Thr Ser Gly Ala Met Leu Thr Gly Glu
                325                 330                 335

Leu Lys Lys Ala Leu Ile Glu Val Leu Gln Pro Leu Ile Ala Glu His
            340                 345                 350

Gln Ala Arg Arg Lys Glu Val Thr Asp Glu Ile Val Lys Glu Phe Met
        355                 360                 365

Thr Pro Arg Lys Leu Ser Phe Asp Phe Gln
    370                 375

<210> SEQ ID NO 13
<211> LENGTH: 401
<212> TYPE: PRT
<213> ORGANISM: Homo sapiens

<400> SEQUENCE: 13

Ser Asn His Gly Pro Asp Ala Thr Glu Ala Glu Asp Phe Val Asp
1               5                   10                  15

Pro Trp Thr Val Gln Thr Ser Ser Ala Lys Gly Ile Asp Tyr Asp Lys
                20                  25                  30

Leu Ile Val Arg Phe Gly Ser Ser Lys Ile Asp Lys Glu Leu Ile Asn
            35                  40                  45

Arg Ile Glu Arg Ala Thr Gly Gln Arg Pro His His Phe Leu Arg Arg
        50                  55                  60

Gly Ile Phe Phe Ser His Arg Asp Met Asn Gln Val Leu Asp Ala Tyr
65                  70                  75                  80

Glu Asn Lys Lys Pro Phe Tyr Leu Tyr Thr Gly Arg Gly Pro Ser Ser
                85                  90                  95

Glu Ala Met His Val Gly His Leu Ile Pro Phe Ile Phe Thr Lys Trp
```

```
                100               105                110
Leu Gln Asp Val Phe Asn Val Pro Leu Val Ile Gln Met Thr Asp Asp
            115                 120                 125

Glu Lys Tyr Leu Trp Lys Asp Leu Thr Leu Asp Gln Ala Tyr Gly Asp
        130                 135                 140

Ala Val Glu Asn Ala Lys Asp Ile Ile Ala Cys Gly Phe Asp Ile Asn
145                 150                 155                 160

Lys Thr Phe Ile Phe Ser Asp Leu Asp Tyr Met Gly Met Ser Ser Gly
                165                 170                 175

Phe Tyr Lys Asn Val Val Lys Ile Gln Lys His Val Thr Phe Asn Gln
            180                 185                 190

Val Lys Gly Ile Phe Gly Phe Thr Asp Ser Asp Cys Ile Gly Lys Ile
        195                 200                 205

Ser Phe Pro Ala Ile Gln Ala Ala Pro Ser Phe Ser Asn Ser Phe Pro
210                 215                 220

Gln Ile Phe Arg Asp Arg Thr Asp Ile Gln Cys Leu Ile Pro Cys Ala
225                 230                 235                 240

Ile Asp Gln Asp Pro Tyr Phe Arg Met Thr Arg Asp Val Ala Pro Arg
                245                 250                 255

Ile Gly Tyr Pro Lys Pro Ala Leu Leu His Ser Thr Phe Phe Pro Ala
            260                 265                 270

Leu Gln Gly Ala Gln Thr Lys Met Ser Ala Ser Asp Pro Asn Ser Ser
        275                 280                 285

Ile Phe Leu Thr Asp Thr Ala Lys Gln Ile Lys Thr Lys Val Asn Lys
        290                 295                 300

His Ala Phe Ser Gly Gly Arg Asp Thr Ile Glu Glu His Arg Gln Phe
305                 310                 315                 320

Gly Gly Asn Cys Asp Val Asp Val Ser Phe Met Tyr Leu Thr Phe Phe
                325                 330                 335

Leu Glu Asp Asp Asp Lys Leu Glu Gln Ile Arg Lys Asp Tyr Thr Ser
            340                 345                 350

Gly Ala Met Leu Thr Gly Glu Leu Lys Lys Ala Leu Ile Glu Val Leu
        355                 360                 365

Gln Pro Leu Ile Ala Glu His Gln Ala Arg Arg Lys Glu Val Thr Asp
        370                 375                 380

Glu Ile Val Lys Glu Phe Met Thr Pro Arg Lys Leu Ser Phe Asp Phe
385                 390                 395                 400

Gln

<210> SEQ ID NO 14
<211> LENGTH: 423
<212> TYPE: PRT
<213> ORGANISM: Artificial Sequence
<220> FEATURE:
<223> OTHER INFORMATION: Recombinant human mini-TrpRS (GD variant)
      construct

<400> SEQUENCE: 14

Ser Tyr Lys Ala Ala Ala Gly Glu Asp Tyr Lys Ala Asp Cys Pro Pro
1               5                   10                  15

Gly Asn Pro Ala Pro Thr Ser Asn His Gly Pro Asp Ala Thr Glu Ala
            20                  25                  30

Glu Glu Asp Phe Val Asp Pro Trp Thr Val Gln Thr Ser Ser Ala Lys
        35                  40                  45

Gly Ile Asp Tyr Asp Lys Leu Ile Val Arg Phe Gly Ser Ser Lys Ile
    50                  55                  60
```

```
Asp Lys Glu Leu Ile Asn Arg Ile Glu Arg Ala Thr Gly Gln Arg Pro
 65                  70                  75                  80

His His Phe Leu Arg Arg Gly Ile Phe Phe Ser His Arg Asp Met Asn
                 85                  90                  95

Gln Val Leu Asp Ala Tyr Glu Asn Lys Lys Pro Phe Tyr Leu Tyr Thr
            100                 105                 110

Gly Arg Gly Pro Ser Ser Glu Ala Met His Val Gly His Leu Ile Pro
        115                 120                 125

Phe Ile Phe Thr Lys Trp Leu Gln Asp Val Phe Asn Val Pro Leu Val
    130                 135                 140

Ile Gln Met Thr Asp Asp Glu Lys Tyr Leu Trp Lys Asp Leu Thr Leu
145                 150                 155                 160

Asp Gln Ala Tyr Gly Asp Ala Val Glu Asn Ala Lys Asp Ile Ile Ala
                165                 170                 175

Cys Gly Phe Asp Ile Asn Lys Thr Phe Ile Phe Ser Asp Leu Asp Tyr
            180                 185                 190

Met Gly Met Ser Ser Gly Phe Tyr Lys Asn Val Val Lys Ile Gln Lys
        195                 200                 205

His Val Thr Phe Asn Gln Val Lys Gly Ile Phe Gly Phe Thr Asp Ser
    210                 215                 220

Asp Cys Ile Gly Lys Ile Ser Phe Pro Ala Ile Gln Ala Ala Pro Ser
225                 230                 235                 240

Phe Ser Asn Ser Phe Pro Gln Ile Phe Arg Asp Arg Thr Asp Ile Gln
                245                 250                 255

Cys Leu Ile Pro Cys Ala Ile Asp Gln Asp Pro Tyr Phe Arg Met Thr
            260                 265                 270

Arg Asp Val Ala Pro Arg Ile Gly Tyr Pro Lys Pro Ala Leu Leu His
        275                 280                 285

Ser Thr Phe Phe Pro Ala Leu Gln Gly Ala Gln Thr Lys Met Ser Ala
    290                 295                 300

Ser Asp Pro Asn Ser Ser Ile Phe Leu Thr Asp Thr Ala Lys Gln Ile
305                 310                 315                 320

Lys Thr Lys Val Asn Lys His Ala Phe Ser Gly Gly Arg Asp Thr Ile
                325                 330                 335

Glu Glu His Arg Gln Phe Gly Gly Asn Cys Asp Val Asp Val Ser Phe
            340                 345                 350

Met Tyr Leu Thr Phe Phe Leu Glu Asp Asp Asp Lys Leu Glu Gln Ile
        355                 360                 365

Arg Lys Asp Tyr Thr Ser Gly Ala Met Leu Thr Gly Glu Leu Lys Lys
    370                 375                 380

Ala Leu Ile Glu Val Leu Gln Pro Leu Ile Ala Glu His Gln Ala Arg
385                 390                 395                 400

Arg Lys Glu Val Thr Asp Glu Ile Val Lys Glu Phe Met Thr Pro Arg
                405                 410                 415

Lys Leu Ser Phe Asp Phe Gln
            420

<210> SEQ ID NO 15
<211> LENGTH: 379
<212> TYPE: PRT
<213> ORGANISM: Artificial Sequence
<220> FEATURE:
<223> OTHER INFORMATION: Recombinant human Met-T2 (GD variant) construct

<400> SEQUENCE: 15
```

```
Met Ser Ala Lys Gly Ile Asp Tyr Asp Lys Leu Ile Val Arg Phe Gly
1               5                   10                  15

Ser Ser Lys Ile Asp Lys Glu Leu Ile Asn Arg Ile Glu Arg Ala Thr
            20                  25                  30

Gly Gln Arg Pro His His Phe Leu Arg Arg Gly Ile Phe Phe Ser His
        35                  40                  45

Arg Asp Met Asn Gln Val Leu Asp Ala Tyr Glu Asn Lys Lys Pro Phe
    50                  55                  60

Tyr Leu Tyr Thr Gly Arg Gly Pro Ser Ser Glu Ala Met His Val Gly
65                  70                  75                  80

His Leu Ile Pro Phe Ile Phe Thr Lys Trp Leu Gln Asp Val Phe Asn
                85                  90                  95

Val Pro Leu Val Ile Gln Met Thr Asp Asp Glu Lys Tyr Leu Trp Lys
            100                 105                 110

Asp Leu Thr Leu Asp Gln Ala Tyr Gly Asp Ala Val Glu Asn Ala Lys
        115                 120                 125

Asp Ile Ile Ala Cys Gly Phe Asp Ile Asn Lys Thr Phe Ile Phe Ser
130                 135                 140

Asp Leu Asp Tyr Met Gly Met Ser Ser Gly Phe Tyr Lys Asn Val Val
145                 150                 155                 160

Lys Ile Gln Lys His Val Thr Phe Asn Gln Val Lys Gly Ile Phe Gly
                165                 170                 175

Phe Thr Asp Ser Asp Cys Ile Gly Lys Ile Ser Phe Pro Ala Ile Gln
            180                 185                 190

Ala Ala Pro Ser Phe Ser Asn Ser Phe Pro Gln Ile Phe Arg Asp Arg
        195                 200                 205

Thr Asp Ile Gln Cys Leu Ile Pro Cys Ala Ile Asp Gln Asp Pro Tyr
210                 215                 220

Phe Arg Met Thr Arg Asp Val Ala Pro Arg Ile Gly Tyr Pro Lys Pro
225                 230                 235                 240

Ala Leu Leu His Ser Thr Phe Phe Pro Ala Leu Gln Gly Ala Gln Thr
                245                 250                 255

Lys Met Ser Ala Ser Asp Pro Asn Ser Ser Ile Phe Leu Thr Asp Thr
            260                 265                 270

Ala Lys Gln Ile Lys Thr Lys Val Asn Lys His Ala Phe Ser Gly Gly
        275                 280                 285

Arg Asp Thr Ile Glu Glu His Arg Gln Phe Gly Gly Asn Cys Asp Val
290                 295                 300

Asp Val Ser Phe Met Tyr Leu Thr Phe Phe Leu Glu Asp Asp Lys
305                 310                 315                 320

Leu Glu Gln Ile Arg Lys Asp Tyr Thr Ser Gly Ala Met Leu Thr Gly
                325                 330                 335

Glu Leu Lys Lys Ala Leu Ile Glu Val Leu Gln Pro Leu Ile Ala Glu
            340                 345                 350

His Gln Ala Arg Arg Lys Glu Val Thr Asp Glu Ile Val Lys Glu Phe
        355                 360                 365

Met Thr Pro Arg Lys Leu Ser Phe Asp Phe Gln
370                 375
```

<210> SEQ ID NO 16
<211> LENGTH: 402
<212> TYPE: PRT
<213> ORGANISM: Artificial Sequence
<220> FEATURE:
<223> OTHER INFORMATION: Recombinant human Met-T1 (GD variant) construct

<400> SEQUENCE: 16

```
Met Ser Asn His Gly Pro Asp Ala Thr Glu Ala Glu Glu Asp Phe Val
1               5                   10                  15

Asp Pro Trp Thr Val Gln Thr Ser Ser Ala Lys Gly Ile Asp Tyr Asp
            20                  25                  30

Lys Leu Ile Val Arg Phe Gly Ser Ser Lys Ile Asp Lys Glu Leu Ile
        35                  40                  45

Asn Arg Ile Glu Arg Ala Thr Gly Gln Arg Pro His His Phe Leu Arg
    50                  55                  60

Arg Gly Ile Phe Phe Ser His Arg Asp Met Asn Gln Val Leu Asp Ala
65                  70                  75                  80

Tyr Glu Asn Lys Lys Pro Phe Tyr Leu Tyr Thr Gly Arg Gly Pro Ser
                85                  90                  95

Ser Glu Ala Met His Val Gly His Leu Ile Pro Phe Ile Phe Thr Lys
            100                 105                 110

Trp Leu Gln Asp Val Phe Asn Val Pro Leu Val Ile Gln Met Thr Asp
        115                 120                 125

Asp Glu Lys Tyr Leu Trp Lys Asp Leu Thr Leu Asp Gln Ala Tyr Gly
    130                 135                 140

Asp Ala Val Glu Asn Ala Lys Asp Ile Ile Ala Cys Gly Phe Asp Ile
145                 150                 155                 160

Asn Lys Thr Phe Ile Phe Ser Asp Leu Asp Tyr Met Gly Met Ser Ser
                165                 170                 175

Gly Phe Tyr Lys Asn Val Val Lys Ile Gln Lys His Val Thr Phe Asn
            180                 185                 190

Gln Val Lys Gly Ile Phe Gly Phe Thr Asp Ser Asp Cys Ile Gly Lys
        195                 200                 205

Ile Ser Phe Pro Ala Ile Gln Ala Ala Pro Ser Phe Ser Asn Ser Phe
210                 215                 220

Pro Gln Ile Phe Arg Asp Arg Thr Asp Ile Gln Cys Leu Ile Pro Cys
225                 230                 235                 240

Ala Ile Asp Gln Asp Pro Tyr Phe Arg Met Thr Arg Asp Val Ala Pro
                245                 250                 255

Arg Ile Gly Tyr Pro Lys Pro Ala Leu Leu His Ser Thr Phe Phe Pro
            260                 265                 270

Ala Leu Gln Gly Ala Gln Thr Lys Met Ser Ala Ser Asp Pro Asn Ser
        275                 280                 285

Ser Ile Phe Leu Thr Asp Thr Ala Lys Gln Ile Lys Thr Lys Val Asn
290                 295                 300

Lys His Ala Phe Ser Gly Gly Arg Asp Thr Ile Glu Glu His Arg Gln
305                 310                 315                 320

Phe Gly Gly Asn Cys Asp Val Asp Val Ser Phe Met Tyr Leu Thr Phe
                325                 330                 335

Phe Leu Glu Asp Asp Lys Leu Glu Gln Ile Arg Lys Asp Tyr Thr
            340                 345                 350

Ser Gly Ala Met Leu Thr Gly Glu Leu Lys Lys Ala Leu Ile Glu Val
        355                 360                 365

Leu Gln Pro Leu Ile Ala Glu His Gln Ala Arg Arg Lys Glu Val Thr
370                 375                 380

Asp Glu Ile Val Lys Glu Phe Met Thr Pro Arg Lys Leu Ser Phe Asp
385                 390                 395                 400

Phe Gln
```

-continued

```
<210> SEQ ID NO 17
<211> LENGTH: 424
<212> TYPE: PRT
<213> ORGANISM: Artificial Sequence
<220> FEATURE:
<223> OTHER INFORMATION: Recombinant human Met-mini-TrpRS (GD variant)
      construct

<400> SEQUENCE: 17
```

| | | | | | | | | | | | | | | | |
|---|---|---|---|---|---|---|---|---|---|---|---|---|---|---|---|
| Met | Ser | Tyr | Lys | Ala | Ala | Gly | Glu | Asp | Tyr | Lys | Ala | Asp | Cys | Pro | |
| 1 | | | | 5 | | | | | 10 | | | | | 15 | |
| Pro | Gly | Asn | Pro | Ala | Pro | Thr | Ser | Asn | His | Gly | Pro | Asp | Ala | Thr | Glu |
| | | | 20 | | | | | 25 | | | | | 30 | | |
| Ala | Glu | Glu | Asp | Phe | Val | Asp | Pro | Trp | Thr | Val | Gln | Thr | Ser | Ser | Ala |
| | | 35 | | | | | 40 | | | | | 45 | | | |
| Lys | Gly | Ile | Asp | Tyr | Asp | Lys | Leu | Ile | Val | Arg | Phe | Gly | Ser | Ser | Lys |
| | 50 | | | | | 55 | | | | | 60 | | | | |
| Ile | Asp | Lys | Glu | Leu | Ile | Asn | Arg | Ile | Glu | Arg | Ala | Thr | Gly | Gln | Arg |
| 65 | | | | | 70 | | | | | 75 | | | | | 80 |
| Pro | His | His | Phe | Leu | Arg | Arg | Gly | Ile | Phe | Phe | Ser | His | Arg | Asp | Met |
| | | | | 85 | | | | | 90 | | | | | 95 | |
| Asn | Gln | Val | Leu | Asp | Ala | Tyr | Glu | Asn | Lys | Lys | Pro | Phe | Tyr | Leu | Tyr |
| | | | 100 | | | | | 105 | | | | | 110 | | |
| Thr | Gly | Arg | Gly | Pro | Ser | Ser | Glu | Ala | Met | His | Val | Gly | His | Leu | Ile |
| | | 115 | | | | | 120 | | | | | 125 | | | |
| Pro | Phe | Ile | Phe | Thr | Lys | Trp | Leu | Gln | Asp | Val | Phe | Asn | Val | Pro | Leu |
| | 130 | | | | | 135 | | | | | 140 | | | | |
| Val | Ile | Gln | Met | Thr | Asp | Asp | Glu | Lys | Tyr | Leu | Trp | Lys | Asp | Leu | Thr |
| 145 | | | | | 150 | | | | | 155 | | | | | 160 |
| Leu | Asp | Gln | Ala | Tyr | Gly | Asp | Ala | Val | Glu | Asn | Ala | Lys | Asp | Ile | Ile |
| | | | | 165 | | | | | 170 | | | | | 175 | |
| Ala | Cys | Gly | Phe | Asp | Ile | Asn | Lys | Thr | Phe | Ile | Phe | Ser | Asp | Leu | Asp |
| | | | 180 | | | | | 185 | | | | | 190 | | |
| Tyr | Met | Gly | Met | Ser | Ser | Gly | Phe | Tyr | Lys | Asn | Val | Val | Lys | Ile | Gln |
| | | 195 | | | | | 200 | | | | | 205 | | | |
| Lys | His | Val | Thr | Phe | Asn | Gln | Val | Lys | Gly | Ile | Phe | Gly | Phe | Thr | Asp |
| | 210 | | | | | 215 | | | | | 220 | | | | |
| Ser | Asp | Cys | Ile | Gly | Lys | Ile | Ser | Phe | Pro | Ala | Ile | Gln | Ala | Ala | Pro |
| 225 | | | | | 230 | | | | | 235 | | | | | 240 |
| Ser | Phe | Ser | Asn | Ser | Phe | Pro | Gln | Ile | Phe | Arg | Asp | Arg | Thr | Asp | Ile |
| | | | | 245 | | | | | 250 | | | | | 255 | |
| Gln | Cys | Leu | Ile | Pro | Cys | Ala | Ile | Asp | Gln | Asp | Pro | Tyr | Phe | Arg | Met |
| | | | 260 | | | | | 265 | | | | | 270 | | |
| Thr | Arg | Asp | Val | Ala | Pro | Arg | Ile | Gly | Tyr | Pro | Lys | Pro | Ala | Leu | Leu |
| | | 275 | | | | | 280 | | | | | 285 | | | |
| His | Ser | Thr | Phe | Phe | Pro | Ala | Leu | Gln | Gly | Ala | Gln | Thr | Lys | Met | Ser |
| | 290 | | | | | 295 | | | | | 300 | | | | |
| Ala | Ser | Asp | Pro | Asn | Ser | Ser | Ile | Phe | Leu | Thr | Asp | Thr | Ala | Lys | Gln |
| 305 | | | | | 310 | | | | | 315 | | | | | 320 |
| Ile | Lys | Thr | Lys | Val | Asn | Lys | His | Ala | Phe | Ser | Gly | Gly | Arg | Asp | Thr |
| | | | | 325 | | | | | 330 | | | | | 335 | |
| Ile | Glu | Glu | His | Arg | Gln | Phe | Gly | Gly | Asn | Cys | Asp | Val | Asp | Val | Ser |
| | | | 340 | | | | | 345 | | | | | 350 | | |
| Phe | Met | Tyr | Leu | Thr | Phe | Phe | Leu | Glu | Asp | Asp | Asp | Lys | Leu | Glu | Gln |
| | | 355 | | | | | 360 | | | | | 365 | | | |
| Ile | Arg | Lys | Asp | Tyr | Thr | Ser | Gly | Ala | Met | Leu | Thr | Gly | Glu | Leu | Lys |

```
    370                 375                 380

Lys Ala Leu Ile Glu Val Leu Gln Pro Leu Ile Ala Glu His Gln Ala
385                 390                 395                 400

Arg Arg Lys Glu Val Thr Asp Glu Ile Val Lys Glu Phe Met Thr Pro
                405                 410                 415

Arg Lys Leu Ser Phe Asp Phe Gln
            420

<210> SEQ ID NO 18
<211> LENGTH: 1134
<212> TYPE: DNA
<213> ORGANISM: Artificial Sequence
<220> FEATURE:
<223> OTHER INFORMATION: Recombinant human T2 (GD variant) construct
<220> FEATURE:
<221> NAME/KEY: CDS
<222> LOCATION: (1)..(1134)

<400> SEQUENCE: 18 agt gca aaa ggc ata gac tac gat aag ctc att gtt cgg ttt gga agt       48
Ser Ala Lys Gly Ile Asp Tyr Asp Lys Leu Ile Val Arg Phe Gly Ser
  1               5                  10                  15 agt aaa att gac aaa gag cta ata aac cga ata gag aga gcc acc ggc       96
Ser Lys Ile Asp Lys Glu Leu Ile Asn Arg Ile Glu Arg Ala Thr Gly
             20                  25                  30 caa aga cca cac cac ttc ctg cgc aga ggc atc ttc ttc tca cac aga      144
Gln Arg Pro His His Phe Leu Arg Arg Gly Ile Phe Phe Ser His Arg
         35                  40                  45 gat atg aat cag gtt ctt gat gcc tat gaa aat aag aag cca ttt tat      192
Asp Met Asn Gln Val Leu Asp Ala Tyr Glu Asn Lys Lys Pro Phe Tyr
     50                  55                  60 ctg tac acg ggc cgg ggc ccc tct tct gaa gca atg cat gta ggt cac      240
Leu Tyr Thr Gly Arg Gly Pro Ser Ser Glu Ala Met His Val Gly His
 65                  70                  75                  80 ctc att cca ttt att ttc aca aag tgg ctc cag gat gta ttt aac gtg      288
Leu Ile Pro Phe Ile Phe Thr Lys Trp Leu Gln Asp Val Phe Asn Val
                 85                  90                  95 ccc ttg gtc atc cag atg acg gat gac gag aag tat ctg tgg aag gac      336
Pro Leu Val Ile Gln Met Thr Asp Asp Glu Lys Tyr Leu Trp Lys Asp
            100                 105                 110 ctg acc ctg gac cag gcc tat ggc gat gct gtt gag aat gcc aag gac      384
Leu Thr Leu Asp Gln Ala Tyr Gly Asp Ala Val Glu Asn Ala Lys Asp
        115                 120                 125 atc atc gcc tgt ggc ttt gac atc aac aag act ttc ata ttc tct gac      432
Ile Ile Ala Cys Gly Phe Asp Ile Asn Lys Thr Phe Ile Phe Ser Asp
    130                 135                 140 ctg gac tac atg ggg atg agc tca ggt ttc tac aaa aat gtg gtg aag      480
Leu Asp Tyr Met Gly Met Ser Ser Gly Phe Tyr Lys Asn Val Val Lys
145                 150                 155                 160 att caa aag cat gtt acc ttc aac caa gtg aaa ggc att ttc ggc ttc      528
Ile Gln Lys His Val Thr Phe Asn Gln Val Lys Gly Ile Phe Gly Phe
                165                 170                 175 act gac agc gac tgc att ggg aag atc agt ttt cct gcc atc cag gct      576
Thr Asp Ser Asp Cys Ile Gly Lys Ile Ser Phe Pro Ala Ile Gln Ala
            180                 185                 190 gct ccc tcc ttc agc aac tca ttc cca cag atc ttc cga gac agg acg      624
Ala Pro Ser Phe Ser Asn Ser Phe Pro Gln Ile Phe Arg Asp Arg Thr
        195                 200                 205 gat atc cag tgc ctt atc cca tgt gcc att gac cag gat cct tac ttt      672
Asp Ile Gln Cys Leu Ile Pro Cys Ala Ile Asp Gln Asp Pro Tyr Phe
    210                 215                 220
```

```
aga atg aca agg gac gtc gcc ccc agg atc ggc tat cct aaa cca gcc    720
Arg Met Thr Arg Asp Val Ala Pro Arg Ile Gly Tyr Pro Lys Pro Ala
225                 230                 235                 240 ctg ttg cac tcc acc ttc ttc cca gcc ctg cag ggc gcc cag acc aaa    768
Leu Leu His Ser Thr Phe Phe Pro Ala Leu Gln Gly Ala Gln Thr Lys
                245                 250                 255 atg agt gcc agc gac cca aac tcc tcc atc ttc ctc acc gac acg gcc    816
Met Ser Ala Ser Asp Pro Asn Ser Ser Ile Phe Leu Thr Asp Thr Ala
            260                 265                 270 aag cag atc aaa acc aag gtc aat aag cat gcg ttt tct gga ggg aga    864
Lys Gln Ile Lys Thr Lys Val Asn Lys His Ala Phe Ser Gly Gly Arg
        275                 280                 285 gac acc atc gag gag cac agg cag ttt ggg ggc aac tgt gat gtg gac    912
Asp Thr Ile Glu Glu His Arg Gln Phe Gly Gly Asn Cys Asp Val Asp
    290                 295                 300 gtg tct ttc atg tac ctg acc ttc ttc ctc gag gac gac gac aag ctc    960
Val Ser Phe Met Tyr Leu Thr Phe Phe Leu Glu Asp Asp Asp Lys Leu
305                 310                 315                 320 gag cag atc agg aag gat tac acc agc gga gcc atg ctc acc ggt gag   1008
Glu Gln Ile Arg Lys Asp Tyr Thr Ser Gly Ala Met Leu Thr Gly Glu
                325                 330                 335 ctc aag aag gca ctc ata gag gtt ctg cag ccc ttg atc gca gag cac   1056
Leu Lys Lys Ala Leu Ile Glu Val Leu Gln Pro Leu Ile Ala Glu His
            340                 345                 350 cag gcc cgg cgc aag gag gtc acg gat gag ata gtg aaa gag ttc atg   1104
Gln Ala Arg Arg Lys Glu Val Thr Asp Glu Ile Val Lys Glu Phe Met
        355                 360                 365 act ccc cgg aag ctg tcc ttc gac ttt cag                           1134
Thr Pro Arg Lys Leu Ser Phe Asp Phe Gln
    370                 375

<210> SEQ ID NO 19
<211> LENGTH: 1137
<212> TYPE: DNA
<213> ORGANISM: Artificial Sequence
<220> FEATURE:
<223> OTHER INFORMATION: Recombinant human Met-T2 (GD variant) construct
<220> FEATURE:
<221> NAME/KEY: CDS
<222> LOCATION: (1)..(1137)

<400> SEQUENCE: 19 atg agt gca aaa ggc ata gac tac gat aag ctc att gtt cgg ttt gga     48
Met Ser Ala Lys Gly Ile Asp Tyr Asp Lys Leu Ile Val Arg Phe Gly
1               5                  10                  15 agt agt aaa att gac aaa gag cta ata aac cga ata gag aga gcc acc     96
Ser Ser Lys Ile Asp Lys Glu Leu Ile Asn Arg Ile Glu Arg Ala Thr
            20                  25                  30 ggc caa aga cca cac cac ttc ctg cgc aga ggc atc ttc ttc tca cac    144
Gly Gln Arg Pro His His Phe Leu Arg Arg Gly Ile Phe Phe Ser His
        35                  40                  45 aga gat atg aat cag gtt ctt gat gcc tat gaa aat aag aag cca ttt    192
Arg Asp Met Asn Gln Val Leu Asp Ala Tyr Glu Asn Lys Lys Pro Phe
    50                  55                  60 tat ctg tac acg ggc cgg ggc ccc tct tct gaa gca atg cat gta ggt    240
Tyr Leu Tyr Thr Gly Arg Gly Pro Ser Ser Glu Ala Met His Val Gly
65                  70                  75                  80 cac ctc att cca ttt att ttc aca aag tgg ctc cag gat gta ttt aac    288
His Leu Ile Pro Phe Ile Phe Thr Lys Trp Leu Gln Asp Val Phe Asn
                85                  90                  95 gtg ccc ttg gtc atc cag atg acg gat gac gag aag tat ctg tgg aag    336
Val Pro Leu Val Ile Gln Met Thr Asp Asp Glu Lys Tyr Leu Trp Lys
            100                 105                 110
```

```
gac ctg acc ctg gac cag gcc tat ggc gat gct gtt gag aat gcc aag      384
Asp Leu Thr Leu Asp Gln Ala Tyr Gly Asp Ala Val Glu Asn Ala Lys
115                 120                 125 gac atc atc gcc tgt ggc ttt gac atc aac aag act ttc ata ttc tct      432
Asp Ile Ile Ala Cys Gly Phe Asp Ile Asn Lys Thr Phe Ile Phe Ser
    130                 135                 140 gac ctg gac tac atg ggg atg agc tca ggt ttc tac aaa aat gtg gtg      480
Asp Leu Asp Tyr Met Gly Met Ser Ser Gly Phe Tyr Lys Asn Val Val
145                 150                 155                 160 aag att caa aag cat gtt acc ttc aac caa gtg aaa ggc att ttc ggc      528
Lys Ile Gln Lys His Val Thr Phe Asn Gln Val Lys Gly Ile Phe Gly
                165                 170                 175 ttc act gac agc gac tgc att ggg aag atc agt ttt cct gcc atc cag      576
Phe Thr Asp Ser Asp Cys Ile Gly Lys Ile Ser Phe Pro Ala Ile Gln
            180                 185                 190 gct gct ccc tcc ttc agc aac tca ttc cca cag atc ttc cga gac agg      624
Ala Ala Pro Ser Phe Ser Asn Ser Phe Pro Gln Ile Phe Arg Asp Arg
        195                 200                 205 acg gat atc cag tgc ctt atc cca tgt gcc att gac cag gat cct tac      672
Thr Asp Ile Gln Cys Leu Ile Pro Cys Ala Ile Asp Gln Asp Pro Tyr
210                 215                 220 ttt aga atg aca agg gac gtc gcc ccc agg atc ggc tat cct aaa cca      720
Phe Arg Met Thr Arg Asp Val Ala Pro Arg Ile Gly Tyr Pro Lys Pro
225                 230                 235                 240 gcc ctg ttg cac tcc acc ttc ttc cca gcc ctg cag ggc gcc cag acc      768
Ala Leu Leu His Ser Thr Phe Phe Pro Ala Leu Gln Gly Ala Gln Thr
                245                 250                 255 aaa atg agt gcc agc gac cca aac tcc tcc atc ttc ctc acc gac acg      816
Lys Met Ser Ala Ser Asp Pro Asn Ser Ser Ile Phe Leu Thr Asp Thr
            260                 265                 270 gcc aag cag atc aaa acc aag gtc aat aag cat gcg ttt tct gga ggg      864
Ala Lys Gln Ile Lys Thr Lys Val Asn Lys His Ala Phe Ser Gly Gly
        275                 280                 285 aga gac acc atc gag gag cac agg cag ttt ggg ggc aac tgt gat gtg      912
Arg Asp Thr Ile Glu Glu His Arg Gln Phe Gly Gly Asn Cys Asp Val
290                 295                 300 gac gtg tct ttc atg tac ctg acc ttc ttc ctc gag gac gac gac aag      960
Asp Val Ser Phe Met Tyr Leu Thr Phe Phe Leu Glu Asp Asp Asp Lys
305                 310                 315                 320 ctc gag cag atc agg aag gat tac acc agc gga gcc atg ctc acc ggt     1008
Leu Glu Gln Ile Arg Lys Asp Tyr Thr Ser Gly Ala Met Leu Thr Gly
                325                 330                 335 gag ctc aag aag gca ctc ata gag gtt ctg cag ccc ttg atc gca gag     1056
Glu Leu Lys Lys Ala Leu Ile Glu Val Leu Gln Pro Leu Ile Ala Glu
            340                 345                 350 cac cag gcc cgg cgc aag gag gtc acg gat gag ata gtg aaa gag ttc     1104
His Gln Ala Arg Arg Lys Glu Val Thr Asp Glu Ile Val Lys Glu Phe
        355                 360                 365 atg act ccc cgg aag ctg tcc ttc gac ttt cag                         1137
Met Thr Pro Arg Lys Leu Ser Phe Asp Phe Gln
    370                 375

<210> SEQ ID NO 20
<211> LENGTH: 1203
<212> TYPE: DNA
<213> ORGANISM: Artificial Sequence
<220> FEATURE:
<223> OTHER INFORMATION: Recombinant human T1 (GD variant) construct
<220> FEATURE:
<221> NAME/KEY: CDS
<222> LOCATION: (1)..(1203)
```

```
<400> SEQUENCE: 20 agt aat cat ggc cca gat gcc aca gaa gct gaa gag gat ttt gtg gac      48
Ser Asn His Gly Pro Asp Ala Thr Glu Ala Glu Glu Asp Phe Val Asp
1               5                  10                  15 cca tgg aca gta cag aca agc agt gca aaa ggc ata gac tac gat aag      96
Pro Trp Thr Val Gln Thr Ser Ser Ala Lys Gly Ile Asp Tyr Asp Lys
                20                  25                  30 ctc att gtt cgg ttt gga agt agt aaa att gac aaa gag cta ata aac     144
Leu Ile Val Arg Phe Gly Ser Ser Lys Ile Asp Lys Glu Leu Ile Asn
            35                  40                  45 cga ata gag aga gcc acc ggc caa aga cca cac cac ttc ctg cgc aga     192
Arg Ile Glu Arg Ala Thr Gly Gln Arg Pro His His Phe Leu Arg Arg
    50                  55                  60 ggc atc ttc ttc tca cac aga gat atg aat cag gtt ctt gat gcc tat     240
Gly Ile Phe Phe Ser His Arg Asp Met Asn Gln Val Leu Asp Ala Tyr
65                  70                  75                  80 gaa aat aag aag cca ttt tat ctg tac acg ggc cgg ggc ccc tct tct     288
Glu Asn Lys Lys Pro Phe Tyr Leu Tyr Thr Gly Arg Gly Pro Ser Ser
                85                  90                  95 gaa gca atg cat gta ggt cac ctc att cca ttt att ttc aca aag tgg     336
Glu Ala Met His Val Gly His Leu Ile Pro Phe Ile Phe Thr Lys Trp
                100                 105                 110 ctc cag gat gta ttt aac gtg ccc ttg gtc atc cag atg acg gat gac     384
Leu Gln Asp Val Phe Asn Val Pro Leu Val Ile Gln Met Thr Asp Asp
            115                 120                 125 gag aag tat ctg tgg aag gac ctg acc ctg gac cag gcc tat ggc gat     432
Glu Lys Tyr Leu Trp Lys Asp Leu Thr Leu Asp Gln Ala Tyr Gly Asp
    130                 135                 140 gct gtt gag aat gcc aag gac atc atc gcc tgt ggc ttt gac atc aac     480
Ala Val Glu Asn Ala Lys Asp Ile Ile Ala Cys Gly Phe Asp Ile Asn
145                 150                 155                 160 aag act ttc ata ttc tct gac ctg gac tac atg ggg atg agc tca ggt     528
Lys Thr Phe Ile Phe Ser Asp Leu Asp Tyr Met Gly Met Ser Ser Gly
                165                 170                 175 ttc tac aaa aat gtg gtg aag att caa aag cat gtt acc ttc aac caa     576
Phe Tyr Lys Asn Val Val Lys Ile Gln Lys His Val Thr Phe Asn Gln
                180                 185                 190 gtg aaa ggc att ttc ggc ttc act gac agc gac tgc att ggg aag atc     624
Val Lys Gly Ile Phe Gly Phe Thr Asp Ser Asp Cys Ile Gly Lys Ile
            195                 200                 205 agt ttt cct gcc atc cag gct gct ccc tcc ttc agc aac tca ttc cca     672
Ser Phe Pro Ala Ile Gln Ala Ala Pro Ser Phe Ser Asn Ser Phe Pro
    210                 215                 220 cag atc ttc cga gac agg acg gat atc cag tgc ctt atc cca tgt gcc     720
Gln Ile Phe Arg Asp Arg Thr Asp Ile Gln Cys Leu Ile Pro Cys Ala
225                 230                 235                 240 att gac cag gat cct tac ttt aga atg aca agg gac gtc gcc ccc agg     768
Ile Asp Gln Asp Pro Tyr Phe Arg Met Thr Arg Asp Val Ala Pro Arg
                245                 250                 255 atc ggc tat cct aaa cca gcc ctg ttg cac tcc acc ttc ttc cca gcc     816
Ile Gly Tyr Pro Lys Pro Ala Leu Leu His Ser Thr Phe Phe Pro Ala
                260                 265                 270 ctg cag ggc gcc cag acc aaa atg agt gcc agc gac cca aac tcc tcc     864
Leu Gln Gly Ala Gln Thr Lys Met Ser Ala Ser Asp Pro Asn Ser Ser
            275                 280                 285 atc ttc ctc acc gac acg gcc aag cag atc aaa acc aag gtc aat aag     912
Ile Phe Leu Thr Asp Thr Ala Lys Gln Ile Lys Thr Lys Val Asn Lys
    290                 295                 300 cat gcg ttt tct gga ggg aga gac acc atc gag gag cac agg cag ttt     960
His Ala Phe Ser Gly Gly Arg Asp Thr Ile Glu Glu His Arg Gln Phe
```

```
                305                 310                 315                 320
ggg ggc aac tgt gat gtg gac gtg tct ttc atg tac ctg acc ttc ttc       1008
Gly Gly Asn Cys Asp Val Asp Val Ser Phe Met Tyr Leu Thr Phe Phe
            325                 330                 335 ctc gag gac gac gac aag ctc gag cag atc agg aag gat tac acc agc       1056
Leu Glu Asp Asp Asp Lys Leu Glu Gln Ile Arg Lys Asp Tyr Thr Ser
        340                 345                 350 gga gcc atg ctc acc ggt gag ctc aag aag gca ctc ata gag gtt ctg       1104
Gly Ala Met Leu Thr Gly Glu Leu Lys Lys Ala Leu Ile Glu Val Leu
    355                 360                 365 cag ccc ttg atc gca gag cac cag gcc cgg cgc aag gag gtc acg gat       1152
Gln Pro Leu Ile Ala Glu His Gln Ala Arg Arg Lys Glu Val Thr Asp
370                 375                 380 gag ata gtg aaa gag ttc atg act ccc cgg aag ctg tcc ttc gac ttt       1200
Glu Ile Val Lys Glu Phe Met Thr Pro Arg Lys Leu Ser Phe Asp Phe
385                 390                 395                 400 cag                                                                   1203
Gln

<210> SEQ ID NO 21
<211> LENGTH: 1206
<212> TYPE: DNA
<213> ORGANISM: Artificial Sequence
<220> FEATURE:
<223> OTHER INFORMATION: Recombinant human Met-T1 (GD variant) construct
<220> FEATURE:
<221> NAME/KEY: CDS
<222> LOCATION: (1)..(1206)

<400> SEQUENCE: 21 atg agt aat cat ggc cca gat gcc aca gaa gct gaa gag gat ttt gtg        48
Met Ser Asn His Gly Pro Asp Ala Thr Glu Ala Glu Glu Asp Phe Val
1               5                   10                  15 gac cca tgg aca gta cag aca agc agt gca aaa ggc ata gac tac gat        96
Asp Pro Trp Thr Val Gln Thr Ser Ser Ala Lys Gly Ile Asp Tyr Asp
            20                  25                  30 aag ctc att gtt cgg ttt gga agt agt aaa att gac aaa gag cta ata       144
Lys Leu Ile Val Arg Phe Gly Ser Ser Lys Ile Asp Lys Glu Leu Ile
        35                  40                  45 aac cga ata gag aga gcc acc ggc caa aga cca cac cac ttc ctg cgc       192
Asn Arg Ile Glu Arg Ala Thr Gly Gln Arg Pro His His Phe Leu Arg
    50                  55                  60 aga ggc atc ttc ttc tca cac aga gat atg aat cag gtt ctt gat gcc       240
Arg Gly Ile Phe Phe Ser His Arg Asp Met Asn Gln Val Leu Asp Ala
65                  70                  75                  80 tat gaa aat aag aag cca ttt tat ctg tac acg ggc cgg ggc ccc tct       288
Tyr Glu Asn Lys Lys Pro Phe Tyr Leu Tyr Thr Gly Arg Gly Pro Ser
                85                  90                  95 tct gaa gca atg cat gta ggt cac ctc att cca ttt att ttc aca aag       336
Ser Glu Ala Met His Val Gly His Leu Ile Pro Phe Ile Phe Thr Lys
            100                 105                 110 tgg ctc cag gat gta ttt aac gtg ccc ttg gtc atc cag atg acg gat       384
Trp Leu Gln Asp Val Phe Asn Val Pro Leu Val Ile Gln Met Thr Asp
        115                 120                 125 gac gag aag tat ctg tgg aag gac ctg acc ctg gac cag gcc tat ggc       432
Asp Glu Lys Tyr Leu Trp Lys Asp Leu Thr Leu Asp Gln Ala Tyr Gly
    130                 135                 140 gat gct gtt gag aat gcc aag gac atc atc gcc tgt ggc ttt gac atc       480
Asp Ala Val Glu Asn Ala Lys Asp Ile Ile Ala Cys Gly Phe Asp Ile
145                 150                 155                 160 aac aag act ttc ata ttc tct gac ctg gac tac atg ggg atg agc tca       528
Asn Lys Thr Phe Ile Phe Ser Asp Leu Asp Tyr Met Gly Met Ser Ser
```

```
                         165                 170                 175
ggt ttc tac aaa aat gtg gtg aag att caa aag cat gtt acc ttc aac         576
Gly Phe Tyr Lys Asn Val Val Lys Ile Gln Lys His Val Thr Phe Asn
            180                 185                 190 caa gtg aaa ggc att ttc ggc ttc act gac agc gac tgc att ggg aag         624
Gln Val Lys Gly Ile Phe Gly Phe Thr Asp Ser Asp Cys Ile Gly Lys
        195                 200                 205 atc agt ttt cct gcc atc cag gct gct ccc tcc ttc agc aac tca ttc         672
Ile Ser Phe Pro Ala Ile Gln Ala Ala Pro Ser Phe Ser Asn Ser Phe
    210                 215                 220 cca cag atc ttc cga gac agg acg gat atc cag tgc ctt atc cca tgt         720
Pro Gln Ile Phe Arg Asp Arg Thr Asp Ile Gln Cys Leu Ile Pro Cys
225                 230                 235                 240 gcc att gac cag gat cct tac ttt aga atg aca agg gac gtc gcc ccc         768
Ala Ile Asp Gln Asp Pro Tyr Phe Arg Met Thr Arg Asp Val Ala Pro
                245                 250                 255 agg atc ggc tat cct aaa cca gcc ctg ttg cac tcc acc ttc ttc cca         816
Arg Ile Gly Tyr Pro Lys Pro Ala Leu Leu His Ser Thr Phe Phe Pro
            260                 265                 270 gcc ctg cag ggc gcc cag acc aaa atg agt gcc agc gac cca aac tcc         864
Ala Leu Gln Gly Ala Gln Thr Lys Met Ser Ala Ser Asp Pro Asn Ser
        275                 280                 285 tcc atc ttc ctc acc gac acg gcc aag cag atc aaa acc aag gtc aat         912
Ser Ile Phe Leu Thr Asp Thr Ala Lys Gln Ile Lys Thr Lys Val Asn
    290                 295                 300 aag cat gcg ttt tct gga ggg aga gac acc atc gag gag cac agg cag         960
Lys His Ala Phe Ser Gly Gly Arg Asp Thr Ile Glu Glu His Arg Gln
305                 310                 315                 320 ttt ggg ggc aac tgt gat gtg gac gtg tct ttc atg tac ctg acc ttc        1008
Phe Gly Gly Asn Cys Asp Val Asp Val Ser Phe Met Tyr Leu Thr Phe
                325                 330                 335 ttc ctc gag gac gac gac aag ctc gag cag atc agg aag gat tac acc        1056
Phe Leu Glu Asp Asp Asp Lys Leu Glu Gln Ile Arg Lys Asp Tyr Thr
            340                 345                 350 agc gga gcc atg ctc acc ggt gag ctc aag aag gca ctc ata gag gtt        1104
Ser Gly Ala Met Leu Thr Gly Glu Leu Lys Lys Ala Leu Ile Glu Val
        355                 360                 365 ctg cag ccc ttg atc gca gag cac cag gcc cgg cgc aag gag gtc acg        1152
Leu Gln Pro Leu Ile Ala Glu His Gln Ala Arg Arg Lys Glu Val Thr
    370                 375                 380 gat gag ata gtg aaa gag ttc atg act ccc cgg aag ctg tcc ttc gac        1200
Asp Glu Ile Val Lys Glu Phe Met Thr Pro Arg Lys Leu Ser Phe Asp
385                 390                 395                 400 ttt cag                                                                 1206
Phe Gln <210> SEQ ID NO 22
<211> LENGTH: 1269
<212> TYPE: DNA
<213> ORGANISM: Artificial Sequence
<220> FEATURE:
<223> OTHER INFORMATION: Recombinant human mini-TrpRS (GD variant)
      construct
<220> FEATURE:
<221> NAME/KEY: CDS
<222> LOCATION: (1)..(1269)

<400> SEQUENCE: 22 agc tac aaa gct gcc gcg ggg gag gat tac aag gct gac tgt cct cca          48
Ser Tyr Lys Ala Ala Ala Gly Glu Asp Tyr Lys Ala Asp Cys Pro Pro
1               5                   10                  15 ggg aac cca gca cct acc agt aat cat ggc cca gat gcc aca gaa gct          96
Gly Asn Pro Ala Pro Thr Ser Asn His Gly Pro Asp Ala Thr Glu Ala
```

-continued

| | | |
|---|---|---|
| Gly Asn Pro Ala Pro Thr Ser Asn His Gly Pro Asp Ala Thr Glu Ala<br>20 25 30 | | |
| gaa gag gat ttt gtg gac cca tgg aca gta cag aca agc agt gca aaa<br>Glu Glu Asp Phe Val Asp Pro Trp Thr Val Gln Thr Ser Ser Ala Lys<br>35 40 45 | 144 | |
| ggc ata gac tac gat aag ctc att gtt cgg ttt gga agt agt aaa att<br>Gly Ile Asp Tyr Asp Lys Leu Ile Val Arg Phe Gly Ser Ser Lys Ile<br>50 55 60 | 192 | |
| gac aaa gag cta ata aac cga ata gag aga gcc acc ggc caa aga cca<br>Asp Lys Glu Leu Ile Asn Arg Ile Glu Arg Ala Thr Gly Gln Arg Pro<br>65 70 75 80 | 240 | |
| cac cac ttc ctg cgc aga ggc atc ttc ttc tca cac aga gat atg aat<br>His His Phe Leu Arg Arg Gly Ile Phe Phe Ser His Arg Asp Met Asn<br>85 90 95 | 288 | |
| cag gtt ctt gat gcc tat gaa aat aag aag cca ttt tat ctg tac acg<br>Gln Val Leu Asp Ala Tyr Glu Asn Lys Lys Pro Phe Tyr Leu Tyr Thr<br>100 105 110 | 336 | |
| ggc cgg ggc ccc tct tct gaa gca atg cat gta ggt cac ctc att cca<br>Gly Arg Gly Pro Ser Ser Glu Ala Met His Val Gly His Leu Ile Pro<br>115 120 125 | 384 | |
| ttt att ttc aca aag tgg ctc cag gat gta ttt aac gtg ccc ttg gtc<br>Phe Ile Phe Thr Lys Trp Leu Gln Asp Val Phe Asn Val Pro Leu Val<br>130 135 140 | 432 | |
| atc cag atg acg gat gac gag aag tat ctg tgg aag gac ctg acc ctg<br>Ile Gln Met Thr Asp Asp Glu Lys Tyr Leu Trp Lys Asp Leu Thr Leu<br>145 150 155 160 | 480 | |
| gac cag gcc tat ggc gat gct gtt gag aat gcc aag gac atc atc gcc<br>Asp Gln Ala Tyr Gly Asp Ala Val Glu Asn Ala Lys Asp Ile Ile Ala<br>165 170 175 | 528 | |
| tgt ggc ttt gac atc aac aag act ttc ata ttc tct gac ctg gac tac<br>Cys Gly Phe Asp Ile Asn Lys Thr Phe Ile Phe Ser Asp Leu Asp Tyr<br>180 185 190 | 576 | |
| atg ggg atg agc tca ggt ttc tac aaa aat gtg gtg aag att caa aag<br>Met Gly Met Ser Ser Gly Phe Tyr Lys Asn Val Val Lys Ile Gln Lys<br>195 200 205 | 624 | |
| cat gtt acc ttc aac caa gtg aaa ggc att ttc ggc ttc act gac agc<br>His Val Thr Phe Asn Gln Val Lys Gly Ile Phe Gly Phe Thr Asp Ser<br>210 215 220 | 672 | |
| gac tgc att ggg aag atc agt ttt cct gcc atc cag gct gct ccc tcc<br>Asp Cys Ile Gly Lys Ile Ser Phe Pro Ala Ile Gln Ala Ala Pro Ser<br>225 230 235 240 | 720 | |
| ttc agc aac tca ttc cca cag atc ttc cga gac agg acg gat atc cag<br>Phe Ser Asn Ser Phe Pro Gln Ile Phe Arg Asp Arg Thr Asp Ile Gln<br>245 250 255 | 768 | |
| tgc ctt atc cca tgt gcc att gac cag gat cct tac ttt aga atg aca<br>Cys Leu Ile Pro Cys Ala Ile Asp Gln Asp Pro Tyr Phe Arg Met Thr<br>260 265 270 | 816 | |
| agg gac gtc gcc ccc agg atc ggc tat cct aaa cca gcc ctg ttg cac<br>Arg Asp Val Ala Pro Arg Ile Gly Tyr Pro Lys Pro Ala Leu Leu His<br>275 280 285 | 864 | |
| tcc acc ttc ttc cca gcc ctg cag ggc gcc cag acc aaa atg agt gcc<br>Ser Thr Phe Phe Pro Ala Leu Gln Gly Ala Gln Thr Lys Met Ser Ala<br>290 295 300 | 912 | |
| agc gac cca aac tcc tcc atc ttc ctc acc gac acg gcc aag cag atc<br>Ser Asp Pro Asn Ser Ser Ile Phe Leu Thr Asp Thr Ala Lys Gln Ile<br>305 310 315 320 | 960 | |
| aaa acc aag gtc aat aag cat gcg ttt tct gga ggg aga gac acc atc<br>Lys Thr Lys Val Asn Lys His Ala Phe Ser Gly Gly Arg Asp Thr Ile<br>325 330 335 | 1008 | |
| gag gag cac agg cag ttt ggg ggc aac tgt gat gtg gac gtg tct ttc | 1056 | |

```
Glu Glu His Arg Gln Phe Gly Gly Asn Cys Asp Val Asp Val Ser Phe
            340                 345                 350 atg tac ctg acc ttc ttc ctc gag gac gac gac aag ctc gag cag atc     1104
Met Tyr Leu Thr Phe Phe Leu Glu Asp Asp Asp Lys Leu Glu Gln Ile
        355                 360                 365 agg aag gat tac acc agc gga gcc atg ctc acc ggt gag ctc aag aag     1152
Arg Lys Asp Tyr Thr Ser Gly Ala Met Leu Thr Gly Glu Leu Lys Lys
370                 375                 380 gca ctc ata gag gtt ctg cag ccc ttg atc gca gag cac cag gcc cgg     1200
Ala Leu Ile Glu Val Leu Gln Pro Leu Ile Ala Glu His Gln Ala Arg
385                 390                 395                 400 cgc aag gag gtc acg gat gag ata gtg aaa gag ttc atg act ccc cgg     1248
Arg Lys Glu Val Thr Asp Glu Ile Val Lys Glu Phe Met Thr Pro Arg
                405                 410                 415 aag ctg tcc ttc gac ttt cag                                         1269
Lys Leu Ser Phe Asp Phe Gln
            420

<210> SEQ ID NO 23
<211> LENGTH: 1272
<212> TYPE: DNA
<213> ORGANISM: Artificial Sequence
<220> FEATURE:
<223> OTHER INFORMATION: Recombinant human Met-mini-TrpRS (GD variant)
      construct
<220> FEATURE:
<221> NAME/KEY: CDS
<222> LOCATION: (1)..(1272)

<400> SEQUENCE: 23 atg agc tac aaa gct gcc gcg ggg gag gat tac aag gct gac tgt cct       48
Met Ser Tyr Lys Ala Ala Ala Gly Glu Asp Tyr Lys Ala Asp Cys Pro
1               5                   10                  15 cca ggg aac cca gca cct acc agt aat cat ggc cca gat gcc aca gaa      96
Pro Gly Asn Pro Ala Pro Thr Ser Asn His Gly Pro Asp Ala Thr Glu
                20                  25                  30 gct gaa gag gat ttt gtg gac cca tgg aca gta cag aca agc agt gca     144
Ala Glu Glu Asp Phe Val Asp Pro Trp Thr Val Gln Thr Ser Ser Ala
            35                  40                  45 aaa ggc ata gac tac gat aag ctc att gtt cgg ttt gga agt agt aaa     192
Lys Gly Ile Asp Tyr Asp Lys Leu Ile Val Arg Phe Gly Ser Ser Lys
        50                  55                  60 att gac aaa gag cta ata aac cga ata gag aga gcc acc ggc caa aga     240
Ile Asp Lys Glu Leu Ile Asn Arg Ile Glu Arg Ala Thr Gly Gln Arg
65                  70                  75                  80 cca cac cac ttc ctg cgc aga ggc atc ttc ttc tca cac aga gat atg     288
Pro His His Phe Leu Arg Arg Gly Ile Phe Phe Ser His Arg Asp Met
                85                  90                  95 aat cag gtt ctt gat gcc tat gaa aat aag aag cca ttt tat ctg tac     336
Asn Gln Val Leu Asp Ala Tyr Glu Asn Lys Lys Pro Phe Tyr Leu Tyr
            100                 105                 110 acg ggc cgg ggc ccc tct tct gaa gca atg cat gta ggt cac ctc att     384
Thr Gly Arg Gly Pro Ser Ser Glu Ala Met His Val Gly His Leu Ile
        115                 120                 125 cca ttt att ttc aca aag tgg ctc cag gat gta ttt aac gtg ccc ttg     432
Pro Phe Ile Phe Thr Lys Trp Leu Gln Asp Val Phe Asn Val Pro Leu
130                 135                 140 gtc atc cag atg acg gat gac gag aag tat ctg tgg aag gac ctg acc     480
Val Ile Gln Met Thr Asp Asp Glu Lys Tyr Leu Trp Lys Asp Leu Thr
145                 150                 155                 160 ctg gac cag gcc tat ggc gat gct gtt gag aat gcc aag gac atc atc     528
Leu Asp Gln Ala Tyr Gly Asp Ala Val Glu Asn Ala Lys Asp Ile Ile
                165                 170                 175
```

```
gcc tgt ggc ttt gac atc aac aag act ttc ata ttc tct gac ctg gac      576
Ala Cys Gly Phe Asp Ile Asn Lys Thr Phe Ile Phe Ser Asp Leu Asp
            180                 185                 190 tac atg ggg atg agc tca ggt ttc tac aaa aat gtg gtg aag att caa      624
Tyr Met Gly Met Ser Ser Gly Phe Tyr Lys Asn Val Val Lys Ile Gln
        195                 200                 205 aag cat gtt acc ttc aac caa gtg aaa ggc att ttc ggc ttc act gac      672
Lys His Val Thr Phe Asn Gln Val Lys Gly Ile Phe Gly Phe Thr Asp
    210                 215                 220 agc gac tgc att ggg aag atc agt ttt cct gcc atc cag gct gct ccc      720
Ser Asp Cys Ile Gly Lys Ile Ser Phe Pro Ala Ile Gln Ala Ala Pro
225                 230                 235                 240 tcc ttc agc aac tca ttc cca cag atc ttc cga gac agg acg gat atc      768
Ser Phe Ser Asn Ser Phe Pro Gln Ile Phe Arg Asp Arg Thr Asp Ile
                245                 250                 255 cag tgc ctt atc cca tgt gcc att gac cag gat cct tac ttt aga atg      816
Gln Cys Leu Ile Pro Cys Ala Ile Asp Gln Asp Pro Tyr Phe Arg Met
            260                 265                 270 aca agg gac gtc gcc ccc agg atc ggc tat cct aaa cca gcc ctg ttg      864
Thr Arg Asp Val Ala Pro Arg Ile Gly Tyr Pro Lys Pro Ala Leu Leu
        275                 280                 285 cac tcc acc ttc ttc cca gcc ctg cag ggc gcc cag acc aaa atg agt      912
His Ser Thr Phe Phe Pro Ala Leu Gln Gly Ala Gln Thr Lys Met Ser
    290                 295                 300 gcc agc gac cca aac tcc tcc atc ttc ctc acc gac acg gcc aag cag      960
Ala Ser Asp Pro Asn Ser Ser Ile Phe Leu Thr Asp Thr Ala Lys Gln
305                 310                 315                 320 atc aaa acc aag gtc aat aag cat gcg ttt tct gga ggg aga gac acc     1008
Ile Lys Thr Lys Val Asn Lys His Ala Phe Ser Gly Gly Arg Asp Thr
                325                 330                 335 atc gag gag cac agg cag ttt ggg ggc aac tgt gat gtg gac gtg tct     1056
Ile Glu Glu His Arg Gln Phe Gly Gly Asn Cys Asp Val Asp Val Ser
            340                 345                 350 ttc atg tac ctg acc ttc ttc ctc gag gac gac gac aag ctc gag cag     1104
Phe Met Tyr Leu Thr Phe Phe Leu Glu Asp Asp Asp Lys Leu Glu Gln
        355                 360                 365 atc agg aag gat tac acc agc gga gcc atg ctc acc ggt gag ctc aag     1152
Ile Arg Lys Asp Tyr Thr Ser Gly Ala Met Leu Thr Gly Glu Leu Lys
    370                 375                 380 aag gca ctc ata gag gtt ctg cag ccc ttg atc gca gag cac cag gcc     1200
Lys Ala Leu Ile Glu Val Leu Gln Pro Leu Ile Ala Glu His Gln Ala
385                 390                 395                 400 cgg cgc aag gag gtc acg gat gag ata gtg aaa gag ttc atg act ccc     1248
Arg Arg Lys Glu Val Thr Asp Glu Ile Val Lys Glu Phe Met Thr Pro
                405                 410                 415 cgg aag ctg tcc ttc gac ttt cag                                     1272
Arg Lys Leu Ser Phe Asp Phe Gln
            420
```

<210> SEQ ID NO 24
<211> LENGTH: 378
<212> TYPE: PRT
<213> ORGANISM: Artificial Sequence
<220> FEATURE:
<223> OTHER INFORMATION: Recombinant human T2 (SY variant) construct

<400> SEQUENCE: 24

```
Ser Ala Lys Gly Ile Asp Tyr Asp Lys Leu Ile Val Arg Phe Gly Ser
1               5                   10                  15

Ser Lys Ile Asp Lys Glu Leu Ile Asn Arg Ile Glu Arg Ala Thr Gly

```
Gln Arg Pro His His Phe Leu Arg Arg Gly Ile Phe Phe Ser His Arg
         35                  40                  45

Asp Met Asn Gln Val Leu Asp Ala Tyr Glu Asn Lys Lys Pro Phe Tyr
 50                  55                  60

Leu Tyr Thr Gly Arg Gly Pro Ser Ser Glu Ala Met His Val Gly His
 65                  70                  75                  80

Leu Ile Pro Phe Ile Phe Thr Lys Trp Leu Gln Asp Val Phe Asn Val
                 85                  90                  95

Pro Leu Val Ile Gln Met Thr Asp Asp Glu Lys Tyr Leu Trp Lys Asp
                100                 105                 110

Leu Thr Leu Asp Gln Ala Tyr Ser Tyr Ala Val Glu Asn Ala Lys Asp
            115                 120                 125

Ile Ile Ala Cys Gly Phe Asp Ile Asn Lys Thr Phe Ile Phe Ser Asp
        130                 135                 140

Leu Asp Tyr Met Gly Met Ser Ser Gly Phe Tyr Lys Asn Val Val Lys
145                 150                 155                 160

Ile Gln Lys His Val Thr Phe Asn Gln Val Lys Gly Ile Phe Gly Phe
                165                 170                 175

Thr Asp Ser Asp Cys Ile Gly Lys Ile Ser Phe Pro Ala Ile Gln Ala
            180                 185                 190

Ala Pro Ser Phe Ser Asn Ser Phe Pro Gln Ile Phe Arg Asp Arg Thr
        195                 200                 205

Asp Ile Gln Cys Leu Ile Pro Cys Ala Ile Asp Gln Asp Pro Tyr Phe
    210                 215                 220

Arg Met Thr Arg Asp Val Ala Pro Arg Ile Gly Tyr Pro Lys Pro Ala
225                 230                 235                 240

Leu Leu His Ser Thr Phe Phe Pro Ala Leu Gln Gly Ala Gln Thr Lys
                245                 250                 255

Met Ser Ala Ser Asp Pro Asn Ser Ser Ile Phe Leu Thr Asp Thr Ala
            260                 265                 270

Lys Gln Ile Lys Thr Lys Val Asn Lys His Ala Phe Ser Gly Gly Arg
        275                 280                 285

Asp Thr Ile Glu Glu His Arg Gln Phe Gly Gly Asn Cys Asp Val Asp
    290                 295                 300

Val Ser Phe Met Tyr Leu Thr Phe Phe Leu Glu Asp Asp Lys Leu
305                 310                 315                 320

Glu Gln Ile Arg Lys Asp Tyr Thr Ser Gly Ala Met Leu Thr Gly Glu
                325                 330                 335

Leu Lys Lys Ala Leu Ile Glu Val Leu Gln Pro Leu Ile Ala Glu His
            340                 345                 350

Gln Ala Arg Arg Lys Glu Val Thr Asp Glu Ile Val Lys Glu Phe Met
        355                 360                 365

Thr Pro Arg Lys Leu Ser Phe Asp Phe Gln
    370                 375

<210> SEQ ID NO 25
<211> LENGTH: 401
<212> TYPE: PRT
<213> ORGANISM: Artificial Sequence
<220> FEATURE:
<223> OTHER INFORMATION: Recombinant human T1 (SY variant) construct

<400> SEQUENCE: 25

Ser Asn His Gly Pro Asp Ala Thr Glu Ala Glu Glu Asp Phe Val Asp
1               5                   10                  15
```

```
Pro Trp Thr Val Gln Thr Ser Ser Ala Lys Gly Ile Asp Tyr Asp Lys
            20                  25                  30

Leu Ile Val Arg Phe Gly Ser Ser Lys Ile Asp Lys Glu Leu Ile Asn
        35                  40                  45

Arg Ile Glu Arg Ala Thr Gly Gln Arg Pro His His Phe Leu Arg Arg
    50                  55                  60

Gly Ile Phe Phe Ser His Arg Asp Met Asn Gln Val Leu Asp Ala Tyr
65                  70                  75                  80

Glu Asn Lys Lys Pro Phe Tyr Leu Tyr Thr Gly Arg Gly Pro Ser Ser
                85                  90                  95

Glu Ala Met His Val Gly His Leu Ile Pro Phe Ile Phe Thr Lys Trp
            100                 105                 110

Leu Gln Asp Val Phe Asn Val Pro Leu Val Ile Gln Met Thr Asp Asp
        115                 120                 125

Glu Lys Tyr Leu Trp Lys Asp Leu Thr Leu Asp Gln Ala Tyr Ser Tyr
    130                 135                 140

Ala Val Glu Asn Ala Lys Asp Ile Ile Ala Cys Gly Phe Asp Ile Asn
145                 150                 155                 160

Lys Thr Phe Ile Phe Ser Asp Leu Asp Tyr Met Gly Met Ser Ser Gly
                165                 170                 175

Phe Tyr Lys Asn Val Val Lys Ile Gln Lys His Val Thr Phe Asn Gln
            180                 185                 190

Val Lys Gly Ile Phe Gly Phe Thr Asp Ser Asp Cys Ile Gly Lys Ile
        195                 200                 205

Ser Phe Pro Ala Ile Gln Ala Ala Pro Ser Phe Ser Asn Ser Phe Pro
210                 215                 220

Gln Ile Phe Arg Asp Arg Thr Asp Ile Gln Cys Leu Ile Pro Cys Ala
225                 230                 235                 240

Ile Asp Gln Asp Pro Tyr Phe Arg Met Thr Arg Asp Val Ala Pro Arg
                245                 250                 255

Ile Gly Tyr Pro Lys Pro Ala Leu Leu His Ser Thr Phe Phe Pro Ala
            260                 265                 270

Leu Gln Gly Ala Gln Thr Lys Met Ser Ala Ser Asp Pro Asn Ser Ser
        275                 280                 285

Ile Phe Leu Thr Asp Thr Ala Lys Gln Ile Lys Thr Lys Val Asn Lys
290                 295                 300

His Ala Phe Ser Gly Gly Arg Asp Thr Ile Glu Glu His Arg Gln Phe
305                 310                 315                 320

Gly Gly Asn Cys Asp Val Asp Val Ser Phe Met Tyr Leu Thr Phe Phe
                325                 330                 335

Leu Glu Asp Asp Asp Lys Leu Glu Gln Ile Arg Lys Asp Tyr Thr Ser
            340                 345                 350

Gly Ala Met Leu Thr Gly Glu Leu Lys Lys Ala Leu Ile Glu Val Leu
        355                 360                 365

Gln Pro Leu Ile Ala Glu His Gln Ala Arg Arg Lys Glu Val Thr Asp
370                 375                 380

Glu Ile Val Lys Glu Phe Met Thr Pro Arg Lys Leu Ser Phe Asp Phe
385                 390                 395                 400

Gln

<210> SEQ ID NO 26
<211> LENGTH: 423
<212> TYPE: PRT
<213> ORGANISM: Artificial Sequence
<220> FEATURE:
```

-continued

<223> OTHER INFORMATION: Recombinant human mini-TrpRS (SY variant) construct

<400> SEQUENCE: 26

```
Ser Tyr Lys Ala Ala Gly Glu Asp Tyr Lys Ala Asp Cys Pro Pro
  1               5                  10                  15

Gly Asn Pro Ala Pro Thr Ser Asn His Gly Pro Asp Ala Thr Glu Ala
             20                  25                  30

Glu Glu Asp Phe Val Asp Pro Trp Thr Val Gln Thr Ser Ser Ala Lys
         35                  40                  45

Gly Ile Asp Tyr Asp Lys Leu Ile Val Arg Phe Gly Ser Ser Lys Ile
     50                  55                  60

Asp Lys Glu Leu Ile Asn Arg Ile Glu Arg Ala Thr Gly Gln Arg Pro
 65                  70                  75                  80

His His Phe Leu Arg Arg Gly Ile Phe Phe Ser His Arg Asp Met Asn
                 85                  90                  95

Gln Val Leu Asp Ala Tyr Glu Asn Lys Lys Pro Phe Tyr Leu Tyr Thr
            100                 105                 110

Gly Arg Gly Pro Ser Ser Glu Ala Met His Val Gly His Leu Ile Pro
        115                 120                 125

Phe Ile Phe Thr Lys Trp Leu Gln Asp Val Phe Asn Val Pro Leu Val
130                 135                 140

Ile Gln Met Thr Asp Asp Glu Lys Tyr Leu Trp Lys Asp Leu Thr Leu
145                 150                 155                 160

Asp Gln Ala Tyr Ser Tyr Ala Val Glu Asn Ala Lys Asp Ile Ile Ala
                165                 170                 175

Cys Gly Phe Asp Ile Asn Lys Thr Phe Ile Phe Ser Asp Leu Asp Tyr
            180                 185                 190

Met Gly Met Ser Ser Gly Phe Tyr Lys Asn Val Val Lys Ile Gln Lys
        195                 200                 205

His Val Thr Phe Asn Gln Val Lys Gly Ile Phe Gly Phe Thr Asp Ser
    210                 215                 220

Asp Cys Ile Gly Lys Ile Ser Phe Pro Ala Ile Gln Ala Ala Pro Ser
225                 230                 235                 240

Phe Ser Asn Ser Phe Pro Gln Ile Phe Arg Asp Arg Thr Asp Ile Gln
                245                 250                 255

Cys Leu Ile Pro Cys Ala Ile Asp Gln Asp Pro Tyr Phe Arg Met Thr
            260                 265                 270

Arg Asp Val Ala Pro Arg Ile Gly Tyr Pro Lys Pro Ala Leu Leu His
        275                 280                 285

Ser Thr Phe Phe Pro Ala Leu Gln Gly Ala Gln Thr Lys Met Ser Ala
    290                 295                 300

Ser Asp Pro Asn Ser Ser Ile Phe Leu Thr Asp Thr Ala Lys Gln Ile
305                 310                 315                 320

Lys Thr Lys Val Asn Lys His Ala Phe Ser Gly Gly Arg Asp Thr Ile
                325                 330                 335

Glu Glu His Arg Gln Phe Gly Gly Asn Cys Asp Val Asp Val Ser Phe
            340                 345                 350

Met Tyr Leu Thr Phe Phe Leu Glu Asp Asp Asp Lys Leu Glu Gln Ile
        355                 360                 365

Arg Lys Asp Tyr Thr Ser Gly Ala Met Leu Thr Gly Glu Leu Lys Lys
    370                 375                 380

Ala Leu Ile Glu Val Leu Gln Pro Leu Ile Ala Glu His Gln Ala Arg
385                 390                 395                 400
```

```
Arg Lys Glu Val Thr Asp Glu Ile Val Lys Glu Phe Met Thr Pro Arg
                405                 410                 415

Lys Leu Ser Phe Asp Phe Gln
            420
```

<210> SEQ ID NO 27
<211> LENGTH: 379
<212> TYPE: PRT
<213> ORGANISM: Artificial Sequence
<220> FEATURE:
<223> OTHER INFORMATION: Recombinant human Met-T2 (SY variant)
      construct

<400> SEQUENCE: 27

```
Met Ser Ala Lys Gly Ile Asp Tyr Asp Lys Leu Ile Val Arg Phe Gly
1               5                   10                  15

Ser Ser Lys Ile Asp Lys Glu Leu Ile Asn Arg Ile Glu Arg Ala Thr
                20                  25                  30

Gly Gln Arg Pro His His Phe Leu Arg Arg Gly Ile Phe Phe Ser His
            35                  40                  45

Arg Asp Met Asn Gln Val Leu Asp Ala Tyr Glu Asn Lys Lys Pro Phe
50                  55                  60

Tyr Leu Tyr Thr Gly Arg Gly Pro Ser Ser Glu Ala Met His Val Gly
65                  70                  75                  80

His Leu Ile Pro Phe Ile Phe Thr Lys Trp Leu Gln Asp Val Phe Asn
                85                  90                  95

Val Pro Leu Val Ile Gln Met Thr Asp Asp Glu Lys Tyr Leu Trp Lys
                100                 105                 110

Asp Leu Thr Leu Asp Gln Ala Tyr Ser Tyr Ala Val Glu Asn Ala Lys
            115                 120                 125

Asp Ile Ile Ala Cys Gly Phe Asp Ile Asn Lys Thr Phe Ile Phe Ser
130                 135                 140

Asp Leu Asp Tyr Met Gly Met Ser Ser Gly Phe Tyr Lys Asn Val Val
145                 150                 155                 160

Lys Ile Gln Lys His Val Thr Phe Asn Gln Val Lys Gly Ile Phe Gly
                165                 170                 175

Phe Thr Asp Ser Asp Cys Ile Gly Lys Ile Ser Phe Pro Ala Ile Gln
            180                 185                 190

Ala Ala Pro Ser Phe Ser Asn Ser Phe Pro Gln Ile Phe Arg Asp Arg
            195                 200                 205

Thr Asp Ile Gln Cys Leu Ile Pro Cys Ala Ile Asp Gln Asp Pro Tyr
210                 215                 220

Phe Arg Met Thr Arg Asp Val Ala Pro Arg Ile Gly Tyr Pro Lys Pro
225                 230                 235                 240

Ala Leu Leu His Ser Thr Phe Phe Pro Ala Leu Gln Gly Ala Gln Thr
                245                 250                 255

Lys Met Ser Ala Ser Asp Pro Asn Ser Ser Ile Phe Leu Thr Asp Thr
            260                 265                 270

Ala Lys Gln Ile Lys Thr Lys Val Asn Lys His Ala Phe Ser Gly Gly
            275                 280                 285

Arg Asp Thr Ile Glu Glu His Arg Gln Phe Gly Gly Asn Cys Asp Val
290                 295                 300

Asp Val Ser Phe Met Tyr Leu Thr Phe Phe Leu Glu Asp Asp Asp Lys
305                 310                 315                 320

Leu Glu Gln Ile Arg Lys Asp Tyr Thr Ser Gly Ala Met Leu Thr Gly
                325                 330                 335
```

Glu Leu Lys Lys Ala Leu Ile Glu Val Leu Gln Pro Leu Ile Ala Glu
                340                 345                 350

His Gln Ala Arg Arg Lys Glu Val Thr Asp Glu Ile Val Lys Glu Phe
            355                 360                 365

Met Thr Pro Arg Lys Leu Ser Phe Asp Phe Gln
    370                 375

<210> SEQ ID NO 28
<211> LENGTH: 402
<212> TYPE: PRT
<213> ORGANISM: Artificial Sequence
<220> FEATURE:
<223> OTHER INFORMATION: Recombinant human Met-T1 (SY variant) construct

<400> SEQUENCE: 28

Met Ser Asn His Gly Pro Asp Ala Thr Glu Ala Glu Glu Asp Phe Val
1               5                   10                  15

Asp Pro Trp Thr Val Gln Thr Ser Ser Ala Lys Gly Ile Asp Tyr Asp
            20                  25                  30

Lys Leu Ile Val Arg Phe Gly Ser Ser Lys Ile Asp Lys Glu Leu Ile
        35                  40                  45

Asn Arg Ile Glu Arg Ala Thr Gly Gln Arg Pro His Phe Leu Arg
50                  55                  60

Arg Gly Ile Phe Phe Ser His Arg Asp Met Asn Gln Val Leu Asp Ala
65                  70                  75                  80

Tyr Glu Asn Lys Lys Pro Phe Tyr Leu Tyr Thr Gly Arg Gly Pro Ser
                85                  90                  95

Ser Glu Ala Met His Val Gly His Leu Ile Pro Phe Ile Phe Thr Lys
            100                 105                 110

Trp Leu Gln Asp Val Phe Asn Val Pro Leu Val Ile Gln Met Thr Asp
        115                 120                 125

Asp Glu Lys Tyr Leu Trp Lys Asp Leu Thr Leu Asp Gln Ala Tyr Ser
    130                 135                 140

Tyr Ala Val Glu Asn Ala Lys Asp Ile Ile Ala Cys Gly Phe Asp Ile
145                 150                 155                 160

Asn Lys Thr Phe Ile Phe Ser Asp Leu Asp Tyr Met Gly Met Ser Ser
                165                 170                 175

Gly Phe Tyr Lys Asn Val Val Lys Ile Gln Lys His Val Thr Phe Asn
            180                 185                 190

Gln Val Lys Gly Ile Phe Gly Phe Thr Asp Ser Asp Cys Ile Gly Lys
        195                 200                 205

Ile Ser Phe Pro Ala Ile Gln Ala Ala Pro Ser Phe Ser Asn Ser Phe
    210                 215                 220

Pro Gln Ile Phe Arg Asp Arg Thr Asp Ile Gln Cys Leu Ile Pro Cys
225                 230                 235                 240

Ala Ile Asp Gln Asp Pro Tyr Phe Arg Met Thr Arg Asp Val Ala Pro
                245                 250                 255

Arg Ile Gly Tyr Pro Lys Pro Ala Leu Leu His Ser Thr Phe Phe Pro
            260                 265                 270

Ala Leu Gln Gly Ala Gln Thr Lys Met Ser Ala Ser Asp Pro Asn Ser
        275                 280                 285

Ser Ile Phe Leu Thr Asp Thr Ala Lys Gln Ile Lys Thr Lys Val Asn
    290                 295                 300

Lys His Ala Phe Ser Gly Gly Arg Asp Thr Ile Glu Glu His Arg Gln
305                 310                 315                 320

Phe Gly Gly Asn Cys Asp Val Asp Val Ser Phe Met Tyr Leu Thr Phe

```
                    325                 330                 335
Phe Leu Glu Asp Asp Lys Leu Glu Gln Ile Arg Lys Asp Tyr Thr
            340                 345                 350

Ser Gly Ala Met Leu Thr Gly Glu Leu Lys Lys Ala Leu Ile Glu Val
            355                 360                 365

Leu Gln Pro Leu Ile Ala Glu His Gln Ala Arg Arg Lys Glu Val Thr
            370                 375                 380

Asp Glu Ile Val Lys Glu Phe Met Thr Pro Arg Lys Leu Ser Phe Asp
385                 390                 395                 400

Phe Gln

<210> SEQ ID NO 29
<211> LENGTH: 424
<212> TYPE: PRT
<213> ORGANISM: Artificial Sequence
<220> FEATURE:
<223> OTHER INFORMATION: Recombinant human Met-mini-TrpRS (SY variant)
      construct

<400> SEQUENCE: 29

Met Ser Tyr Lys Ala Ala Gly Glu Asp Tyr Lys Ala Asp Cys Pro
1               5                   10                  15

Pro Gly Asn Pro Ala Pro Thr Ser Asn His Gly Pro Asp Ala Thr Glu
            20                  25                  30

Ala Glu Glu Asp Phe Val Asp Pro Trp Thr Val Gln Thr Ser Ser Ala
            35                  40                  45

Lys Gly Ile Asp Tyr Asp Lys Leu Ile Val Arg Phe Gly Ser Ser Lys
        50                  55                  60

Ile Asp Lys Glu Leu Ile Asn Arg Ile Glu Arg Ala Thr Gly Gln Arg
65                  70                  75                  80

Pro His His Phe Leu Arg Arg Gly Ile Phe Phe Ser His Arg Asp Met
                85                  90                  95

Asn Gln Val Leu Asp Ala Tyr Glu Asn Lys Lys Pro Phe Tyr Leu Tyr
            100                 105                 110

Thr Gly Arg Gly Pro Ser Ser Glu Ala Met His Val Gly His Leu Ile
            115                 120                 125

Pro Phe Ile Phe Thr Lys Trp Leu Gln Asp Val Phe Asn Val Pro Leu
            130                 135                 140

Val Ile Gln Met Thr Asp Asp Glu Lys Tyr Leu Trp Lys Asp Leu Thr
145                 150                 155                 160

Leu Asp Gln Ala Tyr Ser Tyr Ala Val Glu Asn Ala Lys Asp Ile Ile
                165                 170                 175

Ala Cys Gly Phe Asp Ile Asn Lys Thr Phe Ile Phe Ser Asp Leu Asp
            180                 185                 190

Tyr Met Gly Met Ser Ser Gly Phe Tyr Lys Asn Val Val Lys Ile Gln
            195                 200                 205

Lys His Val Thr Phe Asn Gln Val Lys Gly Ile Phe Gly Phe Thr Asp
            210                 215                 220

Ser Asp Cys Ile Gly Lys Ile Ser Phe Pro Ala Ile Gln Ala Ala Pro
225                 230                 235                 240

Ser Phe Ser Asn Ser Phe Pro Gln Ile Phe Arg Asp Arg Thr Asp Ile
                245                 250                 255

Gln Cys Leu Ile Pro Cys Ala Ile Asp Gln Asp Pro Tyr Phe Arg Met
            260                 265                 270

Thr Arg Asp Val Ala Pro Arg Ile Gly Tyr Pro Lys Pro Ala Leu Leu
            275                 280                 285
```

```
His Ser Thr Phe Phe Pro Ala Leu Gln Gly Ala Gln Thr Lys Met Ser
    290                 295                 300

Ala Ser Asp Pro Asn Ser Ser Ile Phe Leu Thr Asp Thr Ala Lys Gln
305                 310                 315                 320

Ile Lys Thr Lys Val Asn Lys His Ala Phe Ser Gly Gly Arg Asp Thr
                325                 330                 335

Ile Glu Glu His Arg Gln Phe Gly Gly Asn Cys Asp Val Asp Val Ser
            340                 345                 350

Phe Met Tyr Leu Thr Phe Phe Leu Glu Asp Asp Lys Leu Glu Gln
        355                 360                 365

Ile Arg Lys Asp Tyr Thr Ser Gly Ala Met Leu Thr Gly Glu Leu Lys
    370                 375                 380

Lys Ala Leu Ile Glu Val Leu Gln Pro Leu Ile Ala Glu His Gln Ala
385                 390                 395                 400

Arg Arg Lys Glu Val Thr Asp Glu Ile Val Lys Glu Phe Met Thr Pro
                405                 410                 415

Arg Lys Leu Ser Phe Asp Phe Gln
            420
```

```
<210> SEQ ID NO 30
<211> LENGTH: 1134
<212> TYPE: DNA
<213> ORGANISM: Artificial Sequence
<220> FEATURE:
<223> OTHER INFORMATION: Recombinant human T2 (SY variant) construct
<220> FEATURE:
<221> NAME/KEY: CDS
<222> LOCATION: (1)..(1134)
<220> FEATURE:
<221> NAME/KEY: misc_feature
<222> LOCATION: (358)..(360)
<223> OTHER INFORMATION: nnn is agy, tcy or tcr

<400> SEQUENCE: 30
```

```
agt gca aaa ggc ata gac tac gat aag ctc att gtt cgg ttt gga agt    48
Ser Ala Lys Gly Ile Asp Tyr Asp Lys Leu Ile Val Arg Phe Gly Ser
  1               5                  10                  15 agt aaa att gac aaa gag cta ata aac cga ata gag aga gcc acc ggc    96
Ser Lys Ile Asp Lys Glu Leu Ile Asn Arg Ile Glu Arg Ala Thr Gly
             20                  25                  30 caa aga cca cac cac ttc ctg cgc aga ggc atc ttc ttc tca cac aga   144
Gln Arg Pro His His Phe Leu Arg Arg Gly Ile Phe Phe Ser His Arg
         35                  40                  45 gat atg aat cag gtt ctt gat gcc tat gaa aat aag aag cca ttt tat   192
Asp Met Asn Gln Val Leu Asp Ala Tyr Glu Asn Lys Lys Pro Phe Tyr
     50                  55                  60 ctg tac acg ggc cgg ggc ccc tct tct gaa gca atg cat gta ggt cac   240
Leu Tyr Thr Gly Arg Gly Pro Ser Ser Glu Ala Met His Val Gly His
 65                  70                  75                  80 ctc att cca ttt att ttc aca aag tgg ctc cag gat gta ttt aac gtg   288
Leu Ile Pro Phe Ile Phe Thr Lys Trp Leu Gln Asp Val Phe Asn Val
                 85                  90                  95 ccc ttg gtc atc cag atg acg gat gac gag aag tat ctg tgg aag gac   336
Pro Leu Val Ile Gln Met Thr Asp Asp Glu Lys Tyr Leu Trp Lys Asp
            100                 105                 110 ctg acc ctg gac cag gcc tat nnn tay gct gtt gag aat gcc aag gac   384
Leu Thr Leu Asp Gln Ala Tyr Ser Tyr Ala Val Glu Asn Ala Lys Asp
        115                 120                 125 atc atc gcc tgt ggc ttt gac atc aac aag act ttc ata ttc tct gac   432
Ile Ile Ala Cys Gly Phe Asp Ile Asn Lys Thr Phe Ile Phe Ser Asp
    130                 135                 140
```

```
ctg gac tac atg ggg atg agc tca ggt ttc tac aaa aat gtg gtg aag      480
Leu Asp Tyr Met Gly Met Ser Ser Gly Phe Tyr Lys Asn Val Val Lys
145                 150                 155                 160 att caa aag cat gtt acc ttc aac caa gtg aaa ggc att ttc ggc ttc      528
Ile Gln Lys His Val Thr Phe Asn Gln Val Lys Gly Ile Phe Gly Phe
                165                 170                 175 act gac agc gac tgc att ggg aag atc agt ttt cct gcc atc cag gct      576
Thr Asp Ser Asp Cys Ile Gly Lys Ile Ser Phe Pro Ala Ile Gln Ala
            180                 185                 190 gct ccc tcc ttc agc aac tca ttc cca cag atc ttc cga gac agg acg      624
Ala Pro Ser Phe Ser Asn Ser Phe Pro Gln Ile Phe Arg Asp Arg Thr
        195                 200                 205 gat atc cag tgc ctt atc cca tgt gcc att gac cag gat cct tac ttt      672
Asp Ile Gln Cys Leu Ile Pro Cys Ala Ile Asp Gln Asp Pro Tyr Phe
    210                 215                 220 aga atg aca agg gac gtc gcc ccc agg atc ggc tat cct aaa cca gcc      720
Arg Met Thr Arg Asp Val Ala Pro Arg Ile Gly Tyr Pro Lys Pro Ala
225                 230                 235                 240 ctg ttg cac tcc acc ttc ttc cca gcc ctg cag ggc gcc cag acc aaa      768
Leu Leu His Ser Thr Phe Phe Pro Ala Leu Gln Gly Ala Gln Thr Lys
                245                 250                 255 atg agt gcc agc gac cca aac tcc tcc atc ttc ctc acc gac acg gcc      816
Met Ser Ala Ser Asp Pro Asn Ser Ser Ile Phe Leu Thr Asp Thr Ala
            260                 265                 270 aag cag atc aaa acc aag gtc aat aag cat gcg ttt tct gga ggg aga      864
Lys Gln Ile Lys Thr Lys Val Asn Lys His Ala Phe Ser Gly Gly Arg
        275                 280                 285 gac acc atc gag gag cac agg cag ttt ggg ggc aac tgt gat gtg gac      912
Asp Thr Ile Glu Glu His Arg Gln Phe Gly Gly Asn Cys Asp Val Asp
    290                 295                 300 gtg tct ttc atg tac ctg acc ttc ttc ctc gag gac gac gac aag ctc      960
Val Ser Phe Met Tyr Leu Thr Phe Phe Leu Glu Asp Asp Asp Lys Leu
305                 310                 315                 320 gag cag atc agg aag gat tac acc agc gga gcc atg ctc acc ggt gag     1008
Glu Gln Ile Arg Lys Asp Tyr Thr Ser Gly Ala Met Leu Thr Gly Glu
                325                 330                 335 ctc aag aag gca ctc ata gag gtt ctg cag ccc ttg atc gca gag cac     1056
Leu Lys Lys Ala Leu Ile Glu Val Leu Gln Pro Leu Ile Ala Glu His
            340                 345                 350 cag gcc cgg cgc aag gag gtc acg gat gag ata gtg aaa gag ttc atg     1104
Gln Ala Arg Arg Lys Glu Val Thr Asp Glu Ile Val Lys Glu Phe Met
        355                 360                 365 act ccc cgg aag ctg tcc ttc gac ttt cag                             1134
Thr Pro Arg Lys Leu Ser Phe Asp Phe Gln
    370                 375

<210> SEQ ID NO 31
<211> LENGTH: 1137
<212> TYPE: DNA
<213> ORGANISM: Artificial Sequence
<220> FEATURE:
<223> OTHER INFORMATION: Recombinant human Met-T2 (SY variant) construct
<220> FEATURE:
<221> NAME/KEY: CDS
<222> LOCATION: (1)..(1137)
<220> FEATURE:
<221> NAME/KEY: misc_feature
<222> LOCATION: (361)..(363)
<223> OTHER INFORMATION: nnn is agy, tcy or tcr

<400> SEQUENCE: 31 atg agt gca aaa ggc ata gac tac gat aag ctc att gtt cgg ttt gga       48
Met Ser Ala Lys Gly Ile Asp Tyr Asp Lys Leu Ile Val Arg Phe Gly
```

-continued

```
          1               5              10              15
agt agt aaa att gac aaa gag cta ata aac cga ata gag aga gcc acc    96
Ser Ser Lys Ile Asp Lys Glu Leu Ile Asn Arg Ile Glu Arg Ala Thr
            20              25              30 ggc caa aga cca cac cac ttc ctg cgc aga ggc atc ttc ttc tca cac   144
Gly Gln Arg Pro His His Phe Leu Arg Arg Gly Ile Phe Phe Ser His
        35              40              45 aga gat atg aat cag gtt ctt gat gcc tat gaa aat aag aag cca ttt   192
Arg Asp Met Asn Gln Val Leu Asp Ala Tyr Glu Asn Lys Lys Pro Phe
    50              55              60 tat ctg tac acg ggc cgg ggc ccc tct tct gaa gca atg cat gta ggt   240
Tyr Leu Tyr Thr Gly Arg Gly Pro Ser Ser Glu Ala Met His Val Gly
65              70              75              80 cac ctc att cca ttt att ttc aca aag tgg ctc cag gat gta ttt aac   288
His Leu Ile Pro Phe Ile Phe Thr Lys Trp Leu Gln Asp Val Phe Asn
                85              90              95 gtg ccc ttg gtc atc cag atg acg gat gac gag aag tat ctg tgg aag   336
Val Pro Leu Val Ile Gln Met Thr Asp Asp Glu Lys Tyr Leu Trp Lys
            100             105             110 gac ctg acc ctg gac cag gcc tat nnn tay gct gtt gag aat gcc aag   384
Asp Leu Thr Leu Asp Gln Ala Tyr Ser Tyr Ala Val Glu Asn Ala Lys
        115             120             125 gac atc atc gcc tgt ggc ttt gac atc aac aag act ttc ata ttc tct   432
Asp Ile Ile Ala Cys Gly Phe Asp Ile Asn Lys Thr Phe Ile Phe Ser
    130             135             140 gac ctg gac tac atg ggg atg agc tca ggt ttc tac aaa aat gtg gtg   480
Asp Leu Asp Tyr Met Gly Met Ser Ser Gly Phe Tyr Lys Asn Val Val
145             150             155             160 aag att caa aag cat gtt acc ttc aac caa gtg aaa ggc att ttc ggc   528
Lys Ile Gln Lys His Val Thr Phe Asn Gln Val Lys Gly Ile Phe Gly
                165             170             175 ttc act gac agc gac tgc att ggg aag atc agt ttt cct gcc atc cag   576
Phe Thr Asp Ser Asp Cys Ile Gly Lys Ile Ser Phe Pro Ala Ile Gln
            180             185             190 gct gct ccc tcc ttc agc aac tca ttc cca cag atc ttc cga gac agg   624
Ala Ala Pro Ser Phe Ser Asn Ser Phe Pro Gln Ile Phe Arg Asp Arg
        195             200             205 acg gat atc cag tgc ctt atc cca tgt gcc att gac cag gat cct tac   672
Thr Asp Ile Gln Cys Leu Ile Pro Cys Ala Ile Asp Gln Asp Pro Tyr
    210             215             220 ttt aga atg aca agg gac gtc gcc ccc agg atc ggc tat cct aaa cca   720
Phe Arg Met Thr Arg Asp Val Ala Pro Arg Ile Gly Tyr Pro Lys Pro
225             230             235             240 gcc ctg ttg cac tcc acc ttc ttc cca gcc ctg cag ggc gcc cag acc   768
Ala Leu Leu His Ser Thr Phe Phe Pro Ala Leu Gln Gly Ala Gln Thr
                245             250             255 aaa atg agt gcc agc gac cca aac tcc tcc atc ttc ctc acc gac acg   816
Lys Met Ser Ala Ser Asp Pro Asn Ser Ser Ile Phe Leu Thr Asp Thr
            260             265             270 gcc aag cag atc aaa acc aag gtc aat aag cat gcg ttt tct gga ggg   864
Ala Lys Gln Ile Lys Thr Lys Val Asn Lys His Ala Phe Ser Gly Gly
        275             280             285 aga gac acc atc gag gag cac agg cag ttt ggg ggc aac tgt gat gtg   912
Arg Asp Thr Ile Glu Glu His Arg Gln Phe Gly Gly Asn Cys Asp Val
    290             295             300 gac gtg tct ttc atg tac ctg acc ttc ttc ctc gag gac gac gac aag   960
Asp Val Ser Phe Met Tyr Leu Thr Phe Phe Leu Glu Asp Asp Asp Lys
305             310             315             320 ctc gag cag atc agg aag gat tac acc agc gga gcc atg ctc acc ggt  1008
Leu Glu Gln Ile Arg Lys Asp Tyr Thr Ser Gly Ala Met Leu Thr Gly
```

```
                 325                 330                 335
gag ctc aag aag gca ctc ata gag gtt ctg cag ccc ttg atc gca gag    1056
Glu Leu Lys Lys Ala Leu Ile Glu Val Leu Gln Pro Leu Ile Ala Glu
            340                 345                 350 cac cag gcc cgg cgc aag gag gtc acg gat gag ata gtg aaa gag ttc    1104
His Gln Ala Arg Arg Lys Glu Val Thr Asp Glu Ile Val Lys Glu Phe
        355                 360                 365 atg act ccc cgg aag ctg tcc ttc gac ttt cag                        1137
Met Thr Pro Arg Lys Leu Ser Phe Asp Phe Gln
    370                 375

<210> SEQ ID NO 32
<211> LENGTH: 1203
<212> TYPE: DNA
<213> ORGANISM: Artificial Sequence
<220> FEATURE:
<223> OTHER INFORMATION: Recombinant human T1 (SY variant) construct
<220> FEATURE:
<221> NAME/KEY: CDS
<222> LOCATION: (1)..(1203)
<220> FEATURE:
<221> NAME/KEY: misc_feature
<222> LOCATION: (427)..(429)
<223> OTHER INFORMATION: nnn is agy, tcy or tcr

<400> SEQUENCE: 32 agt aat cat ggc cca gat gcc aca gaa gct gaa gag gat ttt gtg gac      48
Ser Asn His Gly Pro Asp Ala Thr Glu Ala Glu Glu Asp Phe Val Asp
  1               5                  10                  15 cca tgg aca gta cag aca agc agt gca aaa ggc ata gac tac gat aag      96
Pro Trp Thr Val Gln Thr Ser Ser Ala Lys Gly Ile Asp Tyr Asp Lys
             20                  25                  30 ctc att gtt cgg ttt gga agt agt aaa att gac aaa gag cta ata aac     144
Leu Ile Val Arg Phe Gly Ser Ser Lys Ile Asp Lys Glu Leu Ile Asn
         35                  40                  45 cga ata gag aga gcc acc ggc caa aga cca cac cac ttc ctg cgc aga     192
Arg Ile Glu Arg Ala Thr Gly Gln Arg Pro His His Phe Leu Arg Arg
     50                  55                  60 ggc atc ttc ttc tca cac aga gat atg aat cag gtt ctt gat gcc tat     240
Gly Ile Phe Phe Ser His Arg Asp Met Asn Gln Val Leu Asp Ala Tyr
 65                  70                  75                  80 gaa aat aag aag cca ttt tat ctg tac acg ggc cgg ggc ccc tct tct     288
Glu Asn Lys Lys Pro Phe Tyr Leu Tyr Thr Gly Arg Gly Pro Ser Ser
                 85                  90                  95 gaa gca atg cat gta ggt cac ctc att cca ttt att ttc aca aag tgg     336
Glu Ala Met His Val Gly His Leu Ile Pro Phe Ile Phe Thr Lys Trp
            100                 105                 110 ctc cag gat gta ttt aac gtg ccc ttg gtc atc cag atg acg gat gac     384
Leu Gln Asp Val Phe Asn Val Pro Leu Val Ile Gln Met Thr Asp Asp
        115                 120                 125 gag aag tat ctg tgg aag gac ctg acc ctg gac cag gcc tat nnn tay     432
Glu Lys Tyr Leu Trp Lys Asp Leu Thr Leu Asp Gln Ala Tyr Ser Tyr
    130                 135                 140 gct gtt gag aat gcc aag gac atc atc gcc tgt ggc ttt gac atc aac     480
Ala Val Glu Asn Ala Lys Asp Ile Ile Ala Cys Gly Phe Asp Ile Asn
145                 150                 155                 160 aag act ttc ata ttc tct gac ctg gac tac atg ggg atg agc tca ggt     528
Lys Thr Phe Ile Phe Ser Asp Leu Asp Tyr Met Gly Met Ser Ser Gly
                165                 170                 175 ttc tac aaa aat gtg gtg aag att caa aag cat gtt acc ttc aac caa     576
Phe Tyr Lys Asn Val Val Lys Ile Gln Lys His Val Thr Phe Asn Gln
            180                 185                 190 gtg aaa ggc att ttc ggc ttc act gac agc gac tgc att ggg aag atc     624
Val Lys Gly Ile Phe Gly Phe Thr Asp Ser Asp Cys Ile Gly Lys Ile
```

```
Val Lys Gly Ile Phe Gly Phe Thr Asp Ser Asp Cys Ile Gly Lys Ile
        195                 200                 205 agt ttt cct gcc atc cag gct gct ccc tcc ttc agc aac tca ttc cca    672
Ser Phe Pro Ala Ile Gln Ala Ala Pro Ser Phe Ser Asn Ser Phe Pro
210                 215                 220 cag atc ttc cga gac agg acg gat atc cag tgc ctt atc cca tgt gcc    720
Gln Ile Phe Arg Asp Arg Thr Asp Ile Gln Cys Leu Ile Pro Cys Ala
225                 230                 235                 240 att gac cag gat cct tac ttt aga atg aca agg gac gtc gcc ccc agg    768
Ile Asp Gln Asp Pro Tyr Phe Arg Met Thr Arg Asp Val Ala Pro Arg
            245                 250                 255 atc ggc tat cct aaa cca gcc ctg ttg cac tcc acc ttc ttc cca gcc    816
Ile Gly Tyr Pro Lys Pro Ala Leu Leu His Ser Thr Phe Phe Pro Ala
        260                 265                 270 ctg cag ggc gcc cag acc aaa atg agt gcc agc gac cca aac tcc tcc    864
Leu Gln Gly Ala Gln Thr Lys Met Ser Ala Ser Asp Pro Asn Ser Ser
    275                 280                 285 atc ttc ctc acc gac acg gcc aag cag atc aaa acc aag gtc aat aag    912
Ile Phe Leu Thr Asp Thr Ala Lys Gln Ile Lys Thr Lys Val Asn Lys
290                 295                 300 cat gcg ttt tct gga ggg aga gac acc atc gag gag cac agg cag ttt    960
His Ala Phe Ser Gly Gly Arg Asp Thr Ile Glu Glu His Arg Gln Phe
305                 310                 315                 320 ggg ggc aac tgt gat gtg gac gtg tct ttc atg tac ctg acc ttc ttc    1008
Gly Gly Asn Cys Asp Val Asp Val Ser Phe Met Tyr Leu Thr Phe Phe
            325                 330                 335 ctc gag gac gac gac aag ctc gag cag atc agg aag gat tac acc agc    1056
Leu Glu Asp Asp Asp Lys Leu Glu Gln Ile Arg Lys Asp Tyr Thr Ser
        340                 345                 350 gga gcc atg ctc acc ggt gag ctc aag aag gca ctc ata gag gtt ctg    1104
Gly Ala Met Leu Thr Gly Glu Leu Lys Lys Ala Leu Ile Glu Val Leu
    355                 360                 365 cag ccc ttg atc gca gag cac cag gcc cgg cgc aag gag gtc acg gat    1152
Gln Pro Leu Ile Ala Glu His Gln Ala Arg Arg Lys Glu Val Thr Asp
370                 375                 380 gag ata gtg aaa gag ttc atg act ccc cgg aag ctg tcc ttc gac ttt    1200
Glu Ile Val Lys Glu Phe Met Thr Pro Arg Lys Leu Ser Phe Asp Phe
385                 390                 395                 400 cag                                                                1203
Gln

<210> SEQ ID NO 33
<211> LENGTH: 1206
<212> TYPE: DNA
<213> ORGANISM: Artificial Sequence
<220> FEATURE:
<223> OTHER INFORMATION: Recombinant human Met-T1 (SY variant) construct
<220> FEATURE:
<221> NAME/KEY: CDS
<222> LOCATION: (1)..(1206)
<220> FEATURE:
<221> NAME/KEY: misc_feature
<222> LOCATION: (430)..(432)
<223> OTHER INFORMATION: nnn is agy, tcy or tcr

<400> SEQUENCE: 33 atg agt aat cat ggc cca gat gcc aca gaa gct gaa gag gat ttt gtg    48
Met Ser Asn His Gly Pro Asp Ala Thr Glu Ala Glu Glu Asp Phe Val
1               5                   10                  15 gac cca tgg aca gta cag aca agc agt gca aaa ggc ata gac tac gat    96
Asp Pro Trp Thr Val Gln Thr Ser Ser Ala Lys Gly Ile Asp Tyr Asp
            20                  25                  30 aag ctc att gtt cgg ttt gga agt agt aaa att gac aaa gag cta ata    144
```

```
                Lys Leu Ile Val Arg Phe Gly Ser Ser Lys Ile Asp Lys Glu Leu Ile
                             35                  40                  45 aac cga ata gag aga gcc acc ggc caa aga cca cac cac ttc ctg cgc            192
Asn Arg Ile Glu Arg Ala Thr Gly Gln Arg Pro His His Phe Leu Arg
         50                  55                  60 aga ggc atc ttc ttc tca cac aga gat atg aat cag gtt ctt gat gcc            240
Arg Gly Ile Phe Phe Ser His Arg Asp Met Asn Gln Val Leu Asp Ala
 65                  70                  75                  80 tat gaa aat aag aag cca ttt tat ctg tac acg ggc cgg ggc ccc tct            288
Tyr Glu Asn Lys Lys Pro Phe Tyr Leu Tyr Thr Gly Arg Gly Pro Ser
                 85                  90                  95 tct gaa gca atg cat gta ggt cac ctc att cca ttt att ttc aca aag            336
Ser Glu Ala Met His Val Gly His Leu Ile Pro Phe Ile Phe Thr Lys
             100                 105                 110 tgg ctc cag gat gta ttt aac gtg ccc ttg gtc atc cag atg acg gat            384
Trp Leu Gln Asp Val Phe Asn Val Pro Leu Val Ile Gln Met Thr Asp
         115                 120                 125 gac gag aag tat ctg tgg aag gac ctg acc ctg gac cag gcc tat nnn            432
Asp Glu Lys Tyr Leu Trp Lys Asp Leu Thr Leu Asp Gln Ala Tyr Ser
130                 135                 140 tay gct gtt gag aat gcc aag gac atc atc gcc tgt ggc ttt gac atc            480
Tyr Ala Val Glu Asn Ala Lys Asp Ile Ile Ala Cys Gly Phe Asp Ile
145                 150                 155                 160 aac aag act ttc ata ttc tct gac ctg gac tac atg ggg atg agc tca            528
Asn Lys Thr Phe Ile Phe Ser Asp Leu Asp Tyr Met Gly Met Ser Ser
                 165                 170                 175 ggt ttc tac aaa aat gtg gtg aag att caa aag cat gtt acc ttc aac            576
Gly Phe Tyr Lys Asn Val Val Lys Ile Gln Lys His Val Thr Phe Asn
             180                 185                 190 caa gtg aaa ggc att ttc ggc ttc act gac agc gac tgc att ggg aag            624
Gln Val Lys Gly Ile Phe Gly Phe Thr Asp Ser Asp Cys Ile Gly Lys
         195                 200                 205 atc agt ttt cct gcc atc cag gct gct ccc tcc ttc agc aac tca ttc            672
Ile Ser Phe Pro Ala Ile Gln Ala Ala Pro Ser Phe Ser Asn Ser Phe
210                 215                 220 cca cag atc ttc cga gac agg acg gat atc cag tgc ctt atc cca tgt            720
Pro Gln Ile Phe Arg Asp Arg Thr Asp Ile Gln Cys Leu Ile Pro Cys
225                 230                 235                 240 gcc att gac cag gat cct tac ttt aga atg aca agg gac gtc gcc ccc            768
Ala Ile Asp Gln Asp Pro Tyr Phe Arg Met Thr Arg Asp Val Ala Pro
                 245                 250                 255 agg atc ggc tat cct aaa cca gcc ttg ttg cac tcc acc ttc ttc cca            816
Arg Ile Gly Tyr Pro Lys Pro Ala Leu Leu His Ser Thr Phe Phe Pro
             260                 265                 270 gcc ctg cag ggc gcc cag acc aaa atg agt gcc agc gac cca aac tcc            864
Ala Leu Gln Gly Ala Gln Thr Lys Met Ser Ala Ser Asp Pro Asn Ser
         275                 280                 285 tcc atc ttc ctc acc gac acg gcc aag cag atc aaa acc aag gtc aat            912
Ser Ile Phe Leu Thr Asp Thr Ala Lys Gln Ile Lys Thr Lys Val Asn
290                 295                 300 aag cat gcg ttt tct gga ggg aga gac acc atc gag gag cac agg cag            960
Lys His Ala Phe Ser Gly Gly Arg Asp Thr Ile Glu Glu His Arg Gln
305                 310                 315                 320 ttt ggg ggc aac tgt gat gtg gac gtg tct ttc atg tac ctg acc ttc           1008
Phe Gly Gly Asn Cys Asp Val Asp Val Ser Phe Met Tyr Leu Thr Phe
                 325                 330                 335 ttc ctc gag gac gac gac aag ctc gag cag atc agg aag gat tac acc           1056
Phe Leu Glu Asp Asp Asp Lys Leu Glu Gln Ile Arg Lys Asp Tyr Thr
             340                 345                 350 agc gga gcc atg ctc acc ggt gag ctc aag aag gca ctc ata gag gtt           1104
```

```
Ser Gly Ala Met Leu Thr Gly Glu Leu Lys Lys Ala Leu Ile Glu Val
        355                 360                 365 ctg cag ccc ttg atc gca gag cac cag gcc cgg cgc aag gag gtc acg      1152
Leu Gln Pro Leu Ile Ala Glu His Gln Ala Arg Arg Lys Glu Val Thr
        370                 375                 380 gat gag ata gtg aaa gag ttc atg act ccc cgg aag ctg tcc ttc gac      1200
Asp Glu Ile Val Lys Glu Phe Met Thr Pro Arg Lys Leu Ser Phe Asp
385                 390                 395                 400 ttt cag                                                               1206
Phe Gln <210> SEQ ID NO 34
<211> LENGTH: 1269
<212> TYPE: DNA
<213> ORGANISM: Artificial Sequence
<220> FEATURE:
<223> OTHER INFORMATION: Recombinant human mini-TrpRS (SY variant)
      construct
<220> FEATURE:
<221> NAME/KEY: CDS
<222> LOCATION: (1)..(1269)
<220> FEATURE:
<221> NAME/KEY: misc_feature
<222> LOCATION: (493)..(495)
<223> OTHER INFORMATION: nnn is agy, tcy or tcr

<400> SEQUENCE: 34 agc tac aaa gct gcc gcg ggg gag gat tac aag gct gac tgt cct cca        48
Ser Tyr Lys Ala Ala Ala Gly Glu Asp Tyr Lys Ala Asp Cys Pro Pro
  1               5                  10                  15 ggg aac cca gca cct acc agt aat cat ggc cca gat gcc aca gaa gct        96
Gly Asn Pro Ala Pro Thr Ser Asn His Gly Pro Asp Ala Thr Glu Ala
             20                  25                  30 gaa gag gat ttt gtg gac cca tgg aca gta cag aca agc agt gca aaa       144
Glu Glu Asp Phe Val Asp Pro Trp Thr Val Gln Thr Ser Ser Ala Lys
         35                  40                  45 ggc ata gac tac gat aag ctc att gtt cgg ttt gga agt agt aaa att       192
Gly Ile Asp Tyr Asp Lys Leu Ile Val Arg Phe Gly Ser Ser Lys Ile
     50                  55                  60 gac aaa gag cta ata aac cga ata gag aga gcc acc ggc caa aga cca       240
Asp Lys Glu Leu Ile Asn Arg Ile Glu Arg Ala Thr Gly Gln Arg Pro
 65                  70                  75                  80 cac cac ttc ctg cgc aga ggc atc ttc ttc tca cac aga gat atg aat       288
His His Phe Leu Arg Arg Gly Ile Phe Phe Ser His Arg Asp Met Asn
                 85                  90                  95 cag gtt ctt gat gcc tat gaa aat aag aag cca ttt tat ctg tac acg       336
Gln Val Leu Asp Ala Tyr Glu Asn Lys Lys Pro Phe Tyr Leu Tyr Thr
            100                 105                 110 ggc cgg ggc ccc tct tct gaa gca atg cat gta ggt cac ctc att cca       384
Gly Arg Gly Pro Ser Ser Glu Ala Met His Val Gly His Leu Ile Pro
        115                 120                 125 ttt att ttc aca aag tgg ctc cag gat gta ttt aac gtg ccc ttg gtc       432
Phe Ile Phe Thr Lys Trp Leu Gln Asp Val Phe Asn Val Pro Leu Val
    130                 135                 140 atc cag atg acg gat gac gag aag tat ctg tgg aag gac ctg acc ctg       480
Ile Gln Met Thr Asp Asp Glu Lys Tyr Leu Trp Lys Asp Leu Thr Leu
145                 150                 155                 160 gac cag gcc tat nnn tay gct gtt gag aat gcc aag gac atc atc gcc       528
Asp Gln Ala Tyr Ser Tyr Ala Val Glu Asn Ala Lys Asp Ile Ile Ala
                165                 170                 175 tgt ggc ttt gac atc aac aag act ttc ata ttc tct gac ctg gac tac       576
Cys Gly Phe Asp Ile Asn Lys Thr Phe Ile Phe Ser Asp Leu Asp Tyr
            180                 185                 190
```

```
atg ggg atg agc tca ggt ttc tac aaa aat gtg gtg aag att caa aag    624
Met Gly Met Ser Ser Gly Phe Tyr Lys Asn Val Val Lys Ile Gln Lys
        195                 200                 205 cat gtt acc ttc aac caa gtg aaa ggc att ttc ggc ttc act gac agc    672
His Val Thr Phe Asn Gln Val Lys Gly Ile Phe Gly Phe Thr Asp Ser
    210                 215                 220 gac tgc att ggg aag atc agt ttt cct gcc atc cag gct gct ccc tcc    720
Asp Cys Ile Gly Lys Ile Ser Phe Pro Ala Ile Gln Ala Ala Pro Ser
225                 230                 235                 240 ttc agc aac tca ttc cca cag atc ttc cga gac agg acg gat atc cag    768
Phe Ser Asn Ser Phe Pro Gln Ile Phe Arg Asp Arg Thr Asp Ile Gln
                245                 250                 255 tgc ctt atc cca tgt gcc att gac cag gat cct tac ttt aga atg aca    816
Cys Leu Ile Pro Cys Ala Ile Asp Gln Asp Pro Tyr Phe Arg Met Thr
            260                 265                 270 agg gac gtc gcc ccc agg atc ggc tat cct aaa cca gcc ctg ttg cac    864
Arg Asp Val Ala Pro Arg Ile Gly Tyr Pro Lys Pro Ala Leu Leu His
        275                 280                 285 tcc acc ttc ttc cca gcc ctg cag ggc gcc cag acc aaa atg agt gcc    912
Ser Thr Phe Phe Pro Ala Leu Gln Gly Ala Gln Thr Lys Met Ser Ala
    290                 295                 300 agc gac cca aac tcc tcc atc ttc ctc acc gac acg gcc aag cag atc    960
Ser Asp Pro Asn Ser Ser Ile Phe Leu Thr Asp Thr Ala Lys Gln Ile
305                 310                 315                 320 aaa acc aag gtc aat aag cat gcg ttt tct gga ggg aga gac acc atc   1008
Lys Thr Lys Val Asn Lys His Ala Phe Ser Gly Gly Arg Asp Thr Ile
                325                 330                 335 gag gag cac agg cag ttt ggg ggc aac tgt gat gtg gac gtg tct ttc   1056
Glu Glu His Arg Gln Phe Gly Gly Asn Cys Asp Val Asp Val Ser Phe
            340                 345                 350 atg tac ctg acc ttc ttc ctc gag gac gac gac aag ctc gag cag atc   1104
Met Tyr Leu Thr Phe Phe Leu Glu Asp Asp Asp Lys Leu Glu Gln Ile
        355                 360                 365 agg aag gat tac acc agc gga gcc atg ctc acc ggt gag ctc aag aag   1152
Arg Lys Asp Tyr Thr Ser Gly Ala Met Leu Thr Gly Glu Leu Lys Lys
    370                 375                 380 gca ctc ata gag gtt ctg cag ccc ttg atc gca gag cac cag gcc cgg   1200
Ala Leu Ile Glu Val Leu Gln Pro Leu Ile Ala Glu His Gln Ala Arg
385                 390                 395                 400 cgc aag gag gtc acg gat gag ata gtg aaa gag ttc atg act ccc cgg   1248
Arg Lys Glu Val Thr Asp Glu Ile Val Lys Glu Phe Met Thr Pro Arg
                405                 410                 415 aag ctg tcc ttc gac ttt cag                                       1269
Lys Leu Ser Phe Asp Phe Gln
            420
```

<210> SEQ ID NO 35
<211> LENGTH: 1272
<212> TYPE: DNA
<213> ORGANISM: Artificial Sequence
<220> FEATURE:
<223> OTHER INFORMATION: Recombinant human Met-mini-TrpRS (SY variant)
      construct
<220> FEATURE:
<221> NAME/KEY: CDS
<222> LOCATION: (1)..(1272)
<220> FEATURE:
<221> NAME/KEY: misc_feature
<222> LOCATION: (496)..(498)
<223> OTHER INFORMATION: nnn is agy, tcy or tcr

<400> SEQUENCE: 35

```
atg agc tac aaa gct gcc gcg ggg gag gat tac aag gct gac tgt cct     48
Met Ser Tyr Lys Ala Ala Ala Gly Glu Asp Tyr Lys Ala Asp Cys Pro
```

```
                1               5              10              15
cca ggg aac cca gca cct acc agt aat cat ggc cca gat gcc aca gaa         96
Pro Gly Asn Pro Ala Pro Thr Ser Asn His Gly Pro Asp Ala Thr Glu
                    20              25              30 gct gaa gag gat ttt gtg gac cca tgg aca gta cag aca agc agt gca        144
Ala Glu Glu Asp Phe Val Asp Pro Trp Thr Val Gln Thr Ser Ser Ala
            35              40              45 aaa ggc ata gac tac gat aag ctc att gtt cgg ttt gga agt agt aaa        192
Lys Gly Ile Asp Tyr Asp Lys Leu Ile Val Arg Phe Gly Ser Ser Lys
        50              55              60 att gac aaa gag cta ata aac cga ata gag aga gcc acc ggc caa aga        240
Ile Asp Lys Glu Leu Ile Asn Arg Ile Glu Arg Ala Thr Gly Gln Arg
65              70              75              80 cca cac cac ttc ctg cgc aga ggc atc ttc ttc tca cac aga gat atg        288
Pro His His Phe Leu Arg Arg Gly Ile Phe Phe Ser His Arg Asp Met
                85              90              95 aat cag gtt ctt gat gcc tat gaa aat aag aag cca ttt tat ctg tac        336
Asn Gln Val Leu Asp Ala Tyr Glu Asn Lys Lys Pro Phe Tyr Leu Tyr
            100             105             110 acg ggc cgg ggc ccc tct tct gaa gca atg cat gta ggt cac ctc att        384
Thr Gly Arg Gly Pro Ser Ser Glu Ala Met His Val Gly His Leu Ile
        115             120             125 cca ttt att ttc aca aag tgg ctc cag gat gta ttt aac gtg ccc ttg        432
Pro Phe Ile Phe Thr Lys Trp Leu Gln Asp Val Phe Asn Val Pro Leu
130             135             140 gtc atc cag atg acg gat gac gag aag tat ctg tgg aag gac ctg acc        480
Val Ile Gln Met Thr Asp Asp Glu Lys Tyr Leu Trp Lys Asp Leu Thr
145             150             155             160 ctg gac cag gcc tat agc tay gct gtt gag aat gcc aag gac atc atc        528
Leu Asp Gln Ala Tyr Ser Tyr Ala Val Glu Asn Ala Lys Asp Ile Ile
                165             170             175 gcc tgt ggc ttt gac atc aac aag act ttc ata ttc tct gac ctg gac        576
Ala Cys Gly Phe Asp Ile Asn Lys Thr Phe Ile Phe Ser Asp Leu Asp
            180             185             190 tac atg ggg atg agc tca ggt ttc tac aaa aat gtg gtg aag att caa        624
Tyr Met Gly Met Ser Ser Gly Phe Tyr Lys Asn Val Val Lys Ile Gln
        195             200             205 aag cat gtt acc ttc aac caa gtg aaa ggc att ttc ggc ttc act gac        672
Lys His Val Thr Phe Asn Gln Val Lys Gly Ile Phe Gly Phe Thr Asp
210             215             220 agc gac tgc att ggg aag atc agt ttt cct gcc atc cag gct gct ccc        720
Ser Asp Cys Ile Gly Lys Ile Ser Phe Pro Ala Ile Gln Ala Ala Pro
225             230             235             240 tcc ttc agc aac tca ttc cca cag atc ttc cga gac agg acg gat atc        768
Ser Phe Ser Asn Ser Phe Pro Gln Ile Phe Arg Asp Arg Thr Asp Ile
                245             250             255 cag tgc ctt atc cca tgt gcc att gac cag gat cct tac ttt aga atg        816
Gln Cys Leu Ile Pro Cys Ala Ile Asp Gln Asp Pro Tyr Phe Arg Met
            260             265             270 aca agg gac gtc gcc ccc agg atc ggc tat cct aaa cca gcc ctg ttg        864
Thr Arg Asp Val Ala Pro Arg Ile Gly Tyr Pro Lys Pro Ala Leu Leu
        275             280             285 cac tcc acc ttc ttc cca gcc ctg cag ggc gcc cag acc aaa atg agt        912
His Ser Thr Phe Phe Pro Ala Leu Gln Gly Ala Gln Thr Lys Met Ser
290             295             300 gcc agc gac cca aac tcc tcc atc ttc ctc acc gac acg gcc aag cag        960
Ala Ser Asp Pro Asn Ser Ser Ile Phe Leu Thr Asp Thr Ala Lys Gln
305             310             315             320 atc aaa acc aag gtc aat aag cat gcg ttt tct gga ggg aga gac acc       1008
Ile Lys Thr Lys Val Asn Lys His Ala Phe Ser Gly Gly Arg Asp Thr
```

```
              325                 330                 335
atc gag gag cac agg cag ttt ggg ggc aac tgt gat gtg gac gtg tct      1056
Ile Glu Glu His Arg Gln Phe Gly Gly Asn Cys Asp Val Asp Val Ser
        340                 345                 350 ttc atg tac ctg acc ttc ttc ctc gag gac gac gac aag ctc gag cag      1104
Phe Met Tyr Leu Thr Phe Phe Leu Glu Asp Asp Asp Lys Leu Glu Gln
            355                 360                 365 atc agg aag gat tac acc agc gga gcc atg ctc acc ggt gag ctc aag      1152
Ile Arg Lys Asp Tyr Thr Ser Gly Ala Met Leu Thr Gly Glu Leu Lys
        370                 375                 380 aag gca ctc ata gag gtt ctg cag ccc ttg atc gca gag cac cag gcc      1200
Lys Ala Leu Ile Glu Val Leu Gln Pro Leu Ile Ala Glu His Gln Ala
385                 390                 395                 400 cgg cgc aag gag gtc acg gat gag ata gtg aaa gag ttc atg act ccc      1248
Arg Arg Lys Glu Val Thr Asp Glu Ile Val Lys Glu Phe Met Thr Pro
            405                 410                 415 cgg aag ctg tcc ttc gac ttt cag                                      1272
Arg Lys Leu Ser Phe Asp Phe Gln
        420
```

<210> SEQ ID NO 36
<211> LENGTH: 378
<212> TYPE: PRT
<213> ORGANISM: Artificial Sequence
<220> FEATURE:
<223> OTHER INFORMATION: Recombinant human T2 (GY variant) construct

<400> SEQUENCE: 36

```
Ser Ala Lys Gly Ile Asp Tyr Asp Lys Leu Ile Val Arg Phe Gly Ser
1               5                   10                  15

Ser Lys Ile Asp Lys Glu Leu Ile Asn Arg Ile Glu Arg Ala Thr Gly
            20                  25                  30

Gln Arg Pro His His Phe Leu Arg Arg Gly Ile Phe Phe Ser His Arg
        35                  40                  45

Asp Met Asn Gln Val Leu Asp Ala Tyr Glu Asn Lys Lys Pro Phe Tyr
    50                  55                  60

Leu Tyr Thr Gly Arg Gly Pro Ser Ser Glu Ala Met His Val Gly His
65                  70                  75                  80

Leu Ile Pro Phe Ile Phe Thr Lys Trp Leu Gln Asp Val Phe Asn Val
                85                  90                  95

Pro Leu Val Ile Gln Met Thr Asp Asp Glu Lys Tyr Leu Trp Lys Asp
            100                 105                 110

Leu Thr Leu Asp Gln Ala Tyr Gly Tyr Ala Val Glu Asn Ala Lys Asp
        115                 120                 125

Ile Ile Ala Cys Gly Phe Asp Ile Asn Lys Thr Phe Ile Phe Ser Asp
    130                 135                 140

Leu Asp Tyr Met Gly Met Ser Ser Gly Phe Tyr Lys Asn Val Val Lys
145                 150                 155                 160

Ile Gln Lys His Val Thr Phe Asn Gln Val Lys Gly Ile Phe Gly Phe
                165                 170                 175

Thr Asp Ser Asp Cys Ile Gly Lys Ile Ser Phe Pro Ala Ile Gln Ala
            180                 185                 190

Ala Pro Ser Phe Ser Asn Ser Phe Pro Gln Ile Phe Arg Asp Arg Thr
        195                 200                 205

Asp Ile Gln Cys Leu Ile Pro Cys Ala Ile Asp Gln Asp Pro Tyr Phe
    210                 215                 220

Arg Met Thr Arg Asp Val Ala Pro Arg Ile Gly Tyr Pro Lys Pro Ala
225                 230                 235                 240
```

```
Leu Leu His Ser Thr Phe Phe Pro Ala Leu Gln Gly Ala Gln Thr Lys
            245                 250                 255

Met Ser Ala Ser Asp Pro Asn Ser Ser Ile Phe Leu Thr Asp Thr Ala
            260                 265                 270

Lys Gln Ile Lys Thr Lys Val Asn Lys His Ala Phe Ser Gly Gly Arg
            275                 280                 285

Asp Thr Ile Glu Glu His Arg Gln Phe Gly Gly Asn Cys Asp Val Asp
290                 295                 300

Val Ser Phe Met Tyr Leu Thr Phe Phe Leu Glu Asp Asp Lys Leu
305                 310                 315                 320

Glu Gln Ile Arg Lys Asp Tyr Thr Ser Gly Ala Met Leu Thr Gly Glu
            325                 330                 335

Leu Lys Lys Ala Leu Ile Glu Val Leu Gln Pro Leu Ile Ala Glu His
            340                 345                 350

Gln Ala Arg Arg Lys Glu Val Thr Asp Glu Ile Val Lys Glu Phe Met
            355                 360                 365

Thr Pro Arg Lys Leu Ser Phe Asp Phe Gln
            370                 375

<210> SEQ ID NO 37
<211> LENGTH: 401
<212> TYPE: PRT
<213> ORGANISM: Artificial Sequence
<220> FEATURE:
<223> OTHER INFORMATION: Recombinant human T1 (GY variant) construct

<400> SEQUENCE: 37

Ser Asn His Gly Pro Asp Ala Thr Glu Ala Glu Glu Asp Phe Val Asp
1               5                   10                  15

Pro Trp Thr Val Gln Thr Ser Ser Ala Lys Gly Ile Asp Tyr Asp Lys
            20                  25                  30

Leu Ile Val Arg Phe Gly Ser Ser Lys Ile Asp Lys Glu Leu Ile Asn
        35                  40                  45

Arg Ile Glu Arg Ala Thr Gly Gln Arg Pro His His Phe Leu Arg Arg
50                  55                  60

Gly Ile Phe Phe Ser His Arg Asp Met Asn Gln Val Leu Asp Ala Tyr
65                  70                  75                  80

Glu Asn Lys Lys Pro Phe Tyr Leu Tyr Thr Gly Arg Gly Pro Ser Ser
            85                  90                  95

Glu Ala Met His Val Gly His Leu Ile Pro Phe Ile Phe Thr Lys Trp
            100                 105                 110

Leu Gln Asp Val Phe Asn Val Pro Leu Val Ile Gln Met Thr Asp Asp
            115                 120                 125

Glu Lys Tyr Leu Trp Lys Asp Leu Thr Leu Asp Gln Ala Tyr Gly Tyr
            130                 135                 140

Ala Val Glu Asn Ala Lys Asp Ile Ile Ala Cys Gly Phe Asp Ile Asn
145                 150                 155                 160

Lys Thr Phe Ile Phe Ser Asp Leu Asp Tyr Met Gly Met Ser Ser Gly
            165                 170                 175

Phe Tyr Lys Asn Val Val Lys Ile Gln Lys His Val Thr Phe Asn Gln
            180                 185                 190

Val Lys Gly Ile Phe Gly Phe Thr Asp Ser Asp Cys Ile Gly Lys Ile
            195                 200                 205

Ser Phe Pro Ala Ile Gln Ala Ala Pro Ser Phe Ser Asn Ser Phe Pro
            210                 215                 220
```

```
Gln Ile Phe Arg Asp Arg Thr Asp Ile Gln Cys Leu Ile Pro Cys Ala
225                 230                 235                 240

Ile Asp Gln Asp Pro Tyr Phe Arg Met Thr Arg Asp Val Ala Pro Arg
                245                 250                 255

Ile Gly Tyr Pro Lys Pro Ala Leu Leu His Ser Thr Phe Phe Pro Ala
            260                 265                 270

Leu Gln Gly Ala Gln Thr Lys Met Ser Ala Ser Asp Pro Asn Ser Ser
        275                 280                 285

Ile Phe Leu Thr Asp Thr Ala Lys Gln Ile Lys Thr Lys Val Asn Lys
    290                 295                 300

His Ala Phe Ser Gly Gly Arg Asp Thr Ile Glu Glu His Arg Gln Phe
305                 310                 315                 320

Gly Gly Asn Cys Asp Val Asp Val Ser Phe Met Tyr Leu Thr Phe Phe
                325                 330                 335

Leu Glu Asp Asp Asp Lys Leu Glu Gln Ile Arg Lys Asp Tyr Thr Ser
                340                 345                 350

Gly Ala Met Leu Thr Gly Glu Leu Lys Lys Ala Leu Ile Glu Val Leu
            355                 360                 365

Gln Pro Leu Ile Ala Glu His Gln Ala Arg Arg Lys Glu Val Thr Asp
        370                 375                 380

Glu Ile Val Lys Glu Phe Met Thr Pro Arg Lys Leu Ser Phe Asp Phe
385                 390                 395                 400

Gln

<210> SEQ ID NO 38
<211> LENGTH: 423
<212> TYPE: PRT
<213> ORGANISM: Artificial Sequence
<220> FEATURE:
<223> OTHER INFORMATION: Recombinant human mini-TrpRS (GY variant)
      construct

<400> SEQUENCE: 38

Ser Tyr Lys Ala Ala Gly Glu Asp Tyr Lys Ala Asp Cys Pro Pro
1               5                   10                  15

Gly Asn Pro Ala Pro Thr Ser Asn His Gly Pro Asp Ala Thr Glu Ala
                20                  25                  30

Glu Glu Asp Phe Val Asp Pro Trp Thr Val Gln Thr Ser Ser Ala Lys
            35                  40                  45

Gly Ile Asp Tyr Asp Lys Leu Ile Val Arg Phe Gly Ser Ser Lys Ile
        50                  55                  60

Asp Lys Glu Leu Ile Asn Arg Ile Glu Arg Ala Thr Gly Gln Arg Pro
65                  70                  75                  80

His His Phe Leu Arg Arg Gly Ile Phe Phe Ser His Arg Asp Met Asn
                85                  90                  95

Gln Val Leu Asp Ala Tyr Glu Asn Lys Lys Pro Phe Tyr Leu Tyr Thr
                100                 105                 110

Gly Arg Gly Pro Ser Ser Glu Ala Met His Val Gly His Leu Ile Pro
            115                 120                 125

Phe Ile Phe Thr Lys Trp Leu Gln Asp Val Phe Asn Val Pro Leu Val
        130                 135                 140

Ile Gln Met Thr Asp Asp Glu Lys Tyr Leu Trp Lys Asp Leu Thr Leu
145                 150                 155                 160

Asp Gln Ala Tyr Gly Tyr Ala Val Glu Asn Ala Lys Asp Ile Ile Ala
                165                 170                 175

Cys Gly Phe Asp Ile Asn Lys Thr Phe Ile Phe Ser Asp Leu Asp Tyr
```

```
                        180                 185                 190
Met Gly Met Ser Ser Gly Phe Tyr Lys Asn Val Val Lys Ile Gln Lys
            195                 200                 205

His Val Thr Phe Asn Gln Val Lys Gly Ile Phe Gly Phe Thr Asp Ser
            210                 215                 220

Asp Cys Ile Gly Lys Ile Ser Phe Pro Ala Ile Gln Ala Ala Pro Ser
225                 230                 235                 240

Phe Ser Asn Ser Phe Pro Gln Ile Phe Arg Asp Arg Thr Asp Ile Gln
                245                 250                 255

Cys Leu Ile Pro Cys Ala Ile Asp Gln Asp Pro Tyr Phe Arg Met Thr
            260                 265                 270

Arg Asp Val Ala Pro Arg Ile Gly Tyr Pro Lys Pro Ala Leu Leu His
            275                 280                 285

Ser Thr Phe Phe Pro Ala Leu Gln Gly Ala Gln Thr Lys Met Ser Ala
            290                 295                 300

Ser Asp Pro Asn Ser Ser Ile Phe Leu Thr Asp Thr Ala Lys Gln Ile
305                 310                 315                 320

Lys Thr Lys Val Asn Lys His Ala Phe Ser Gly Gly Arg Asp Thr Ile
                325                 330                 335

Glu Glu His Arg Gln Phe Gly Gly Asn Cys Asp Val Asp Val Ser Phe
            340                 345                 350

Met Tyr Leu Thr Phe Phe Leu Glu Asp Asp Lys Leu Glu Gln Ile
            355                 360                 365

Arg Lys Asp Tyr Thr Ser Gly Ala Met Leu Thr Gly Glu Leu Lys Lys
            370                 375                 380

Ala Leu Ile Glu Val Leu Gln Pro Leu Ile Ala Glu His Gln Ala Arg
385                 390                 395                 400

Arg Lys Glu Val Thr Asp Glu Ile Val Lys Glu Phe Met Thr Pro Arg
                405                 410                 415

Lys Leu Ser Phe Asp Phe Gln
            420

<210> SEQ ID NO 39
<211> LENGTH: 379
<212> TYPE: PRT
<213> ORGANISM: Artificial Sequence
<220> FEATURE:
<223> OTHER INFORMATION: Recombinant human Met-T2 (GY variant) construct

<400> SEQUENCE: 39

Met Ser Ala Lys Gly Ile Asp Tyr Asp Lys Leu Ile Val Arg Phe Gly
1               5                   10                  15

Ser Ser Lys Ile Asp Lys Glu Leu Ile Asn Arg Ile Glu Arg Ala Thr
            20                  25                  30

Gly Gln Arg Pro His His Phe Leu Arg Arg Gly Ile Phe Phe Ser His
            35                  40                  45

Arg Asp Met Asn Gln Val Leu Asp Ala Tyr Glu Asn Lys Lys Pro Phe
            50                  55                  60

Tyr Leu Tyr Thr Gly Arg Gly Pro Ser Ser Glu Ala Met His Val Gly
65                  70                  75                  80

His Leu Ile Pro Phe Ile Phe Thr Lys Trp Leu Gln Asp Val Phe Asn
                85                  90                  95

Val Pro Leu Val Ile Gln Met Thr Asp Asp Glu Lys Tyr Leu Trp Lys
            100                 105                 110

Asp Leu Thr Leu Asp Gln Ala Tyr Gly Tyr Ala Val Glu Asn Ala Lys
            115                 120                 125
```

```
Asp Ile Ile Ala Cys Gly Phe Asp Ile Asn Lys Thr Phe Ile Phe Ser
    130                 135                 140

Asp Leu Asp Tyr Met Gly Met Ser Ser Gly Phe Tyr Lys Asn Val Val
145                 150                 155                 160

Lys Ile Gln Lys His Val Thr Phe Asn Gln Val Lys Gly Ile Phe Gly
                165                 170                 175

Phe Thr Asp Ser Asp Cys Ile Gly Lys Ile Ser Phe Pro Ala Ile Gln
                180                 185                 190

Ala Ala Pro Ser Phe Ser Asn Ser Phe Pro Gln Ile Phe Arg Asp Arg
                195                 200                 205

Thr Asp Ile Gln Cys Leu Ile Pro Cys Ala Ile Asp Gln Asp Pro Tyr
    210                 215                 220

Phe Arg Met Thr Arg Asp Val Ala Pro Arg Ile Gly Tyr Pro Lys Pro
225                 230                 235                 240

Ala Leu Leu His Ser Thr Phe Phe Pro Ala Leu Gln Gly Ala Gln Thr
                245                 250                 255

Lys Met Ser Ala Ser Asp Pro Asn Ser Ser Ile Phe Leu Thr Asp Thr
                260                 265                 270

Ala Lys Gln Ile Lys Thr Lys Val Asn Lys His Ala Phe Ser Gly Gly
                275                 280                 285

Arg Asp Thr Ile Glu Glu His Arg Gln Phe Gly Gly Asn Cys Asp Val
    290                 295                 300

Asp Val Ser Phe Met Tyr Leu Thr Phe Phe Leu Glu Asp Asp Lys
305                 310                 315                 320

Leu Glu Gln Ile Arg Lys Asp Tyr Thr Ser Gly Ala Met Leu Thr Gly
                325                 330                 335

Glu Leu Lys Lys Ala Leu Ile Glu Val Leu Gln Pro Leu Ile Ala Glu
                340                 345                 350

His Gln Ala Arg Arg Lys Glu Val Thr Asp Glu Ile Val Lys Glu Phe
                355                 360                 365

Met Thr Pro Arg Lys Leu Ser Phe Asp Phe Gln
                370                 375

<210> SEQ ID NO 40
<211> LENGTH: 402
<212> TYPE: PRT
<213> ORGANISM: Artificial Sequence
<220> FEATURE:
<223> OTHER INFORMATION: Recombinant human Met-T1 (GY variant) construct

<400> SEQUENCE: 40

Met Ser Asn His Gly Pro Asp Ala Thr Glu Ala Glu Asp Phe Val
1               5                   10                  15

Asp Pro Trp Thr Val Gln Thr Ser Ser Ala Lys Gly Ile Asp Tyr Asp
                20                  25                  30

Lys Leu Ile Val Arg Phe Gly Ser Ser Lys Ile Asp Lys Glu Leu Ile
            35                  40                  45

Asn Arg Ile Glu Arg Ala Thr Gly Gln Arg Pro His His Phe Leu Arg
        50                  55                  60

Arg Gly Ile Phe Phe Ser His Arg Asp Met Asn Gln Val Leu Asp Ala
65                  70                  75                  80

Tyr Glu Asn Lys Lys Pro Phe Tyr Leu Tyr Thr Gly Arg Gly Pro Ser
                85                  90                  95

Ser Glu Ala Met His Val Gly His Leu Ile Pro Phe Ile Phe Thr Lys
                100                 105                 110
```

```
Trp Leu Gln Asp Val Phe Asn Val Pro Leu Val Ile Gln Met Thr Asp
        115                 120                 125

Asp Glu Lys Tyr Leu Trp Lys Asp Leu Thr Leu Asp Gln Ala Tyr Gly
    130                 135                 140

Tyr Ala Val Glu Asn Ala Lys Asp Ile Ile Ala Cys Gly Phe Asp Ile
145                 150                 155                 160

Asn Lys Thr Phe Ile Phe Ser Asp Leu Asp Tyr Met Gly Met Ser Ser
                165                 170                 175

Gly Phe Tyr Lys Asn Val Val Lys Ile Gln Lys His Val Thr Phe Asn
            180                 185                 190

Gln Val Lys Gly Ile Phe Gly Phe Thr Asp Ser Asp Cys Ile Gly Lys
        195                 200                 205

Ile Ser Phe Pro Ala Ile Gln Ala Ala Pro Ser Phe Ser Asn Ser Phe
    210                 215                 220

Pro Gln Ile Phe Arg Asp Arg Thr Asp Ile Gln Cys Leu Ile Pro Cys
225                 230                 235                 240

Ala Ile Asp Gln Asp Pro Tyr Phe Arg Met Thr Arg Asp Val Ala Pro
                245                 250                 255

Arg Ile Gly Tyr Pro Lys Pro Ala Leu Leu His Ser Thr Phe Phe Pro
            260                 265                 270

Ala Leu Gln Gly Ala Gln Thr Lys Met Ser Ala Ser Asp Pro Asn Ser
        275                 280                 285

Ser Ile Phe Leu Thr Asp Thr Ala Lys Gln Ile Lys Thr Lys Val Asn
    290                 295                 300

Lys His Ala Phe Ser Gly Gly Arg Asp Thr Ile Glu Glu His Arg Gln
305                 310                 315                 320

Phe Gly Gly Asn Cys Asp Val Asp Val Ser Phe Met Tyr Leu Thr Phe
                325                 330                 335

Phe Leu Glu Asp Asp Asp Lys Leu Glu Gln Ile Arg Lys Asp Tyr Thr
            340                 345                 350

Ser Gly Ala Met Leu Thr Gly Glu Leu Lys Lys Ala Leu Ile Glu Val
        355                 360                 365

Leu Gln Pro Leu Ile Ala Glu His Gln Ala Arg Arg Lys Glu Val Thr
    370                 375                 380

Asp Glu Ile Val Lys Glu Phe Met Thr Pro Arg Lys Leu Ser Phe Asp
385                 390                 395                 400

Phe Gln

<210> SEQ ID NO 41
<211> LENGTH: 424
<212> TYPE: PRT
<213> ORGANISM: Artificial Sequence
<220> FEATURE:
<223> OTHER INFORMATION: Recombinant human Met-mini-TrpRS (GY variant)
      construct

<400> SEQUENCE: 41

Met Ser Tyr Lys Ala Ala Ala Gly Glu Asp Tyr Lys Ala Asp Cys Pro
1               5                   10                  15

Pro Gly Asn Pro Ala Pro Thr Ser Asn His Gly Pro Asp Ala Thr Glu
            20                  25                  30

Ala Glu Glu Asp Phe Val Asp Pro Trp Thr Val Gln Thr Ser Ser Ala
        35                  40                  45

Lys Gly Ile Asp Tyr Asp Lys Leu Ile Val Arg Phe Gly Ser Ser Lys
    50                  55                  60

Ile Asp Lys Glu Leu Ile Asn Arg Ile Glu Arg Ala Thr Gly Gln Arg
```

```
                65                  70                  75                  80
Pro His His Phe Leu Arg Arg Gly Ile Phe Phe Ser His Arg Asp Met
                        85                  90                  95

Asn Gln Val Leu Asp Ala Tyr Glu Asn Lys Pro Phe Tyr Leu Tyr
                100                 105                 110

Thr Gly Arg Gly Pro Ser Ser Glu Ala Met His Val Gly His Leu Ile
                115                 120                 125

Pro Phe Ile Phe Thr Lys Trp Leu Gln Asp Val Phe Asn Val Pro Leu
            130                 135                 140

Val Ile Gln Met Thr Asp Asp Glu Lys Tyr Leu Trp Lys Asp Leu Thr
145                 150                 155                 160

Leu Asp Gln Ala Tyr Gly Tyr Ala Val Glu Asn Ala Lys Asp Ile Ile
                165                 170                 175

Ala Cys Gly Phe Asp Ile Asn Lys Thr Phe Ile Phe Ser Asp Leu Asp
                180                 185                 190

Tyr Met Gly Met Ser Ser Gly Phe Tyr Lys Asn Val Val Lys Ile Gln
                195                 200                 205

Lys His Val Thr Phe Asn Gln Val Lys Gly Ile Phe Gly Phe Thr Asp
210                 215                 220

Ser Asp Cys Ile Gly Lys Ile Ser Phe Pro Ala Ile Gln Ala Ala Pro
225                 230                 235                 240

Ser Phe Ser Asn Ser Phe Pro Gln Ile Phe Arg Asp Arg Thr Asp Ile
                245                 250                 255

Gln Cys Leu Ile Pro Cys Ala Ile Asp Gln Asp Pro Tyr Phe Arg Met
                260                 265                 270

Thr Arg Asp Val Ala Pro Arg Ile Gly Tyr Pro Lys Pro Ala Leu Leu
            275                 280                 285

His Ser Thr Phe Phe Pro Ala Leu Gln Gly Ala Gln Thr Lys Met Ser
290                 295                 300

Ala Ser Asp Pro Asn Ser Ser Ile Phe Leu Thr Asp Thr Ala Lys Gln
305                 310                 315                 320

Ile Lys Thr Lys Val Asn Lys His Ala Phe Ser Gly Gly Arg Asp Thr
                325                 330                 335

Ile Glu Glu His Arg Gln Phe Gly Gly Asn Cys Asp Val Asp Val Ser
                340                 345                 350

Phe Met Tyr Leu Thr Phe Phe Leu Glu Asp Asp Lys Leu Glu Gln
            355                 360                 365

Ile Arg Lys Asp Tyr Thr Ser Gly Ala Met Leu Thr Gly Glu Leu Lys
            370                 375                 380

Lys Ala Leu Ile Glu Val Leu Gln Pro Leu Ile Ala Glu His Gln Ala
385                 390                 395                 400

Arg Arg Lys Glu Val Thr Asp Glu Ile Val Lys Glu Phe Met Thr Pro
                405                 410                 415

Arg Lys Leu Ser Phe Asp Phe Gln
                420

<210> SEQ ID NO 42
<211> LENGTH: 1134
<212> TYPE: DNA
<213> ORGANISM: Artificial Sequence
<220> FEATURE:
<223> OTHER INFORMATION: Recombinant human T2 (GY variant) construct
<220> FEATURE:
<221> NAME/KEY: CDS
<222> LOCATION: (1)..(1134)
<220> FEATURE:
<221> NAME/KEY: modified_base
```

<222> LOCATION: (360)
<223> OTHER INFORMATION: a, t, c or g

<400> SEQUENCE: 42

| | | | | | | | | | | | | | | | | |
|---|---|---|---|---|---|---|---|---|---|---|---|---|---|---|---|---|
| agt | gca | aaa | ggc | ata | gac | tac | gat | aag | ctc | att | gtt | cgg | ttt | gga | agt | 48 |
| Ser | Ala | Lys | Gly | Ile | Asp | Tyr | Asp | Lys | Leu | Ile | Val | Arg | Phe | Gly | Ser | |
| 1 | | | | 5 | | | | | 10 | | | | | 15 | | |
| agt | aaa | att | gac | aaa | gag | cta | ata | aac | cga | ata | gag | aga | gcc | acc | ggc | 96 |
| Ser | Lys | Ile | Asp | Lys | Glu | Leu | Ile | Asn | Arg | Ile | Glu | Arg | Ala | Thr | Gly | |
| | | | 20 | | | | | 25 | | | | | 30 | | | |
| caa | aga | cca | cac | cac | ttc | ctg | cgc | aga | ggc | atc | ttc | ttc | tca | cac | aga | 144 |
| Gln | Arg | Pro | His | His | Phe | Leu | Arg | Arg | Gly | Ile | Phe | Phe | Ser | His | Arg | |
| | | 35 | | | | | 40 | | | | | 45 | | | | |
| gat | atg | aat | cag | gtt | ctt | gat | gcc | tat | gaa | aat | aag | aag | cca | ttt | tat | 192 |
| Asp | Met | Asn | Gln | Val | Leu | Asp | Ala | Tyr | Glu | Asn | Lys | Lys | Pro | Phe | Tyr | |
| 50 | | | | | 55 | | | | | 60 | | | | | | |
| ctg | tac | acg | ggc | cgg | ggc | ccc | tct | tct | gaa | gca | atg | cat | gta | ggt | cac | 240 |
| Leu | Tyr | Thr | Gly | Arg | Gly | Pro | Ser | Ser | Glu | Ala | Met | His | Val | Gly | His | |
| 65 | | | | 70 | | | | | 75 | | | | | 80 | | |
| ctc | att | cca | ttt | att | ttc | aca | aag | tgg | ctc | cag | gat | gta | ttt | aac | gtg | 288 |
| Leu | Ile | Pro | Phe | Ile | Phe | Thr | Lys | Trp | Leu | Gln | Asp | Val | Phe | Asn | Val | |
| | | | | 85 | | | | | 90 | | | | | 95 | | |
| ccc | ttg | gtc | atc | cag | atg | acg | gat | gac | gag | aag | tat | ctg | tgg | aag | gac | 336 |
| Pro | Leu | Val | Ile | Gln | Met | Thr | Asp | Asp | Glu | Lys | Tyr | Leu | Trp | Lys | Asp | |
| | | | 100 | | | | | 105 | | | | | 110 | | | |
| ctg | acc | ctg | gac | cag | gcc | tat | ggn | tay | gct | gtt | gag | aat | gcc | aag | gac | 384 |
| Leu | Thr | Leu | Asp | Gln | Ala | Tyr | Gly | Tyr | Ala | Val | Glu | Asn | Ala | Lys | Asp | |
| | | 115 | | | | | 120 | | | | | 125 | | | | |
| atc | atc | gcc | tgt | ggc | ttt | gac | atc | aac | aag | act | ttc | ata | ttc | tct | gac | 432 |
| Ile | Ile | Ala | Cys | Gly | Phe | Asp | Ile | Asn | Lys | Thr | Phe | Ile | Phe | Ser | Asp | |
| | 130 | | | | | 135 | | | | | 140 | | | | | |
| ctg | gac | tac | atg | ggg | atg | agc | tca | ggt | ttc | tac | aaa | aat | gtg | gtg | aag | 480 |
| Leu | Asp | Tyr | Met | Gly | Met | Ser | Ser | Gly | Phe | Tyr | Lys | Asn | Val | Val | Lys | |
| 145 | | | | | 150 | | | | | 155 | | | | | 160 | |
| att | caa | aag | cat | gtt | acc | ttc | aac | caa | gtg | aaa | ggc | att | ttc | ggc | ttc | 528 |
| Ile | Gln | Lys | His | Val | Thr | Phe | Asn | Gln | Val | Lys | Gly | Ile | Phe | Gly | Phe | |
| | | | | 165 | | | | | 170 | | | | | 175 | | |
| act | gac | agc | gac | tgc | att | ggg | aag | atc | agt | ttt | cct | gcc | atc | cag | gct | 576 |
| Thr | Asp | Ser | Asp | Cys | Ile | Gly | Lys | Ile | Ser | Phe | Pro | Ala | Ile | Gln | Ala | |
| | | | 180 | | | | | 185 | | | | | 190 | | | |
| gct | ccc | tcc | ttc | agc | aac | tca | ttc | cca | cag | atc | ttc | cga | gac | agg | acg | 624 |
| Ala | Pro | Ser | Phe | Ser | Asn | Ser | Phe | Pro | Gln | Ile | Phe | Arg | Asp | Arg | Thr | |
| | | 195 | | | | | 200 | | | | | 205 | | | | |
| gat | atc | cag | tgc | ctt | atc | cca | tgt | gcc | att | gac | cag | gat | cct | tac | ttt | 672 |
| Asp | Ile | Gln | Cys | Leu | Ile | Pro | Cys | Ala | Ile | Asp | Gln | Asp | Pro | Tyr | Phe | |
| | 210 | | | | | 215 | | | | | 220 | | | | | |
| aga | atg | aca | agg | gac | gtc | gcc | ccc | agg | atc | ggc | tat | cct | aaa | cca | gcc | 720 |
| Arg | Met | Thr | Arg | Asp | Val | Ala | Pro | Arg | Ile | Gly | Tyr | Pro | Lys | Pro | Ala | |
| 225 | | | | | 230 | | | | | 235 | | | | | 240 | |
| ctg | ttg | cac | tcc | acc | ttc | ttc | cca | gcc | ctg | cag | ggc | gcc | cag | acc | aaa | 768 |
| Leu | Leu | His | Ser | Thr | Phe | Phe | Pro | Ala | Leu | Gln | Gly | Ala | Gln | Thr | Lys | |
| | | | | 245 | | | | | 250 | | | | | 255 | | |
| atg | agt | gcc | agc | gac | cca | aac | tcc | tcc | atc | ttc | ctc | acc | gac | acg | gcc | 816 |
| Met | Ser | Ala | Ser | Asp | Pro | Asn | Ser | Ser | Ile | Phe | Leu | Thr | Asp | Thr | Ala | |
| | | | 260 | | | | | 265 | | | | | 270 | | | |
| aag | cag | atc | aaa | acc | aag | gtc | aat | aag | cat | gcg | ttt | tct | gga | ggg | aga | 864 |
| Lys | Gln | Ile | Lys | Thr | Lys | Val | Asn | Lys | His | Ala | Phe | Ser | Gly | Gly | Arg | |
| | | 275 | | | | | 280 | | | | | 285 | | | | |
| gac | acc | atc | gag | gag | cac | agg | cag | ttt | ggg | ggc | aac | tgt | gat | gtg | gac | 912 |
| Asp | Thr | Ile | Glu | Glu | His | Arg | Gln | Phe | Gly | Gly | Asn | Cys | Asp | Val | Asp | |
| | 290 | | | | | 295 | | | | | 300 | | | | | |

```
gtg tct ttc atg tac ctg acc ttc ttc ctc gag gac gac gac aag ctc    960
Val Ser Phe Met Tyr Leu Thr Phe Phe Leu Glu Asp Asp Asp Lys Leu
305                 310                 315                 320 gag cag atc agg aag gat tac acc agc gga gcc atg ctc acc ggt gag   1008
Glu Gln Ile Arg Lys Asp Tyr Thr Ser Gly Ala Met Leu Thr Gly Glu
            325                 330                 335 ctc aag aag gca ctc ata gag gtt ctg cag ccc ttg atc gca gag cac   1056
Leu Lys Lys Ala Leu Ile Glu Val Leu Gln Pro Leu Ile Ala Glu His
        340                 345                 350 cag gcc cgg cgc aag gag gtc acg gat gag ata gtg aaa gag ttc atg   1104
Gln Ala Arg Arg Lys Glu Val Thr Asp Glu Ile Val Lys Glu Phe Met
    355                 360                 365 act ccc cgg aag ctg tcc ttc gac ttt cag                           1134
Thr Pro Arg Lys Leu Ser Phe Asp Phe Gln
370                 375

<210> SEQ ID NO 43
<211> LENGTH: 1137
<212> TYPE: DNA
<213> ORGANISM: Artificial Sequence
<220> FEATURE:
<223> OTHER INFORMATION: Recombinant human Met-T2 (GY variant) construct
<220> FEATURE:
<221> NAME/KEY: CDS
<222> LOCATION: (1)..(1137)
<220> FEATURE:
<221> NAME/KEY: modified_base
<222> LOCATION: (363)
<223> OTHER INFORMATION: a, t, c or g

<400> SEQUENCE: 43 atg agt gca aaa ggc ata gac tac gat aag ctc att gtt cgg ttt gga     48
Met Ser Ala Lys Gly Ile Asp Tyr Asp Lys Leu Ile Val Arg Phe Gly
1               5                  10                  15 agt agt aaa att gac aaa gag cta ata aac cga ata gag aga gcc acc     96
Ser Ser Lys Ile Asp Lys Glu Leu Ile Asn Arg Ile Glu Arg Ala Thr
            20                  25                  30 ggc caa aga cca cac cac ttc ctg cgc aga ggc atc ttc ttc tca cac    144
Gly Gln Arg Pro His His Phe Leu Arg Arg Gly Ile Phe Phe Ser His
        35                  40                  45 aga gat atg aat cag gtt ctt gat gcc tat gaa aat aag aag cca ttt    192
Arg Asp Met Asn Gln Val Leu Asp Ala Tyr Glu Asn Lys Lys Pro Phe
    50                  55                  60 tat ctg tac acg ggc cgg ggc ccc tct tct gaa gca atg cat gta ggt    240
Tyr Leu Tyr Thr Gly Arg Gly Pro Ser Ser Glu Ala Met His Val Gly
65                  70                  75                  80 cac ctc att cca ttt att ttc aca aag tgg ctc cag gat gta ttt aac    288
His Leu Ile Pro Phe Ile Phe Thr Lys Trp Leu Gln Asp Val Phe Asn
                85                  90                  95 gtg ccc ttg gtc atc cag atg acg gat gac gag aag tat ctg tgg aag    336
Val Pro Leu Val Ile Gln Met Thr Asp Asp Glu Lys Tyr Leu Trp Lys
            100                 105                 110 gac ctg acc ctg gac cag gcc tat ggn tay gct gtt gag aat gcc aag    384
Asp Leu Thr Leu Asp Gln Ala Tyr Gly Tyr Ala Val Glu Asn Ala Lys
        115                 120                 125 gac atc atc gcc tgt ggc ttt gac atc aac aag act ttc ata ttc tct    432
Asp Ile Ile Ala Cys Gly Phe Asp Ile Asn Lys Thr Phe Ile Phe Ser
    130                 135                 140 gac ctg gac tac atg ggg atg agc tca ggt ttc tac aaa aat gtg gtg    480
Asp Leu Asp Tyr Met Gly Met Ser Ser Gly Phe Tyr Lys Asn Val Val
145                 150                 155                 160 aag att caa aag cat gtt acc ttc aac caa gtg aaa ggc att ttc ggc    528
Lys Ile Gln Lys His Val Thr Phe Asn Gln Val Lys Gly Ile Phe Gly
```

```
ttc act gac agc gac tgc att ggg aag atc agt ttt cct gcc atc cag      576
Phe Thr Asp Ser Asp Cys Ile Gly Lys Ile Ser Phe Pro Ala Ile Gln
            180                 185                 190 gct gct ccc tcc ttc agc aac tca ttc cca cag atc ttc cga gac agg      624
Ala Ala Pro Ser Phe Ser Asn Ser Phe Pro Gln Ile Phe Arg Asp Arg
        195                 200                 205 acg gat atc cag tgc ctt atc cca tgt gcc att gac cag gat cct tac      672
Thr Asp Ile Gln Cys Leu Ile Pro Cys Ala Ile Asp Gln Asp Pro Tyr
    210                 215                 220 ttt aga atg aca agg gac gtc gcc ccc agg atc ggc tat cct aaa cca      720
Phe Arg Met Thr Arg Asp Val Ala Pro Arg Ile Gly Tyr Pro Lys Pro
225                 230                 235                 240 gcc ctg ttg cac tcc acc ttc ttc cca gcc ctg cag ggc gcc cag acc      768
Ala Leu Leu His Ser Thr Phe Phe Pro Ala Leu Gln Gly Ala Gln Thr
                245                 250                 255 aaa atg agt gcc agc gac cca aac tcc tcc atc ttc ctc acc gac acg      816
Lys Met Ser Ala Ser Asp Pro Asn Ser Ser Ile Phe Leu Thr Asp Thr
            260                 265                 270 gcc aag cag atc aaa acc aag gtc aat aag cat gcg ttt tct gga ggg      864
Ala Lys Gln Ile Lys Thr Lys Val Asn Lys His Ala Phe Ser Gly Gly
        275                 280                 285 aga gac acc atc gag gag cac agg cag ttt ggg ggc aac tgt gat gtg      912
Arg Asp Thr Ile Glu Glu His Arg Gln Phe Gly Gly Asn Cys Asp Val
    290                 295                 300 gac gtg tct ttc atg tac ctg acc ttc ttc ctc gag gac gac gac aag      960
Asp Val Ser Phe Met Tyr Leu Thr Phe Phe Leu Glu Asp Asp Asp Lys
305                 310                 315                 320 ctc gag cag atc agg aag gat tac acc agc gga gcc atg ctc acc ggt     1008
Leu Glu Gln Ile Arg Lys Asp Tyr Thr Ser Gly Ala Met Leu Thr Gly
                325                 330                 335 gag ctc aag aag gca ctc ata gag gtt ctg cag ccc ttg atc gca gag     1056
Glu Leu Lys Lys Ala Leu Ile Glu Val Leu Gln Pro Leu Ile Ala Glu
            340                 345                 350 cac cag gcc cgg cgc aag gag gtc acg gat gag ata gtg aaa gag ttc     1104
His Gln Ala Arg Arg Lys Glu Val Thr Asp Glu Ile Val Lys Glu Phe
        355                 360                 365 atg act ccc cgg aag ctg tcc ttc gac ttt cag                         1137
Met Thr Pro Arg Lys Leu Ser Phe Asp Phe Gln
    370                 375

<210> SEQ ID NO 44
<211> LENGTH: 1203
<212> TYPE: DNA
<213> ORGANISM: Artificial Sequence
<220> FEATURE:
<223> OTHER INFORMATION: Recombinant human T1 (GY variant) construct
<220> FEATURE:
<221> NAME/KEY: CDS
<222> LOCATION: (1)..(1203)
<220> FEATURE:
<221> NAME/KEY: modified_base
<222> LOCATION: (429)
<223> OTHER INFORMATION: a, t, c or g

<400> SEQUENCE: 44 agt aat cat ggc cca gat gcc aca gaa gct gaa gag gat ttt gtg gac       48
Ser Asn His Gly Pro Asp Ala Thr Glu Ala Glu Glu Asp Phe Val Asp
1               5                   10                  15 cca tgg aca gta cag aca agc agt gca aaa ggc ata gac tac gat aag       96
Pro Trp Thr Val Gln Thr Ser Ser Ala Lys Gly Ile Asp Tyr Asp Lys
            20                  25                  30 ctc att gtt cgg ttt gga agt agt aaa att gac aaa gag cta ata aac      144
```

-continued

```
Leu Ile Val Arg Phe Gly Ser Ser Lys Ile Asp Lys Glu Leu Ile Asn
         35                  40                  45 cga ata gag aga gcc acc ggc caa aga cca cac cac ttc ctg cgc aga       192
Arg Ile Glu Arg Ala Thr Gly Gln Arg Pro His His Phe Leu Arg Arg
 50                  55                  60 ggc atc ttc ttc tca cac aga gat atg aat cag gtt ctt gat gcc tat       240
Gly Ile Phe Phe Ser His Arg Asp Met Asn Gln Val Leu Asp Ala Tyr
 65                  70                  75                  80 gaa aat aag aag cca ttt tat ctg tac acg ggc cgg ggc ccc tct tct       288
Glu Asn Lys Lys Pro Phe Tyr Leu Tyr Thr Gly Arg Gly Pro Ser Ser
                 85                  90                  95 gaa gca atg cat gta ggt cac ctc att cca ttt att ttc aca aag tgg       336
Glu Ala Met His Val Gly His Leu Ile Pro Phe Ile Phe Thr Lys Trp
            100                 105                 110 ctc cag gat gta ttt aac gtg ccc ttg gtc atc cag atg acg gat gac       384
Leu Gln Asp Val Phe Asn Val Pro Leu Val Ile Gln Met Thr Asp Asp
        115                 120                 125 gag aag tat ctg tgg aag gac ctg acc ctg gac cag gcc tat ggn tay       432
Glu Lys Tyr Leu Trp Lys Asp Leu Thr Leu Asp Gln Ala Tyr Gly Tyr
130                 135                 140 gct gtt gag aat gcc aag gac atc atc gcc tgt ggc ttt gac atc aac       480
Ala Val Glu Asn Ala Lys Asp Ile Ile Ala Cys Gly Phe Asp Ile Asn
145                 150                 155                 160 aag act ttc ata ttc tct gac ctg gac tac atg ggg atg agc tca ggt       528
Lys Thr Phe Ile Phe Ser Asp Leu Asp Tyr Met Gly Met Ser Ser Gly
                165                 170                 175 ttc tac aaa aat gtg gtg aag att caa aag cat gtt acc ttc aac caa       576
Phe Tyr Lys Asn Val Val Lys Ile Gln Lys His Val Thr Phe Asn Gln
            180                 185                 190 gtg aaa ggc att ttc ggc ttc act gac agc gac tgc att ggg aag atc       624
Val Lys Gly Ile Phe Gly Phe Thr Asp Ser Asp Cys Ile Gly Lys Ile
        195                 200                 205 agt ttt cct gcc atc cag gct gct ccc tcc ttc agc aac tca ttc cca       672
Ser Phe Pro Ala Ile Gln Ala Ala Pro Ser Phe Ser Asn Ser Phe Pro
210                 215                 220 cag atc ttc cga gac agg acg gat atc cag tgc ctt atc cca tgt gcc       720
Gln Ile Phe Arg Asp Arg Thr Asp Ile Gln Cys Leu Ile Pro Cys Ala
225                 230                 235                 240 att gac cag gat cct tac ttt aga atg aca agg gac gtc gcc ccc agg       768
Ile Asp Gln Asp Pro Tyr Phe Arg Met Thr Arg Asp Val Ala Pro Arg
                245                 250                 255 atc ggc tat cct aaa cca gcc ctg ttg cac tcc acc ttc ttc cca gcc       816
Ile Gly Tyr Pro Lys Pro Ala Leu Leu His Ser Thr Phe Phe Pro Ala
            260                 265                 270 ctg cag ggc gcc cag acc aaa atg agt gcc agc gac cca aac tcc tcc       864
Leu Gln Gly Ala Gln Thr Lys Met Ser Ala Ser Asp Pro Asn Ser Ser
        275                 280                 285 atc ttc ctc acc gac acg gcc aag cag atc aaa acc aag gtc aat aag       912
Ile Phe Leu Thr Asp Thr Ala Lys Gln Ile Lys Thr Lys Val Asn Lys
290                 295                 300 cat gcg ttt tct gga ggg aga gac acc atc gag gag cac agg cag ttt       960
His Ala Phe Ser Gly Gly Arg Asp Thr Ile Glu Glu His Arg Gln Phe
305                 310                 315                 320 ggg ggc aac tgt gat gtg gac gtg tct ttc atg tac ctg acc ttc ttc      1008
Gly Gly Asn Cys Asp Val Asp Val Ser Phe Met Tyr Leu Thr Phe Phe
                325                 330                 335 ctc gag gac gac gac aag ctc gag cag atc agg aag gat tac acc agc      1056
Leu Glu Asp Asp Asp Lys Leu Glu Gln Ile Arg Lys Asp Tyr Thr Ser
            340                 345                 350 gga gcc atg ctc acc ggt gag ctc aag aag gca ctc ata gag gtt ctg      1104
```

-continued

```
                Gly Ala Met Leu Thr Gly Glu Leu Lys Lys Ala Leu Ile Glu Val Leu
                                355                 360                 365 cag ccc ttg atc gca gag cac cag gcc cgg cgc aag gag gtc acg gat         1152
Gln Pro Leu Ile Ala Glu His Gln Ala Arg Arg Lys Glu Val Thr Asp
    370                 375                 380 gag ata gtg aaa gag ttc atg act ccc cgg aag ctg tcc ttc gac ttt         1200
Glu Ile Val Lys Glu Phe Met Thr Pro Arg Lys Leu Ser Phe Asp Phe
385                 390                 395                 400 cag                                                                     1203
Gln <210> SEQ ID NO 45
<211> LENGTH: 1206
<212> TYPE: DNA
<213> ORGANISM: Artificial Sequence
<220> FEATURE:
<223> OTHER INFORMATION: Recombinant human Met-T1 (GY variant) construct
<220> FEATURE:
<221> NAME/KEY: CDS
<222> LOCATION: (1)..(1206)
<220> FEATURE:
<221> NAME/KEY: modified_base
<222> LOCATION: (432)
<223> OTHER INFORMATION: a, t, c or g

<400> SEQUENCE: 45 atg agt aat cat ggc cca gat gcc aca gaa gct gaa gag gat ttt gtg        48
Met Ser Asn His Gly Pro Asp Ala Thr Glu Ala Glu Glu Asp Phe Val
1               5                   10                  15 gac cca tgg aca gta cag aca agc agt gca aaa ggc ata gac tac gat        96
Asp Pro Trp Thr Val Gln Thr Ser Ser Ala Lys Gly Ile Asp Tyr Asp
                20                  25                  30 aag ctc att gtt cgg ttt gga agt agt aaa att gac aaa gag cta ata       144
Lys Leu Ile Val Arg Phe Gly Ser Ser Lys Ile Asp Lys Glu Leu Ile
            35                  40                  45 aac cga ata gag aga gcc acc ggc caa aga cca cac cac ttc ctg cgc       192
Asn Arg Ile Glu Arg Ala Thr Gly Gln Arg Pro His His Phe Leu Arg
        50                  55                  60 aga ggc atc ttc ttc tca cac aga gat atg aat cag gtt ctt gat gcc       240
Arg Gly Ile Phe Phe Ser His Arg Asp Met Asn Gln Val Leu Asp Ala
65                  70                  75                  80 tat gaa aat aag aag cca ttt tat ctg tac acg ggc cgg ggc ccc tct       288
Tyr Glu Asn Lys Lys Pro Phe Tyr Leu Tyr Thr Gly Arg Gly Pro Ser
                85                  90                  95 tct gaa gca atg cat gta ggt cac ctc att cca ttt att ttc aca aag       336
Ser Glu Ala Met His Val Gly His Leu Ile Pro Phe Ile Phe Thr Lys
                100                 105                 110 tgg ctc cag gat gta ttt aac gtg ccc ttg gtc atc cag atg acg gat       384
Trp Leu Gln Asp Val Phe Asn Val Pro Leu Val Ile Gln Met Thr Asp
            115                 120                 125 gac gag aag tat ctg tgg aag gac ctg acc ctg gac cag gcc tat ggn       432
Asp Glu Lys Tyr Leu Trp Lys Asp Leu Thr Leu Asp Gln Ala Tyr Gly
        130                 135                 140 tay gct gtt gag aat gcc aag gac atc atc gcc tgt ggc ttt gac atc       480
Tyr Ala Val Glu Asn Ala Lys Asp Ile Ile Ala Cys Gly Phe Asp Ile
145                 150                 155                 160 aac aag act ttc ata ttc tct gac ctg gac tac atg ggg atg agc tca       528
Asn Lys Thr Phe Ile Phe Ser Asp Leu Asp Tyr Met Gly Met Ser Ser
                165                 170                 175 ggt ttc tac aaa aat gtg gtg aag att caa aag cat gtt acc ttc aac       576
Gly Phe Tyr Lys Asn Val Val Lys Ile Gln Lys His Val Thr Phe Asn
            180                 185                 190 caa gtg aaa ggc att ttc ggc ttc act gac agc gac tgc att ggg aag       624
Gln Val Lys Gly Ile Phe Gly Phe Thr Asp Ser Asp Cys Ile Gly Lys
```

```
                                        Gln Val Lys Gly Ile Phe Gly Phe Thr Asp Ser Asp Cys Ile Gly Lys
                                            195                 200                 205 atc agt ttt cct gcc atc cag gct gct ccc tcc ttc agc aac tca ttc           672
Ile Ser Phe Pro Ala Ile Gln Ala Ala Pro Ser Phe Ser Asn Ser Phe
    210                 215                 220 cca cag atc ttc cga gac agg acg gat atc cag tgc ctt atc cca tgt           720
Pro Gln Ile Phe Arg Asp Arg Thr Asp Ile Gln Cys Leu Ile Pro Cys
225                 230                 235                 240 gcc att gac cag gat cct tac ttt aga atg aca agg gac gtc gcc ccc           768
Ala Ile Asp Gln Asp Pro Tyr Phe Arg Met Thr Arg Asp Val Ala Pro
                245                 250                 255 agg atc ggc tat cct aaa cca gcc ctg ttg cac tcc acc ttc ttc cca           816
Arg Ile Gly Tyr Pro Lys Pro Ala Leu Leu His Ser Thr Phe Phe Pro
            260                 265                 270 gcc ctg cag ggc gcc cag acc aaa atg agt gcc agc gac cca aac tcc           864
Ala Leu Gln Gly Ala Gln Thr Lys Met Ser Ala Ser Asp Pro Asn Ser
        275                 280                 285 tcc atc ttc ctc acc gac acg gcc aag cag atc aaa acc aag gtc aat           912
Ser Ile Phe Leu Thr Asp Thr Ala Lys Gln Ile Lys Thr Lys Val Asn
    290                 295                 300 aag cat gcg ttt tct gga ggg aga gac acc atc gag gag cac agg cag           960
Lys His Ala Phe Ser Gly Gly Arg Asp Thr Ile Glu Glu His Arg Gln
305                 310                 315                 320 ttt ggg ggc aac tgt gat gtg gac gtg tct ttc atg tac ctg acc ttc          1008
Phe Gly Gly Asn Cys Asp Val Asp Val Ser Phe Met Tyr Leu Thr Phe
                325                 330                 335 ttc ctc gag gac gac gac aag ctc gag cag atc agg aag gat tac acc          1056
Phe Leu Glu Asp Asp Asp Lys Leu Glu Gln Ile Arg Lys Asp Tyr Thr
            340                 345                 350 agc gga gcc atg ctc acc ggt gag ctc aag aag gca ctc ata gag gtt          1104
Ser Gly Ala Met Leu Thr Gly Glu Leu Lys Lys Ala Leu Ile Glu Val
        355                 360                 365 ctg cag ccc ttg atc gca gag cac cag gcc cgg cgc aag gag gtc acg          1152
Leu Gln Pro Leu Ile Ala Glu His Gln Ala Arg Arg Lys Glu Val Thr
    370                 375                 380 gat gag ata gtg aaa gag ttc atg act ccc cgg aag ctg tcc ttc gac          1200
Asp Glu Ile Val Lys Glu Phe Met Thr Pro Arg Lys Leu Ser Phe Asp
385                 390                 395                 400 ttt cag                                                                   1206
Phe Gln <210> SEQ ID NO 46
<211> LENGTH: 1269
<212> TYPE: DNA
<213> ORGANISM: Artificial Sequence
<220> FEATURE:
<223> OTHER INFORMATION: Recombinant human mini-TrpRS (GY variant)
      construct
<220> FEATURE:
<221> NAME/KEY: CDS
<222> LOCATION: (1)..(1269)
<220> FEATURE:
<221> NAME/KEY: modified_base
<222> LOCATION: (495)
<223> OTHER INFORMATION: a, t, c or g

<400> SEQUENCE: 46 agc tac aaa gct gcc gcg ggg gag gat tac aag gct gac tgt cct cca            48
Ser Tyr Lys Ala Ala Ala Gly Glu Asp Tyr Lys Ala Asp Cys Pro Pro
  1               5                  10                  15 ggg aac cca gca cct acc agt aat cat ggc cca gat gcc aca gaa gct            96
Gly Asn Pro Ala Pro Thr Ser Asn His Gly Pro Asp Ala Thr Glu Ala
                20                  25                  30
```

```
gaa gag gat ttt gtg gac cca tgg aca gta cag aca agc agt gca aaa      144
Glu Glu Asp Phe Val Asp Pro Trp Thr Val Gln Thr Ser Ser Ala Lys
         35                  40                  45 ggc ata gac tac gat aag ctc att gtt cgg ttt gga agt agt aaa att      192
Gly Ile Asp Tyr Asp Lys Leu Ile Val Arg Phe Gly Ser Ser Lys Ile
 50                  55                  60 gac aaa gag cta ata aac cga ata gag aga gcc acc ggc caa aga cca      240
Asp Lys Glu Leu Ile Asn Arg Ile Glu Arg Ala Thr Gly Gln Arg Pro
 65                  70                  75                  80 cac cac ttc ctg cgc aga ggc atc ttc ttc tca cac aga gat atg aat      288
His His Phe Leu Arg Arg Gly Ile Phe Phe Ser His Arg Asp Met Asn
                 85                  90                  95 cag gtt ctt gat gcc tat gaa aat aag aag cca ttt tat ctg tac acg      336
Gln Val Leu Asp Ala Tyr Glu Asn Lys Lys Pro Phe Tyr Leu Tyr Thr
            100                 105                 110 ggc cgg ggc ccc tct tct gaa gca atg cat gta ggt cac ctc att cca      384
Gly Arg Gly Pro Ser Ser Glu Ala Met His Val Gly His Leu Ile Pro
        115                 120                 125 ttt att ttc aca aag tgg ctc cag gat gta ttt aac gtg ccc ttg gtc      432
Phe Ile Phe Thr Lys Trp Leu Gln Asp Val Phe Asn Val Pro Leu Val
130                 135                 140 atc cag atg acg gat gac gag aag tat ctg tgg aag gac ctg acc ctg      480
Ile Gln Met Thr Asp Asp Glu Lys Tyr Leu Trp Lys Asp Leu Thr Leu
145                 150                 155                 160 gac cag gcc tat ggn tay gct gtt gag aat gcc aag gac atc atc gcc      528
Asp Gln Ala Tyr Gly Tyr Ala Val Glu Asn Ala Lys Asp Ile Ile Ala
                165                 170                 175 tgt ggc ttt gac atc aac aag act ttc ata ttc tct gac ctg gac tac      576
Cys Gly Phe Asp Ile Asn Lys Thr Phe Ile Phe Ser Asp Leu Asp Tyr
            180                 185                 190 atg ggg atg agc tca ggt ttc tac aaa aat gtg gtg aag att caa aag      624
Met Gly Met Ser Ser Gly Phe Tyr Lys Asn Val Val Lys Ile Gln Lys
        195                 200                 205 cat gtt acc ttc aac caa gtg aaa ggc att ttc ggc ttc act gac agc      672
His Val Thr Phe Asn Gln Val Lys Gly Ile Phe Gly Phe Thr Asp Ser
210                 215                 220 gac tgc att ggg aag atc agt ttt cct gcc atc cag gct gct ccc tcc      720
Asp Cys Ile Gly Lys Ile Ser Phe Pro Ala Ile Gln Ala Ala Pro Ser
225                 230                 235                 240 ttc agc aac tca ttc cca cag atc ttc cga gac agg acg gat atc cag      768
Phe Ser Asn Ser Phe Pro Gln Ile Phe Arg Asp Arg Thr Asp Ile Gln
                245                 250                 255 tgc ctt atc cca tgt gcc att gac cag gat cct tac ttt aga atg aca      816
Cys Leu Ile Pro Cys Ala Ile Asp Gln Asp Pro Tyr Phe Arg Met Thr
            260                 265                 270 agg gac gtc gcc ccc agg atc ggc tat cct aaa cca gcc ctg ttg cac      864
Arg Asp Val Ala Pro Arg Ile Gly Tyr Pro Lys Pro Ala Leu Leu His
        275                 280                 285 tcc acc ttc ttc cca gcc ctg cag ggc gcc cag acc aaa atg agt gcc      912
Ser Thr Phe Phe Pro Ala Leu Gln Gly Ala Gln Thr Lys Met Ser Ala
290                 295                 300 agc gac cca aac tcc tcc atc ttc ctc acc gac acg gcc aag cag atc      960
Ser Asp Pro Asn Ser Ser Ile Phe Leu Thr Asp Thr Ala Lys Gln Ile
305                 310                 315                 320 aaa acc aag gtc aat aag cat gcg ttt tct gga ggg aga gac acc atc     1008
Lys Thr Lys Val Asn Lys His Ala Phe Ser Gly Gly Arg Asp Thr Ile
                325                 330                 335 gag gag cac agg cag ttt ggg ggc aac tgt gat gtg gac gtg tct ttc     1056
Glu Glu His Arg Gln Phe Gly Gly Asn Cys Asp Val Asp Val Ser Phe
            340                 345                 350
```

-continued

```
atg tac ctg acc ttc ttc ctc gag gac gac gac aag ctc gag cag atc      1104
Met Tyr Leu Thr Phe Phe Leu Glu Asp Asp Asp Lys Leu Glu Gln Ile
        355                 360                 365 agg aag gat tac acc agc gga gcc atg ctc acc ggt gag ctc aag aag      1152
Arg Lys Asp Tyr Thr Ser Gly Ala Met Leu Thr Gly Glu Leu Lys Lys
370                 375                 380 gca ctc ata gag gtt ctg cag ccc ttg atc gca gag cac cag gcc cgg      1200
Ala Leu Ile Glu Val Leu Gln Pro Leu Ile Ala Glu His Gln Ala Arg
385                 390                 395                 400 cgc aag gag gtc acg gat gag ata gtg aaa gag ttc atg act ccc cgg      1248
Arg Lys Glu Val Thr Asp Glu Ile Val Lys Glu Phe Met Thr Pro Arg
        405                 410                 415 aag ctg tcc ttc gac ttt cag                                          1269
Lys Leu Ser Phe Asp Phe Gln
            420
```

<210> SEQ ID NO 47
<211> LENGTH: 1272
<212> TYPE: DNA
<213> ORGANISM: Artificial Sequence
<220> FEATURE:
<223> OTHER INFORMATION: Recombinant human Met-mini-TrpRS (GY variant) construct
<220> FEATURE:
<221> NAME/KEY: CDS
<222> LOCATION: (1)..(1272)
<220> FEATURE:
<221> NAME/KEY: modified_base
<222> LOCATION: (498)
<223> OTHER INFORMATION: a, t, c or g

<400> SEQUENCE: 47

```
atg agc tac aaa gct gcc gcg ggg gag gat tac aag gct gac tgt cct      48
Met Ser Tyr Lys Ala Ala Ala Gly Glu Asp Tyr Lys Ala Asp Cys Pro
1               5                   10                  15 cca ggg aac cca gca cct acc agt aat cat ggc cca gat gcc aca gaa      96
Pro Gly Asn Pro Ala Pro Thr Ser Asn His Gly Pro Asp Ala Thr Glu
            20                  25                  30 gct gaa gag gat ttt gtg gac cca tgg aca gta cag aca agc agt gca      144
Ala Glu Glu Asp Phe Val Asp Pro Trp Thr Val Gln Thr Ser Ser Ala
        35                  40                  45 aaa ggc ata gac tac gat aag ctc att gtt cgg ttt gga agt agt aaa      192
Lys Gly Ile Asp Tyr Asp Lys Leu Ile Val Arg Phe Gly Ser Ser Lys
50                  55                  60 att gac aaa gag cta ata aac cga ata gag aga gcc acc ggc caa aga      240
Ile Asp Lys Glu Leu Ile Asn Arg Ile Glu Arg Ala Thr Gly Gln Arg
65                  70                  75                  80 cca cac cac ttc ctg cgc aga ggc atc ttc ttc tca cac aga gat atg      288
Pro His His Phe Leu Arg Arg Gly Ile Phe Phe Ser His Arg Asp Met
                85                  90                  95 aat cag gtt ctt gat gcc tat gaa aat aag aag cca ttt tat ctg tac      336
Asn Gln Val Leu Asp Ala Tyr Glu Asn Lys Lys Pro Phe Tyr Leu Tyr
            100                 105                 110 acg ggc cgg ggc ccc tct tct gaa gca atg cat gta ggt cac ctc att      384
Thr Gly Arg Gly Pro Ser Ser Glu Ala Met His Val Gly His Leu Ile
        115                 120                 125 cca ttt att ttc aca aag tgg ctc cag gat gta ttt aac gtg ccc ttg      432
Pro Phe Ile Phe Thr Lys Trp Leu Gln Asp Val Phe Asn Val Pro Leu
130                 135                 140 gtc atc cag atg acg gat gac gag aag tat ctg tgg aag gac ctg acc      480
Val Ile Gln Met Thr Asp Asp Glu Lys Tyr Leu Trp Lys Asp Leu Thr
145                 150                 155                 160 ctg gac cag gcc tat ggn tay gct gtt gag aat gcc aag gac atc atc      528
Leu Asp Gln Ala Tyr Gly Tyr Ala Val Glu Asn Ala Lys Asp Ile Ile
```

```
                165                 170                 175
gcc tgt ggc ttt gac atc aac aag act ttc ata ttc tct gac ctg gac     576
Ala Cys Gly Phe Asp Ile Asn Lys Thr Phe Ile Phe Ser Asp Leu Asp
            180                 185                 190 tac atg ggg atg agc tca ggt ttc tac aaa aat gtg gtg aag att caa     624
Tyr Met Gly Met Ser Ser Gly Phe Tyr Lys Asn Val Val Lys Ile Gln
        195                 200                 205 aag cat gtt acc ttc aac caa gtg aaa ggc att ttc ggc ttc act gac     672
Lys His Val Thr Phe Asn Gln Val Lys Gly Ile Phe Gly Phe Thr Asp
    210                 215                 220 agc gac tgc att ggg aag atc agt ttt cct gcc atc cag gct gct ccc     720
Ser Asp Cys Ile Gly Lys Ile Ser Phe Pro Ala Ile Gln Ala Ala Pro
225                 230                 235                 240 tcc ttc agc aac tca ttc cca cag atc ttc cga gac agg acg gat atc     768
Ser Phe Ser Asn Ser Phe Pro Gln Ile Phe Arg Asp Arg Thr Asp Ile
                245                 250                 255 cag tgc ctt atc cca tgt gcc att gac cag gat cct tac ttt aga atg     816
Gln Cys Leu Ile Pro Cys Ala Ile Asp Gln Asp Pro Tyr Phe Arg Met
            260                 265                 270 aca agg gac gtc gcc ccc agg atc ggc tat cct aaa cca gcc ctg ttg     864
Thr Arg Asp Val Ala Pro Arg Ile Gly Tyr Pro Lys Pro Ala Leu Leu
        275                 280                 285 cac tcc acc ttc ttc cca gcc ctg cag ggc gcc cag acc aaa atg agt     912
His Ser Thr Phe Phe Pro Ala Leu Gln Gly Ala Gln Thr Lys Met Ser
    290                 295                 300 gcc agc gac cca aac tcc tcc atc ttc ctc acc gac acg gcc aag cag     960
Ala Ser Asp Pro Asn Ser Ser Ile Phe Leu Thr Asp Thr Ala Lys Gln
305                 310                 315                 320 atc aaa acc aag gtc aat aag cat gcg ttt tct gga ggg aga gac acc    1008
Ile Lys Thr Lys Val Asn Lys His Ala Phe Ser Gly Gly Arg Asp Thr
                325                 330                 335 atc gag gag cac agg cag ttt ggg ggc aac tgt gat gtg gac gtg tct    1056
Ile Glu Glu His Arg Gln Phe Gly Gly Asn Cys Asp Val Asp Val Ser
            340                 345                 350 ttc atg tac ctg acc ttc ttc ctc gag gac gac gac aag ctc gag cag    1104
Phe Met Tyr Leu Thr Phe Phe Leu Glu Asp Asp Asp Lys Leu Glu Gln
        355                 360                 365 atc agg aag gat tac acc agc gga gcc atg ctc acc ggt gag ctc aag    1152
Ile Arg Lys Asp Tyr Thr Ser Gly Ala Met Leu Thr Gly Glu Leu Lys
    370                 375                 380 aag gca ctc ata gag gtt ctg cag ccc ttg atc gca gag cac cag gcc    1200
Lys Ala Leu Ile Glu Val Leu Gln Pro Leu Ile Ala Glu His Gln Ala
385                 390                 395                 400 cgg cgc aag gag gtc acg gat gag ata gtg aaa gag ttc atg act ccc    1248
Arg Arg Lys Glu Val Thr Asp Glu Ile Val Lys Glu Phe Met Thr Pro
                405                 410                 415 cgg aag ctg tcc ttc gac ttt cag                                    1272
Arg Lys Leu Ser Phe Asp Phe Gln
            420

<210> SEQ ID NO 48
<211> LENGTH: 378
<212> TYPE: PRT
<213> ORGANISM: Artificial Sequence
<220> FEATURE:
<223> OTHER INFORMATION: Recombinant human T2 (SD variant) construct

<400> SEQUENCE: 48

Ser Ala Lys Gly Ile Asp Tyr Asp Lys Leu Ile Val Arg Phe Gly Ser
1               5                   10                  15

Ser Lys Ile Asp Lys Glu Leu Ile Asn Arg Ile Glu Arg Ala Thr Gly
```

```
                    20                  25                  30
Gln Arg Pro His His Phe Leu Arg Arg Gly Ile Phe Phe Ser His Arg
                35                  40                  45

Asp Met Asn Gln Val Leu Asp Ala Tyr Glu Asn Lys Lys Pro Phe Tyr
         50                  55                  60

Leu Tyr Thr Gly Arg Gly Pro Ser Ser Glu Ala Met His Val Gly His
 65                  70                  75                  80

Leu Ile Pro Phe Ile Phe Thr Lys Trp Leu Gln Asp Val Phe Asn Val
                 85                  90                  95

Pro Leu Val Ile Gln Met Thr Asp Asp Glu Lys Tyr Leu Trp Lys Asp
                100                 105                 110

Leu Thr Leu Asp Gln Ala Tyr Ser Asp Ala Val Glu Asn Ala Lys Asp
             115                 120                 125

Ile Ile Ala Cys Gly Phe Asp Ile Asn Lys Thr Phe Ile Phe Ser Asp
         130                 135                 140

Leu Asp Tyr Met Gly Met Ser Ser Gly Phe Tyr Lys Asn Val Val Lys
145                 150                 155                 160

Ile Gln Lys His Val Thr Phe Asn Gln Val Lys Gly Ile Phe Gly Phe
                165                 170                 175

Thr Asp Ser Asp Cys Ile Gly Lys Ile Ser Phe Pro Ala Ile Gln Ala
                180                 185                 190

Ala Pro Ser Phe Ser Asn Ser Phe Pro Gln Ile Phe Arg Asp Arg Thr
            195                 200                 205

Asp Ile Gln Cys Leu Ile Pro Cys Ala Ile Asp Gln Asp Pro Tyr Phe
        210                 215                 220

Arg Met Thr Arg Asp Val Ala Pro Arg Ile Gly Tyr Pro Lys Pro Ala
225                 230                 235                 240

Leu Leu His Ser Thr Phe Phe Pro Ala Leu Gln Gly Ala Gln Thr Lys
                245                 250                 255

Met Ser Ala Ser Asp Pro Asn Ser Ser Ile Phe Leu Thr Asp Thr Ala
            260                 265                 270

Lys Gln Ile Lys Thr Lys Val Asn Lys His Ala Phe Ser Gly Gly Arg
        275                 280                 285

Asp Thr Ile Glu Glu His Arg Gln Phe Gly Gly Asn Cys Asp Val Asp
    290                 295                 300

Val Ser Phe Met Tyr Leu Thr Phe Phe Leu Glu Asp Asp Lys Leu
305                 310                 315                 320

Glu Gln Ile Arg Lys Asp Tyr Thr Ser Gly Ala Met Leu Thr Gly Glu
                325                 330                 335

Leu Lys Lys Ala Leu Ile Glu Val Leu Gln Pro Leu Ile Ala Glu His
            340                 345                 350

Gln Ala Arg Arg Lys Glu Val Thr Asp Glu Ile Val Lys Glu Phe Met
        355                 360                 365

Thr Pro Arg Lys Leu Ser Phe Asp Phe Gln
    370                 375

<210> SEQ ID NO 49
<211> LENGTH: 401
<212> TYPE: PRT
<213> ORGANISM: Artificial Sequence
<220> FEATURE:
<223> OTHER INFORMATION: Recombinant human T1 (SD variant) construct

<400> SEQUENCE: 49

Ser Asn His Gly Pro Asp Ala Thr Glu Ala Glu Glu Asp Phe Val Asp
1               5                   10                  15
```

Pro Trp Thr Val Gln Thr Ser Ser Ala Lys Gly Ile Asp Tyr Asp Lys
             20                  25                  30

Leu Ile Val Arg Phe Gly Ser Ser Lys Ile Asp Lys Glu Leu Ile Asn
         35                  40                  45

Arg Ile Glu Arg Ala Thr Gly Gln Arg Pro His His Phe Leu Arg Arg
     50                  55                  60

Gly Ile Phe Phe Ser His Arg Asp Met Asn Gln Val Leu Asp Ala Tyr
65                  70                  75                  80

Glu Asn Lys Lys Pro Phe Tyr Leu Tyr Thr Gly Arg Gly Pro Ser Ser
                 85                  90                  95

Glu Ala Met His Val Gly His Leu Ile Pro Phe Ile Phe Thr Lys Trp
             100                 105                 110

Leu Gln Asp Val Phe Asn Val Pro Leu Val Ile Gln Met Thr Asp Asp
         115                 120                 125

Glu Lys Tyr Leu Trp Lys Asp Leu Thr Leu Asp Gln Ala Tyr Ser Asp
     130                 135                 140

Ala Val Glu Asn Ala Lys Asp Ile Ile Ala Cys Gly Phe Asp Ile Asn
145                 150                 155                 160

Lys Thr Phe Ile Phe Ser Asp Leu Asp Tyr Met Gly Met Ser Ser Gly
                 165                 170                 175

Phe Tyr Lys Asn Val Val Lys Ile Gln Lys His Val Thr Phe Asn Gln
             180                 185                 190

Val Lys Gly Ile Phe Gly Phe Thr Asp Ser Asp Cys Ile Gly Lys Ile
         195                 200                 205

Ser Phe Pro Ala Ile Gln Ala Ala Pro Ser Phe Ser Asn Ser Phe Pro
210                 215                 220

Gln Ile Phe Arg Asp Arg Thr Asp Ile Gln Cys Leu Ile Pro Cys Ala
225                 230                 235                 240

Ile Asp Gln Asp Pro Tyr Phe Arg Met Thr Arg Asp Val Ala Pro Arg
                 245                 250                 255

Ile Gly Tyr Pro Lys Pro Ala Leu Leu His Ser Thr Phe Phe Pro Ala
         260                 265                 270

Leu Gln Gly Ala Gln Thr Lys Met Ser Ala Ser Asp Pro Asn Ser Ser
     275                 280                 285

Ile Phe Leu Thr Asp Thr Ala Lys Gln Ile Lys Thr Lys Val Asn Lys
290                 295                 300

His Ala Phe Ser Gly Gly Arg Asp Thr Ile Glu Glu His Arg Gln Phe
305                 310                 315                 320

Gly Gly Asn Cys Asp Val Asp Val Ser Phe Met Tyr Leu Thr Phe Phe
                 325                 330                 335

Leu Glu Asp Asp Asp Lys Leu Glu Gln Ile Arg Lys Asp Tyr Thr Ser
             340                 345                 350

Gly Ala Met Leu Thr Gly Glu Leu Lys Lys Ala Leu Ile Glu Val Leu
         355                 360                 365

Gln Pro Leu Ile Ala Glu His Gln Ala Arg Arg Lys Glu Val Thr Asp
     370                 375                 380

Glu Ile Val Lys Glu Phe Met Thr Pro Arg Lys Leu Ser Phe Asp Phe
385                 390                 395                 400

Gln

<210> SEQ ID NO 50
<211> LENGTH: 423
<212> TYPE: PRT
<213> ORGANISM: Artificial Sequence
<220> FEATURE:
<223> OTHER INFORMATION: Recombinant human mini-TrpRS (SD variant) construct

<400> SEQUENCE: 50

```
Ser Tyr Lys Ala Ala Gly Glu Asp Tyr Lys Ala Asp Cys Pro Pro
1               5                   10                  15

Gly Asn Pro Ala Pro Thr Ser Asn His Gly Pro Asp Ala Thr Glu Ala
            20                  25                  30

Glu Glu Asp Phe Val Asp Pro Trp Thr Val Gln Thr Ser Ser Ala Lys
            35                  40                  45

Gly Ile Asp Tyr Asp Lys Leu Ile Val Arg Phe Gly Ser Ser Lys Ile
        50                  55                  60

Asp Lys Glu Leu Ile Asn Arg Ile Glu Arg Ala Thr Gly Gln Arg Pro
65                  70                  75                  80

His His Phe Leu Arg Arg Gly Ile Phe Phe Ser His Arg Asp Met Asn
                85                  90                  95

Gln Val Leu Asp Ala Tyr Glu Asn Lys Lys Pro Phe Tyr Leu Tyr Thr
            100                 105                 110

Gly Arg Gly Pro Ser Ser Glu Ala Met His Val Gly His Leu Ile Pro
        115                 120                 125

Phe Ile Phe Thr Lys Trp Leu Gln Asp Val Phe Asn Val Pro Leu Val
130                 135                 140

Ile Gln Met Thr Asp Asp Glu Lys Tyr Leu Trp Lys Asp Leu Thr Leu
145                 150                 155                 160

Asp Gln Ala Tyr Ser Asp Ala Val Glu Asn Ala Lys Asp Ile Ile Ala
                165                 170                 175

Cys Gly Phe Asp Ile Asn Lys Thr Phe Ile Phe Ser Asp Leu Asp Tyr
            180                 185                 190

Met Gly Met Ser Ser Gly Phe Tyr Lys Asn Val Val Lys Ile Gln Lys
        195                 200                 205

His Val Thr Phe Asn Gln Val Lys Gly Ile Phe Gly Phe Thr Asp Ser
210                 215                 220

Asp Cys Ile Gly Lys Ile Ser Phe Pro Ala Ile Gln Ala Ala Pro Ser
225                 230                 235                 240

Phe Ser Asn Ser Phe Pro Gln Ile Phe Arg Asp Arg Thr Asp Ile Gln
                245                 250                 255

Cys Leu Ile Pro Cys Ala Ile Asp Gln Asp Pro Tyr Phe Arg Met Thr
            260                 265                 270

Arg Asp Val Ala Pro Arg Ile Gly Tyr Pro Lys Pro Ala Leu Leu His
        275                 280                 285

Ser Thr Phe Phe Pro Ala Leu Gln Gly Ala Gln Thr Lys Met Ser Ala
290                 295                 300

Ser Asp Pro Asn Ser Ser Ile Phe Leu Thr Asp Thr Ala Lys Gln Ile
305                 310                 315                 320

Lys Thr Lys Val Asn Lys His Ala Phe Ser Gly Gly Arg Asp Thr Ile
                325                 330                 335

Glu Glu His Arg Gln Phe Gly Gly Asn Cys Asp Val Asp Val Ser Phe
            340                 345                 350

Met Tyr Leu Thr Phe Phe Leu Glu Asp Asp Lys Leu Glu Gln Ile
        355                 360                 365

Arg Lys Asp Tyr Thr Ser Gly Ala Met Leu Thr Gly Glu Leu Lys Lys
370                 375                 380

Ala Leu Ile Glu Val Leu Gln Pro Leu Ile Ala Glu His Gln Ala Arg
385                 390                 395                 400
```

Arg Lys Glu Val Thr Asp Glu Ile Val Lys Glu Phe Met Thr Pro Arg
            405                 410                 415

Lys Leu Ser Phe Asp Phe Gln
            420

<210> SEQ ID NO 51
<211> LENGTH: 379
<212> TYPE: PRT
<213> ORGANISM: Artificial Sequence
<220> FEATURE:
<223> OTHER INFORMATION: Recombinant human Met-T2 (SD variant) construct

<400> SEQUENCE: 51

Met Ser Ala Lys Gly Ile Asp Tyr Asp Lys Leu Ile Val Arg Phe Gly
1               5                   10                  15

Ser Ser Lys Ile Asp Lys Glu Leu Ile Asn Arg Ile Glu Arg Ala Thr
            20                  25                  30

Gly Gln Arg Pro His His Phe Leu Arg Arg Gly Ile Phe Phe Ser His
            35                  40                  45

Arg Asp Met Asn Gln Val Leu Asp Ala Tyr Glu Asn Lys Lys Pro Phe
50                  55                  60

Tyr Leu Tyr Thr Gly Arg Gly Pro Ser Ser Glu Ala Met His Val Gly
65                  70                  75                  80

His Leu Ile Pro Phe Ile Phe Thr Lys Trp Leu Gln Asp Val Phe Asn
                85                  90                  95

Val Pro Leu Val Ile Gln Met Thr Asp Asp Glu Lys Tyr Leu Trp Lys
            100                 105                 110

Asp Leu Thr Leu Asp Gln Ala Tyr Ser Asp Ala Val Glu Asn Ala Lys
            115                 120                 125

Asp Ile Ile Ala Cys Gly Phe Asp Ile Asn Lys Thr Phe Ile Phe Ser
            130                 135                 140

Asp Leu Asp Tyr Met Gly Met Ser Ser Gly Phe Tyr Lys Asn Val Val
145                 150                 155                 160

Lys Ile Gln Lys His Val Thr Phe Asn Gln Val Lys Gly Ile Phe Gly
                165                 170                 175

Phe Thr Asp Ser Asp Cys Ile Gly Lys Ile Ser Phe Pro Ala Ile Gln
            180                 185                 190

Ala Ala Pro Ser Phe Ser Asn Ser Phe Pro Gln Ile Phe Arg Asp Arg
            195                 200                 205

Thr Asp Ile Gln Cys Leu Ile Pro Cys Ala Ile Asp Gln Asp Pro Tyr
            210                 215                 220

Phe Arg Met Thr Arg Asp Val Ala Pro Arg Ile Gly Tyr Pro Lys Pro
225                 230                 235                 240

Ala Leu Leu His Ser Thr Phe Phe Pro Ala Leu Gln Gly Ala Gln Thr
                245                 250                 255

Lys Met Ser Ala Ser Asp Pro Asn Ser Ser Ile Phe Leu Thr Asp Thr
            260                 265                 270

Ala Lys Gln Ile Lys Thr Lys Val Asn Lys His Ala Phe Ser Gly Gly
            275                 280                 285

Arg Asp Thr Ile Glu Glu His Arg Gln Phe Gly Gly Asn Cys Asp Val
            290                 295                 300

Asp Val Ser Phe Met Tyr Leu Thr Phe Phe Leu Glu Asp Asp Asp Lys
305                 310                 315                 320

Leu Glu Gln Ile Arg Lys Asp Tyr Thr Ser Gly Ala Met Leu Thr Gly
                325                 330                 335

```
Glu Leu Lys Lys Ala Leu Ile Glu Val Leu Gln Pro Leu Ile Ala Glu
            340                 345                 350

His Gln Ala Arg Arg Lys Glu Val Thr Asp Glu Ile Val Lys Glu Phe
            355                 360                 365

Met Thr Pro Arg Lys Leu Ser Phe Asp Phe Gln
    370                 375

<210> SEQ ID NO 52
<211> LENGTH: 402
<212> TYPE: PRT
<213> ORGANISM: Artificial Sequence
<220> FEATURE:
<223> OTHER INFORMATION: Recombinant human Met-T1 (SD variant) construct

<400> SEQUENCE: 52

Met Ser Asn His Gly Pro Asp Ala Thr Glu Ala Glu Glu Asp Phe Val
1               5                   10                  15

Asp Pro Trp Thr Val Gln Thr Ser Ser Ala Lys Gly Ile Asp Tyr Asp
            20                  25                  30

Lys Leu Ile Val Arg Phe Gly Ser Ser Lys Ile Asp Lys Glu Leu Ile
            35                  40                  45

Asn Arg Ile Glu Arg Ala Thr Gly Gln Arg Pro His His Phe Leu Arg
        50                  55                  60

Arg Gly Ile Phe Phe Ser His Arg Asp Met Asn Gln Val Leu Asp Ala
65                  70                  75                  80

Tyr Glu Asn Lys Lys Pro Phe Tyr Leu Tyr Thr Gly Arg Gly Pro Ser
                85                  90                  95

Ser Glu Ala Met His Val Gly His Leu Ile Pro Phe Ile Phe Thr Lys
            100                 105                 110

Trp Leu Gln Asp Val Phe Asn Val Pro Leu Val Ile Gln Met Thr Asp
            115                 120                 125

Asp Glu Lys Tyr Leu Trp Lys Asp Leu Thr Leu Asp Gln Ala Tyr Ser
        130                 135                 140

Asp Ala Val Glu Asn Ala Lys Asp Ile Ile Ala Cys Gly Phe Asp Ile
145                 150                 155                 160

Asn Lys Thr Phe Ile Phe Ser Asp Leu Asp Tyr Met Gly Met Ser Ser
                165                 170                 175

Gly Phe Tyr Lys Asn Val Val Lys Ile Gln Lys His Val Thr Phe Asn
            180                 185                 190

Gln Val Lys Gly Ile Phe Gly Phe Thr Asp Ser Asp Cys Ile Gly Lys
            195                 200                 205

Ile Ser Phe Pro Ala Ile Gln Ala Ala Pro Ser Phe Ser Asn Ser Phe
        210                 215                 220

Pro Gln Ile Phe Arg Asp Arg Thr Asp Ile Gln Cys Leu Ile Pro Cys
225                 230                 235                 240

Ala Ile Asp Gln Asp Pro Tyr Phe Arg Met Thr Arg Asp Val Ala Pro
                245                 250                 255

Arg Ile Gly Tyr Pro Lys Pro Ala Leu Leu His Ser Thr Phe Phe Pro
            260                 265                 270

Ala Leu Gln Gly Ala Gln Thr Lys Met Ser Ala Ser Asp Pro Asn Ser
            275                 280                 285

Ser Ile Phe Leu Thr Asp Thr Ala Lys Gln Ile Lys Thr Lys Val Asn
        290                 295                 300

Lys His Ala Phe Ser Gly Gly Arg Asp Thr Ile Glu Glu His Arg Gln
305                 310                 315                 320

Phe Gly Gly Asn Cys Asp Val Asp Val Ser Phe Met Tyr Leu Thr Phe
```

```
                325                 330                 335
Phe Leu Glu Asp Asp Lys Leu Glu Gln Ile Arg Lys Asp Tyr Thr
            340                 345                 350
Ser Gly Ala Met Leu Thr Gly Glu Leu Lys Lys Ala Leu Ile Glu Val
            355                 360                 365
Leu Gln Pro Leu Ile Ala Glu His Gln Ala Arg Arg Lys Glu Val Thr
            370                 375                 380
Asp Glu Ile Val Lys Glu Phe Met Thr Pro Arg Lys Leu Ser Phe Asp
385                 390                 395                 400
Phe Gln

<210> SEQ ID NO 53
<211> LENGTH: 424
<212> TYPE: PRT
<213> ORGANISM: Artificial Sequence
<220> FEATURE:
<223> OTHER INFORMATION: Recombinant human Met-mini-TrpRS (SD variant)
      construct

<400> SEQUENCE: 53

Met Ser Tyr Lys Ala Ala Gly Glu Asp Tyr Lys Ala Asp Cys Pro
1               5                   10                  15
Pro Gly Asn Pro Ala Pro Thr Ser Asn His Gly Pro Asp Ala Thr Glu
            20                  25                  30
Ala Glu Glu Asp Phe Val Asp Pro Trp Thr Val Gln Thr Ser Ser Ala
            35                  40                  45
Lys Gly Ile Asp Tyr Asp Lys Leu Ile Val Arg Phe Gly Ser Ser Lys
            50                  55                  60
Ile Asp Lys Glu Leu Ile Asn Arg Ile Glu Arg Ala Thr Gly Gln Arg
65                  70                  75                  80
Pro His His Phe Leu Arg Arg Gly Ile Phe Phe Ser His Arg Asp Met
                85                  90                  95
Asn Gln Val Leu Asp Ala Tyr Glu Asn Lys Lys Pro Phe Tyr Leu Tyr
            100                 105                 110
Thr Gly Arg Gly Pro Ser Ser Glu Ala Met His Val Gly His Leu Ile
            115                 120                 125
Pro Phe Ile Phe Thr Lys Trp Leu Gln Asp Val Phe Asn Val Pro Leu
        130                 135                 140
Val Ile Gln Met Thr Asp Asp Glu Lys Tyr Leu Trp Lys Asp Leu Thr
145                 150                 155                 160
Leu Asp Gln Ala Tyr Ser Asp Ala Val Glu Asn Ala Lys Asp Ile Ile
                165                 170                 175
Ala Cys Gly Phe Asp Ile Asn Lys Thr Phe Ile Phe Ser Asp Leu Asp
            180                 185                 190
Tyr Met Gly Met Ser Ser Gly Phe Tyr Lys Asn Val Val Lys Ile Gln
            195                 200                 205
Lys His Val Thr Phe Asn Gln Val Lys Gly Ile Phe Gly Phe Thr Asp
        210                 215                 220
Ser Asp Cys Ile Gly Lys Ile Ser Phe Pro Ala Ile Gln Ala Ala Pro
225                 230                 235                 240
Ser Phe Ser Asn Ser Phe Pro Gln Ile Phe Arg Asp Arg Thr Asp Ile
                245                 250                 255
Gln Cys Leu Ile Pro Cys Ala Ile Asp Gln Asp Pro Tyr Phe Arg Met
            260                 265                 270
Thr Arg Asp Val Ala Pro Arg Ile Gly Tyr Pro Lys Pro Ala Leu Leu
            275                 280                 285
```

```
His Ser Thr Phe Phe Pro Ala Leu Gln Gly Ala Gln Thr Lys Met Ser
    290                 295                 300

Ala Ser Asp Pro Asn Ser Ser Ile Phe Leu Thr Asp Thr Ala Lys Gln
305                 310                 315                 320

Ile Lys Thr Lys Val Asn Lys His Ala Phe Ser Gly Gly Arg Asp Thr
                325                 330                 335

Ile Glu His Arg Gln Phe Gly Gly Asn Cys Asp Val Asp Val Ser
            340                 345                 350

Phe Met Tyr Leu Thr Phe Phe Leu Glu Asp Asp Lys Leu Glu Gln
        355                 360                 365

Ile Arg Lys Asp Tyr Thr Ser Gly Ala Met Leu Thr Gly Glu Leu Lys
370                 375                 380

Lys Ala Leu Ile Glu Val Leu Gln Pro Leu Ile Ala Glu His Gln Ala
385                 390                 395                 400

Arg Arg Lys Glu Val Thr Asp Glu Ile Val Lys Glu Phe Met Thr Pro
                405                 410                 415

Arg Lys Leu Ser Phe Asp Phe Gln
            420
```

```
<210> SEQ ID NO 54
<211> LENGTH: 1134
<212> TYPE: DNA
<213> ORGANISM: Artificial Sequence
<220> FEATURE:
<223> OTHER INFORMATION: Recombinant human T2 (SD variant) construct
<220> FEATURE:
<221> NAME/KEY: CDS
<222> LOCATION: (1)..(1134)
<220> FEATURE:
<221> NAME/KEY: misc_feature
<222> LOCATION: (358)..(360)
<223> OTHER INFORMATION: nnn is agy, tcy or tcr

<400> SEQUENCE: 54
```

```
agt gca aaa ggc ata gac tac gat aag ctc att gtt cgg ttt gga agt    48
Ser Ala Lys Gly Ile Asp Tyr Asp Lys Leu Ile Val Arg Phe Gly Ser
  1               5                  10                  15 agt aaa att gac aaa gag cta ata aac cga ata gag aga gcc acc ggc    96
Ser Lys Ile Asp Lys Glu Leu Ile Asn Arg Ile Glu Arg Ala Thr Gly
             20                  25                  30 caa aga cca cac cac ttc ctg cgc aga ggc atc ttc ttc tca cac aga   144
Gln Arg Pro His His Phe Leu Arg Arg Gly Ile Phe Phe Ser His Arg
         35                  40                  45 gat atg aat cag gtt ctt gat gcc tat gaa aat aag aag cca ttt tat   192
Asp Met Asn Gln Val Leu Asp Ala Tyr Glu Asn Lys Lys Pro Phe Tyr
     50                  55                  60 ctg tac acg ggc cgg ggc ccc tct tct gaa gca atg cat gta ggt cac   240
Leu Tyr Thr Gly Arg Gly Pro Ser Ser Glu Ala Met His Val Gly His
 65                  70                  75                  80 ctc att cca ttt att ttc aca aag tgg ctc cag gat gta ttt aac gtg   288
Leu Ile Pro Phe Ile Phe Thr Lys Trp Leu Gln Asp Val Phe Asn Val
                 85                  90                  95 ccc ttg gtc atc cag atg acg gat gac gag aag tat ctg tgg aag gac   336
Pro Leu Val Ile Gln Met Thr Asp Asp Glu Lys Tyr Leu Trp Lys Asp
            100                 105                 110 ctg acc ctg gac cag gcc tat nnn gay gct gtt gag aat gcc aag gac   384
Leu Thr Leu Asp Gln Ala Tyr Ser Asp Ala Val Glu Asn Ala Lys Asp
        115                 120                 125 atc atc gcc tgt ggc ttt gac atc aac aag act ttc ata ttc tct gac   432
Ile Ile Ala Cys Gly Phe Asp Ile Asn Lys Thr Phe Ile Phe Ser Asp
    130                 135                 140
```

```
ctg gac tac atg ggg atg agc tca ggt ttc tac aaa aat gtg gtg aag    480
Leu Asp Tyr Met Gly Met Ser Ser Gly Phe Tyr Lys Asn Val Val Lys
145                 150                 155                 160 att caa aag cat gtt acc ttc aac caa gtg aaa ggc att ttc ggc ttc    528
Ile Gln Lys His Val Thr Phe Asn Gln Val Lys Gly Ile Phe Gly Phe
                165                 170                 175 act gac agc gac tgc att ggg aag atc agt ttt cct gcc atc cag gct    576
Thr Asp Ser Asp Cys Ile Gly Lys Ile Ser Phe Pro Ala Ile Gln Ala
            180                 185                 190 gct ccc tcc ttc agc aac tca ttc cca cag atc ttc cga gac agg acg    624
Ala Pro Ser Phe Ser Asn Ser Phe Pro Gln Ile Phe Arg Asp Arg Thr
        195                 200                 205 gat atc cag tgc ctt atc cca tgt gcc att gac cag gat cct tac ttt    672
Asp Ile Gln Cys Leu Ile Pro Cys Ala Ile Asp Gln Asp Pro Tyr Phe
    210                 215                 220 aga atg aca agg gac gtc gcc ccc agg atc ggc tat cct aaa cca gcc    720
Arg Met Thr Arg Asp Val Ala Pro Arg Ile Gly Tyr Pro Lys Pro Ala
225                 230                 235                 240 ctg ttg cac tcc acc ttc ttc cca gcc ctg cag ggc gcc cag acc aaa    768
Leu Leu His Ser Thr Phe Phe Pro Ala Leu Gln Gly Ala Gln Thr Lys
                245                 250                 255 atg agt gcc agc gac cca aac tcc tcc atc ttc ctc acc gac acg gcc    816
Met Ser Ala Ser Asp Pro Asn Ser Ser Ile Phe Leu Thr Asp Thr Ala
            260                 265                 270 aag cag atc aaa acc aag gtc aat aag cat gcg ttt tct gga ggg aga    864
Lys Gln Ile Lys Thr Lys Val Asn Lys His Ala Phe Ser Gly Gly Arg
        275                 280                 285 gac acc atc gag gag cac agg cag ttt ggg ggc aac tgt gat gtg gac    912
Asp Thr Ile Glu Glu His Arg Gln Phe Gly Gly Asn Cys Asp Val Asp
    290                 295                 300 gtg tct ttc atg tac ctg acc ttc ttc ctc gag gac gac gac aag ctc    960
Val Ser Phe Met Tyr Leu Thr Phe Phe Leu Glu Asp Asp Asp Lys Leu
305                 310                 315                 320 gag cag atc agg aag gat tac acc agc gga gcc atg ctc acc ggt gag   1008
Glu Gln Ile Arg Lys Asp Tyr Thr Ser Gly Ala Met Leu Thr Gly Glu
                325                 330                 335 ctc aag aag gca ctc ata gag gtt ctg cag ccc ttg atc gca gag cac   1056
Leu Lys Lys Ala Leu Ile Glu Val Leu Gln Pro Leu Ile Ala Glu His
            340                 345                 350 cag gcc cgg cgc aag gag gtc acg gat gag ata gtg aaa gag ttc atg   1104
Gln Ala Arg Arg Lys Glu Val Thr Asp Glu Ile Val Lys Glu Phe Met
        355                 360                 365 act ccc cgg aag ctg tcc ttc gac ttt cag                           1134
Thr Pro Arg Lys Leu Ser Phe Asp Phe Gln
    370                 375
```

<210> SEQ ID NO 55
<211> LENGTH: 1137
<212> TYPE: DNA
<213> ORGANISM: Artificial Sequence
<220> FEATURE:
<223> OTHER INFORMATION: Recombinant human Met-T2 (SD variant) construct
<220> FEATURE:
<221> NAME/KEY: CDS
<222> LOCATION: (1)..(1137)
<220> FEATURE:
<221> NAME/KEY: misc_feature
<222> LOCATION: (361)..(363)
<223> OTHER INFORMATION: nnn is agy, tcy or tcr

<400> SEQUENCE: 55

```
atg agt gca aaa ggc ata gac tac gat aag ctc att gtt cgg ttt gga     48
Met Ser Ala Lys Gly Ile Asp Tyr Asp Lys Leu Ile Val Arg Phe Gly
```

```
              1               5              10              15
agt agt aaa att gac aaa gag cta ata aac cga ata gag aga gcc acc        96
Ser Ser Lys Ile Asp Lys Glu Leu Ile Asn Arg Ile Glu Arg Ala Thr
             20              25              30 ggc caa aga cca cac cac ttc ctg cgc aga ggc atc ttc ttc tca cac       144
Gly Gln Arg Pro His His Phe Leu Arg Arg Gly Ile Phe Phe Ser His
         35              40              45 aga gat atg aat cag gtt ctt gat gcc tat gaa aat aag aag cca ttt       192
Arg Asp Met Asn Gln Val Leu Asp Ala Tyr Glu Asn Lys Lys Pro Phe
     50              55              60 tat ctg tac acg ggc cgg ggc ccc tct tct gaa gca atg cat gta ggt       240
Tyr Leu Tyr Thr Gly Arg Gly Pro Ser Ser Glu Ala Met His Val Gly
 65              70              75              80 cac ctc att cca ttt att ttc aca aag tgg ctc cag gat gta ttt aac       288
His Leu Ile Pro Phe Ile Phe Thr Lys Trp Leu Gln Asp Val Phe Asn
             85              90              95 gtg ccc ttg gtc atc cag atg acg gat gac gag aag tat ctg tgg aag       336
Val Pro Leu Val Ile Gln Met Thr Asp Asp Glu Lys Tyr Leu Trp Lys
        100             105             110 gac ctg acc ctg gac cag gcc tat nnn gay gct gtt gag aat gcc aag       384
Asp Leu Thr Leu Asp Gln Ala Tyr Ser Asp Ala Val Glu Asn Ala Lys
    115             120             125 gac atc atc gcc tgt ggc ttt gac atc aac aag act ttc ata ttc tct       432
Asp Ile Ile Ala Cys Gly Phe Asp Ile Asn Lys Thr Phe Ile Phe Ser
130             135             140 gac ctg gac tac atg ggg atg agc tca ggt ttc tac aaa aat gtg gtg       480
Asp Leu Asp Tyr Met Gly Met Ser Ser Gly Phe Tyr Lys Asn Val Val
145             150             155             160 aag att caa aag cat gtt acc ttc aac caa gtg aaa ggc att ttc ggc       528
Lys Ile Gln Lys His Val Thr Phe Asn Gln Val Lys Gly Ile Phe Gly
            165             170             175 ttc act gac agc gac tgc att ggg aag atc agt ttt cct gcc atc cag       576
Phe Thr Asp Ser Asp Cys Ile Gly Lys Ile Ser Phe Pro Ala Ile Gln
        180             185             190 gct gct ccc tcc ttc agc aac tca ttc cca cag atc ttc cga gac agg       624
Ala Ala Pro Ser Phe Ser Asn Ser Phe Pro Gln Ile Phe Arg Asp Arg
    195             200             205 acg gat atc cag tgc ctt atc cca tgt gcc att gac cag gat cct tac       672
Thr Asp Ile Gln Cys Leu Ile Pro Cys Ala Ile Asp Gln Asp Pro Tyr
210             215             220 ttt aga atg aca agg gac gtc gcc ccc agg atc ggt tat cct aaa cca       720
Phe Arg Met Thr Arg Asp Val Ala Pro Arg Ile Gly Tyr Pro Lys Pro
225             230             235             240 gcc ctg ttg cac tcc acc ttc ttc cca gcc ctg cag ggc gcc cag acc       768
Ala Leu Leu His Ser Thr Phe Phe Pro Ala Leu Gln Gly Ala Gln Thr
            245             250             255 aaa atg agt gcc agc gac cca aac tcc tcc atc ttc ctc acc gac acg       816
Lys Met Ser Ala Ser Asp Pro Asn Ser Ser Ile Phe Leu Thr Asp Thr
        260             265             270 gcc aag cag atc aaa acc aag gtc aat aag cat gcg ttt tct gga ggg       864
Ala Lys Gln Ile Lys Thr Lys Val Asn Lys His Ala Phe Ser Gly Gly
    275             280             285 aga gac acc atc gag gag cac agg cag ttt ggg ggc aac tgt gat gtg       912
Arg Asp Thr Ile Glu Glu His Arg Gln Phe Gly Gly Asn Cys Asp Val
290             295             300 gac gtg tct ttc atg tac ctg acc ttc ttc ctc gag gac gac gac aag       960
Asp Val Ser Phe Met Tyr Leu Thr Phe Phe Leu Glu Asp Asp Asp Lys
305             310             315             320 ctc gag cag atc agg aag gat tac acc agc gga gcc atg ctc acc ggt      1008
Leu Glu Gln Ile Arg Lys Asp Tyr Thr Ser Gly Ala Met Leu Thr Gly
```

```
                    325                 330                 335
gag ctc aag aag gca ctc ata gag gtt ctg cag ccc ttg atc gca gag      1056
Glu Leu Lys Lys Ala Leu Ile Glu Val Leu Gln Pro Leu Ile Ala Glu
        340                 345                 350 cac cag gcc cgg cgc aag gag gtc acg gat gag ata gtg aaa gag ttc      1104
His Gln Ala Arg Arg Lys Glu Val Thr Asp Glu Ile Val Lys Glu Phe
            355                 360                 365 atg act ccc cgg aag ctg tcc ttc gac ttt cag                          1137
Met Thr Pro Arg Lys Leu Ser Phe Asp Phe Gln
        370                 375

<210> SEQ ID NO 56
<211> LENGTH: 1203
<212> TYPE: DNA
<213> ORGANISM: Artificial Sequence
<220> FEATURE:
<223> OTHER INFORMATION: Recombinant human T1 (SD variant) construct
<220> FEATURE:
<221> NAME/KEY: CDS
<222> LOCATION: (1)..(1203)
<220> FEATURE:
<221> NAME/KEY: misc_feature
<222> LOCATION: (427)..(429)
<223> OTHER INFORMATION: nnn is agy, tcy or tcr

<400> SEQUENCE: 56 agt aat cat ggc cca gat gcc aca gaa gct gaa gag gat ttt gtg gac       48
Ser Asn His Gly Pro Asp Ala Thr Glu Ala Glu Glu Asp Phe Val Asp
  1               5                  10                  15 cca tgg aca gta cag aca agc agt gca aaa ggc ata gac tac gat aag       96
Pro Trp Thr Val Gln Thr Ser Ser Ala Lys Gly Ile Asp Tyr Asp Lys
             20                  25                  30 ctc att gtt cgg ttt gga agt agt aaa att gac aaa gag cta ata aac      144
Leu Ile Val Arg Phe Gly Ser Ser Lys Ile Asp Lys Glu Leu Ile Asn
         35                  40                  45 cga ata gag aga gcc acc ggc caa aga cca cac cac ttc ctg cgc aga      192
Arg Ile Glu Arg Ala Thr Gly Gln Arg Pro His His Phe Leu Arg Arg
     50                  55                  60 ggc atc ttc ttc tca cac aga gat atg aat cag gtt ctt gat gcc tat      240
Gly Ile Phe Phe Ser His Arg Asp Met Asn Gln Val Leu Asp Ala Tyr
 65                  70                  75                  80 gaa aat aag aag cca ttt tat ctg tac acg ggc cgg ggc ccc tct tct      288
Glu Asn Lys Lys Pro Phe Tyr Leu Tyr Thr Gly Arg Gly Pro Ser Ser
                 85                  90                  95 gaa gca atg cat gta ggt cac ctc att cca ttt att ttc aca aag tgg      336
Glu Ala Met His Val Gly His Leu Ile Pro Phe Ile Phe Thr Lys Trp
            100                 105                 110 ctc cag gat gta ttt aac gtg ccc ttg gtc atc cag atg acg gat gac      384
Leu Gln Asp Val Phe Asn Val Pro Leu Val Ile Gln Met Thr Asp Asp
        115                 120                 125 gag aag tat ctg tgg aag gac ctg acc ctg gac cag gcc tat nnn gay      432
Glu Lys Tyr Leu Trp Lys Asp Leu Thr Leu Asp Gln Ala Tyr Ser Asp
    130                 135                 140 gct gtt gag aat gcc aag gac atc atc gcc tgt ggc ttt gac atc aac      480
Ala Val Glu Asn Ala Lys Asp Ile Ile Ala Cys Gly Phe Asp Ile Asn
145                 150                 155                 160 aag act ttc ata ttc tct gac ctg gac tac atg ggg atg agc tca ggt      528
Lys Thr Phe Ile Phe Ser Asp Leu Asp Tyr Met Gly Met Ser Ser Gly
                165                 170                 175 ttc tac aaa aat gtg gtg aag att caa aag cat gtt acc ttc aac caa      576
Phe Tyr Lys Asn Val Val Lys Ile Gln Lys His Val Thr Phe Asn Gln
            180                 185                 190 gtg aaa ggc att ttc ggc ttc act gac agc gac tgc att ggg aag atc      624
```

```
                  Val Lys Gly Ile Phe Gly Phe Thr Asp Ser Asp Cys Ile Gly Lys Ile
                          195                 200                 205 agt ttt cct gcc atc cag gct gct ccc tcc ttc agc aac tca ttc cca         672
Ser Phe Pro Ala Ile Gln Ala Ala Pro Ser Phe Ser Asn Ser Phe Pro
    210                 215                 220 cag atc ttc cga gac agg acg gat atc cag tgc ctt atc cca tgt gcc         720
Gln Ile Phe Arg Asp Arg Thr Asp Ile Gln Cys Leu Ile Pro Cys Ala
225                 230                 235                 240 att gac cag gat cct tac ttt aga atg aca agg gac gtc gcc ccc agg         768
Ile Asp Gln Asp Pro Tyr Phe Arg Met Thr Arg Asp Val Ala Pro Arg
                245                 250                 255 atc ggc tat cct aaa cca gcc ctg ttg cac tcc acc ttc ttc cca gcc         816
Ile Gly Tyr Pro Lys Pro Ala Leu Leu His Ser Thr Phe Phe Pro Ala
            260                 265                 270 ctg cag ggc gcc cag acc aaa atg agt gcc agc gac cca aac tcc tcc         864
Leu Gln Gly Ala Gln Thr Lys Met Ser Ala Ser Asp Pro Asn Ser Ser
        275                 280                 285 atc ttc ctc acc gac acg gcc aag cag atc aaa acc aag gtc aat aag         912
Ile Phe Leu Thr Asp Thr Ala Lys Gln Ile Lys Thr Lys Val Asn Lys
    290                 295                 300 cat gcg ttt tct gga ggg aga gac acc atc gag gag cac agg cag ttt         960
His Ala Phe Ser Gly Gly Arg Asp Thr Ile Glu Glu His Arg Gln Phe
305                 310                 315                 320 ggg ggc aac tgt gat gtg gac gtg tct ttc atg tac ctg acc ttc ttc        1008
Gly Gly Asn Cys Asp Val Asp Val Ser Phe Met Tyr Leu Thr Phe Phe
                325                 330                 335 ctc gag gac gac gac aag ctc gag cag atc agg aag gat tac acc agc        1056
Leu Glu Asp Asp Asp Lys Leu Glu Gln Ile Arg Lys Asp Tyr Thr Ser
            340                 345                 350 gga gcc atg ctc acc ggt gag ctc aag aag gca ctc ata gag gtt ctg        1104
Gly Ala Met Leu Thr Gly Glu Leu Lys Lys Ala Leu Ile Glu Val Leu
        355                 360                 365 cag ccc ttg atc gca gag cac cag gcc cgg cgc aag gag gtc acg gat        1152
Gln Pro Leu Ile Ala Glu His Gln Ala Arg Arg Lys Glu Val Thr Asp
    370                 375                 380 gag ata gtg aaa gag ttc atg act ccc cgg aag ctg tcc ttc gac ttt        1200
Glu Ile Val Lys Glu Phe Met Thr Pro Arg Lys Leu Ser Phe Asp Phe
385                 390                 395                 400 cag                                                                    1203
Gln

<210> SEQ ID NO 57
<211> LENGTH: 1206
<212> TYPE: DNA
<213> ORGANISM: Artificial Sequence
<220> FEATURE:
<223> OTHER INFORMATION: Recombinant human Met-T1 (SD variant) construct
<220> FEATURE:
<221> NAME/KEY: CDS
<222> LOCATION: (1)..(1206)
<220> FEATURE:
<221> NAME/KEY: misc_feature
<222> LOCATION: (430)..(432)
<223> OTHER INFORMATION: nnn is agy, tcy or tcr

<400> SEQUENCE: 57 atg agt aat cat ggc cca gat gcc aca gaa gct gaa gag gat ttt gtg          48
Met Ser Asn His Gly Pro Asp Ala Thr Glu Ala Glu Glu Asp Phe Val
1               5                   10                  15 gac cca tgg aca gta cag aca agc agt gca aaa ggc ata gac tac gat          96
Asp Pro Trp Thr Val Gln Thr Ser Ser Ala Lys Gly Ile Asp Tyr Asp
                20                  25                  30 aag ctc att gtt cgg ttt gga agt agt aaa att gac aaa gag cta ata         144
```

-continued

```
                Lys Leu Ile Val Arg Phe Gly Ser Ser Lys Ile Asp Lys Glu Leu Ile
                             35                  40                  45 aac cga ata gag aga gcc acc ggc caa aga cca cac cac ttc ctg cgc          192
Asn Arg Ile Glu Arg Ala Thr Gly Gln Arg Pro His His Phe Leu Arg
         50                  55                  60 aga ggc atc ttc ttc tca cac aga gat atg aat cag gtt ctt gat gcc          240
Arg Gly Ile Phe Phe Ser His Arg Asp Met Asn Gln Val Leu Asp Ala
 65                  70                  75                  80 tat gaa aat aag aag cca ttt tat ctg tac acg ggc cgg ggc ccc tct          288
Tyr Glu Asn Lys Lys Pro Phe Tyr Leu Tyr Thr Gly Arg Gly Pro Ser
                 85                  90                  95 tct gaa gca atg cat gta ggt cac ctc att cca ttt att ttc aca aag          336
Ser Glu Ala Met His Val Gly His Leu Ile Pro Phe Ile Phe Thr Lys
            100                 105                 110 tgg ctc cag gat gta ttt aac gtg ccc ttg gtc atc cag atg acg gat          384
Trp Leu Gln Asp Val Phe Asn Val Pro Leu Val Ile Gln Met Thr Asp
        115                 120                 125 gac gag aag tat ctg tgg aag gac ctg acc ctg gac cag gcc tat nnn          432
Asp Glu Lys Tyr Leu Trp Lys Asp Leu Thr Leu Asp Gln Ala Tyr Ser
130                 135                 140 gay gct gtt gag aat gcc aag gac atc atc gcc tgt ggc ttt gac atc          480
Asp Ala Val Glu Asn Ala Lys Asp Ile Ile Ala Cys Gly Phe Asp Ile
145                 150                 155                 160 aac aag act ttc ata ttc tct gac ctg gac tac atg ggg atg agc tca          528
Asn Lys Thr Phe Ile Phe Ser Asp Leu Asp Tyr Met Gly Met Ser Ser
                165                 170                 175 ggt ttc tac aaa aat gtg gtg aag att caa aag cat gtt acc ttc aac          576
Gly Phe Tyr Lys Asn Val Val Lys Ile Gln Lys His Val Thr Phe Asn
            180                 185                 190 caa gtg aaa ggc att ttc ggc ttc act gac agc gac tgc att ggg aag          624
Gln Val Lys Gly Ile Phe Gly Phe Thr Asp Ser Asp Cys Ile Gly Lys
        195                 200                 205 atc agt ttt cct gcc atc cag gct gct ccc tcc ttc agc aac tca ttc          672
Ile Ser Phe Pro Ala Ile Gln Ala Ala Pro Ser Phe Ser Asn Ser Phe
    210                 215                 220 cca cag atc ttc cga gac agg acg gat atc cag tgc ctt atc cca tgt          720
Pro Gln Ile Phe Arg Asp Arg Thr Asp Ile Gln Cys Leu Ile Pro Cys
225                 230                 235                 240 gcc att gac cag gat cct tac ttt aga atg aca agg gac gtc gcc ccc          768
Ala Ile Asp Gln Asp Pro Tyr Phe Arg Met Thr Arg Asp Val Ala Pro
                245                 250                 255 agg atc ggc tat cct aaa cca gcc ctg ttg cac tcc acc ttc ttc cca          816
Arg Ile Gly Tyr Pro Lys Pro Ala Leu Leu His Ser Thr Phe Phe Pro
            260                 265                 270 gcc ctg cag ggc gcc cag acc aaa atg agt gcc agc gac cca aac tcc          864
Ala Leu Gln Gly Ala Gln Thr Lys Met Ser Ala Ser Asp Pro Asn Ser
        275                 280                 285 tcc atc ttc ctc acc gac acg gcc aag cag atc aaa acc aag gtc aat          912
Ser Ile Phe Leu Thr Asp Thr Ala Lys Gln Ile Lys Thr Lys Val Asn
    290                 295                 300 aag cat gcg ttt tct gga ggg aga gac acc atc gag gag cac agg cag          960
Lys His Ala Phe Ser Gly Gly Arg Asp Thr Ile Glu Glu His Arg Gln
305                 310                 315                 320 ttt ggg ggc aac tgt gat gtg gac gtg tct ttc atg tac ctg acc ttc         1008
Phe Gly Gly Asn Cys Asp Val Asp Val Ser Phe Met Tyr Leu Thr Phe
                325                 330                 335 ttc ctc gag gac gac gac aag ctc gag cag atc agg aag gat tac acc         1056
Phe Leu Glu Asp Asp Asp Lys Leu Glu Gln Ile Arg Lys Asp Tyr Thr
            340                 345                 350 agc gga gcc atg ctc acc ggt gag ctc aag aag gca ctc ata gag gtt         1104
```

```
Ser Gly Ala Met Leu Thr Gly Glu Leu Lys Lys Ala Leu Ile Glu Val
        355                 360                 365 ctg cag ccc ttg atc gca gag cac cag gcc cgg cgc aag gag gtc acg    1152
Leu Gln Pro Leu Ile Ala Glu His Gln Ala Arg Arg Lys Glu Val Thr
    370                 375                 380 gat gag ata gtg aaa gag ttc atg act ccc cgg aag ctg tcc ttc gac    1200
Asp Glu Ile Val Lys Glu Phe Met Thr Pro Arg Lys Leu Ser Phe Asp
385                 390                 395                 400 ttt cag                                                             1206
Phe Gln <210> SEQ ID NO 58
<211> LENGTH: 1269
<212> TYPE: DNA
<213> ORGANISM: Artificial Sequence
<220> FEATURE:
<223> OTHER INFORMATION: Recombinant human mini-TrpRS (SD variant)
      construct
<220> FEATURE:
<221> NAME/KEY: CDS
<222> LOCATION: (1)..(1269)
<220> FEATURE:
<221> NAME/KEY: misc_feature
<222> LOCATION: (493)..(495)
<223> OTHER INFORMATION: nnn is agy, tcy or tcr

<400> SEQUENCE: 58 agc tac aaa gct gcc gcg ggg gag gat tac aag gct gac tgt cct cca    48
Ser Tyr Lys Ala Ala Ala Gly Glu Asp Tyr Lys Ala Asp Cys Pro Pro
1               5                   10                  15 ggg aac cca gca cct acc agt aat cat ggc cca gat gcc aca gaa gct    96
Gly Asn Pro Ala Pro Thr Ser Asn His Gly Pro Asp Ala Thr Glu Ala
            20                  25                  30 gaa gag gat ttt gtg gac cca tgg aca gta cag aca agc agt gca aaa    144
Glu Glu Asp Phe Val Asp Pro Trp Thr Val Gln Thr Ser Ser Ala Lys
        35                  40                  45 ggc ata gac tac gat aag ctc att gtt cgg ttt gga agt agt aaa att    192
Gly Ile Asp Tyr Asp Lys Leu Ile Val Arg Phe Gly Ser Ser Lys Ile
    50                  55                  60 gac aaa gag cta ata aac cga ata gag aga gcc acc ggc caa aga cca    240
Asp Lys Glu Leu Ile Asn Arg Ile Glu Arg Ala Thr Gly Gln Arg Pro
65                  70                  75                  80 cac cac ttc ctg cgc aga ggc atc ttc ttc tca cac aga gat atg aat    288
His His Phe Leu Arg Arg Gly Ile Phe Phe Ser His Arg Asp Met Asn
                85                  90                  95 cag gtt ctt gat gcc tat gaa aat aag aag cca ttt tat ctg tac acg    336
Gln Val Leu Asp Ala Tyr Glu Asn Lys Lys Pro Phe Tyr Leu Tyr Thr
            100                 105                 110 ggc cgg ggc ccc tct tct gaa gca atg cat gta ggt cac ctc att cca    384
Gly Arg Gly Pro Ser Ser Glu Ala Met His Val Gly His Leu Ile Pro
        115                 120                 125 ttt att ttc aca aag tgg ctc cag gat gta ttt aac gtg ccc ttg gtc    432
Phe Ile Phe Thr Lys Trp Leu Gln Asp Val Phe Asn Val Pro Leu Val
    130                 135                 140 atc cag atg acg gat gac gag aag tat ctg tgg aag gac ctg acc ctg    480
Ile Gln Met Thr Asp Asp Glu Lys Tyr Leu Trp Lys Asp Leu Thr Leu
145                 150                 155                 160 gac cag gcc tat nnn gay gct gtt gag aat gcc aag gac atc atc gcc    528
Asp Gln Ala Tyr Ser Asp Ala Val Glu Asn Ala Lys Asp Ile Ile Ala
                165                 170                 175 tgt ggc ttt gac atc aac aag act ttc ata ttc tct gac ctg gac tac    576
Cys Gly Phe Asp Ile Asn Lys Thr Phe Ile Phe Ser Asp Leu Asp Tyr
            180                 185                 190
```

```
atg ggg atg agc tca ggt ttc tac aaa aat gtg gtg aag att caa aag      624
Met Gly Met Ser Ser Gly Phe Tyr Lys Asn Val Val Lys Ile Gln Lys
        195                 200                 205 cat gtt acc ttc aac caa gtg aaa ggc att ttc ggc ttc act gac agc      672
His Val Thr Phe Asn Gln Val Lys Gly Ile Phe Gly Phe Thr Asp Ser
    210                 215                 220 gac tgc att ggg aag atc agt ttt cct gcc atc cag gct gct ccc tcc      720
Asp Cys Ile Gly Lys Ile Ser Phe Pro Ala Ile Gln Ala Ala Pro Ser
225                 230                 235                 240 ttc agc aac tca ttc cca cag atc ttc cga gac agg acg gat atc cag      768
Phe Ser Asn Ser Phe Pro Gln Ile Phe Arg Asp Arg Thr Asp Ile Gln
                245                 250                 255 tgc ctt atc cca tgt gcc att gac cag gat cct tac ttt aga atg aca      816
Cys Leu Ile Pro Cys Ala Ile Asp Gln Asp Pro Tyr Phe Arg Met Thr
            260                 265                 270 agg gac gtc gcc ccc agg atc ggc tat cct aaa cca gcc ctg ttg cac      864
Arg Asp Val Ala Pro Arg Ile Gly Tyr Pro Lys Pro Ala Leu Leu His
        275                 280                 285 tcc acc ttc ttc cca gcc ctg cag ggc gcc cag acc aaa atg agt gcc      912
Ser Thr Phe Phe Pro Ala Leu Gln Gly Ala Gln Thr Lys Met Ser Ala
    290                 295                 300 agc gac cca aac tcc tcc atc ttc ctc acc gac acg gcc aag cag atc      960
Ser Asp Pro Asn Ser Ser Ile Phe Leu Thr Asp Thr Ala Lys Gln Ile
305                 310                 315                 320 aaa acc aag gtc aat aag cat gcg ttt tct gga ggg aga gac acc atc     1008
Lys Thr Lys Val Asn Lys His Ala Phe Ser Gly Gly Arg Asp Thr Ile
                325                 330                 335 gag gag cac agg cag ttt ggg ggc aac tgt gat gtg gac gtg tct ttc     1056
Glu Glu His Arg Gln Phe Gly Gly Asn Cys Asp Val Asp Val Ser Phe
            340                 345                 350 atg tac ctg acc ttc ttc ctc gag gac gac gac aag ctc gag cag atc     1104
Met Tyr Leu Thr Phe Phe Leu Glu Asp Asp Asp Lys Leu Glu Gln Ile
        355                 360                 365 agg aag gat tac acc agc gga gcc atg ctc acc ggt gag ctc aag aag     1152
Arg Lys Asp Tyr Thr Ser Gly Ala Met Leu Thr Gly Glu Leu Lys Lys
    370                 375                 380 gca ctc ata gag gtt ctg cag ccc ttg atc gca gag cac cag gcc cgg     1200
Ala Leu Ile Glu Val Leu Gln Pro Leu Ile Ala Glu His Gln Ala Arg
385                 390                 395                 400 cgc aag gag gtc acg gat gag ata gtg aaa gag ttc atg act ccc cgg     1248
Arg Lys Glu Val Thr Asp Glu Ile Val Lys Glu Phe Met Thr Pro Arg
                405                 410                 415 aag ctg tcc ttc gac ttt cag                                         1269
Lys Leu Ser Phe Asp Phe Gln
            420

<210> SEQ ID NO 59
<211> LENGTH: 1272
<212> TYPE: DNA
<213> ORGANISM: Artificial Sequence
<220> FEATURE:
<223> OTHER INFORMATION: Recombinant human Met-mini-TrpRS (SD variant)
      construct
<220> FEATURE:
<221> NAME/KEY: CDS
<222> LOCATION: (1)..(1272)
<220> FEATURE:
<221> NAME/KEY: misc_feature
<222> LOCATION: (496)..(498)
<223> OTHER INFORMATION: nnn is agy, tcy or tcr

<400> SEQUENCE: 59 atg agc tac aaa gct gcc gcg ggg gag gat tac aag gct gac tgt cct       48
Met Ser Tyr Lys Ala Ala Ala Gly Glu Asp Tyr Lys Ala Asp Cys Pro
```

-continued

| | 1 | | | 5 | | | | 10 | | | | 15 | | | |
|---|---|---|---|---|---|---|---|---|---|---|---|---|---|---|---|
| cca | ggg | aac | cca | gca | cct | acc | agt | aat | cat | ggc | cca | gat | gcc | aca | gaa | 96 |
| Pro | Gly | Asn | Pro | Ala | Pro | Thr | Ser | Asn | His | Gly | Pro | Asp | Ala | Thr | Glu | |
| | | | 20 | | | | | 25 | | | | | 30 | | | |

| gct | gaa | gag | gat | ttt | gtg | gac | cca | tgg | aca | gta | cag | aca | agc | agt | gca | 144 |
| Ala | Glu | Glu | Asp | Phe | Val | Asp | Pro | Trp | Thr | Val | Gln | Thr | Ser | Ser | Ala | |
| | 35 | | | | | 40 | | | | | 45 | | | | | |

| aaa | ggc | ata | gac | tac | gat | aag | ctc | att | gtt | cgg | ttt | gga | agt | agt | aaa | 192 |
| Lys | Gly | Ile | Asp | Tyr | Asp | Lys | Leu | Ile | Val | Arg | Phe | Gly | Ser | Ser | Lys | |
| 50 | | | | | 55 | | | | | 60 | | | | | | |

| att | gac | aaa | gag | cta | ata | aac | cga | ata | gag | aga | gcc | acc | ggc | caa | aga | 240 |
| Ile | Asp | Lys | Glu | Leu | Ile | Asn | Arg | Ile | Glu | Arg | Ala | Thr | Gly | Gln | Arg | |
| 65 | | | | 70 | | | | | 75 | | | | | 80 | | |

| cca | cac | cac | ttc | ctg | cgc | aga | ggc | atc | ttc | ttc | tca | cac | aga | gat | atg | 288 |
| Pro | His | His | Phe | Leu | Arg | Arg | Gly | Ile | Phe | Phe | Ser | His | Arg | Asp | Met | |
| | | | | 85 | | | | | 90 | | | | | 95 | | |

| aat | cag | gtt | ctt | gat | gcc | tat | gaa | aat | aag | aag | cca | ttt | tat | ctg | tac | 336 |
| Asn | Gln | Val | Leu | Asp | Ala | Tyr | Glu | Asn | Lys | Lys | Pro | Phe | Tyr | Leu | Tyr | |
| | | | 100 | | | | | 105 | | | | | 110 | | | |

| acg | ggc | cgg | ggc | ccc | tct | tct | gaa | gca | atg | cat | gta | ggt | cac | ctc | att | 384 |
| Thr | Gly | Arg | Gly | Pro | Ser | Ser | Glu | Ala | Met | His | Val | Gly | His | Leu | Ile | |
| | | 115 | | | | | 120 | | | | | 125 | | | | |

| cca | ttt | att | ttc | aca | aag | tgg | ctc | cag | gat | gta | ttt | aac | gtg | ccc | ttg | 432 |
| Pro | Phe | Ile | Phe | Thr | Lys | Trp | Leu | Gln | Asp | Val | Phe | Asn | Val | Pro | Leu | |
| | 130 | | | | | 135 | | | | | 140 | | | | | |

| gtc | atc | cag | atg | acg | gat | gac | gag | aag | tat | ctg | tgg | aag | gac | ctg | acc | 480 |
| Val | Ile | Gln | Met | Thr | Asp | Asp | Glu | Lys | Tyr | Leu | Trp | Lys | Asp | Leu | Thr | |
| 145 | | | | | 150 | | | | | 155 | | | | | 160 | |

| ctg | gac | cag | gcc | tat | nnn | gay | gct | gtt | gag | aat | gcc | aag | gac | atc | atc | 528 |
| Leu | Asp | Gln | Ala | Tyr | Ser | Asp | Ala | Val | Glu | Asn | Ala | Lys | Asp | Ile | Ile | |
| | | | | 165 | | | | | 170 | | | | | 175 | | |

| gcc | tgt | ggc | ttt | gac | atc | aac | aag | act | ttc | ata | ttc | tct | gac | ctg | gac | 576 |
| Ala | Cys | Gly | Phe | Asp | Ile | Asn | Lys | Thr | Phe | Ile | Phe | Ser | Asp | Leu | Asp | |
| | | | 180 | | | | | 185 | | | | | 190 | | | |

| tac | atg | ggg | atg | agc | tca | ggt | ttc | tac | aaa | aat | gtg | gtg | aag | att | caa | 624 |
| Tyr | Met | Gly | Met | Ser | Ser | Gly | Phe | Tyr | Lys | Asn | Val | Val | Lys | Ile | Gln | |
| | | 195 | | | | | 200 | | | | | 205 | | | | |

| aag | cat | gtt | acc | ttc | aac | caa | gtg | aaa | ggc | att | ttc | ggc | ttc | act | gac | 672 |
| Lys | His | Val | Thr | Phe | Asn | Gln | Val | Lys | Gly | Ile | Phe | Gly | Phe | Thr | Asp | |
| | 210 | | | | | 215 | | | | | 220 | | | | | |

| agc | gac | tgc | att | ggg | aag | atc | agt | ttt | cct | gcc | atc | cag | gct | gct | ccc | 720 |
| Ser | Asp | Cys | Ile | Gly | Lys | Ile | Ser | Phe | Pro | Ala | Ile | Gln | Ala | Ala | Pro | |
| 225 | | | | 230 | | | | | 235 | | | | | 240 | | |

| tcc | ttc | agc | aac | tca | ttc | cca | cag | atc | ttc | cga | gac | agg | acg | gat | atc | 768 |
| Ser | Phe | Ser | Asn | Ser | Phe | Pro | Gln | Ile | Phe | Arg | Asp | Arg | Thr | Asp | Ile | |
| | | | | 245 | | | | | 250 | | | | | 255 | | |

| cag | tgc | ctt | atc | cca | tgt | gcc | att | gac | cag | gat | cct | tac | ttt | aga | atg | 816 |
| Gln | Cys | Leu | Ile | Pro | Cys | Ala | Ile | Asp | Gln | Asp | Pro | Tyr | Phe | Arg | Met | |
| | | | 260 | | | | | 265 | | | | | 270 | | | |

| aca | agg | gac | gtc | gcc | ccc | agg | atc | ggc | tat | cct | aaa | cca | gcc | ctg | ttg | 864 |
| Thr | Arg | Asp | Val | Ala | Pro | Arg | Ile | Gly | Tyr | Pro | Lys | Pro | Ala | Leu | Leu | |
| | | 275 | | | | | 280 | | | | | 285 | | | | |

| cac | tcc | acc | ttc | ttc | cca | gcc | ctg | cag | ggc | gcc | cag | acc | aaa | atg | agt | 912 |
| His | Ser | Thr | Phe | Phe | Pro | Ala | Leu | Gln | Gly | Ala | Gln | Thr | Lys | Met | Ser | |
| | 290 | | | | | 295 | | | | | 300 | | | | | |

| gcc | agc | gac | cca | aac | tcc | tcc | atc | ttc | ctc | acc | gac | acg | gcc | aag | cag | 960 |
| Ala | Ser | Asp | Pro | Asn | Ser | Ser | Ile | Phe | Leu | Thr | Asp | Thr | Ala | Lys | Gln | |
| 305 | | | | 310 | | | | | 315 | | | | | 320 | | |

| atc | aaa | acc | aag | gtc | aat | aag | cat | gcg | ttt | tct | gga | ggg | aga | gac | acc | 1008 |
| Ile | Lys | Thr | Lys | Val | Asn | Lys | His | Ala | Phe | Ser | Gly | Gly | Arg | Asp | Thr | |

```
                     325                 330                 335
atc gag gag cac agg cag ttt ggg ggc aac tgt gat gtg gac gtg tct    1056
Ile Glu Glu His Arg Gln Phe Gly Gly Asn Cys Asp Val Asp Val Ser
            340                 345                 350 ttc atg tac ctg acc ttc ttc ctc gag gac gac gac aag ctc gag cag    1104
Phe Met Tyr Leu Thr Phe Phe Leu Glu Asp Asp Asp Lys Leu Glu Gln
        355                 360                 365 atc agg aag gat tac acc agc gga gcc atg ctc acc ggt gag ctc aag    1152
Ile Arg Lys Asp Tyr Thr Ser Gly Ala Met Leu Thr Gly Glu Leu Lys
    370                 375                 380 aag gca ctc ata gag gtt ctg cag ccc ttg atc gca gag cac cag gcc    1200
Lys Ala Leu Ile Glu Val Leu Gln Pro Leu Ile Ala Glu His Gln Ala
385                 390                 395                 400 cgg cgc aag gag gtc acg gat gag ata gtg aaa gag ttc atg act ccc    1248
Arg Arg Lys Glu Val Thr Asp Glu Ile Val Lys Glu Phe Met Thr Pro
                405                 410                 415 cgg aag ctg tcc ttc gac ttt cag                                    1272
Arg Lys Leu Ser Phe Asp Phe Gln
            420

<210> SEQ ID NO 60
<211> LENGTH: 56
<212> TYPE: PRT
<213> ORGANISM: Homo sapiens

<400> SEQUENCE: 60

Asp Leu Asp Tyr Met Gly Met Ser Ser Gly Phe Tyr Lys Asn Val Val
1               5                   10                  15

Lys Ile Gln Lys His Val Thr Phe Asn Gln Val Lys Gly Ile Phe Gly
            20                  25                  30

Phe Thr Asp Ser Asp Cys Ile Gly Lys Ile Ser Phe Pro Ala Ile Gln
        35                  40                  45

Ala Ala Pro Ser Phe Ser Asn Ser
    50                  55

<210> SEQ ID NO 61
<211> LENGTH: 471
<212> TYPE: PRT
<213> ORGANISM: Artificial Sequence
<220> FEATURE:
<223> OTHER INFORMATION: Description of Artificial Sequence: Recombinant
      human GD variant protein

<400> SEQUENCE: 61

Met Pro Asn Ser Glu Pro Ala Ser Leu Leu Glu Leu Phe Asn Ser Ile
1               5                   10                  15

Ala Thr Gln Gly Glu Leu Val Arg Ser Leu Lys Ala Gly Asn Ala Ser
            20                  25                  30

Lys Asp Glu Ile Asp Ser Ala Val Lys Met Leu Val Ser Leu Lys Met
        35                  40                  45

Ser Tyr Lys Ala Ala Ala Gly Glu Asp Tyr Lys Ala Asp Cys Pro Pro
    50                  55                  60

Gly Asn Pro Ala Pro Thr Ser Asn His Gly Pro Asp Ala Thr Glu Ala
65                  70                  75                  80

Glu Glu Asp Phe Val Asp Pro Trp Thr Val Gln Thr Ser Ser Ala Lys
                85                  90                  95

Gly Ile Asp Tyr Asp Lys Leu Ile Val Arg Phe Gly Ser Ser Lys Ile
            100                 105                 110

Asp Lys Glu Leu Ile Asn Arg Ile Glu Arg Ala Thr Gly Gln Arg Pro
        115                 120                 125
```

His His Phe Leu Arg Arg Gly Ile Phe Phe Ser His Arg Asp Met Asn
            130                 135                 140

Gln Val Leu Asp Ala Tyr Glu Asn Lys Lys Pro Phe Tyr Leu Tyr Thr
145                 150                 155                 160

Gly Arg Gly Pro Ser Ser Glu Ala Met His Val Gly His Leu Ile Pro
                165                 170                 175

Phe Ile Phe Thr Lys Trp Leu Gln Asp Val Phe Asn Val Pro Leu Val
            180                 185                 190

Ile Gln Met Thr Asp Asp Glu Lys Tyr Leu Trp Lys Asp Leu Thr Leu
            195                 200                 205

Asp Gln Ala Tyr Gly Asp Ala Val Glu Asn Ala Lys Asp Ile Ile Ala
            210                 215                 220

Cys Gly Phe Asp Ile Asn Lys Thr Phe Ile Phe Ser Asp Leu Asp Tyr
225                 230                 235                 240

Met Gly Met Ser Ser Gly Phe Tyr Lys Asn Val Val Lys Ile Gln Lys
                245                 250                 255

His Val Thr Phe Asn Gln Val Lys Gly Ile Phe Gly Phe Thr Asp Ser
            260                 265                 270

Asp Cys Ile Gly Lys Ile Ser Phe Pro Ala Ile Gln Ala Ala Pro Ser
            275                 280                 285

Phe Ser Asn Ser Phe Pro Gln Ile Phe Arg Asp Arg Thr Asp Ile Gln
290                 295                 300

Cys Leu Ile Pro Cys Ala Ile Asp Gln Asp Pro Tyr Phe Arg Met Thr
305                 310                 315                 320

Arg Asp Val Ala Pro Arg Ile Gly Tyr Pro Lys Pro Ala Leu Leu His
                325                 330                 335

Ser Thr Phe Phe Pro Ala Leu Gln Gly Ala Gln Thr Lys Met Ser Ala
            340                 345                 350

Ser Asp Pro Asn Ser Ser Ile Phe Leu Thr Asp Thr Ala Lys Gln Ile
            355                 360                 365

Lys Thr Lys Val Asn Lys His Ala Phe Ser Gly Gly Arg Asp Thr Ile
            370                 375                 380

Glu Glu His Arg Gln Phe Gly Gly Asn Cys Asp Val Asp Val Ser Phe
385                 390                 395                 400

Met Tyr Leu Thr Phe Phe Leu Glu Asp Asp Lys Leu Glu Gln Ile
                405                 410                 415

Arg Lys Asp Tyr Thr Ser Gly Ala Met Leu Thr Gly Glu Leu Lys Lys
            420                 425                 430

Ala Leu Ile Glu Val Leu Gln Pro Leu Ile Ala Glu His Gln Ala Arg
            435                 440                 445

Arg Lys Glu Val Thr Asp Glu Ile Val Lys Glu Phe Met Thr Pro Arg
            450                 455                 460

Lys Leu Ser Phe Asp Phe Gln
465                 470

<210> SEQ ID NO 62
<211> LENGTH: 470
<212> TYPE: PRT
<213> ORGANISM: Artificial Sequence
<220> FEATURE:
<223> OTHER INFORMATION: Description of Artificial Sequence: Recombinant
      human GD variant protein

<400> SEQUENCE: 62

Pro Asn Ser Glu Pro Ala Ser Leu Leu Glu Leu Phe Asn Ser Ile Ala
1               5                   10                  15

Thr Gln Gly Glu Leu Val Arg Ser Leu Lys Ala Gly Asn Ala Ser Lys
                20                  25                  30

Asp Glu Ile Asp Ser Ala Val Lys Met Leu Val Ser Leu Lys Met Ser
            35                  40                  45

Tyr Lys Ala Ala Ala Gly Glu Asp Tyr Lys Ala Asp Cys Pro Pro Gly
50                  55                  60

Asn Pro Ala Pro Thr Ser Asn His Gly Pro Asp Ala Thr Glu Ala Glu
65                  70                  75                  80

Glu Asp Phe Val Asp Pro Trp Thr Val Gln Thr Ser Ala Lys Gly
                85                  90                  95

Ile Asp Tyr Asp Lys Leu Ile Val Arg Phe Gly Ser Ser Lys Ile Asp
            100                 105                 110

Lys Glu Leu Ile Asn Arg Ile Glu Arg Ala Thr Gly Gln Arg Pro His
            115                 120                 125

His Phe Leu Arg Arg Gly Ile Phe Phe Ser His Arg Asp Met Asn Gln
130                 135                 140

Val Leu Asp Ala Tyr Glu Asn Lys Lys Pro Phe Tyr Leu Tyr Thr Gly
145                 150                 155                 160

Arg Gly Pro Ser Ser Glu Ala Met His Val Gly His Leu Ile Pro Phe
                165                 170                 175

Ile Phe Thr Lys Trp Leu Gln Asp Val Phe Asn Val Pro Leu Val Ile
            180                 185                 190

Gln Met Thr Asp Asp Glu Lys Tyr Leu Trp Lys Asp Leu Thr Leu Asp
            195                 200                 205

Gln Ala Tyr Gly Asp Ala Val Glu Asn Ala Lys Asp Ile Ile Ala Cys
210                 215                 220

Gly Phe Asp Ile Asn Lys Thr Phe Ile Phe Ser Asp Leu Asp Tyr Met
225                 230                 235                 240

Gly Met Ser Ser Gly Phe Tyr Lys Asn Val Val Lys Ile Gln Lys His
                245                 250                 255

Val Thr Phe Asn Gln Val Lys Gly Ile Phe Gly Phe Thr Asp Ser Asp
            260                 265                 270

Cys Ile Gly Lys Ile Ser Phe Pro Ala Ile Gln Ala Ala Pro Ser Phe
            275                 280                 285

Ser Asn Ser Phe Pro Gln Ile Phe Arg Asp Arg Thr Asp Ile Gln Cys
290                 295                 300

Leu Ile Pro Cys Ala Ile Asp Gln Asp Pro Tyr Phe Arg Met Thr Arg
305                 310                 315                 320

Asp Val Ala Pro Arg Ile Gly Tyr Pro Lys Pro Ala Leu Leu His Ser
                325                 330                 335

Thr Phe Phe Pro Ala Leu Gln Gly Ala Gln Thr Lys Met Ser Ala Ser
            340                 345                 350

Asp Pro Asn Ser Ser Ile Phe Leu Thr Asp Thr Ala Lys Gln Ile Lys
            355                 360                 365

Thr Lys Val Asn Lys His Ala Phe Ser Gly Gly Arg Asp Thr Ile Glu
370                 375                 380

Glu His Arg Gln Phe Gly Gly Asn Cys Asp Val Asp Val Ser Phe Met
385                 390                 395                 400

Tyr Leu Thr Phe Phe Leu Glu Asp Asp Lys Leu Glu Gln Ile Arg
                405                 410                 415

Lys Asp Tyr Thr Ser Gly Ala Met Leu Thr Gly Glu Leu Lys Lys Ala
            420                 425                 430

Leu Ile Glu Val Leu Gln Pro Leu Ile Ala Glu His Gln Ala Arg Arg

```
                435                 440                 445
Lys Glu Val Thr Asp Glu Ile Val Lys Glu Phe Met Thr Pro Arg Lys
    450                 455                 460

Leu Ser Phe Asp Phe Gln
465                 470

<210> SEQ ID NO 63
<211> LENGTH: 471
<212> TYPE: PRT
<213> ORGANISM: Artificial Sequence
<220> FEATURE:
<223> OTHER INFORMATION: Description of Artificial Sequence: Recombinant
      human SY variant protein

<400> SEQUENCE: 63

Met Pro Asn Ser Glu Pro Ala Ser Leu Leu Glu Leu Phe Asn Ser Ile
1               5                   10                  15

Ala Thr Gln Gly Glu Leu Val Arg Ser Leu Lys Ala Gly Asn Ala Ser
            20                  25                  30

Lys Asp Glu Ile Asp Ser Ala Val Lys Met Leu Val Ser Leu Lys Met
        35                  40                  45

Ser Tyr Lys Ala Ala Ala Gly Glu Asp Tyr Lys Ala Asp Cys Pro Pro
50                  55                  60

Gly Asn Pro Ala Pro Thr Ser Asn His Gly Pro Asp Ala Thr Glu Ala
65                  70                  75                  80

Glu Glu Asp Phe Val Asp Pro Trp Thr Val Gln Thr Ser Ser Ala Lys
                85                  90                  95

Gly Ile Asp Tyr Asp Lys Leu Ile Val Arg Phe Gly Ser Ser Lys Ile
            100                 105                 110

Asp Lys Glu Leu Ile Asn Arg Ile Glu Arg Ala Thr Gly Gln Arg Pro
        115                 120                 125

His His Phe Leu Arg Arg Gly Ile Phe Phe Ser His Arg Asp Met Asn
130                 135                 140

Gln Val Leu Asp Ala Tyr Glu Asn Lys Lys Pro Phe Tyr Leu Tyr Thr
145                 150                 155                 160

Gly Arg Gly Pro Ser Ser Glu Ala Met His Val Gly His Leu Ile Pro
                165                 170                 175

Phe Ile Phe Thr Lys Trp Leu Gln Asp Val Phe Asn Val Pro Leu Val
            180                 185                 190

Ile Gln Met Thr Asp Asp Glu Lys Tyr Leu Trp Lys Asp Leu Thr Leu
        195                 200                 205

Asp Gln Ala Tyr Ser Tyr Ala Val Glu Asn Ala Lys Asp Ile Ile Ala
210                 215                 220

Cys Gly Phe Asp Ile Asn Lys Thr Phe Ile Phe Ser Asp Leu Asp Tyr
225                 230                 235                 240

Met Gly Met Ser Ser Gly Phe Tyr Lys Asn Val Val Lys Ile Gln Lys
                245                 250                 255

His Val Thr Phe Asn Gln Val Lys Gly Ile Phe Gly Phe Thr Asp Ser
            260                 265                 270

Asp Cys Ile Gly Lys Ile Ser Phe Pro Ala Ile Gln Ala Ala Pro Ser
        275                 280                 285

Phe Ser Asn Ser Phe Pro Gln Ile Phe Arg Asp Arg Thr Asp Ile Gln
    290                 295                 300

Cys Leu Ile Pro Cys Ala Ile Asp Gln Asp Pro Tyr Phe Arg Met Thr
305                 310                 315                 320

Arg Asp Val Ala Pro Arg Ile Gly Tyr Pro Lys Pro Ala Leu Leu His
```

```
                    325                 330                 335
Ser Thr Phe Phe Pro Ala Leu Gln Gly Ala Gln Thr Lys Met Ser Ala
                340                 345                 350

Ser Asp Pro Asn Ser Ser Ile Phe Leu Thr Asp Thr Ala Lys Gln Ile
            355                 360                 365

Lys Thr Lys Val Asn Lys His Ala Phe Ser Gly Gly Arg Asp Thr Ile
        370                 375                 380

Glu Glu His Arg Gln Phe Gly Gly Asn Cys Asp Val Asp Val Ser Phe
385                 390                 395                 400

Met Tyr Leu Thr Phe Phe Leu Glu Asp Asp Lys Leu Gly Gln Ile
                405                 410                 415

Arg Lys Asp Tyr Thr Ser Gly Ala Met Leu Thr Gly Glu Leu Lys Lys
                420                 425                 430

Ala Leu Ile Glu Val Leu Gln Pro Leu Ile Ala Glu His Gln Ala Arg
                435                 440                 445

Arg Lys Glu Val Thr Asp Glu Ile Val Lys Glu Phe Met Thr Pro Arg
            450                 455                 460

Lys Leu Ser Phe Asp Phe Gln
465                 470

<210> SEQ ID NO 64
<211> LENGTH: 470
<212> TYPE: PRT
<213> ORGANISM: Artificial Sequence
<220> FEATURE:
<223> OTHER INFORMATION: Description of Artificial Sequence: Recombinant
      human SY variant protein

<400> SEQUENCE: 64

Pro Asn Ser Glu Pro Ala Ser Leu Leu Glu Leu Phe Asn Ser Ile Ala
1               5                   10                  15

Thr Gln Gly Glu Leu Val Arg Ser Leu Lys Ala Gly Asn Ala Ser Lys
                20                  25                  30

Asp Glu Ile Asp Ser Ala Val Lys Met Leu Val Ser Leu Lys Met Ser
            35                  40                  45

Tyr Lys Ala Ala Ala Gly Glu Asp Tyr Lys Ala Asp Cys Pro Pro Gly
        50                  55                  60

Asn Pro Ala Pro Thr Ser Asn His Gly Pro Asp Ala Thr Glu Ala Glu
65                  70                  75                  80

Glu Asp Phe Val Asp Pro Trp Thr Val Gln Thr Ser Ser Ala Lys Gly
                85                  90                  95

Ile Asp Tyr Asp Lys Leu Ile Val Arg Phe Gly Ser Ser Lys Ile Asp
            100                 105                 110

Lys Glu Leu Ile Asn Arg Ile Glu Arg Ala Thr Gly Gln Arg Pro His
        115                 120                 125

His Phe Leu Arg Arg Gly Ile Phe Phe Ser His Arg Asp Met Asn Gln
    130                 135                 140

Val Leu Asp Ala Tyr Glu Asn Lys Lys Pro Phe Tyr Leu Tyr Thr Gly
145                 150                 155                 160

Arg Gly Pro Ser Ser Glu Ala Met His Val Gly His Leu Ile Pro Phe
                165                 170                 175

Ile Phe Thr Lys Trp Leu Gln Asp Val Phe Asn Val Pro Leu Val Ile
            180                 185                 190

Gln Met Thr Asp Asp Glu Lys Tyr Leu Trp Lys Asp Leu Thr Leu Asp
        195                 200                 205

Gln Ala Tyr Ser Tyr Ala Val Glu Asn Ala Lys Asp Ile Ile Ala Cys
```

```
            210                 215                 220
Gly Phe Asp Ile Asn Lys Thr Phe Ile Phe Ser Asp Leu Asp Tyr Met
225                 230                 235                 240

Gly Met Ser Ser Gly Phe Tyr Lys Asn Val Val Lys Ile Gln Lys His
                245                 250                 255

Val Thr Phe Asn Gln Val Lys Gly Ile Phe Gly Phe Thr Asp Ser Asp
                260                 265                 270

Cys Ile Gly Lys Ile Ser Phe Pro Ala Ile Gln Ala Ala Pro Ser Phe
            275                 280                 285

Ser Asn Ser Phe Pro Gln Ile Phe Arg Asp Arg Thr Asp Ile Gln Cys
        290                 295                 300

Leu Ile Pro Cys Ala Ile Asp Gln Asp Pro Tyr Phe Arg Met Thr Arg
305                 310                 315                 320

Asp Val Ala Pro Arg Ile Gly Tyr Pro Lys Pro Ala Leu Leu His Ser
                325                 330                 335

Thr Phe Phe Pro Ala Leu Gln Gly Ala Gln Thr Lys Met Ser Ala Ser
                340                 345                 350

Asp Pro Asn Ser Ser Ile Phe Leu Thr Asp Thr Ala Lys Gln Ile Lys
            355                 360                 365

Thr Lys Val Asn Lys His Ala Phe Ser Gly Gly Arg Asp Thr Ile Glu
        370                 375                 380

Glu His Arg Gln Phe Gly Gly Asn Cys Asp Val Asp Val Ser Phe Met
385                 390                 395                 400

Tyr Leu Thr Phe Phe Leu Glu Asp Asp Lys Leu Glu Gln Ile Arg
                405                 410                 415

Lys Asp Tyr Thr Ser Gly Ala Met Leu Thr Gly Glu Leu Lys Lys Ala
                420                 425                 430

Leu Ile Glu Val Leu Gln Pro Leu Ile Ala Glu His Gln Ala Arg Arg
            435                 440                 445

Lys Glu Val Thr Asp Glu Ile Val Lys Glu Phe Met Thr Pro Arg Lys
        450                 455                 460

Leu Ser Phe Asp Phe Gln
465                 470

<210> SEQ ID NO 65
<211> LENGTH: 471
<212> TYPE: PRT
<213> ORGANISM: Artificial Sequence
<220> FEATURE:
<223> OTHER INFORMATION: Description of Artificial Sequence: Recombinant
      human GY variant protein

<400> SEQUENCE: 65

Met Pro Asn Ser Glu Pro Ala Ser Leu Leu Glu Leu Phe Asn Ser Ile
1               5                   10                  15

Ala Thr Gln Gly Glu Leu Val Arg Ser Leu Lys Ala Gly Asn Ala Ser
                20                  25                  30

Lys Asp Glu Ile Asp Ser Ala Val Lys Met Leu Val Ser Leu Lys Met
            35                  40                  45

Ser Tyr Lys Ala Ala Ala Gly Glu Asp Tyr Lys Ala Asp Cys Pro Pro
        50                  55                  60

Gly Asn Pro Ala Pro Thr Ser Asn His Gly Pro Asp Ala Thr Glu Ala
65                  70                  75                  80

Glu Glu Asp Phe Val Asp Pro Trp Thr Val Gln Thr Ser Ser Ala Lys
                85                  90                  95

Gly Ile Asp Tyr Asp Lys Leu Ile Val Arg Phe Gly Ser Ser Lys Ile
```

```
                          100                 105                 110
Asp Lys Glu Leu Ile Asn Arg Ile Glu Arg Ala Thr Gly Gln Arg Pro
            115                 120                 125

His His Phe Leu Arg Arg Gly Ile Phe Phe Ser His Arg Asp Met Asn
        130                 135                 140

Gln Val Leu Asp Ala Tyr Glu Asn Lys Lys Pro Phe Tyr Leu Tyr Thr
145                 150                 155                 160

Gly Arg Gly Pro Ser Ser Glu Ala Met His Val Gly His Leu Ile Pro
                165                 170                 175

Phe Ile Phe Thr Lys Trp Leu Gln Asp Val Phe Asn Val Pro Leu Val
            180                 185                 190

Ile Gln Met Thr Asp Asp Glu Lys Tyr Leu Trp Lys Asp Leu Thr Leu
        195                 200                 205

Asp Gln Ala Tyr Gly Tyr Ala Val Glu Asn Ala Lys Asp Ile Ile Ala
        210                 215                 220

Cys Gly Phe Asp Ile Asn Lys Thr Phe Ile Phe Ser Asp Leu Asp Tyr
225                 230                 235                 240

Met Gly Met Ser Ser Gly Phe Tyr Lys Asn Val Val Lys Ile Gln Lys
                245                 250                 255

His Val Thr Phe Asn Gln Val Lys Gly Ile Phe Gly Phe Thr Asp Ser
            260                 265                 270

Asp Cys Ile Gly Lys Ile Ser Phe Pro Ala Ile Gln Ala Ala Pro Ser
        275                 280                 285

Phe Ser Asn Ser Phe Pro Gln Ile Phe Arg Asp Arg Thr Asp Ile Gln
        290                 295                 300

Cys Leu Ile Pro Cys Ala Ile Asp Gln Asp Pro Tyr Phe Arg Met Thr
305                 310                 315                 320

Arg Asp Val Ala Pro Arg Ile Gly Tyr Pro Lys Pro Ala Leu Leu His
                325                 330                 335

Ser Thr Phe Phe Pro Ala Leu Gln Gly Ala Gln Thr Lys Met Ser Ala
            340                 345                 350

Ser Asp Pro Asn Ser Ser Ile Phe Leu Thr Asp Thr Ala Lys Gln Ile
        355                 360                 365

Lys Thr Lys Val Asn Lys His Ala Phe Ser Gly Gly Arg Asp Thr Ile
370                 375                 380

Glu Glu His Arg Gln Phe Gly Gly Asn Cys Asp Val Asp Val Ser Phe
385                 390                 395                 400

Met Tyr Leu Thr Phe Phe Leu Glu Asp Asp Lys Leu Glu Gln Ile
                405                 410                 415

Arg Lys Asp Tyr Thr Ser Gly Ala Met Leu Thr Gly Glu Leu Lys Lys
            420                 425                 430

Ala Leu Ile Glu Val Leu Gln Pro Leu Ile Ala Glu His Gln Ala Arg
        435                 440                 445

Arg Lys Glu Val Thr Asp Glu Ile Val Lys Glu Phe Met Thr Pro Arg
        450                 455                 460

Lys Leu Ser Phe Asp Phe Gln
465                 470

<210> SEQ ID NO 66
<211> LENGTH: 470
<212> TYPE: PRT
<213> ORGANISM: Artificial Sequence
<220> FEATURE:
<223> OTHER INFORMATION: Description of Artificial Sequence: Recombinant
      human G

<400> SEQUENCE: 66

```
Pro Asn Ser Glu Pro Ala Ser Leu Leu Glu Leu Phe Asn Ser Ile Ala
1               5                   10                  15

Thr Gln Gly Glu Leu Val Arg Ser Leu Lys Ala Gly Asn Ala Ser Lys
            20                  25                  30

Asp Glu Ile Asp Ser Ala Val Lys Met Leu Val Ser Leu Lys Met Ser
        35                  40                  45

Tyr Lys Ala Ala Ala Gly Glu Asp Tyr Lys Ala Asp Cys Pro Pro Gly
    50                  55                  60

Asn Pro Ala Pro Thr Ser Asn His Gly Pro Asp Ala Thr Glu Ala Glu
65                  70                  75                  80

Glu Asp Phe Val Asp Pro Trp Thr Val Gln Thr Ser Ala Lys Gly
                85                  90                  95

Ile Asp Tyr Asp Lys Leu Ile Val Arg Phe Gly Ser Ser Lys Ile Asp
                100                 105                 110

Lys Glu Leu Ile Asn Arg Ile Glu Arg Ala Thr Gly Gln Arg Pro His
            115                 120                 125

His Phe Leu Arg Arg Gly Ile Phe Phe Ser His Arg Asp Met Asn Gln
130                 135                 140

Val Leu Asp Ala Tyr Glu Asn Lys Lys Pro Phe Tyr Leu Tyr Thr Gly
145                 150                 155                 160

Arg Gly Pro Ser Ser Glu Ala Met His Val Gly His Leu Ile Pro Phe
                165                 170                 175

Ile Phe Thr Lys Trp Leu Gln Asp Val Phe Asn Val Pro Leu Val Ile
                180                 185                 190

Gln Met Thr Asp Asp Glu Lys Tyr Leu Trp Lys Asp Leu Thr Leu Asp
            195                 200                 205

Gln Ala Tyr Gly Tyr Ala Val Glu Asn Ala Lys Asp Ile Ile Ala Cys
210                 215                 220

Gly Phe Asp Ile Asn Lys Thr Phe Ile Phe Ser Asp Leu Asp Tyr Met
225                 230                 235                 240

Gly Met Ser Ser Gly Phe Tyr Lys Asn Val Val Lys Ile Gln Lys His
                245                 250                 255

Val Thr Phe Asn Gln Val Lys Gly Ile Phe Gly Phe Thr Asp Ser Asp
                260                 265                 270

Cys Ile Gly Lys Ile Ser Phe Pro Ala Ile Gln Ala Ala Pro Ser Phe
            275                 280                 285

Ser Asn Ser Phe Pro Gln Ile Phe Arg Asp Arg Thr Asp Ile Gln Cys
290                 295                 300

Leu Ile Pro Cys Ala Ile Asp Gln Asp Pro Tyr Phe Arg Met Thr Arg
305                 310                 315                 320

Asp Val Ala Pro Arg Ile Gly Tyr Pro Lys Pro Ala Leu Leu His Ser
                325                 330                 335

Thr Phe Phe Pro Ala Leu Gln Gly Ala Gln Thr Lys Met Ser Ala Ser
                340                 345                 350

Asp Pro Asn Ser Ser Ile Phe Leu Thr Asp Thr Ala Lys Gln Ile Lys
            355                 360                 365

Thr Lys Val Asn Lys His Ala Phe Ser Gly Gly Arg Asp Thr Ile Glu
370                 375                 380

Glu His Arg Gln Phe Gly Gly Asn Cys Asp Val Asp Val Ser Phe Met
385                 390                 395                 400

Tyr Leu Thr Phe Phe Leu Glu Asp Asp Lys Leu Glu Gln Ile Arg
                405                 410                 415
```

```
Lys Asp Tyr Thr Ser Gly Ala Met Leu Thr Gly Glu Leu Lys Lys Ala
                420                 425                 430

Leu Ile Glu Val Leu Gln Pro Leu Ile Ala Glu His Gln Ala Arg Arg
            435                 440                 445

Lys Glu Val Thr Asp Glu Ile Val Lys Glu Phe Met Thr Pro Arg Lys
    450                 455                 460

Leu Ser Phe Asp Phe Gln
465             470

<210> SEQ ID NO 67
<211> LENGTH: 471
<212> TYPE: PRT
<213> ORGANISM: Artificial Sequence
<220> FEATURE:
<223> OTHER INFORMATION: Description of Artificial Sequence: Recombinant
      human SD variant protein

<400> SEQUENCE: 67

Met Pro Asn Ser Glu Pro Ala Ser Leu Leu Glu Leu Phe Asn Ser Ile
1               5                   10                  15

Ala Thr Gln Gly Glu Leu Val Arg Ser Leu Lys Ala Gly Asn Ala Ser
            20                  25                  30

Lys Asp Glu Ile Asp Ser Ala Val Lys Met Leu Val Ser Leu Lys Met
        35                  40                  45

Ser Tyr Lys Ala Ala Ala Gly Glu Asp Tyr Lys Ala Asp Cys Pro Pro
50                  55                  60

Gly Asn Pro Ala Pro Thr Ser Asn His Gly Pro Asp Ala Thr Glu Ala
65                  70                  75                  80

Glu Glu Asp Phe Val Asp Pro Trp Thr Val Gln Thr Ser Ser Ala Lys
                85                  90                  95

Gly Ile Asp Tyr Asp Lys Leu Ile Val Arg Phe Gly Ser Ser Lys Ile
            100                 105                 110

Asp Lys Glu Leu Ile Asn Arg Ile Glu Arg Ala Thr Gly Gln Arg Pro
        115                 120                 125

His His Phe Leu Arg Arg Gly Ile Phe Phe Ser His Arg Asp Met Asn
    130                 135                 140

Gln Val Leu Asp Ala Tyr Glu Asn Lys Lys Pro Phe Tyr Leu Tyr Thr
145                 150                 155                 160

Gly Arg Gly Pro Ser Ser Glu Ala Met His Val Gly His Leu Ile Pro
                165                 170                 175

Phe Ile Phe Thr Lys Trp Leu Gln Asp Val Phe Asn Val Pro Leu Val
            180                 185                 190

Ile Gln Met Thr Asp Asp Glu Lys Tyr Leu Trp Lys Asp Leu Thr Leu
        195                 200                 205

Asp Gln Ala Tyr Ser Asp Ala Val Glu Asn Ala Lys Asp Ile Ile Ala
    210                 215                 220

Cys Gly Phe Asp Ile Asn Lys Thr Phe Ile Phe Ser Asp Leu Asp Tyr
225                 230                 235                 240

Met Gly Met Ser Ser Gly Phe Tyr Lys Asn Val Val Lys Ile Gln Lys
                245                 250                 255

His Val Thr Phe Asn Gln Val Lys Gly Ile Phe Gly Phe Thr Asp Ser
            260                 265                 270

Asp Cys Ile Gly Lys Ile Ser Phe Pro Ala Ile Gln Ala Ala Pro Ser
        275                 280                 285

Phe Ser Asn Ser Phe Pro Gln Ile Phe Arg Asp Arg Thr Asp Ile Gln
    290                 295                 300
```

```
Cys Leu Ile Pro Cys Ala Ile Asp Gln Asp Pro Tyr Phe Arg Met Thr
305                 310                 315                 320

Arg Asp Val Ala Pro Arg Ile Gly Tyr Pro Lys Pro Ala Leu Leu His
            325                 330                 335

Ser Thr Phe Phe Pro Ala Leu Gln Gly Ala Gln Thr Lys Met Ser Ala
        340                 345                 350

Ser Asp Pro Asn Ser Ser Ile Phe Leu Thr Asp Thr Ala Lys Gln Ile
    355                 360                 365

Lys Thr Lys Val Asn Lys His Ala Phe Ser Gly Gly Arg Asp Thr Ile
370                 375                 380

Glu Glu His Arg Gln Phe Gly Gly Asn Cys Asp Val Asp Val Ser Phe
385                 390                 395                 400

Met Tyr Leu Thr Phe Phe Leu Glu Asp Asp Lys Leu Glu Gln Ile
            405                 410                 415

Arg Lys Asp Tyr Thr Ser Gly Ala Met Leu Thr Gly Glu Leu Lys Lys
            420                 425                 430

Ala Leu Ile Glu Val Leu Gln Pro Leu Ile Ala Glu His Gln Ala Arg
            435                 440                 445

Arg Lys Glu Val Thr Asp Glu Ile Val Lys Glu Phe Met Thr Pro Arg
450                 455                 460

Lys Leu Ser Phe Asp Phe Gln
465                 470

<210> SEQ ID NO 68
<211> LENGTH: 470
<212> TYPE: PRT
<213> ORGANISM: Artificial Sequence
<220> FEATURE:
<223> OTHER INFORMATION: Description of Artificial Sequence: Recombinant
      human SD variant protein

<400> SEQUENCE: 68

Pro Asn Ser Glu Pro Ala Ser Leu Leu Glu Leu Phe Asn Ser Ile Ala
1               5                   10                  15

Thr Gln Gly Glu Leu Val Arg Ser Leu Lys Ala Gly Asn Ala Ser Lys
            20                  25                  30

Asp Glu Ile Asp Ser Ala Val Lys Met Leu Val Ser Leu Lys Met Ser
        35                  40                  45

Tyr Lys Ala Ala Ala Gly Glu Asp Tyr Lys Ala Asp Cys Pro Pro Gly
    50                  55                  60

Asn Pro Ala Pro Thr Ser Asn His Gly Pro Asp Ala Thr Glu Ala Glu
65                  70                  75                  80

Glu Asp Phe Val Asp Pro Trp Thr Val Gln Thr Ser Ser Ala Lys Gly
            85                  90                  95

Ile Asp Tyr Asp Lys Leu Ile Val Arg Phe Gly Ser Ser Lys Ile Asp
            100                 105                 110

Lys Glu Leu Ile Asn Arg Ile Glu Arg Ala Thr Gly Gln Arg Pro His
        115                 120                 125

His Phe Leu Arg Arg Gly Ile Phe Phe Ser His Arg Asp Met Asn Gln
    130                 135                 140

Val Leu Asp Ala Tyr Glu Asn Lys Lys Pro Phe Tyr Leu Tyr Thr Gly
145                 150                 155                 160

Arg Gly Pro Ser Ser Glu Ala Met His Val Gly His Leu Ile Pro Phe
            165                 170                 175

Ile Phe Thr Lys Trp Leu Gln Asp Val Phe Asn Val Pro Leu Val Ile
            180                 185                 190
```

Gln Met Thr Asp Asp Glu Lys Tyr Leu Trp Lys Asp Leu Thr Leu Asp
    195                 200                 205

Gln Ala Tyr Ser Asp Ala Val Glu Asn Ala Lys Asp Ile Ile Ala Cys
    210                 215                 220

Gly Phe Asp Ile Asn Lys Thr Phe Ile Phe Ser Asp Leu Asp Tyr Met
225                 230                 235                 240

Gly Met Ser Ser Gly Phe Tyr Lys Asn Val Val Lys Ile Gln Lys His
                245                 250                 255

Val Thr Phe Asn Gln Val Lys Gly Ile Phe Gly Phe Thr Asp Ser Asp
        260                 265                 270

Cys Ile Gly Lys Ile Ser Phe Pro Ala Ile Gln Ala Ala Pro Ser Phe
    275                 280                 285

Ser Asn Ser Phe Pro Gln Ile Phe Arg Asp Arg Thr Asp Ile Gln Cys
    290                 295                 300

Leu Ile Pro Cys Ala Ile Asp Gln Asp Pro Tyr Phe Arg Met Thr Arg
305                 310                 315                 320

Asp Val Ala Pro Arg Ile Gly Tyr Pro Lys Pro Ala Leu Leu His Ser
                325                 330                 335

Thr Phe Phe Pro Ala Leu Gln Gly Ala Gln Thr Lys Met Ser Ala Ser
        340                 345                 350

Asp Pro Asn Ser Ser Ile Phe Leu Thr Asp Thr Ala Lys Gln Ile Lys
    355                 360                 365

Thr Lys Val Asn Lys His Ala Phe Ser Gly Gly Arg Asp Thr Ile Glu
    370                 375                 380

Glu His Arg Gln Phe Gly Gly Asn Cys Asp Val Asp Val Ser Phe Met
385                 390                 395                 400

Tyr Leu Thr Phe Phe Leu Glu Asp Asp Asp Lys Leu Glu Gln Ile Arg
                405                 410                 415

Lys Asp Tyr Thr Ser Gly Ala Met Leu Thr Gly Glu Leu Lys Lys Ala
        420                 425                 430

Leu Ile Glu Val Leu Gln Pro Leu Ile Ala Glu His Gln Ala Arg Arg
    435                 440                 445

Lys Glu Val Thr Asp Glu Ile Val Lys Glu Phe Met Thr Pro Arg Lys
    450                 455                 460

Leu Ser Phe Asp Phe Gln
465                 470

<210> SEQ ID NO 69
<211> LENGTH: 12
<212> TYPE: PRT
<213> ORGANISM: Artificial Sequence
<220> FEATURE:
<223> OTHER INFORMATION: Description of Artificial Sequence: C-terminal
      peptide

<400> SEQUENCE: 69

Phe Met Thr Pro Arg Lys Leu Ser Phe Asp Phe Gln
1               5                   10

<210> SEQ ID NO 70
<211> LENGTH: 6389
<212> TYPE: DNA
<213> ORGANISM: Artificial Sequence
<220> FEATURE:
<223> OTHER INFORMATION: Description of Artificial Sequence: Plasmid 01
      - pET24b+ with a NdeI/HindIII inSt of Hu T2-WRS (SY variant)
      without 6-H Tag

<400> SEQUENCE: 70

```
tggcgaatgg gacgcgccct gtagcggcgc attaagcgcg gcgggtgtgg tggttacgcg    60
cagcgtgacc gctacacttg ccagcgccct agcgcccgct cctttcgctt tcttcccttc   120
ctttctcgcc acgttcgccg gctttccccg tcaagctcta aatcggggc tccctttagg   180 gttccgattt agtgctttac ggcacctcga ccccaaaaaa cttgattagg gtgatggttc   240
acgtagtggg ccatcgccct gatagacggt ttttcgccct ttgacgttgg agtccacgtt   300
ctttaatagt ggactcttgt tccaaactgg aacaacactc aaccctatct cggtctattc   360
ttttgattta aagggatttt tgccgatttc ggcctattgg ttaaaaaatg agctgattta   420
acaaaatttt aacgcgaatt ttaacaaaat attaacgttt acaatttcag gtggcacttt   480
tcggggaaat gtgcgcggaa cccctatttg tttatttttc taaatacatt caaatatgta   540
tccgctcatg aattaattct tagaaaaact catcgagcat caaatgaaac tgcaatttat   600
tcatatcagg attatcaata ccatattttt gaaaagccg tttctgtaat gaaggagaaa   660
actcaccgag gcagttccat aggatggcaa gatcctggta tcggtctgcg attccgactc   720
gtccaacatc aatacaacct attaatttcc cctcgtcaaa aataaggtta tcaagtgaga   780
aatcaccatg agtgacgact gaatccggtg agaatggcaa aagtttatgc atttcttttcc   840 agacttgttc aacaggccag ccattacgct cgtcatcaaa atcactcgca tcaaccaaac   900
cgttattcat tcgtgattgc gcctgagcga gacgaaatac gcgatcgctg ttaaaaggac   960
aattacaaac aggaatcgaa tgcaaccggc gcaggaacac tgccagcgca tcaacaatat  1020
tttcacctga atcaggatat tcttctaata cctggaatgc tgttttcccg gggatcgcag  1080
tggtgagtaa ccatgcatca tcaggagtac ggataaaatg cttgatggtc ggaagaggca  1140
taaattccgt cagccagttt agtctgacca tctcatctgt aacatcattg gcaacgctac  1200
ctttgccatg tttcagaaac aactctggcg catcgggctt cccatacaat cgatagattg  1260
tcgcacctga ttgcccgaca ttatcgcgag cccatttata cccatataaa tcagcatcca  1320
tgttggaatt taatcgcggc ctagagcaag acgtttcccg ttgaatatgg ctcataacac  1380
cccttgtatt actgtttatg taagcagaca gttttattgt tcatgaccaa aatcccttaa  1440
cgtgagtttt cgttccactg agcgtcagac cccgtagaaa agatcaaagg atcttcttga  1500
gatccttttt ttctgcgcgt aatctgctgc ttgcaaacaa aaaaaccacc gctaccagcg  1560
gtggtttgtt tgccggatca agagctacca actcttttc cgaaggtaac tggcttcagc  1620
agagcgcaga taccaaatac tgtccttcta gtgtagccgt agttaggcca ccacttcaag  1680
aactctgtag caccgcctac atacctcgct ctgctaatcc tgttaccagt ggctgctgcc  1740
agtggcgata agtcgtgtct taccgggttg gactcaagac gatagttacc ggataaggcg  1800
cagcggtcgg gctgaacggg gggttcgtgc acacagccca gcttggagcg aacgacctac  1860
accgaactga gatacctaca gcgtgagcta tgagaaagcg ccacgcttcc cgaagggaga  1920
aaggcggaca ggtatccggt aagcggcagg gtcggaacag gagagcgcac gagggagctt  1980
ccagggggaa acgcctggta tctttatagt cctgtcgggt ttcgccacct ctgacttgag  2040
cgtcgatttt tgtgatgctc gtcagggggg cggagcctat ggaaaaacgc cagcaacgcg  2100 gccttttac ggttcctggc ctttgctgg cttttgctc acatgttctt tcctgcgtta   2160
tcccctgatt ctgtggataa ccgtattacc gcctttgagt gagctgatac cgctcgccgc  2220
agccgaacga ccgagcgcag cgagtcagtg agcgaggaag cggaagagcg cctgatgcgg  2280
tattttctcc ttacgcatct gtgcggtatt tcacaccgca tatatggtgc actctcagta  2340
caatctgctc tgatgccgca tagttaagcc agtatacact ccgctatcgc tacgtgactg  2400
```

```
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccgagag gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
```

```
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatataca tatgagtgca aaaggcatag actacgataa    5100
gctcattgtt cggtttggaa gtagtaaaat tgacaaagag ctaataaacc gaatagagag    5160
agccaccggc caaagaccac accacttcct gcgcagaggc atcttcttct cacacagaga    5220
tatgaatcag gttcttgatg cctatgaaaa taagaagcca ttttatctgt cacgggccg     5280
gggcccctct tctgaagcaa tgcatgtagg tcacctcatt ccatttattt tcacaaagtg    5340
gctccaggat gtatttaacg tgcccttggt catccagatg acggatgacg agaagtatct    5400
gtggaaggac ctgaccctgg accaggccta tagctatgct gtggagaatg ccaaggacat    5460
catcgcctgt ggcttttgaca tcaacaagac tttcatattc tctgacctgg actacatggg    5520
gatgagctca ggtttctaca aaaatgtggt gaagattcaa aagcatgtta ccttcaacca    5580
agtgaaaggc attttcggct tcactgacag cgactgcatt gggaagatca gttttcctgc    5640
catccaggct gctccctcct tcagcaactc attcccacag atcttccgag acaggacgga    5700
tatccagtgc cttatcccat gtgccattga ccaggatcct tactttagaa tgacaaggga    5760
cgtcgccccc aggatcggct atcctaaacc agccctgttg cactccacct tcttcccagc    5820
cctgcagggc gcccagacca aaatgagtgc cagcgacccc aactcctcca tcttcctcac    5880
cgacacggcc aagcagatca aaaccaaggt caataagcat gcgttttctg gagggagaga    5940
caccatcgag gagcacaggc agtttggggg caactgtgat gtggacgtgt ctttcatgta    6000
cctgaccttc ttcctcgagg acgacgacaa gctcgagcag atcaggaagg attacaccag    6060
cggagccatg ctcaccggtg agctcaagaa ggcactcata gaggttctgc agcccttgat    6120
cgcagagcac caggcccggc gcaaggaggt cacggatgag atagtgaaag agttcatgac    6180
tccccggaag ctgtccttcg actttcagtg aaagcttgcg gccgcactcg agcaccacca    6240
ccaccaccac tgagatccgg ctgctaacaa agcccgaaag gaagctgagt tggctgctgc    6300
caccgctgag caataactag cataacccct ggggcctcct aaacgggtct tgaggggttt    6360
tttgctgaaa ggaggaacta tatccggat                                      6389
```

<210> SEQ ID NO 71  
<211> LENGTH: 4742  
<212> TYPE: DNA  
<213> ORGANISM: Artificial Sequence  
<220> FEATURE:  
<223> OTHER INFORMATION: Description of Artificial Sequence: Plasmid 02: pET20b+ with a NdeI/HindIII inSt of Hu T2-WRS (SY variant), with 6-H Tag

<400> SEQUENCE: 71

```
tggcgaatgg gacgcgccct gtagcggcgc attaagcgcg gcgggtgtgg tggttacgcg    60
cagcgtgacc gctacacttg ccagcgccct agcgcccgct cctttcgctt tcttcccttc   120
ctttctcgcc acgttcgccg gctttccccg tcaagctcta aatcgggggc tccctttagg   180
gttccgattt agtgctttac ggcacctcga ccccaaaaaa cttgattagg gtgatggttc   240
acgtagtggg ccatcgccct gatagacggt ttttcgccct ttgacgttgg agtccacgtt   300
ctttaatagt ggactcttgt tccaaactgg aacaacactc aacccatctc tggtctattc   360
ttttgattta taagggattt tgccgatttc ggcctattgg ttaaaaaatg agctgattta   420
```

```
acaaaaattt aacgcgaatt ttaacaaaat attaacgttt acaatttcag gtggcacttt    480
tcggggaaat gtgcgcggaa cccctatttg tttattttc taaatacatt caaatatgta    540
tccgctcatg agacaataac cctgataaat gcttcaataa tattgaaaaa ggaagagtat    600
gagtattcaa catttccgtg tcgcccttat tccctttttt gcggcatttt gccttcctgt    660
ttttgctcac ccagaaacgc tggtgaaagt aaaagatgct gaagatcagt tgggtgcacg    720
agtgggttac atcgaactgg atctcaacag cggtaagatc cttgagagtt ttcgccccga    780
agaacgtttt ccaatgatga gcacttttaa agttctgcta tgtggcgcgg tattatcccg    840
tattgacgcc gggcaagagc aactcggtcg ccgcatacac tattctcaga atgacttggt    900
tgagtactca ccagtcacag aaaagcatct tacggatggc atgacagtaa gagaattatg    960
cagtgctgcc ataaccatga gtgataacac tgcggccaac ttacttctga caacgatcgg    1020
aggaccgaag gagctaaccg cttttttgca caacatgggg gatcatgtaa ctcgccttga    1080
tcgttgggaa ccggagctga atgaagccat accaaacgac gagcgtgaca ccacgatgcc    1140
tgcagcaatg gcaacaacgt tgcgcaaact attaactggc gaactactta ctctagcttc    1200
ccggcaacaa ttaatagact ggatggaggc ggataaagtt gcaggaccac ttctgcgctc    1260
ggcccttccg gctggctggt ttattgctga taaatctgga gccggtgagc gtgggtctcg    1320
cggtatcatt gcagcactgg ggccagatgg taagccctcc cgtatcgtag ttatctacac    1380 gacgggagt caggcaacta tggatgaacg aaatagacag atcgctgaga taggtgcctc    1440
actgattaag cattggtaac tgtcagacca agtttactca tatatacttt agattgattt    1500
aaaacttcat ttttaattta aaaggatcta ggtgaagatc cttttttgata atctcatgac    1560 caaaatccct aacgtgagt tttcgttcca ctgagcgtca gaccccgtag aaaagatcaa    1620
aggatcttct tgagatcctt ttttttctgcg cgtaatctgc tgcttgcaaa caaaaaaacc    1680
accgctacca gcggtggttt gtttgccgga tcaagagcta ccaactcttt ttccgaaggt    1740
aactggcttc agcagagcgc agataccaaa tactgtcctt ctagtgtagc cgtagttagg    1800
ccaccacttc aagaactctg tagcaccgcc tacatacctc gctctgctaa tcctgttacc    1860
agtggctgct gccagtggcg ataagtcgtg tcttaccggg ttggactcaa gacgatagtt    1920
accggataag gcgcagcggt cgggctgaac ggggggttcg tgcacacagc ccagcttgga    1980
gcgaacgacc tacaccgaac tgagatacct acagcgtgag ctatgagaaa gcgccacgct    2040
tcccgaaggg agaaaggcgg acaggtatcc ggtaagcggc agggtcggaa caggagagcg    2100
cacgagggag cttccagggg gaaacgcctg gtatctttat agtcctgtcg ggtttcgcca    2160
cctctgactt gagcgtcgat ttttgtgatg ctcgtcaggg gggcggagcc tatggaaaaa    2220
cgccagcaac gcggcctttt tacggttcct ggccttttgc tggccttttg ctcacatgtt    2280
ctttcctgcg ttatccctg attctgtgga taaccgtatt accgcctttg agtgagctga    2340
taccgctcgc cgcagccgaa cgaccgagcg cagcgagtca gtgagcgagg aagcggaaga    2400
gcgcctgatg cggtattttc tccttacgca tctgtgcggt atttcacacc gcatatatgg    2460
tgcactctca gtacaatctg ctctgatgcc gcatagttaa gccagtatac actccgctat    2520
cgctacgtga ctgggtcatg gctgcgcccc gacacccgcc aacacccgct gacgcgccct    2580
gacgggcttg tctgctcccg gcatccgctt acagacaagc tgtgaccgtc tccgggagct    2640
gcatgtgtca gaggttttca ccgtcatcac cgaaacgcgc gaggcagctg cggtaaagct    2700
catcagcgtg gtcgtgaagc gattcacaga tgtctgcctg ttcatccgcg tccagctcgt    2760
tgagtttctc cagaagcgtt aatgtctggc ttctgataaa gcgggccatg ttaagggcgg    2820
```

```
ttttttcctg tttggtcact gatgcctccg tgtaaggggg atttctgttc atggggtaa      2880
tgataccgat gaaacgagag aggatgctca cgatacgggt tactgatgat gaacatgccc      2940
ggttactgga acgttgtgag ggtaaacaac tggcggtatg gatgcggcgg gaccagagaa      3000
aaatcactca gggtcaatgc cagcgcttcg ttaatacaga tgtaggtgtt ccacagggta      3060
gccagcagca tcctgcgatg cagatccgga acataatggt gcagggcgct gacttccgcg      3120
tttccagact ttacgaaaca cggaaaccga agaccattca tgttgttgct caggtcgcag      3180
acgttttgca gcagcagtcg cttcacgttc gctcgcgtat cggtgattca ttctgctaac      3240
cagtaaggca accccgccag cctagccggg tcctcaacga caggagcacg atcatgcgca      3300
cccgtggcca ggacccaacg ctgcccgaga tctcgatccc gcgaaattaa tacgactcac      3360
tataggagac cacaacggt ttccctctag aaataatttt gtttaacttt aagaaggaga      3420
tatacatatg agtgcaaaag gcatagacta cgataagctc attgttcggt ttggaagtag      3480
taaaattgac aaagagctaa taaaccgaat agagagagcc accggccaaa gaccacacca      3540
cttcctgcgc agaggcatct tcttctcaca cagagatatg aatcaggttc ttgatgccta      3600
tgaaaataag aagccatttt atctgtacac gggccgggc ccctcttctg aagcaatgca      3660
tgtaggtcac ctcattccat ttattttcac aaagtggctc caggatgtat ttaacgtgcc      3720
cttggtcatc cagatgacgg atgacgagaa gtatctgtgg aaggacctga ccctggacca      3780
ggcctatagc tatgctgtgg agaatgccaa ggacatcatc gcctgtggct ttgacatcaa      3840
caagactttc atattctctg acctggacta catgggatg agctcaggtt tctacaaaaa      3900
tgtggtgaag attcaaaagc atgttacctt caaccaagtg aaaggcattt tcggcttcac      3960
tgacagcgac tgcattggga agatcagttt tcctgccatc caggctgctc cctccttcag      4020
caactcattc ccacagatct tccgagacag gacggatatc cagtgcctta tcccatgtgc      4080
cattgaccag gatccttact ttagaatgac aagggacgtc gcccccagga tcggctatcc      4140
taaaccagcc ctgttgcact ccaccttctt cccagccctg cagggcgccc agaccaaaat      4200
gagtgccagc gaccccaact cctccatctt cctcaccgac acggccaagc agatcaaaac      4260
caaggtcaat aagcatgcgt tttctggagg gagagacacc atcgaggagc acaggcagtt      4320
tgggggcaac tgtgatgtgg acgtgtcttt catgtacctg accttcttcc tcgaggacga      4380
cgacaagctc gagcagatca ggaaggatta ccagcgcgga gccatgctca ccggtgagct      4440
caagaaggca ctcatagagg ttctgcagcc cttgatcgca gagcaccagg cccggcgcaa      4500
ggaggtcacg gatgagatag tgaaagagtt catgactccc cggaagctgt ccttcgactt      4560
tcagaagctt gcggccgcac tcgagcacca ccaccaccac cactgagatc cggctgctaa      4620
caaagcccga aggaagctg agttggctgc tgccaccgct gagcaataac tagcataacc      4680
ccttggggcc tctaaacggg tcttgagggg ttttttgctg aaaggaggaa ctatatccgg      4740
at                                                                     4742

<210> SEQ ID NO 72
<211> LENGTH: 4769
<212> TYPE: DNA
<213> ORGANISM: Artificial Sequence
<220> FEATURE:
<223> OTHER INFORMATION: Description of Artificial Sequence: Plasmid
      04 pET20b+ with a NdeI/HindIII inSt of T2-WRS (SY variant), 6-H
      Tag w/Tombin Cleavage Site

<400> SEQUENCE: 72
tggcgaatgg gacgcgccct gtagcggcgc attaagcgcg gcgggtgtgg tggttacgcg      60
```

```
cagcgtgacc gctacacttg ccagcgccct agcgcccgct cctttcgctt tcttcccttc    120
cttcctcgcc acgttcgccg gctttccccg tcaagctcta aatcggggc tcccttagg       180 gttccgattt agtgctttac ggcacctcga ccccaaaaaa cttgattagg gtgatggttc    240
acgtagtggg ccatcgccct gatagacggt ttttcgccct ttgacgttgg agtccacgtt    300
ctttaatagt ggactcttgt tccaaactgg aacaacactc aaccctatct cggtctattc    360
ttttgattta tagggatttt tgccgattc ggcctattgg ttaaaaatg agctgattta      420 acaaaatttt aacgcgaatt ttaacaaaat attaacgttt acaatttcag gtggcacttt    480
tcggggaaat gtgcgcggaa ccccttattg ttttattttc taaatacatt caaatatgta    540
tccgctcatg agacaataac cctgataaat gcttcaataa tattgaaaaa ggaagagtat    600
gagtattcaa catttccgtg tcgcccttat tccttttttt gcggcatttt gccttcctgt    660
ttttgctcac ccagaaacgc tggtgaaagt aaaagatgct gaagatcagt tgggtgcacg    720
agtgggttac atcgaactgg atctcaacag cggtaagatc cttgagagtt ttcgccccga    780
agaacgtttt ccaatgatga gcacttttaa agttctgcta tgtggcgcgg tattatcccg    840
tattgacgcc gggcaagagc aactcggtcg ccgcatacac tattctcaga atgacttggt    900
tgagtactca ccagtcacag aaaagcatct tacggatggc atgacagtaa gagaattatg    960
cagtgctgcc ataaccatga gtgataacac tgcggccaac ttacttctga caacgatcgg    1020
aggaccgaag gagctaaccg cttttttgca caacatgggg gatcatgtaa ctcgccttga    1080
tcgttgggaa ccggagctga atgaagccat accaaacgac gagcgtgaca ccacgatgcc    1140
tgcagcaatg gcaacaacgt tgcgcaaact attaactggc gaactactta ctctagcttc    1200
ccggcaacaa ttaatagact ggatggaggc ggataaagtt gcaggaccac ttctgcgctc    1260
ggcccttccg gctggctggt ttattgctga taaatctgga gccggtgagc gtgggtctcg    1320
cggtatcatt gcagcactgg ggccagatgg taagccctcc cgtatcgtag ttatctacac    1380 gacgggagt caggcaacta tggatgaacg aaatagacag atcgctgaga taggtgcctc    1440
actgattaag cattggtaac tgtcagacca agtttactca tatatacttt agattgattt    1500
aaaacttcat ttttaattta aaaggatcta ggtgaagatc ctttttgata atctcatgac    1560
caaaatccct aacgtgagt tttcgttcca ctgagcgtca ccccgtag aaaagatcaa        1620 aggatcttct tgagatcctt ttttctgcg cgtaatctgc tgcttgcaaa caaaaaaacc     1680
accgctacca gcggtggttt gtttgccgga tcaagagcta ccaactcttt ttccgaaggt    1740
aactggcttc agcagagcgc agataccaaa tactgtcctt ctagtgtagc cgtagttagg    1800
ccaccacttc aagaactctg tagcaccgcc tacatacctc gctctgctaa tcctgttacc    1860
agtggctgct gccagtggcg ataagtcgtg tcttaccggg ttggactcaa gacgatagtt    1920
accggataag gcgcagcggt cgggctgaac ggggggttcg tgcacacagc ccagcttgga    1980
gcgaacgacc tacaccgaac tgagatacct acagcgtgag ctatgagaaa gcgccacgct    2040
tcccgaaggg agaaaggcgg acaggtatcc ggtaagcggc agggtcggaa caggagagcg    2100
cacgagggag cttccagggg gaaacgcctg gtatctttat agtcctgtcg gtttcgccac    2160
cctctgactt gagcgtcgat ttttgtgatg ctcgtcaggg gggcggagcc tatggaaaaa    2220
cgccagcaac gcggcctttt tacgttcct ggccttttgc tggcctttg ctcacatgtt      2280 ctttcctgcg ttatccctg attctgtgga taaccgtatt accgcctttg agtgagctga    2340
taccgctcgc cgcagccgaa cgaccgagcg cagcgagtca gtgagcgagg aagcggaaga    2400
gcgcctgatg cggtattttc tccttacgca tctgtgcggt atttcacacc gcatatatgg    2460
```

| | |
|---|---|
| tgcactctca gtacaatctg ctctgatgcc gcatagttaa gccagtatac actccgctat | 2520 |
| cgctacgtga ctgggtcatg gctgcgcccc gacacccgcc aacacccgct gacgcgccct | 2580 |
| gacgggcttg tctgctcccg gcatccgctt acagacaagc tgtgaccgtc tccgggagct | 2640 |
| gcatgtgtca gaggttttca ccgtcatcac cgaaacgcgc gaggcagctg cggtaaagct | 2700 |
| catcagcgtg gtcgtgaagc gattcacaga tgtctgcctg ttcatccgcg tccagctcgt | 2760 |
| tgagtttctc cagaagcgtt aatgtctggc ttctgataaa gcgggccatg ttaagggcgg | 2820 |
| ttttttcctg tttggtcact gatgcctccg tgtaaggggg atttctgttc atggggtaa | 2880 |
| tgataccgat gaaacgagag aggatgctca cgatacgggt tactgatgat gaacatgccc | 2940 |
| ggttactgga acgttgtgag ggtaaacaac tggcggtatg gatgcggcgg gaccagagaa | 3000 |
| aaatcactca gggtcaatgc cagcgcttcg ttaatacaga tgtaggtgtt ccacagggta | 3060 |
| gccagcagca tcctgcgatg cagatccgga acataatggt gcagggcgct gacttccgcg | 3120 |
| tttccagact ttacgaaaca cggaaaccga agaccattca tgttgttgct caggtcgcag | 3180 |
| acgttttgca gcagcagtcg cttcacgttc gctcgcgtat cggtgattca ttctgctaac | 3240 |
| cagtaaggca accccgccag cctagccggg tcctcaacga caggagcacg atcatgcgca | 3300 |
| cccgtggcca ggacccaacg ctgcccgaga tctcgatccc gcgaaattaa tacgactcac | 3360 |
| tataggagac cacaacggt ttccctctag aaataatttt gtttaacttt aagaaggaga | 3420 |
| tatacatatg agtgcaaaag gcatagacta cgataagctc attgttcggt ttggaagtag | 3480 |
| taaaattgac aaagagctaa taaaccgaat agagagagcc accggccaaa gaccacacca | 3540 |
| cttcctgcgc agaggcatct tcttctcaca cagagatatg aatcaggttc ttgatgccta | 3600 |
| tgaaaataag aagccatttt atctgtacac gggccgggc ccctcttctg aagcaatgca | 3660 |
| tgtaggtcac ctcattccat ttattttcac aaagtggctc caggatgtat ttaacgtgcc | 3720 |
| cttggtcatc cagatgacgg atgacgagaa gtatctgtgg aaggacctga ccctggacca | 3780 |
| ggcctatagc tatgctgtgg agaatgccaa ggacatcatc gcctgtggct ttgacatcaa | 3840 |
| caagactttc atattctctg acctggacta catggggatg agctcaggtt tctacaaaaa | 3900 |
| tgtggtgaag attcaaaagc atgttacctt caaccaagtg aaaggcattt tcggcttcac | 3960 |
| tgacagcgac tgcattggga agatcagttt tcctgccatc caggctgctc cctccttcag | 4020 |
| caactcattc ccacagatct tccgagacag gacggatatc cagtgcctta tcccatgtgc | 4080 |
| cattgaccag gatccttact ttagaatgac aagggacgtc gcccccagga tcggctatcc | 4140 |
| taaaccagcc ctgttgcact ccaccttctt cccagccctg cagggcgccc agaccaaaat | 4200 |
| gagtgccagc gaccccaact cctccatctt cctcaccgac acggccaagc agatcaaaac | 4260 |
| caaggtcaat aagcatgcgt tttctggagg gagagacacc atcgaggagc acaggcagtt | 4320 |
| tgggggcaac tgtgatgtgg acgtgtcttt catgtacctg accttcttcc tcgaggacga | 4380 |
| cgacaagctc gagcagatca ggaaggatta caccagcgga gccatgctca ccggtgagct | 4440 |
| caagaaggca ctcatagagg ttctgcagcc cttgatcgca gagcaccagg cccggcgcaa | 4500 |
| ggaggtcacg gatgagatag tgaaagagtt catgactccc cggaagctgt ccttcgactt | 4560 |
| tcagtcttct ggtctggtgc cacgcggttc taagcttgcg gccgcactcg agcaccacca | 4620 |
| ccaccaccac tgagatccgg ctgctaacaa agcccgaaag gaagctgagt tggctgctgc | 4680 |
| caccgctgag caataactag cataacccct tggggcctct aaacgggtct tgaggggttt | 4740 |
| tttgctgaaa ggaggaacta tatccggat | 4769 |

<210> SEQ ID NO 73

<211> LENGTH: 6326
<212> TYPE: DNA
<213> ORGANISM: Artificial Sequence
<220> FEATURE:
<223> OTHER INFORMATION: Description of Artificial Sequence: Plasmid 06 pET24b+ with a NdeI/XhoI inSt of Hu mini-YRS, 6-H Tag

<400> SEQUENCE: 73

```
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcggggggc tcccttttagg     180
gttccgattt agtgctttac ggcacctcga ccccaaaaaa cttgattagg gtgatggttc     240
acgtagtggg ccatcgccct gatagacggt ttttcgccct tgacgttgg agtccacgtt      300
ctttaatagt ggactcttgt tccaaactgg aacaacactc aaccctatct cggtctattc     360
ttttgattta agggatttt gccgatttc ggcctattgg ttaaaaatg agctgattta        420
acaaaattt aacgcgaatt ttaacaaaat attaacgttt acaatttcag gtggcacttt      480
tcggggaaat gtgcgcggaa ccctatttg tttattttc taaatacatt caaatatgta       540
tccgctcatg aattaattct tagaaaaact catcgagcat caaatgaaac tgcaatttat     600
tcatatcagg attatcaata ccatatttt gaaaaagccg tttctgtaat gaaggagaaa      660
actcaccgag gcagttccat aggatggcaa gatcctggta tcggtctgcg attccgactc     720
gtccaacatc aatacaacct attaatttcc cctcgtcaaa aataaggtta tcaagtgaga     780
aatcaccatg agtgacgact gaatccggtg agaatggcaa aagtttatgc atttctttcc     840
agacttgttc aacaggccag ccattacgct cgtcatcaaa atcactcgca tcaaccaaac     900
cgttattcat tcgtgattgc gcctgagcga cgaaatac gcgatcgctg ttaaaaggac       960
aattacaaac aggaatcgaa tgcaaccggc gcaggaacac tgccagcgca tcaacaatat    1020
tttcacctga atcaggatat tcttctaata cctggaatgc tgttttcccg gggatcgcag    1080
tggtgagtaa ccatgcatca tcaggagtac ggataaaatg cttgatggtc ggaagaggca    1140
taaattccgt cagccagttt agtctgacca tctcatctgt aacatcattg gcaacgctac    1200
ctttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
cccttgtatt actgtttatg taagcagaca gttttattgt tcatgaccaa atcccttaa    1440
cgtgagtttt cgttccactg agcgtcagac cccgtagaaa agatcaaagg atcttcttga    1500
gatcctttt tctgcgcgt aatctgctgc ttgcaaacaa aaaaaccacc gctaccagcg     1560
gtggtttgtt tgccggatca agagctacca actcttttc cgaaggtaac tggcttcagc    1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata gtcgtgtct taccggggttg gactcaagac gatagttacc ggataaggcg    1800
cagcggtcgg gctgaacggg gggttcgtgc acacagccca gcttggagcg aacgacctac    1860
accgaactga tacctacag cgtgagcta tgagaaagcg ccacgcttcc gaagggaga       1920
aaggcggaca ggtatccggt aagcggcagg gtcggaacag gagagcgcac gagggagctt    1980
ccagggggaa acgcctggta tctttatagt cctgtcgggt ttcgccacct ctgacttgag    2040
cgtcgatttt tgtgatgctc gtcagggggg cggagcctat ggaaaaacgc cagcaacgcg    2100
gcctttttac ggttcctggc cttttgctgg cctttttgctc acatgttctt tcctgcgtta    2160
```

```
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccgagag ctgccggca cctgtcctac   3360 gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccgaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
```

```
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc aacagtccc     4800 ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccgccac gatgcgtccg gcgtagagga tcgagatctc gatcccgcga     4980
aattaatacg actcactata ggggaattgt gagcggataa caattcccct ctagaaataa    5040
ttttgtttaa ctttaagaag gagatataca tatgggggac gctcccagcc ctgaagagaa    5100
actgcacctt atcacccgga acctgcagga ggttctgggg gaagagaagc tgaaggagat    5160
actgaaggag cgggaactta aaatttactg gggaacggca accacgggca aaccacatgt    5220
ggcttacttt gtgcccatgt caaagattgc agacttctta aaggcagggt gtgaggtaac    5280
aattctgttt gcggacctcc acgcatacct ggataacatg aaagcccat gggaacttct     5340 agaactccga gtcagttact atgagaatgt gatcaaagca atgctggaga gcattggtgt    5400
gcccttggag aagctcaagt tcatcaaagg cactgattac cagctcagca aagagtacac    5460
actagatgtg tacagactct cctccgtggt cacacagcac gattccaaga aggctggagc    5520
tgaggtggta aagcaggtgg agcacccttt gctgagtggc ctcttatacc ccggactgca    5580
ggctttggat gaagagtatt taaaagtaga tgcccaattt ggaggcattg atcagagaaa    5640
gattttcacc tttgcagaga agtacctccc tgcacttggc tattcaaaac gggtccatct    5700
gatgaatcct atggttccag gattaacagg cagcaaaatg agctcttcag aagaggagtc    5760
caagattgat ctccttgatc ggaaggagga tgtgaagaaa aaactgaaga aggccttctg    5820
tgagccagga aatgtggaga acaatggggt tctgtccttc atcaagcatg tccttttcc     5880 ccttaagtcc gagtttgtga tcctacgaga tgagaaatgg ggtggaaaca aacctacac     5940 agcttacgtg gacctggaaa aggactttgc tgctgaggtt gtacatcctg gagacctgaa    6000
gaattctgtt gaagtcgcac tgaacaagtt gctggatcca atccgggaaa agtttaatac    6060
ccctgccctg aaaaaactgg ccagcgctgc ctacccagat ccctcaaagc agaagccaat    6120
ggccaaaggc cctgccaaga attcagaacc agaggaggtc atcctcgagc accaccacca    6180
ccaccactga gatccggctg ctaacaaagc ccgaaaggaa gctgagttgg ctgctgccac    6240
cgctgagcaa taactagcat aaccccttgg ggcctctaaa cgggtcttga ggggttttt     6300 gctgaaagga ggaactatat ccggat                                         6326
```

<210> SEQ ID NO 74
<211> LENGTH: 6563
<212> TYPE: DNA
<213> ORGANISM: Artificial Sequence
<220> FEATURE:
<223> OTHER INFORMATION: Description of Artificial Sequence: Plasmid 07 pET24b+ with a NdeI/HindIII inSt of Hu mini-WRS, (SY variant) 6-H Tag

<400> SEQUENCE: 74

```
tggcgaatgg gacgcgccct gtagcggcgc attaagcgcg gcgggtgtgg tggttacgcg     60
cagcgtgacc gctacacttg ccagcgccct agcgcccgct cctttcgctt tcttcccttc    120
ctttctcgcc acgttcgccg gctttccccg tcaagctcta aatcggggc tccctttagg     180 gttccgattt agtgctttac ggcacctcga ccccaaaaaa cttgattagg gtgatggttc    240
```

```
acgtagtggg ccatcgccct gatagacggt ttttcgccct ttgacgttgg agtccacgtt    300
ctttaatagt ggactcttgt tccaaactgg aacaacactc aaccctatct cggtctattc    360
ttttgattta tagggatttt tgccgatttc ggcctattgg ttaaaaaatg agctgattta    420
acaaaaattt aacgcgaatt ttaacaaaat attaacgttt acaatttcag gtggcacttt    480
tcggggaaat gtgcgcggaa ccectatttg tttatttttc taaatacatt caaatatgta    540
tccgctcatg aattaattct tagaaaaact catcgagcat caaatgaaac tgcaatttat    600
tcatatcagg attatcaata ccatattttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat    1020
tttcacctga atcaggatat tcttctaata cctggaatgc tgttttcccg gggatcgcag    1080
tggtgagtaa ccatgcatca tcaggagtac ggataaaatg cttgatggtc ggaagaggca    1140
taaattccgt cagccagttt agtctgacca tctcatctgt aacatcattg gcaacgctac    1200
ctttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
cccttgtatt actgtttatg taagcagaca gttttattgt tcatgaccaa aatcccttaa    1440
cgtgagtttt cgttccactg agcgtcagac cccgtagaaa agatcaaagg atcttcttga    1500
gatccttttt ttctgcgcgt aatctgctgc ttgcaaacaa aaaaaccacc gctaccagcg    1560
gtggtttgtt tgccggatca agagctacca actcttttc cgaaggtaac tggcttcagc    1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata gtcgtgtct taccggggttg gactcaagac gatagttacc ggataaggcg    1800
cagcggtcgg gctgaacggg gggttcgtgc acacagccca gcttggagcg aacgacctac    1860
accgaactga gatacctaca gcgtgagcta tgagaaagcg ccacgcttcc cgaagggaga    1920
aaggcggaca ggtatccggt aagcggcagg gtcggaacag gagagcgcac gagggagctt    1980
ccagggggaa acgcctggta tctttatagt cctgtcgggt ttcgccacct ctgacttgag    2040
cgtcgatttt tgtgatgctc gtcaggggggg cggagcctat ggaaaaacgc cagcaacgcg    2100
gcctttttac ggttcctggc cttttgctgg ccttttgctc acatgttctt tcctgcgtta    2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
```

```
aagcgttaat gtctggcttc tgataaagcg ggccatgtta agggcggttt tttcctgttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag gtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg tgtccggga    4680 tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
```

```
ttttgtttaa ctttaagaag gagatataca tatgagctac aaagctgccg cgggggagga    5100
ttacaaggct gactgtcctc cagggaaccc agcacctacc agtaatcatg cccagatgc     5160 cacagaagct gaagaggatt ttgtggaccc atggacagta cagacaagca gtgcaaaagg    5220
catagactac gataagctca ttgttcggtt tggaagtagt aaaattgaca aagagctaat    5280
aaaccgaata gagagagcca ccggccaaag accacaccac ttcctgcgca gaggcatctt    5340
cttctcacac agagatatga atcaggttct tgatgcctat gaaaataaga agccatttta    5400
tctgtacacg ggccggggcc cctcttctga agcaatgcat gtaggtcacc tcattccatt    5460
tattttcaca aagtggctcc aggatgtatt taacgtgccc ttggtcatcc agatgacgga    5520
tgacgagaag tatctgtgga aggacctgac cctggaccag gcctatagct atgctgtgga    5580
gaatgccaag gacatcatcg cctgtggctt tgacatcaac aagactttca tattctctga    5640
cctggactac atggggatga gctcaggttt ctacaaaaat gtggtgaaga ttcaaaagca    5700
tgttaccttc aaccaagtga aaggcatttt cggcttcact gacagcgact gcattgggaa    5760
gatcagtttt cctgccatcc aggctgctcc ctccttcagc aactcattcc cacagatctt    5820
ccgagacagg acgatatcc agtgcctat cccatgtgcc attgaccagg atccttactt      5880
tagaatgaca agggacgtcg cccccaggat cggctatcct aaaccagccc tgttgcactc    5940
caccttcttc ccagccctgc agggcgccca gaccaaaatg agtgccagcg accccaactc    6000
ctccatcttc ctcaccgaca cggccaagca gatcaaaacc aaggtcaata gcatgcgtt    6060 ttctggaggg agagacacca tcgaggagca caggcagttt gggggcaact gtgatgtgga    6120
cgtgtctttc atgtacctga ccttcttcct cgaggacgac gacaagctcg agcagatcag    6180
gaaggattac accagcggag ccatgctcac cggtgagctc aagaaggcac tcatagaggt    6240
tctgcagccc ttgatcgcag agcaccaggc ccggcgcaag gaggtcacgg atgagatagt    6300
gaaagagttc atgactcccc ggaagctgtc cttcgacttt cagaagcttg cggccgcact    6360
cgagcaccac caccaccacc actgaaagct tgcggccgca ctcgagcacc accaccacca    6420
ccactgagat ccggctgcta acaaagcccg aaaggaagct gagttggctg ctgccaccgc    6480
tgagcaataa ctagcataac cccttggggc ctctaaacgg gtcttgaggg gttttttgct    6540
gaaaggagga actatatccg gat                                            6563
```

<210> SEQ ID NO 75
<211> LENGTH: 6329
<212> TYPE: DNA
<213> ORGANISM: Artificial Sequence
<220> FEATURE:
<223> OTHER INFORMATION: Description of Artificial Sequence: Plasmid
      09: pET24b+ with a NdeI/XhoI inSt of Hu mini-YRS, No H Tag

<400> SEQUENCE: 75

```
tggcgaatgg gacgcgccct gtagcggcgc attaagcgcg gcgggtgtgg tggttacgcg     60
cagcgtgacc gctacacttg ccagcgccct agcgcccgct cctttcgctt tcttcccttc    120
ctttctcgcc acgttcgccg gctttccccg tcaagctcta aatcggggc tccctttagg    180 gttccgattt agtgctttac ggcacctcga ccccaaaaaa cttgattagg gtgatggttc    240
acgtagtggg ccatcgccct gatagacggt ttttcgccct ttgacgttgg agtccacgtt    300
ctttaatagt ggactcttgt tccaaactgg aacaacactc aaccctatct cggtctattc    360
ttttgattta aagggatt tgccgatttc ggcctattgg ttaaaaaatg agctgattta    420
acaaaaattt aacgcgaatt ttaacaaaat attaacgttt acaatttcag gtggcacttt    480
```

```
tcggggaaat gtgcgcggaa cccctatttg tttattttc taaatacatt caaatatgta    540
tccgctcatg aattaattct tagaaaaact catcgagcat caaatgaaac tgcaatttat    600
tcatatcagg attatcaata ccatattttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa aagtttatgc atttcttttcc   840 agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200 cttttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actcttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata gtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100 gccttttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac cccgctgac gcgccctgac gggcttgtct   2460
gctcccggca tccgcttaca cagaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt ttcctgtttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
```

```
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccgaaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgcggcccac gatgcgtccg gcgtagagga tcgagatctc gatcccgcga   4980
aattaatacg actcactata gggaattgt gagcggataa caattcccct ctagaaataa   5040
ttttgtttaa ctttaagaag gagatataca tatggggggac gctcccagcc ctgaagagaa   5100
actgcacctt atcacccgga acctgcagga ggttctgggg gaagagaagc tgaaggagat   5160
actgaaggag cggaaactta aaatttactg gggaacggca accacgggca aaccacatgt   5220
ggcttacttt gtgcccatgt caaagattgc agacttctta aaggcagggt gtgaggtaac   5280
```

```
aattctgttt gcggacctcc acgcatacct ggataacatg aaagccccat gggaacttct    5340
agaactccga gtcagttact atgagaatgt gatcaaagca atgctggaga gcattggtgt    5400
gcccttggag aagctcaagt tcatcaaagg cactgattac cagctcagca aagagtacac    5460
actagatgtg tacagactct cctccgtggt cacacagcac gattccaaga aggctggagc    5520
tgaggtggta aagcaggtgg agcacccttt gctgagtggc ctcttatacc ccggactgca    5580
ggctttggat gaagagtatt taaaagtaga tgcccaattt ggaggcattg atcagagaaa    5640
gattttcacc tttgcagaga agtacctccc tgcacttggc tattcaaaac gggtccatct    5700
gatgaatcct atggttccag gattaacagg cagcaaaatg agctcttcag aagaggagtc    5760
caagattgat ctccttgatc ggaaggagga tgtgaagaaa aaactgaaga aggccttctg    5820
tgagccagga aatgtggaga acaatggggt tctgtccttc atcaagcatg tccttttcc     5880 ccttaagtcc gagtttgtga tcctacgaga tgagaaatgg ggtggaaaca aaacctacac    5940
agcttacgtg gacctggaaa aggactttgc tgctgaggtt gtacatcctg gagacctgaa    6000
gaattctgtt gaagtcgcac tgaacaagtt gctggatcca atccgggaaa agtttaatac    6060
ccctgccctg aaaaaactgg ccagcgctgc ctacccagat ccctcaaagc agaagccaat    6120
ggccaaaggc cctgccaaga attcagaacc agaggaggtc atctgactcg agcaccacca    6180
ccaccaccac tgagatccgg ctgctaacaa agcccgaaag gaagctgagt tggctgctgc    6240
caccgctgag caataactag cataacccct tggggcctct aaacgggtct tgaggggttt    6300
tttgctgaaa ggaggaacta tatccggat                                      6329
```

<210> SEQ ID NO 76
<211> LENGTH: 13
<212> TYPE: PRT
<213> ORGANISM: Artificial Sequence
<220> FEATURE:
<223> OTHER INFORMATION: Synthetic

<400> SEQUENCE: 76

Lys Leu Ala Ala Ala Leu Glu His His His His His His
1               5                   10